US009464055B2

(12) United States Patent
DeCorte et al.

(10) Patent No.: US 9,464,055 B2
(45) Date of Patent: Oct. 11, 2016

(54) QUINOLINE DERIVATIVES USEFUL AS CB-1 INVERSE AGONISTS

(71) Applicant: JANSSEN PHARMACEUTICA NV, Beerse (BE)

(72) Inventors: Bart DeCorte, Southampton, PA (US); Mark Macielag, Lower Gwynedd, PA (US); Michael Greco, Lansdale, PA (US); Yue-Mei Zhang, Wellesley, MA (US); Christopher Teleha, Fort Washington, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/615,575

(22) Filed: Feb. 6, 2015

(65) Prior Publication Data
US 2015/0239845 A1    Aug. 27, 2015

Related U.S. Application Data

(60) Provisional application No. 61/945,208, filed on Feb. 27, 2014.

(51) Int. Cl.
*C07D 215/44* (2006.01)
*C07D 417/14* (2006.01)
*C07D 409/14* (2006.01)
*C07D 417/06* (2006.01)
*C07D 405/14* (2006.01)
*C07D 401/12* (2006.01)
*C07D 401/14* (2006.01)
*C07D 409/06* (2006.01)
*C07D 215/04* (2006.01)
*C07D 215/42* (2006.01)
*C07D 401/04* (2006.01)

(52) U.S. Cl.
CPC ......... *C07D 215/44* (2013.01); *C07D 215/04* (2013.01); *C07D 215/42* (2013.01); *C07D 401/04* (2013.01); *C07D 401/12* (2013.01); *C07D 401/14* (2013.01); *C07D 405/14* (2013.01); *C07D 409/06* (2013.01); *C07D 409/14* (2013.01); *C07D 417/06* (2013.01); *C07D 417/14* (2013.01)

(58) Field of Classification Search
None
See application file for complete search history.

(56) References Cited

U.S. PATENT DOCUMENTS 8,871,756 B2 * 10/2014 Chen .................... C07D 413/04
514/210.21

* cited by examiner

*Primary Examiner* — Timothy R Rozof
(74) *Attorney, Agent, or Firm* — Thomas J. Dodd

(57) ABSTRACT

The present invention is directed to quinoline derivatives, pharmaceutical compositions containing said derivatives and their use in the treatment of disorders and conditions mediated by the CB-1 receptor; more particularly, in the treatment of disorders and conditions responsive to inverse agonism of the CB-1 receptor. For example, the compounds of the present invention are useful in the treatment of metabolic disorders.

16 Claims, No Drawings

QUINOLINE DERIVATIVES USEFUL AS CB-1 INVERSE AGONISTS

CROSS REFERENCE TO RELATED APPLICATIONS

This application claims the benefit of U.S. Provisional Application 61/945,208, filed on Feb. 27, 2014, which is incorporated by reference herein in its entirety.

FIELD OF THE INVENTION

The present invention is directed to quinoline derivatives, pharmaceutical compositions containing said derivatives and their use in the treatment of disorders and conditions mediated by the CB-1 receptor; more particularly, in the treatment of disorders and conditions responsive to inverse agonism of the CB-1 receptor. For example, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/skeletal muscle, to avoid the adverse effects.

Thus there remains a need for peripherally restricted cannabanoid-1 receptor (CB1R) inverse agonists for the treatment of, for example metabolic disorders, such as obesity, Type II diabetes mellitus, Syndrome X.

SUMMARY OF THE INVENTION

The present invention is directed to CB-1 inverse agonists, more particularly quinoline and quinolone derivatives, compounds of formula (A)

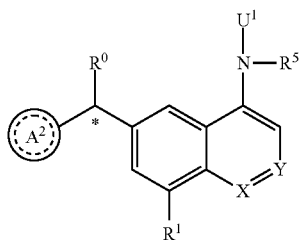

(A)

and stereoisomers, tautomers and pharmaceutically acceptable salts thereof; and compounds of formula (B)

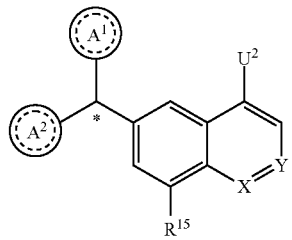

(B)

and stereoisomers, tautomers and pharmaceutically acceptable salts thereof.

In an embodiment, the present invention is directed to compounds of formula (I)

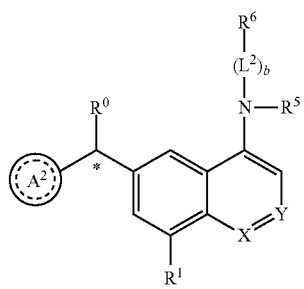

(I)

and stereoisomers, tautomers and pharmaceutically acceptable salts thereof. In another embodiment, the present invention is directed to compounds of formula (II)

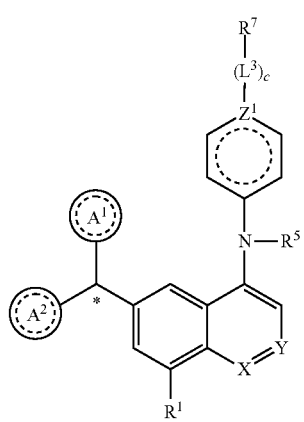

(II)

and stereoisomers, tautomers and pharmaceutically acceptable salts thereof. In another embodiment, the present invention is directed to compounds of formula (III)

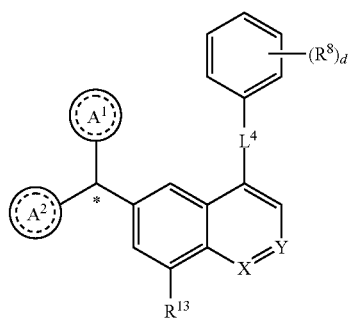

(III)

and stereoisomers, tautomers and pharmaceutically acceptable salts thereof. In another embodiment, the present invention is directed to compounds of formula (IV)

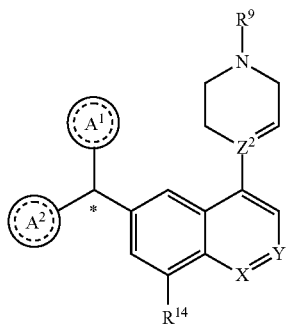

(IV)

and stereoisomers, tautomers and pharmaceutically acceptable salts thereof.

The present invention is directed to compounds of formula (A)

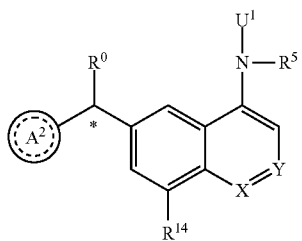

(A)

wherein $U^1$ is selected from the group consisting of

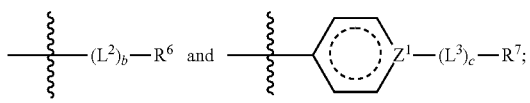

$R^0$ is selected from the group consisting of

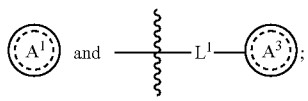

provided that when $U^1$ is

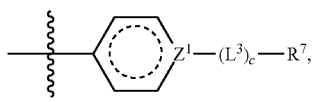

then $R^0$ is

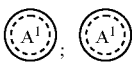

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^AR^B$; wherein $R^A$ and $R^B$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

$L^1$ is selected from the group consisting of —O—, —CH₂—,

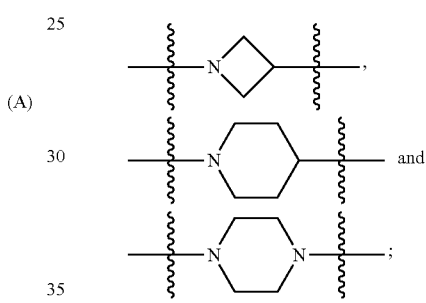

and

;

wherein the azetidin-1,3-diyl, piperidin-1,4-diyl or piperazin-1,4-diyl group is bound to the —CH— portion of the core structure of the compounds of formula (I) at the 1-position;

is phenyl; wherein the phenyl is optionally substituted with one or more substituents, independently selected from the group consisting of halogen, —OH, —CN, $C_{1-4}$alkyl, fluorinated $C_{1-2}$alkyl, $C_{1-4}$alkoxy and fluorinated $C_{1-2}$alkoxy;

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^CR^D$; wherein $R^C$ and $R^D$ are each independently selected from the group consisting of hydrogen, $C_{1-4}$alkyl and —(C$_{2-4}$ alkyl)-O—(C$_{1-4}$alkyl); provided that each substituent is bound to a carbon atom of the ring;

R$^1$ is selected from the group consisting of hydrogen, halogen, —(C$_{1-4}$alkyl)-O—(C$_{1-2}$ alkyl), —(C$_{1-4}$alkyl)-OH, —(C$_{3-4}$alkenyl)-O—(C$_{1-2}$ alkyl), —(C$_{3-4}$alkenyl)-OH, —OH, —C$_{1-4}$alkyl, —O—(C$_{1-4}$alkyl), —O—(C$_{1-4}$alkyl)-CO$_2$H, —O—(C$_{1-4}$alkyl)-C(O)O—(C$_{1-4}$alkyl), —O—(C$_{2-4}$ alkyl)-NH$_2$, —O—(C$_{1-4}$alkyl)-C(O)—NH$_2$, —O—(C$_{2-4}$ alkyl)-NH—C(O)—(C$_{1-2}$ alkyl), —O—(C$_{2-4}$alkyl)-NH—C(O)O—(C$_{1-4}$alkyl) and —NR$^E$R$^F$;

wherein R$^E$ and R$^F$ are each independently selected from the group consisting of hydrogen, C$_{1-4}$alkyl, —(C$_{1-4}$alkyl)-OH, —(C$_{1-4}$alkyl)-CO$_2$H, —(C$_{1-4}$alkyl)-C(O)O—(C$_{1-4}$ alkyl), —(C$_{1-4}$alkyl)-O—(C$_{1-4}$alkyl)-(C$_{1-4}$alkyl)-NH$_2$ and 1-((halogenated C$_{1-2}$alkyl)-sulfonyl))-piperidin-4-yl; alternatively, R$^E$ and R$^F$ are taken together with the nitrogen atom to which they are bound to form a 5 to 6 membered, saturated ring selected from the group consisting of pyrrolidin-1-yl, 1-(pyrrolidin-2-one), piperidin-1-yl, piperiazin-1-yl, 4-methyl-piperazin-1-yl and morpholin-4-yl;

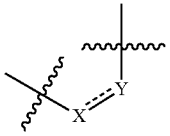

is selected from the group consisting of

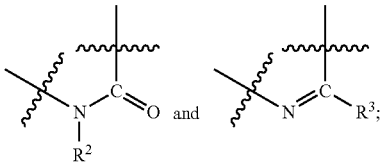

R$^2$ is selected from the group consisting of hydrogen, —(C$_{1-4}$alkyl), —(C$_{2-4}$alkyl)-O—(C$_{1-4}$alkyl), —(C$_{1-4}$alkyl)-CO$_2$H, —(C$_{1-4}$alkyl)-C(O)O—(C$_{1-4}$alkyl) and —(C$_{1-4}$alkyl)-C(O)—NR$^L$R$^M$; wherein R$^L$ and R$^M$ are each independently selected from the group consisting of hydrogen and C$_{1-4}$alkyl;

R$^3$ is selected from the group consisting of hydrogen and —OR$^4$;

wherein R$^4$ is selected from the group consisting of —C$_{1-12}$alkyl, -(hydroxy substituted C$_{2-12}$alkyl), —(C$_{1-12}$alkyl)-N$_3$, (C$_{2-12}$alkyl)-NR$^J$R$^K$, —(C$_{2-12}$alkyl)-O—(C$_{1-12}$ alkyl), —(C$_{2-12}$alkyl)-O—(C$_{1-12}$alkyl)-CN, —(C$_{2-12}$ alkyl)-O—(C$_{1-12}$alkyl)-CO$_2$H, —(C$_{2-12}$alkyl)-O—(C$_{1-12}$ alkyl)-C(O)—O—(C$_{1-6}$ alkyl), —(C$_{2-12}$alkyl)-O—(C$_{1-12}$ alkyl)-C(O)—NR$^J$R$^K$, —(C$_{1-12}$alkyl)-CO$_2$H, —(C$_{1-12}$ alkyl)-C(O)O—(C$_{1-6}$alkyl), —(C$_{2-12}$alkyl)-OC(O)—(C$_{1-6}$ alkyl), —(C$_{2-12}$alkyl)-OC(O)—NR$^J$R$^K$, —(C$_{1-12}$alkyl)-C(O)—NR$^J$R$^K$, —(C$_{2-12}$alkyl)-NR$^J$—C(O)—(C$_{1-6}$alkyl), —(C$_{2-12}$ alkyl)-NR$^J$—C(O)—(C$_{1-12}$alkyl)-OH, —(C$_{2-12}$ alkyl)-NR$^J$—SO$_2$—(C$_{1-6}$alkyl), and —SO$_2$-(halogenated C$_{1-6}$alkyl); wherein R$^J$ and R$^K$ are each independently selected from the group consisting of hydrogen, C$_{1-6}$alkyl and hydroxy substituted C$_{2-6}$alkyl;

provided that when R$^1$ is selected from the group consisting of —(C$_{1-4}$alkyl)-O—(C$_{1-2}$alkyl), —(C$_{1-4}$alkyl)-OH, —(C$_{3-4}$alkenyl)-O—(C$_{1-2}$ alkyl), —(C$_{3-4}$alkenyl)-OH, —O—(C$_{1-4}$alkyl)-CO$_2$H, —O—(C$_{1-4}$alkyl)-C(O)O—(C$_{1-4}$ alkyl), —O—(C$_{2-4}$alkyl)-NH$_2$, —O—(C$_{1-4}$alkyl)-C(O)—NH$_2$, —O—(C$_{2-4}$alkyl)-NH—C(O)—(C$_{1-2}$ alkyl), —O—(C$_{2-4}$alkyl)-NH—C(O)O—(C$_{1-4}$alkyl) and —NR$^E$R$^F$; and wherein R$^E$ and R$^F$ are other than hydrogen or C$_{1-4}$alkyl, then R$^3$ is selected from the group consisting of hydrogen and —O—C$_{1-4}$alkyl;

provided further that when R$^1$ is other than hydrogen, then R$^2$ is hydrogen;

R$^5$ is selected from the group consisting of hydrogen and C$_{1-4}$alkyl;

b is an integer from 0 to 1;

L$^2$ is selected from the group consisting of —CH$_2$—, —CH$_2$CH$_2$—, —CH(CH$_3$)— and cycloprop-1,2-diyl;

R$^6$ is selected from the group consisting of azetidin-3-yl, pyrrolidin-3-yl, piperidin-4-yl, piperazin-1-yl, morpholin-4-yl, phenyl, pyrid-2-yl, pyrid-3-yl, pyrid-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the R$^6$ ring structures is optionally substituted with one substituent selected from the group consisting of halogen, hydroxy, cyano, C$_{1-4}$alkyl, halogenated C$_{1-4}$alkyl, hydroxy substituted C$_{1-12}$alkyl, C$_{1-4}$alkoxy, halogenated C$_{1-4}$alkoxy, —(C$_{1-4}$alkyl)-O—(C$_{1-4}$alkyl), —(C$_{1-4}$ alkyl)-CO$_2$H, —(C$_{1-4}$alkyl)-C(O)O—(C$_{1-4}$alkyl), —(C$_{1-4}$ alkyl)-C(O)—NR$^P$R$^Q$, —O—(C$_{1-4}$alkyl)-O—(C$_{1-4}$alkyl), —O—(C$_{1-4}$alkyl)-CO$_2$H, —O—(C$_{1-4}$alkyl)-C(O)O—(C$_{1-4}$ alkyl), —O—(C$_{1-4}$alkyl)-C(O)—NR$^P$R$^Q$, —C(O)—(C$_{1-4}$ alkyl), —C(O)-(halogenated C$_{1-4}$alkyl), —C(O)—(C$_{1-4}$ alkyl)-CO$_2$H, —C(O)—(C$_{1-4}$alkyl)-C(O)O—(C$_{1-4}$alkyl), —C(O)—NR$^P$R$^Q$, —C(O)—(C$_{1-4}$alkyl)-C(O)—NR$^P$R$^Q$, —CO$_2$H, —C(O)O—(C$_{1-4}$alkyl), —C(O)O—(C$_{1-4}$alkyl)-OC(O)O—(C$_{1-4}$alkyl), —C(=NR$^P$)—NR$^Q$—C(O)O—(C$_{1-4}$ alkyl), —C(=NH)—NH$_2$, —C(=N-Boc)-NH(Boc), —NR$^P$R$^Q$, —NR$^P$—C(O)—(C$_{1-4}$alkyl), —NR$^Q$—SO$_2$—(C$_{1-4}$alkyl), —SO$_2$—(C$_{1-4}$alkyl), —SO$_2$-(halogenated C$_{1-4}$alkyl), —SO$_2$—(C$_{1-4}$alkyl)-OH, —SO$_2$—(C$_{1-4}$alkyl)-C(O)O—(C$_{1-4}$alkyl), —SO$_2$—NR$^P$R$^Q$ and —SO$_2$—(C$_{1-4}$ alkyl)-C(O)—NR$^P$R$^Q$; and wherein R$^P$ and R$^Q$ are each independently selected from the group consisting of hydrogen and C$_{1-4}$alkyl;

and wherein R$^6$ is phenyl; the phenyl is further optionally substituted with an additional substituent selected from the group consisting of halogen, hydroxy, cyano, C$_{1-4}$alkyl, halogenated C$_{1-4}$alkyl, C$_{1-4}$alkoxy and halogenated C$_{1-4}$alkoxy;

provided that when R$^6$ is piperazin-1-yl or morpholin-4-yl, then b is 1 and L$^2$ is —CH$_2$CH$_2$—;

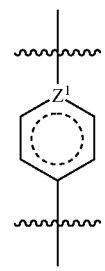

is selected from the group consisting of

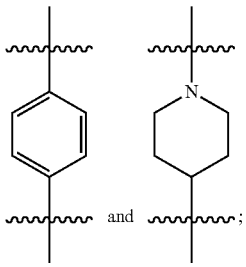 [SMILES: *c1ccc(*)cc1 ; *C1CCN(*)CC1]

and;

wherein $Z^1$ is C or N, respectively; and wherein the

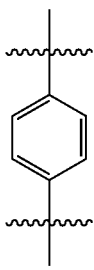 [SMILES: *c1ccc(*)cc1]

is optionally substituted at the ortho-position relative to $Z^1$ with a substituent selected from the group consisting of halogen and $C_{1-4}$alkyl;

c is an integer from 0 to 1;

$L^3$ is selected from the group consisting of —$CH_2$—, —CH($CH_3$)—, —CH($CH_2CH_3$)—, —C(O)— and —$SO_2$—;

$R^7$ is selected from the group consisting of azetidin-3-yl, pyrrolidin-1-yl, piperidin-4-yl, piperazin-1-yl, morpholin-4-yl, phenyl, pyrid-2-yl, pyrid-3-yl, pyrid-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^7$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)—($C_{1-4}$alkyl)-C(O)—$NR^PR^Q$, —$CO_2H$, —C(O)O—($C_{1-4}$alkyl), —C(O)O—($C_{1-4}$alkyl)-OC(O)O—($C_{1-4}$alkyl), —C(=$NR^P$)—$NR^Q$—C(O)O—($C_{1-4}$ alkyl), —C(=NH)—$NH_2$, —C(=N-Boc)-NH(Boc), —$NR^PR^Q$, —$NR^P$—C(O)—($C_{1-4}$alkyl), —$NR^Q$—$SO_2$—($C_{1-4}$alkyl), —$SO_2$—($C_{1-4}$alkyl), —$SO_2$-(halogenated $C_{1-4}$alkyl), —$SO_2$—($C_{1-4}$alkyl)-OH, —$SO_2$—($C_{1-4}$alkyl)-C(O)O—($C_{1-4}$alkyl), —$SO_2$—$NR^PR^Q$ and —$SO_2$—($C_{1-4}$alkyl)-C(O)—$NR^PR^Q$; and wherein $R^P$ and $R^Q$ are each independently selected from the group consisting of hydrogen and $C_{1-4}$alkyl;

and wherein $R^7$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

provided that when

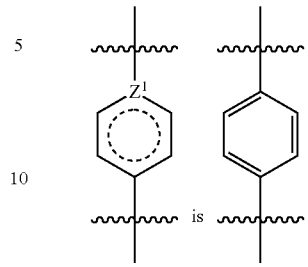

is and c is 0 (i.e $L^3$ is absent); then $R^7$ is phenyl;

provided that when

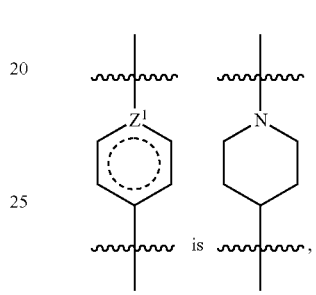

is, c is an integer from 0 to 1, and $L^3$ is —$CH_2$—, then $R^7$ is selected from the group consisting of azetidin-3-yl, piperidin-4-yl, phenyl, pyrid-2-yl, pyrid-3-yl, pyrid-4-yl, thien-2-yl, thein-3-yl, furan-2-yl, furan-3-yl, pyrimidin-2-yl, pyrazin-2-yl, cyclopropyl, cyclobutyl, cyclopentyl and cyclohexyl;

and stereoisomers, tautomers and pharmaceutically acceptable salts thereof.

The present invention is further directed to compounds of formula (B)

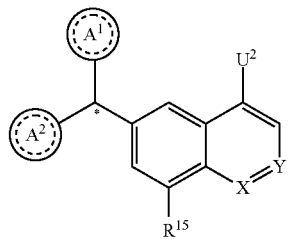

(B)

wherein
$U^2$ is selected from the group consisting of

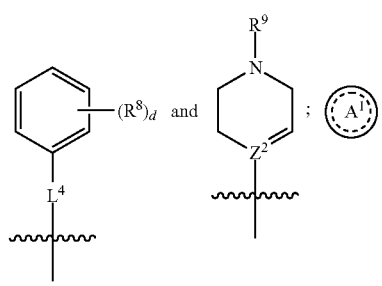

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^AR^B$; wherein $R^A$ and $R^B$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^CR^D$; wherein $R^C$ and $R^D$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

$R^{15}$ is selected from the group consisting of hydrogen, halogen, —OH, —$C_{1-4}$alkyl, —O—($C_{1-4}$alkyl), —$NH_2$, —NH($C_{1-4}$alkyl) and —N($C_{1-4}$alkyl)$_2$;

provided that when $U^2$ is

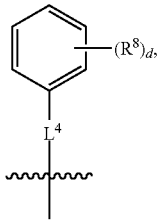

then $R^{15}$ is selected from the group consisting of hydrogen and —O—($C_{1-4}$alkyl);

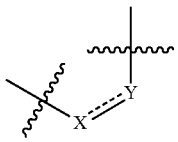

is selected from the group consisting of

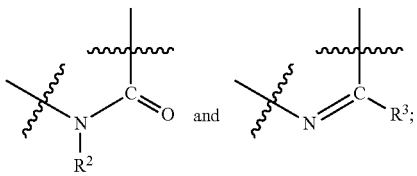

$R^2$ is selected from the group consisting of hydrogen, —($C_{1-4}$alkyl), —($C_{2-4}$alkyl)-O—($C_{1-4}$alkyl), —($C_{1-4}$alkyl)-$CO_2H$, —($C_{1-4}$alkyl)-C(O)O—($C_{1-4}$alkyl) and —($C_{1-4}$alkyl)-C(O)—$NR^LR^M$; wherein $R^L$ and $R^M$ are each independently selected from the group consisting of hydrogen and $C_{1-4}$alkyl;

$R^3$ is selected from the group consisting of hydrogen and —$OR^4$;

wherein $R^4$ is selected from the group consisting of —$C_{1-12}$alkyl, -(hydroxy substituted $C_{2-12}$alkyl), —($C_{1-12}$alkyl)-$N_3$, —($C_{2-12}$alkyl)-$NR^JR^K$, —($C_{2-12}$alkyl)-O—($C_{1-12}$alkyl), —($C_{2-12}$alkyl)-O—($C_{2-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$alkyl), —($C_{1-12}$alkyl)-O—($C_{1-12}$alkyl)-C(O)—$NR^JR^K$, —($C_{1-12}$alkyl)-$CO_2H$, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—$NR^JR^K$, —($C_{1-12}$alkyl)-C(O)—$NR^JR^K$, —($C_{2-12}$alkyl)-$NR^J$—C(O)—($C_{1-6}$alkyl), —($C_{2-12}$alkyl)-$NR^J$—C(O)—($C_{1-12}$alkyl)-OH, —($C_{2-12}$alkyl)-$NR^J$—$SO_2$—($C_{1-6}$alkyl), and —$SO_2$-(halogenated $C_{1-12}$alkyl); wherein $R^J$ and $R^K$ are each independently selected from the group consisting of hydrogen, $C_{1-6}$alkyl and hydroxy substituted $C_{2-6}$alkyl;

provided that when that when $R^{15}$ is other than hydrogen, then $R^2$ is hydrogen;

$L^4$ is selected from the group consisting of —$CH_2$—, —$CH_2CH_2$— and —CH=CH—;

d is an integer from 0 to 2; and each $R^8$ is independently selected from the group consisting of halogen, cyano, $C_{1-4}$alkyl, halogenated $C_{1-4}$alkyl, $C_{1-4}$alkoxy and halogenated $C_{1-4}$alkoxy;

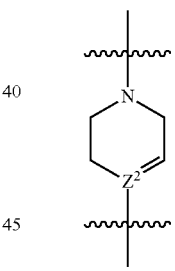

is selected from the group consisting of

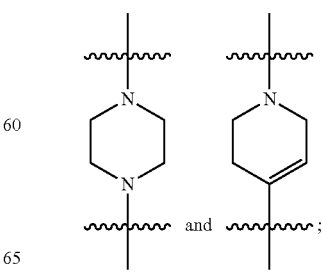

wherein $Z^2$ is N and "----" represents a single bond or alternatively, $Z^2$ is C and "----" represents a double bond;

$R^9$ is selected from the group consisting of hydrogen, —C(O)O—($C_{1-4}$alkyl), —C(O)—($C_{1-4}$alkyl), —C(O)-(halogenated $C_{1-4}$alkyl) and —SO$_2$-(halogenated $C_{1-4}$alkyl);

provided that when

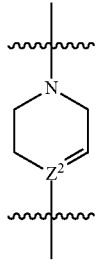

is piperazin-1-yl, then $R^9$ is other than hydrogen;

and stereoisomers, tautomers and pharmaceutically acceptable salts thereof.

In an embodiment, the present invention is directed to compounds of formula (I)

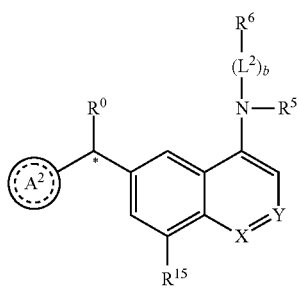

(I)

wherein
$R^0$ is selected from the group consisting of

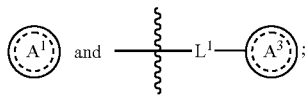

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

$L^1$ is selected from the group consisting of —O—, —CH$_2$—,

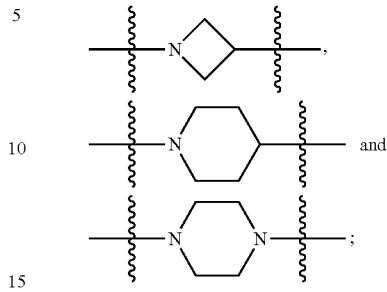

and wherein the azetidin-1,3-diyl, piperidin-1,4-diyl or piperazin-1,4-diyl group is bound to the —CH— portion of the core structure of the compounds of formula (I) at the 1-position;

is phenyl; wherein the phenyl is optionally substituted with one or more substituents, independently selected from the group consisting of halogen, —OH, —CN, $C_{1-4}$alkyl, fluorinated $C_{1-2}$alkyl, $C_{1-4}$alkoxy and fluorinated $C_{1-2}$alkoxy;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^C$R$^D$; wherein R$^C$ and R$^D$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

$R^1$ is selected from the group consisting of hydrogen, halogen, —($C_{1-4}$alkyl)-O—($C_{1-2}$alkyl), —($C_{1-4}$alkyl)-OH, —($C_{3-4}$alkenyl)-O—($C_{1-2}$alkyl), —($C_{3-4}$alkenyl)-OH, —OH, —$C_{1-4}$alkyl, —O—($C_{1-4}$alkyl), —O—($C_{1-4}$alkyl)-CO$_2$H, —O—($C_{1-4}$alkyl)-C(O)O—($C_{1-4}$alkyl), —O—($C_{2-4}$ alkyl)-NH$_2$, —O—($C_{1-4}$alkyl)-C(O)—NH$_2$, —O—($C_{2-4}$ alkyl)-NH—C(O)—($C_{1-2}$alkyl), —O—($C_{2-4}$alkyl)-NH—C(O)O—($C_{1-4}$alkyl) and —NR$^E$R$^F$;

wherein R$^E$ and R$^F$ are each independently selected from the group consisting of hydrogen, $C_{1-4}$alkyl, —($C_{1-4}$alkyl)-OH, —($C_{1-4}$alkyl)-CO$_2$H, —($C_{1-4}$alkyl)-C(O)O—($C_{1-4}$ alkyl), —($C_{1-4}$alkyl)-O—($C_{1-4}$alkyl)-($C_{1-4}$alkyl)-NH$_2$ and 1-((halogenated $C_{1-2}$alkyl)-sulfonyl))-piperidin-4-yl; alternatively, R$^E$ and R$^F$ are taken together with the nitrogen atom to which they are bound to form a 5 to 6 membered, saturated ring selected from the group consisting of pyrrolidin-1-yl, 1-(pyrrolidin-2-one), piperidin-1-yl, piperiazin-1-yl, 4-methyl-piperazin-1-yl and morpholin-4-yl;

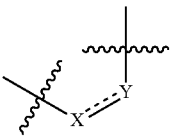

is selected from the group consisting of

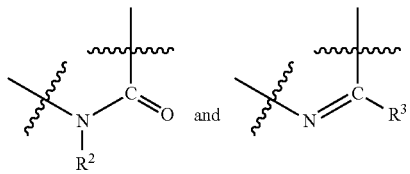

and;

$R^2$ is selected from the group consisting of hydrogen, —($C_{1-4}$alkyl), —($C_{2-4}$alkyl)-O—($C_{1-4}$alkyl), —($C_{1-4}$alkyl)-$CO_2H$, —($C_{1-4}$alkyl)-C(O)O—($C_{1-4}$alkyl) and —($C_{1-4}$alkyl)-C(O)—$NR^LR^M$; wherein $R^L$ and $R^M$ are each independently selected from the group consisting of hydrogen and $C_{1-4}$alkyl;

$R^3$ is selected from the group consisting of hydrogen and —$OR^4$;

wherein $R^4$ is selected from the group consisting of —$C_{1-12}$alkyl, -(hydroxy substituted $C_{2-12}$alkyl), —($C_{1-12}$alkyl)-$N_3$, ($C_{2-12}$alkyl)-$NR^JR^K$, —($C_{2-12}$alkyl)-O—($C_{1-12}$alkyl), —($C_{2-12}$alkyl)-O—($C_{1-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$alkyl), —($C_{2-12}$alkyl)-O—($C_{1-12}$alkyl)-C(O)—$NR^JR^K$, —($C_{1-12}$alkyl)-$CO_2H$, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—$NR^JR^K$, ($C_{1-12}$alkyl)-C(O)—$NR^JR^K$, —($C_{2-12}$alkyl)-$NR^J$—C(O)—($C_{1-6}$alkyl), —($C_{2-12}$alkyl)-$NR^J$—C(O)—($C_{1-12}$alkyl)-OH, —($C_{2-12}$alkyl)-$NR^J$—$SO_2$—($C_{1-6}$alkyl), and —$SO_2$-(halogenated $C_{1-6}$alkyl); wherein $R^J$ and $R^K$ are each independently selected from the group consisting of hydrogen, $C_{1-6}$alkyl and hydroxy substituted $C_{2-6}$alkyl;

provided that when $R^1$ is selected from the group consisting of —($C_{1-4}$alkyl)-O—($C_{1-2}$ alkyl), —($C_{1-4}$alkyl)-OH, —($C_{3-4}$alkenyl)-O—($C_{1-2}$ alkyl), —($C_{3-4}$alkenyl)-OH, —O—($C_{1-4}$alkyl)-$CO_2H$, —O—($C_{1-4}$alkyl)-C(O)O—($C_{1-4}$alkyl), —O—($C_{2-4}$alkyl)-$NH_2$, —O—($C_{1-4}$alkyl)-C(O)—$NH_2$, —O—($C_{2-4}$alkyl)-NH—C(O)—($C_{1-2}$ alkyl), —O—($C_{2-4}$alkyl)-NH—C(O)O—($C_{1-4}$alkyl) and —$NR^ER^F$; and wherein $R^E$ and $R^F$ are other than hydrogen or $C_{1-4}$alkyl, then $R^3$ is selected from the group consisting of hydrogen and —O—$C_{1-4}$alkyl;

provided further that when $R^1$ is other than hydrogen, then $R^2$ is hydrogen;

$R^5$ is selected from the group consisting of hydrogen and $C_{1-4}$alkyl;

b is an integer from 0 to 1;

$L^2$ is selected from the group consisting of —$CH_2$—, —$CH_2CH_2$—, —CH($CH_3$)— and cycloprop-1,2-diyl;

$R^6$ is selected from the group consisting of azetidin-3-yl, pyrrolidin-3-yl, piperidin-4-yl, piperazin-1-yl, morpholin-4-yl, phenyl, pyrid-2-yl, pyrid-3-yl, pyrid-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^6$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)—($C_{1-4}$alkyl)-C(O)—$NR^PR^Q$, —$CO_2H$, —C(O)O—($C_{1-4}$alkyl), —C(O)O—($C_{1-4}$alkyl)-OC(O)O—($C_{1-4}$alkyl), —C(=$NR^P$)—$NR^Q$—C(O)O—($C_{1-4}$ alkyl), —C(=NH)—$NH_2$, —C(=N-Boc)-NH(Boc), —$NR^PR^Q$, —$NR^P$—C(O)—($C_{1-4}$alkyl), —$NR^Q$—$SO_2$—($C_{1-4}$alkyl), —$SO_2$—($C_{1-4}$alkyl), —$SO_2$-(halogenated $C_{1-4}$alkyl), —$SO_2$—($C_{1-4}$alkyl)-OH, —$SO_2$—($C_{1-4}$alkyl)-C(O)O—($C_{1-4}$alkyl), —$SO_2$—$NR^PR^Q$ and —$SO_2$—($C_{1-4}$alkyl)-C(O)—$NR^PR^Q$; and wherein $R^P$ and $R^Q$ are each independently selected from the group consisting of hydrogen and $C_{1-4}$alkyl;

and wherein $R^6$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

provided that when $R^6$ is piperazin-1-yl or morpholin-4-yl, then b is 1 and $L^2$ is —$CH_2CH_2$—;

and stereoisomers, tautomers and pharmaceutically acceptable salts thereof.

In another embodiment, the present invention is directed to compounds of formula (II)

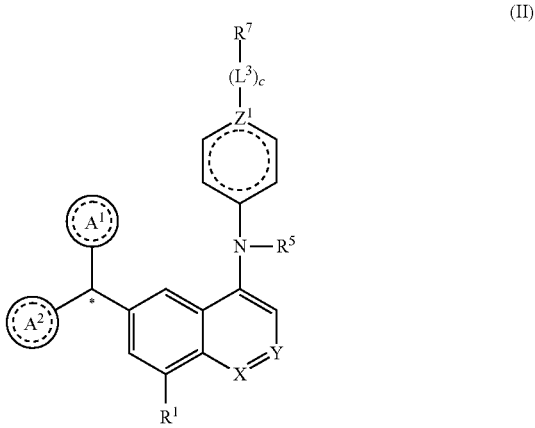

(II)

wherein

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, C$_{1-4}$alkyl and —(C$_{2-4}$ alkyl)-O—(C$_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, cyano, —C(O)OH, C(O)O—C$_{1-4}$alkyl and NR$^C$R$^D$; wherein R$^C$ and R$^D$ are each independently selected from the group consisting of hydrogen, C$_{1-4}$alkyl and —(C$_{2-4}$ alkyl)-O—(C$_{1-4}$alkyl); provided that each substituent is bound to a carbon atom of the ring;

R$^1$ is selected from the group consisting of hydrogen, halogen, —(C$_{1-4}$alkyl)-O—(C$_{1-2}$alkyl), —(C$_{1-4}$alkyl)-OH, —(C$_{3-4}$alkenyl)-O—(C$_{1-2}$ alkyl), —(C$_{3-4}$alkenyl)-OH, —OH, —C$_{1-4}$alkyl, —O—(C$_{1-4}$alkyl), —O—(C$_{1-4}$alkyl)-CO$_2$H, —O—(C$_{1-4}$alkyl)-C(O)O—(C$_{1-4}$alkyl), —O—(C$_{2-4}$ alkyl)-NH$_2$, —O—(C$_{1-4}$alkyl)-C(O)—NH$_2$, —O—(C$_{2-4}$ alkyl)-NH—C(O)—(C$_{1-2}$ alkyl), —O—(C$_{2-4}$alkyl)-NH—C(O)O—(C$_{1-4}$alkyl) and —NR$^E$R$^F$;

wherein R$^E$ and R$^F$ are each independently selected from the group consisting of hydrogen, C$_{1-4}$alkyl, —(C$_{2-4}$alkyl)-OH, —(C$_{1-4}$alkyl)-CO$_2$H, —(C$_{1-4}$alkyl)-C(O)O—(C$_{1-4}$ alkyl), —(C$_{2-4}$alkyl)-O—(C$_{1-4}$alkyl)-(C$_{1-4}$alkyl)-NH$_2$ and 1-((halogenated C$_{1-2}$alkyl)-sulfonyl))-piperidin-4-yl; alternatively, R$^E$ and R$^F$ are taken together with the nitrogen atom to which they are bound to form a 5 to 6 membered, saturated ring selected from the group consisting of pyrrolidin-1-yl, 1-(pyrrolidin-2-one), piperidin-1-yl, piperiazin-1-yl, 4-methyl-piperazin-1-yl and morpholin-4-yl;

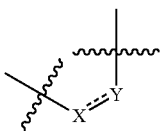

is selected from the group consisting of

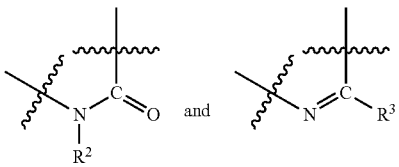

and;

R$^2$ is selected from the group consisting of hydrogen, —(C$_{1-4}$alkyl), —(C$_{2-4}$alkyl)-O—(C$_{1-4}$alkyl), —(C$_{1-4}$alkyl)-CO$_2$H, —(C$_{1-4}$alkyl)-C(O)O—(C$_{1-4}$alkyl) and —(C$_{1-4}$alkyl)-C(O)—NR$^L$R$^M$; wherein R$^L$ and R$^M$ are each independently selected from the group consisting of hydrogen and C$_{1-4}$alkyl;

R$^3$ is selected from the group consisting of hydrogen and —OR$^4$;

wherein R$^4$ is selected from the group consisting of —C$_{1-12}$alkyl, -(hydroxy substituted C$_{2-12}$alkyl), —(C$_{1-12}$alkyl)-N$_3$, —(C$_{2-12}$alkyl)-NR$^J$R$^K$, —(C$_{2-12}$alkyl)-O—(C$_{1-12}$alkyl), —(C$_{2-12}$alkyl)-O—(C$_{1-12}$alkyl)-CN, —(C$_{2-12}$ alkyl)-O—(C$_{1-12}$alkyl)-CO$_2$H, —(C$_{2-12}$alkyl)-O—(C$_{1-12}$ alkyl)-C(O)—O—(C$_{1-6}$ alkyl), —(C$_{6-12}$alkyl)-O—(C$_{1-12}$ alkyl)-C(O)—NR$^J$R$^K$, —(C$_{1-12}$alkyl)-CO$_2$H, —(C$_{1-12}$ alkyl)-C(O)O—(C$_{1-6}$alkyl), —(C$_{2-12}$alkyl)-OC(O)—(C$_{1-6}$ alkyl), —(C$_{2-12}$alkyl)-OC(O)—NR$^J$R$^K$, —(C$_{1-12}$alkyl)-C(O)—NR$^J$R$^K$, —(C$_{2-12}$alkyl)-NR$^J$—C(O)—(C$_{1-6}$alkyl), —(C$_{2-12}$alkyl)-NR$^J$—C(O)—(C$_{1-12}$alkyl)-OH, —(C$_{2-12}$ alkyl)-NR$^J$—SO$_2$—(C$_{1-6}$alkyl), and —SO$_2$-(halogenated C$_{1-12}$alkyl); wherein R$^J$ and R$^K$ are each independently selected from the group consisting of hydrogen, C$_{1-6}$alkyl and hydroxy substituted C$_{2-6}$alkyl;

provided that when R$^1$ is selected from the group consisting of —(C$_{1-4}$alkyl)-O—(C$_{1-2}$ alkyl), —(C$_{1-4}$alkyl)-OH, —(C$_{3-4}$alkenyl)-O—(C$_{1-2}$ alkyl), —(C$_{3-4}$alkenyl)-OH, —O—(C$_{1-4}$alkyl)-CO$_2$H, —O—(C$_{1-4}$alkyl)-C(O)O—(C$_{1-4}$ alkyl), —O—(C$_{2-4}$alkyl)-NH$_2$, —O—(C$_{1-4}$alkyl)-C(O)—NH$_2$, —O—(C$_{2-4}$alkyl)-NH—C(O)—(C$_{1-2}$ alkyl), —O—(C$_{2-4}$alkyl)-NH—C(O)O—(C$_{1-4}$alkyl) and —NR$^E$R$^F$; and wherein R$^E$ and R$^F$ are other than hydrogen or C$_{1-4}$alkyl, then R$^3$ is selected from the group consisting of hydrogen and —O—C$_{1-4}$alkyl;

provided further that when R$^1$ is other than hydrogen, then R$^2$ is hydrogen;

R$^5$ is selected from the group consisting of hydrogen and C$_{1-4}$alkyl;

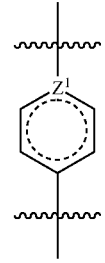

is selected from the group consisting of

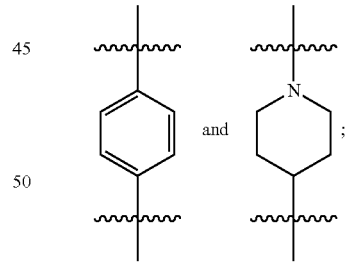

wherein Z$^1$ is C or N, respectively; and wherein the

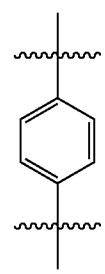 [SMILES: *c1ccc(*)cc1]

is optionally substituted at the ortho-position relative to $Z^1$ with a substituent selected from the group consisting of halogen and $C_{1-4}$alkyl;

c is an integer from 0 to 1;

$L^3$ is selected from the group consisting of —CH$_2$—, —CH(CH$_3$)—, —CH(CH$_2$CH$_3$)—, —C(O)— and —SO$_2$—;

$R^7$ is selected from the group consisting of azetidin-3-yl, pyrrolidin-1-yl, piperidin-4-yl, piperazin-1-yl, morpholin-4-yl, phenyl, pyrid-2-yl, pyrid-3-yl, pyrid-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^7$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-CO$_2$H, —($C_{1-4}$alkyl)-C(O)O—($C_{1-4}$alkyl), —($C_{1-4}$alkyl)-C(O)—NR$^P$R$^Q$, —O—($C_{1-4}$alkyl)-O—($C_{1-4}$alkyl), —O—($C_{1-4}$alkyl)-CO$_2$H, —O—($C_{1-4}$alkyl)-C(O)O—($C_{1-4}$alkyl), —O—($C_{1-4}$alkyl)-C(O)—NR$^P$R$^Q$, —C(O)—($C_{1-4}$alkyl), —C(O)-(halogenated $C_{1-4}$alkyl), —C(O)—($C_{1-4}$alkyl)-CO$_2$H, —C(O)—($C_{1-4}$alkyl)-C(O)O—($C_{1-4}$alkyl), —C(O)—NR$^P$R$^Q$, —C(O)—($C_{1-4}$alkyl)-C(O)—NR$^P$R$^Q$, —CO$_2$H, —C(O)O—($C_{1-4}$alkyl), —C(O)O—($C_{1-4}$alkyl)-OC(O)O—($C_{1-4}$alkyl), —C(=NR$^P$)—NR$^Q$—C(O)O—($C_{1-4}$ alkyl), —C(=NH)—NH$_2$, —C(=N-Boc)-NH(Boc), —NR$^P$R$^Q$, —NR$^P$—C(O)—($C_{1-4}$alkyl), —NR$^Q$—SO$_2$—($C_{1-4}$alkyl), —SO$_2$—($C_{1-4}$alkyl), —SO$_2$-(halogenated $C_{1-4}$alkyl), —SO$_2$—($C_{1-4}$alkyl)-OH, —SO$_2$—($C_{1-4}$alkyl)-C(O)O—($C_{1-4}$alkyl), —SO$_2$—NR$^P$R$^Q$ and —SO$_2$—($C_{1-4}$alkyl)-C(O)—NR$^P$R$^Q$; and wherein R$^P$ and R$^Q$ are each independently selected from the group consisting of hydrogen and $C_{1-4}$alkyl;

and wherein $R^7$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

provided that when

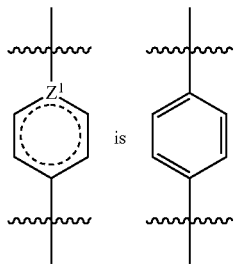

is and c is 0 (i.e $L^3$ is absent); then $R^7$ is phenyl;

provided that when

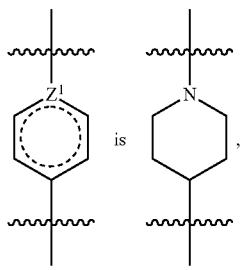

is

, c is an integer from 0 to 1, and $L^3$ is —CH$_2$—, then $R^7$ is selected from the group consisting of azetidin-3-yl, piperidin-4-yl, phenyl, pyrid-2-yl, pyrid-3-yl, pyrid-4-yl, thien-2-yl, thein-3-yl, furan-2-yl, furan-3-yl, pyrimidin-2-yl, pyrazin-2-yl, cyclopropyl, cyclobutyl, cyclopentyl and cyclohexyl;

and stereoisomers, tautomers and pharmaceutically acceptable salts thereof.

In another embodiment, the present invention is directed to compounds of formula (III)

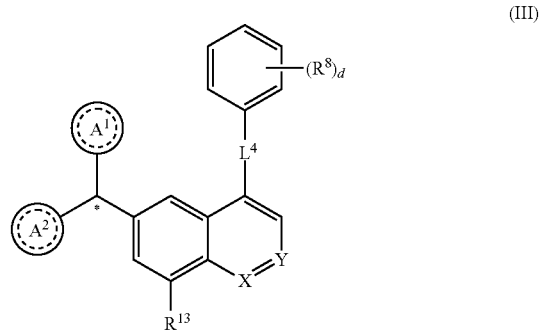

(III)

wherein

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^C$R$^D$; wherein R$^C$ and R$^D$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

$R^{13}$ is selected from the group consisting of hydrogen and —O—($C_{1-4}$alkyl);

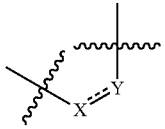

is selected from the group consisting of

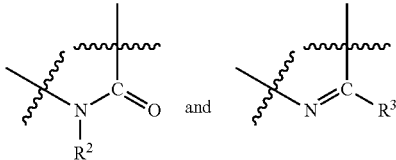

and;

$R^2$ is selected from the group consisting of hydrogen, —($C_{1-4}$alkyl), —($C_{2-4}$alkyl)-O—($C_{1-4}$alkyl), —($C_{1-4}$alkyl)-CO$_2$H, —($C_{1-4}$alkyl)-C(O)O—($C_{1-4}$alkyl) and —($C_{1-4}$alkyl)-C(O)—NR$^L$R$^M$; wherein R$^L$ and R$^M$ are each independently selected from the group consisting of hydrogen and $C_{1-4}$alkyl;

$R^3$ is selected from the group consisting of hydrogen and —OR$^4$;

wherein $R^4$ is selected from the group consisting of —$C_{1-12}$alkyl, -(hydroxy substituted $C_{2-12}$alkyl), —($C_{1-12}$ alkyl)-N$_3$, —($C_{2-12}$alkyl)-NR$^J$R$^K$, —($C_{2-12}$alkyl)-O—($C_{1-12}$ alkyl), —($C_{2-12}$alkyl)-O—($C_{1-12}$alkyl)-CN, —($C_{2-12}$ alkyl)-O—($C_{1-12}$alkyl)-CO$_2$H, —($C_{2-12}$alkyl)-O—($C_{1-12}$ alkyl)-C(O)—O—($C_{1-6}$ alkyl), —($C_{2-12}$alkyl)-O—($C_{1-12}$ alkyl)-C(O)—NR$^J$R$^K$, —($C_{1-12}$alkyl)-CO$_2$H, —($C_{1-12}$ alkyl)-C(O)O—($C_{1-6}$alkyl), —($C_{2-12}$alkyl)-OC(O)—($C_{1-6}$ alkyl), —($C_{2-12}$alkyl)-OC(O)—NR$^J$R$^K$, —($C_{1-12}$alkyl)-C(O)—NR$^J$R$^K$, —($C_{2-12}$alkyl)-NR$^J$—C(O)—($C_{1-6}$alkyl), —($C_{2-12}$alkyl)-NR$^J$—C(O)—($C_{1-12}$alkyl)-OH, —($C_{2-12}$ alkyl)-NR$^J$—SO$_2$—($C_{1-6}$alkyl), and —SO$_2$-(halogenated $C_{1-12}$alkyl); wherein R$^J$ and R$^K$ are each independently selected from the group consisting of hydrogen, $C_{1-6}$alkyl and hydroxy substituted $C_{2-6}$alkyl;

provided that when $R^{13}$ is —O—($C_{1-4}$alkyl), then $R^2$ is hydrogen;

$L^4$ is selected from the group consisting of —CH$_2$—, —CH$_2$CH$_2$— and —CH=CH—;

d is an integer from 0 to 2;

each $R^8$ is independently selected from the group consisting of halogen, cyano, $C_{1-4}$alkyl, halogenated $C_{1-4}$alkyl, $C_{1-4}$alkoxy and halogenated $C_{1-4}$alkoxy;

and stereoisomers, tautomers and pharmaceutically acceptable salts thereof.

In another embodiment, the present invention is directed to compounds of formula (IV)

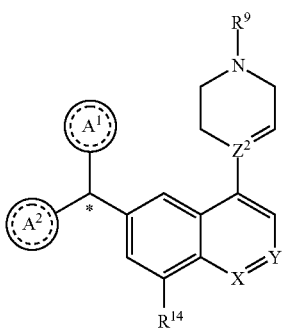

(IV)

wherein

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^C$R$^D$; wherein R$^C$ and R$^D$ are each independently selected from the group consisting of hydrogen, $C_{1-4}$alkyl and —($C_{2-4}$ alkyl)-O—($C_{1-4}$alkyl); provided that each substituent is bound to a carbon atom of the ring;

$R^{14}$ is selected from the group consisting of hydrogen, halogen, —OH, —$C_{1-4}$alkyl, —O—($C_{1-4}$alkyl), —NH$_2$, —NH($C_{1-4}$alkyl) and —N($C_{1-4}$alkyl)$_2$;

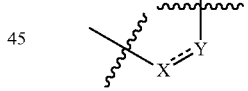

is selected from the group consisting of

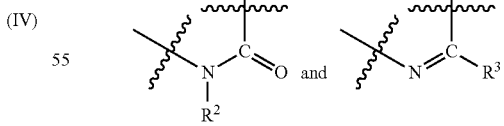

and;

$R^2$ is selected from the group consisting of hydrogen, —($C_{1-4}$alkyl), —($C_{2-4}$alkyl)-O—($C_{1-4}$alkyl), —($C_{1-4}$alkyl)-CO$_2$H, —($C_{1-4}$alkyl)-C(O)O—($C_{1-4}$alkyl) and —($C_{1-4}$ alkyl)-C(O)—NR$^L$R$^M$; wherein R$^L$ and R$^M$ are each independently selected from the group consisting of hydrogen and $C_{1-4}$alkyl;

$R^3$ is selected from the group consisting of hydrogen and —OR$^4$;

wherein $R^4$ is selected from the group consisting of —$C_{1-12}$alkyl, -(hydroxy substituted $C_{2-12}$alkyl), —($C_{1-12}$alkyl)-$N_3$, —($C_{2-12}$alkyl)-$NR^JR^K$, —($C_{2-12}$alkyl)-O—($C_{1-12}$alkyl), —($C_{2-12}$alkyl)-O—($C_{2-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$alkyl), —($C_{1-12}$alkyl)-O—($C_{1-12}$alkyl)-C(O)—$NR^JR^K$, —($C_{1-12}$alkyl)-$CO_2H$, —($C_{1-12}$alkyl)-C(O)—O—($C_{1-6}$alkyl), —($C_{2-12}$alkyl)-OC(O)—($C_{1-6}$ alkyl), —($C_{2-12}$alkyl)-OC(O)—$NR^JR^K$, —($C_{1-12}$alkyl)-C(O)—$NR^JR^K$, —($C_{2-12}$alkyl)-$NR^J$—C(O)—($C_{1-6}$alkyl), —($C_{2-12}$alkyl)-$NR^J$—C(O)—($C_{1-12}$alkyl)-OH, —($C_{2-12}$ alkyl)-$NR^J$—$SO_2$—($C_{1-6}$alkyl), and —$SO_2$-(halogenated $C_{1-6}$alkyl); wherein $R^J$ and $R^K$ are each independently selected from the group consisting of hydrogen, $C_{1-6}$alkyl and hydroxy substituted $C_{2-6}$alkyl;

provided that when $R^{14}$ is other than hydrogen, then $R^2$ is hydrogen;

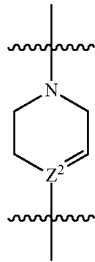

is selected from the group consisting of

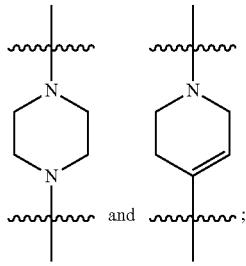

wherein $Z^2$ is N and " ----- " represents a single bond or alternatively, $Z^2$ is C and " ----- " represents a double bond;

$R^9$ is selected from the group consisting of hydrogen, —C(O)O—($C_{1-4}$alkyl), —C(O)—($C_{1-4}$alkyl), —C(O)-(halogenated $C_{1-4}$alkyl) and —$SO_2$-(halogenated $C_{1-4}$alkyl);

provided that when

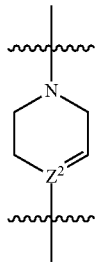

is piperazin-1-yl, then $R^9$ is other than hydrogen;

and stereoisomers, tautomers and pharmaceutically acceptable salts thereof.

The present invention is further directed to processes for the preparation of the compounds of formula (I). The present invention is further directed to processes for the preparation of the compounds of formula (II). The present invention is further directed to processes for the preparation of the compounds of formula (III). The present invention is further directed to processes for the preparation of the compounds of formula (IV). The present invention is further directed to a product prepared according to any of the process(es) described herein.

The present invention is further directed to intermediate compounds useful in the synthesis of the compounds of formula (I), as described and defined in the synthesis schemes and examples which follow herein. The present invention is further directed to intermediate compounds useful in the synthesis of the compounds of formula (II), as described and defined in the synthesis schemes and examples which follow herein. The present invention is further directed to intermediate compounds useful in the synthesis of the compounds of formula (III), as described and defined in the synthesis schemes and examples which follow herein. The present invention is further directed to intermediate compounds useful in the synthesis of the compounds of formula (IV), as described and defined in the synthesis schemes and examples which follow herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

In an embodiment, the present invention is directed to a compound of formula (I) or a compound of formula (II) for use as a medicament. In another embodiment, the present invention is directed to a compound of formula (I) or a compound of formula (II) for use in the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain). In another embodiment, the present invention is directed to a composition comprising a compound of formula (I) for the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain Another example of the invention is the use of any of the compounds described herein in the preparation of a medicament for treating: (a) obesity, (b) Type I diabetes, (c) Type II diabetes, (d) gestational diabetes, (e) latent autoimmune diabetes of adults (LADA), (f) pre-diabetes, (g) insulin resistance, (h) inadequate glucose tolerance, (i) dyslipidemia (including, but not limited to elevated triglycerides and LDL, and low HDL), (j) nonalcoholic steatohepatitis (NASH), (k) cirrhosis, (l) fatty liver disease, (m) atherosclerosis, (n) hypertension, (o) inflammatory bowel disease, (p) Alzheimer's disease, (q) osteoporosis, (r) multiple sclerosis, (s) traumatic brain injury, (t) arthritis, or (u) neuropathic pain, in a subject in need thereof. In another example, the present invention is directed to a compound as described herein for use in method for treating a disorder selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain, in a subject in need thereof.

In additional embodiments the present invention is as described herein.

DETAILED DESCRIPTION OF THE INVENTION

The present invention is directed to compounds of formula (A)

(A)

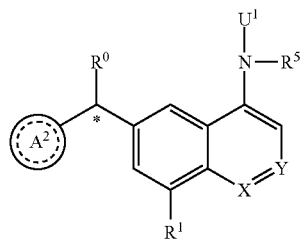

wherein $R^0$, $R^1$, $R^5$, $U^1$,

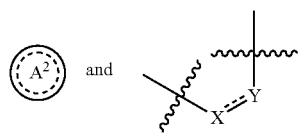

are as herein defined, and stereoisomers, tautomers and pharmaceutically acceptable salts thereof. The present invention is further directed to compounds of formula (B)

(B)

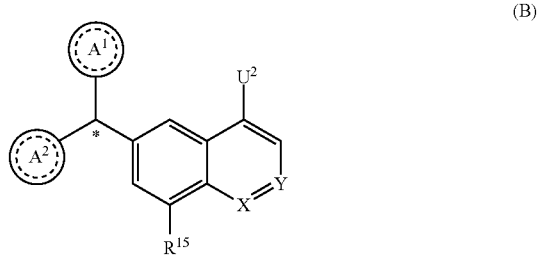

wherein $R^{15}$, $U^2$.

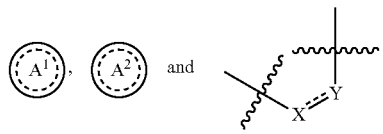

are as herein defined, and stereoisomers, tautomers and pharmaceutically acceptable salts thereof.

The compounds of formula (A) and the compounds of formula (B) of the present invention are CB-1 receptor inverse agonists, useful in the treatment of metabolic disorders, including but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

In an embodiment, the present invention is directed to compounds of formula (I)

(I)

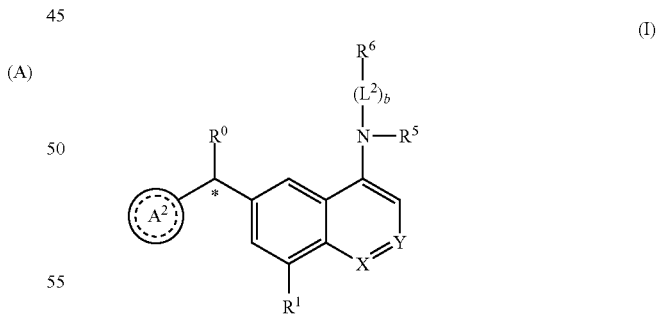

wherein

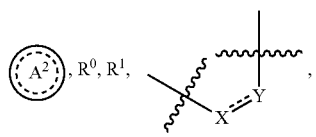

$R^5$, b, $L^2$ and $R^6$ are as herein defined, and stereoisomers, tautomers and pharmaceutically acceptable salts thereof.

In another embodiment, the present invention is directed to compounds of formula (II)

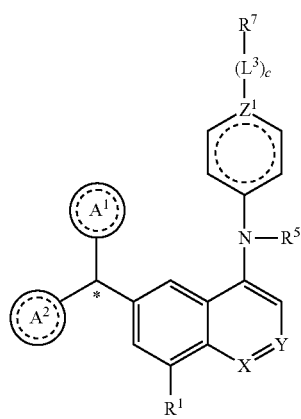
(II)

wherein

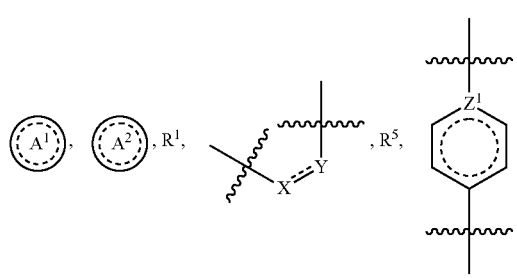

c, $L^3$ and $R^7$ are as herein defined, and stereoisomers, tautomers and pharmaceutically acceptable salts thereof.

In another embodiment, present invention is directed to compounds of formula (III)

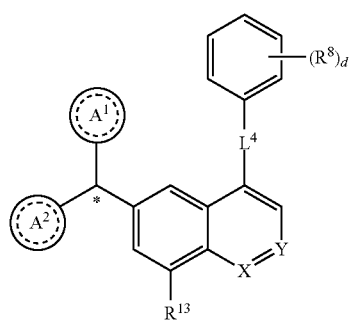
(III)

wherein

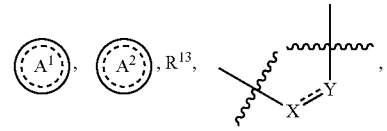

$L^4$, d and $R^8$ are as herein defined, and stereoisomers, tautomers and pharmaceutically acceptable salts thereof.

In another embodiment, present invention is directed to compounds of formula (IV)

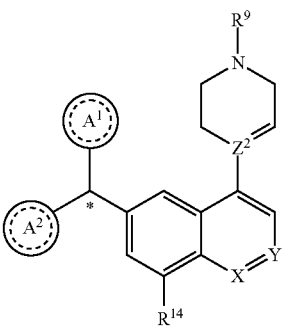
(IV)

wherein

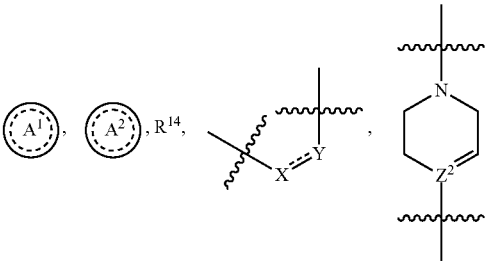

and $R^9$ are as herein defined, and stereoisomers, tautomers and pharmaceutically acceptable salts thereof.

The compounds of formula (I), the compounds of formula (II), the compounds of formula (III) and the compounds of formula (IV) of the present invention are CB-1 receptor inverse agonists, useful in the treatment of metabolic disorders including, but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

One skilled in the art will recognize that wherein the compounds of formula (A), (B), (I), (II), (III) and/or (IV) of the present invention,

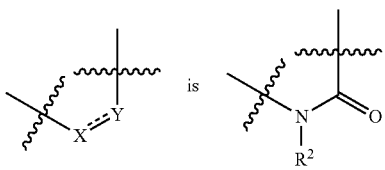 is 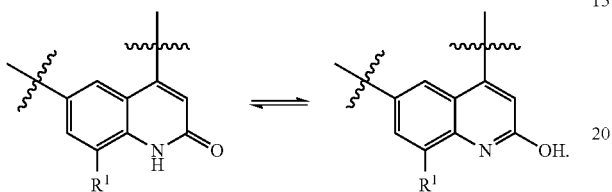

and R² is hydrogen, said compounds may exists as tautomers. More particularly, the quinoline/quinolone core may be present in either of the following keto/enol tautomeric forms or as a mixture of said keto/enol tautomeric forms:

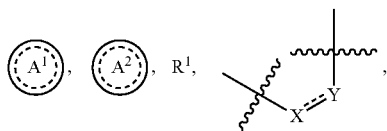

One skilled in the art will further recognize that some variables (e.g.

R², R³, etc.) appear in the definition of two or more of the compounds of formula (A), compounds of formula (B), compounds of formula (I), compounds of formula (II), compounds of formula (III) and compounds of formula (IV). One skilled in the art will further recognize that the selection of substituent(s) for any particularly variable in any compound of formula (A), compound of formula (B), compound of formula (I), compound of formula (II), compound of formula (III) and/or compound of formula (IV), is not intended to limit said variable in any of the others of the compounds of formula (A), compounds of formula (B), compounds of formula (I), compounds of formula (II), compounds of formula (III) and/or compounds of formula (IV).

More particularly, one skilled in the art will recognize that wherein a particular substituent or group of substituents is selected for a given variable for a compound of formula (A), said selection is not intended to limit the scope of said variable for compounds of formula (B), compounds of formula (I), compounds of formula (II), compounds of formula (III) and/or compounds of formula (IV). Similarly, the selection of a particular substituent for a given variable for a compound of formula (B), is not intended to limit the scope of said variable for compounds of formula (A), compounds of formula (I), compounds of formula (II), compounds of formula (III) and/or compounds of formula (IV). Similarly, the selection of a particular substituent for a given variable for a compound of formula (I), is not intended to limit the scope of said variable for compounds of formula (A), compounds of formula (B), compounds of formula (II), compounds of formula (III) and/or compounds of formula (IV). Similarly, the selection of a particular substituent for a given variable for a compound of formula (II), is not intended to limit the scope of said variable for compounds of formula (A), compounds of formula (B), compounds of formula (I), compounds of formula (III) and/or compounds of formula (IV). Similarly, the selection of a particular substituent for a given variable for a compound of formula (III), is not intended to limit the scope of said variable for compounds of formula (A), compounds of formula (B), compounds of formula (I), compounds of formula (II) and/or compounds of formula (IV). Similarly, the selection of a particular substituent for a given variable for a compound of formula (IV), is not intended to limit the scope of said variable for compounds of formula (A), compounds of formula (B), compounds of formula (I), compounds of formula (II) and/or compounds of formula (III).

In an embodiment of the present invention,

is selected from the group consisting of phenyl, thiazolyl and benzothiazolyl; wherein the phenyl or thiazolyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, and $NR^A R^B$; wherein $R^A$ and $R^B$ are each independently selected from the group consisting of hydrogen, $C_{1-4}$alkyl and —($C_2$alkyl)-O—($C_{1-2}$alkyl); provided that each substituent is bound to a carbon atom of the ring. In another embodiment of the present invention,

is selected from the group consisting of phenyl and thiazolyl; wherein the phenyl is substituted with a halogen. In another embodiment of the present invention,

is phenyl; wherein the phenyl is substituted with a substituent selected from the group consisting of halogen and $C_{1-2}$alkoxy. In another embodiment of the present invention,

is phenyl; wherein the phenyl is substituted with a halogen.

In an embodiment of the present invention, is selected from the group consisting of 4-chlorophenyl and 4-methoxyphenyl. In another embodiment of the present invention,

is selected from the group consisting of phenyl, 4-chlorophenyl and 4-fluorophenyl. In another embodiment of the present invention,

is 4-chlorophenyl.

In an embodiment of the present invention, $L^1$ is selected from the group consisting of —O—, —CH$_2$—,

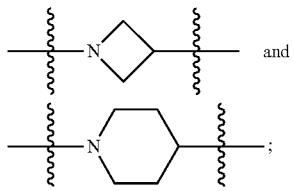

wherein the azetidin-1,3-diyl or piperidin-1,4-diyl group is bound to the —CH— portion of the core structure of the compounds of formula (I) at the 1-position.

In another embodiment of the present invention, $L^1$ is selected from the group consisting in —O—, —CH$_2$— and

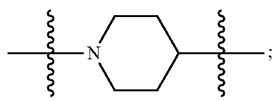

wherein the piperidin-1,4-diyl group is bound to the —CH— portion of the core structure of the compounds of formula (I) at the 1-position.

In another embodiment of the present invention, $L^1$ is selected from the group consisting in —O— and

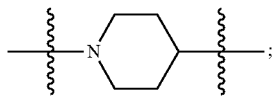

wherein the piperidin-1,4-diyl group is bound to the —CH— portion of the core structure of the compounds of formula (I) at the 1-position.

In an embodiment of the present invention,

is phenyl; wherein the phenyl is optionally substituted with one to two substituents, independently selected from the group consisting of halogen, —OH, C$_{1-4}$alkyl, fluorinated C$_{1-2}$alkyl, C$_{1-4}$alkoxy and fluorinated C$_{1-2}$alkoxy. In another embodiment of the present invention,

is phenyl; wherein the phenyl is substituted with a halogen.
In another embodiment of the present invention,

is selected from the group consisting of phenyl, 4-fluorophenyl and 4-chlorophenyl. In another embodiment of the present invention,

is selected from the group consisting of phenyl and 4-chlorophenyl.

In another embodiment of the present invention, $L^1$ is —O—; and

is 4-chlorophenyl.

In an embodiment of the present invention,

is selected from the group consisting of phenyl, thiazolyl, pyridyl and benzothiazolyl; wherein the phenyl, thiazolyl or pyridyl is optionally substituted with one to two substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, and NR$^C$R$^D$; wherein R$^C$ and R$^D$ are each independently selected from the group consisting of hydrogen, C$_{1-4}$alkyl and —(C$_{2-2}$alkyl)-O—(C$_{1-2}$ alkyl); provided that each substituent is bound to a carbon atom of the ring. In another embodiment of the present invention,

is selected from the group consisting of phenyl, thiazolyl, pyridyl and benzothiazolyl; wherein the phenyl or pyridyl is optionally substituted with one to two substituents independently selected from the group consisting of halogen, hydroxy, C$_{1-2}$ alkoxy, fluorinated C$_{1-2}$ alkyl and —NR$^C$R$^D$; wherein R$^C$ and R$^D$ are each independently selected from the group consisting of hydrogen and —(C$_2$alkyl)-O—(C$_{1-2}$ alkyl). In an embodiment of the present invention,

is selected from the group consisting of phenyl, thiazolyl and thienyl; wherein the phenyl or thienyl is optionally substituted with a substituent selected from the group consisting of halogen and $C_{1-2}$alkoxy.

In another embodiment of the present invention,

is selected from the group consisting of 4-chlorophenyl, 4-fluorophenyl, 3,4-dichlorophenyl, 4-hydroxyphenyl, 4-methoxyphenyl, 4-trifluoromethylphenyl, 4-(methoxyethylamino)-phenyl, thiazol-2-yl, 4-chloro-pyridyl, benzothiazol-2-yl and benzo[d][1,3]dioxol-5-yl. In another embodiment of the present invention,

is selected from the group consisting of 4-chlorophenyl, 3,4-dichlorophenyl, 4-hydroxyphenyl, 4-methoxyphenyl, 4-trifluoromethylphenyl, 4-(methoxyethylamino)-phenyl, thiazol-2-yl, 6-chloro-pyrid-3-yl, benzothiazol-2-yl and benzo[d][1,3]dioxol-5-yl. In another embodiment of the present invention,

is selected from the group consisting of 4-chlorophenyl, 3,4-dichlorophenyl, 4-hydroxyphenyl, 4-trifluoromethylphenyl, 4-(methoxyethylamino)-phenyl, thiazol-2-yl, 6-chloro-pyrid-3-yl, benzothiazol-2-yl and benzo[d][1,3]dioxol-5-yl. In another embodiment of the present invention,

is selected from the group consisting of 4-chlorophenyl, 3,4-dichlorophenyl, 4-hydroxyphenyl, 4-trifluoromethylphenyl, 4-(methoxyethylamino)-phenyl, thiazol-2-yl, 6-chloro-pyrid-3-yl and benzo[d][1,3]dioxol-5-yl. In another embodiment of the present invention,

is selected from the group consisting of 4-chlorophenyl and thiazol-2-yl.

In an embodiment of the present invention,

is selected from the group consisting of phenyl, 4-chlorophenyl, 4-methoxyphenyl, thiazol-2-yl, thiazol-4-yl, thien-2-yl, thien-3-yl and 5-chloro-thien-2-yl. In an embodiment of the present invention,

is selected from the group consisting of phenyl, 4-chlorophenyl, 4-methoxyphenyl, thiazol-2-yl, thiazol-4-yl, thien-2-yl and thien-3-yl. In an embodiment of the present invention,

is selected from the group consisting of 4-chlorophenyl, thiazol-2-yl, thiazol-4-yl and thien-3-yl. In an embodiment of the present invention,

is selected from the group consisting of 4-chlorophenyl, thiazol-2-yl, thien-2-yl and thien-3-yl.

In another embodiment of the present invention,

is phenyl; wherein the phenyl is substituted with a halogen. In another embodiment of the present invention,

is 4-chlorophenyl.

In an embodiment of the present invention, $R^1$ is selected from the group consisting of hydrogen, halogen, —($C_{1-4}$ alkyl)-O—($C_{1-2}$alkyl), —($C_{1-4}$alkyl)-OH, —($C_{3-4}$alkenyl)-O—($C_{1-2}$alkyl), —($C_{3-4}$alkenyl)-OH, —OH, —$C_{1-4}$alkyl, —O—($C_{1-4}$alkyl), —O—($C_{1-4}$alkyl)-$CO_2$H, —O—($C_{1-4}$ alkyl)-C(O)O—($C_{1-4}$alkyl), —O—($C_{2-4}$alkyl)-$NH_2$, —O—($C_{1-4}$alkyl)-C(O)—$NH_2$, —O—($C_{2-4}$alkyl)-NH—C(O)—($C_{1-2}$alkyl), —O—($C_{2-4}$alkyl)-NH—C(O)O—($C_{1-4}$ alkyl) and —$NR^E R^F$; wherein $R^E$ and $R^F$ are each independently selected from the group consisting of hydrogen, $C_{1-4}$alkyl, —($C_{2-4}$alkyl)-OH, —($C_{1-4}$alkyl)-$CO_2$H, —($C_{1-4}$ alkyl)-C(O)O—($C_{1-4}$alkyl), —O—($C_{2-4}$alkyl)-O—($C_{1-4}$alkyl), —($C_{1-4}$ alkyl)-$NH_2$ and 1-((fluorinated $C_{1-2}$alkyl)-sulfonyl))-piperidin-4-yl; alternatively, $R^E$ and $R^F$ are taken together with the nitrogen atom to which they are bound to form a 5 to 6 membered, saturated ring selected from the group consisting of pyrrolidin-1-yl, 1-(pyrrolidin-2-one), piperidin-1-yl, piperazin-1-yl, 4-methyl-piperazin-1-yl and morpholin-4-yl.

In another embodiment of the present invention, $R^1$ is selected from the group consisting of hydrogen, halogen, —($C_{1-4}$alkyl)-O—($C_{1-2}$alkyl), —($C_{1-4}$alkyl)-OH, —($C_{3-4}$alkenyl)-O—($C_{1-2}$alkyl), —($C_{3-4}$alkenyl)-OH, —OH, —O—($C_{1-2}$alkyl), —O—($C_{1-4}$alkyl)-$CO_2H$, —O—($C_{1-4}$alkyl), —C(O)O—($C_{1-4}$alkyl), —O—($C_{1-4}$alkyl), —C(O)—$NH_2$, —O—($C_{2-4}$alkyl)-$NH_2$, —O—($C_{2-4}$alkyl)-NH—C(O)—($C_{1-2}$alkyl), —O—($C_{2-4}$alkyl)-NH—C(O)O—($C_{1-4}$alkyl), and —$NR^ER^F$; wherein $R^E$ and $R^F$ are each independently selected from the group consisting of hydrogen, $C_{1-4}$alkyl, —($C_{2-2}$alkyl)-O—($C_{1-2}$alkyl), —($C_{1-4}$alkyl)-$CO_2H$, —($C_{1-2}$alkyl)-C(O)O—($C_{1-2}$alkyl), —($C_{1-4}$alkyl)-$NH_2$, and 1-(fluorinated $C_{1-2}$alkyl)-sulfonyl))-piperidin-4-yl; alternatively, $R^E$ and $R^F$ are taken together with the nitrogen atom to which they are bound to form 1-pyrrolidin-2-one.

In an embodiment of the present invention, $R^1$ is selected from the group consisting of hydrogen, halogen, —$C_{1-4}$alkyl, —O—($C_{1-4}$alkyl), —O—($C_{1-2}$alkyl)-$CO_2H$, —O—($C_{1-2}$alkyl)-C(O)O—($C_{1-4}$alkyl), —O—($C_2$alkyl)-$NH_2$ and —$NR^ER^F$; wherein $R^E$ and $R^F$ are each independently selected from the group consisting of hydrogen, $C_{1-4}$alkyl, —($C_{1-2}$alkyl)-$CO_2H$, —($C_{1-2}$alkyl)-C(O)O—($C_{1-4}$alkyl), —($C_2$alkyl)-O—($C_{1-2}$alkyl) and 1-((fluorinated $C_{1-2}$alkyl)-sulfonyl))-piperidin-4-yl; alternatively, $R^E$ and $R^F$ are taken together with the nitrogen atom to which they are bound to form a 5 to 6 membered, saturated ring selected from the group consisting of pyrrolidin-1-yl, 1-(pyrrolidin-2-one), piperidin-1-yl, piperiazin-1-yl, 4-methyl-piperazin-1-yl and morpholin-4-yl.

In another embodiment of the present invention, $R^1$ is selected from the group consisting of hydrogen, bromo, —$CH_2CH_2CH_2$—$OCH_3$, —$CH_2CH_2CH_2$—OH, —CH═CH—$CH_2$—$OCH_3$, —CH═CH—$CH_2$—$CH_2OH$, —OH, —$OCH_3$, —O—$CH_2CH_2CH_2CH_2$—$CO_2H$, —O—$CH_2CH_2CH_2CH_2$—C(O)O—C($CH_3$)$_3$, —O—$CH_2CH_2CH_2CH_2$—C(O)$NH_2$, —O—$CH_2CH_2CH_2CH_2$—$NH_2$, —O—$CH_2CH_2CH_2CH_2$—NH—C(O)—$CH_3$, —O—$CH_2CH_2CH_2$—NH—C(O)—O—C($CH_3$)$_3$, —O—$CH_2$—$CO_2H$, —O—$CH_2$—C(O)O—$CH_2CH_3$, —O—$CH_2CH_2CH_2$—C(O)O—$CH_2CH_3$, —NH—$CH_2CH_2CH_2CH_3$, —NH—$CH_2CH_2$—$OCH_3$, —NH—$CH_2CH_2CH_2$—$CO_2H$, —NH—$CH_2CH_2CH_2$—C(O)O—$CH_2CH_3$, —NH—$CH_2CH_2CH_2CH_2$—$NH_2$, —NH-(1-trifluoromethyl-sulfonyl-piperidin-4-yl) and 1-pyrrolidin-2-one.

In another embodiment of the present invention, $R^1$ is selected from the group consisting of hydrogen, bromo, —$CH_2CH_2CH_2$—$OCH_3$, —$CH_2CH_2CH_2$—OH, —CH═CH—$CH_2$—$OCH_3$, —CH═CH—$CH_2$—$CH_2OH$, —OH, —$OCH_3$, —O—$CH_2CH_2CH_2CH_2$—$CO_2H$, —O—$CH_2CH_2CH_2CH_2$—C(O)$NH_2$, —O—$CH_2CH_2CH_2CH_2$—$NH_2$, —O—$CH_2CH_2CH_2CH_2$—NH—C(O)—$CH_3$, —O—$CH_2CH_2CH_2CH_2$—NH—C(O)—O—C($CH_3$)$_3$, —O—$CH_2$—C(O)O—$CH_2CH_3$, —O—$CH_2CH_2CH_2CH_2$—C(O)O—$CH_2CH_3$, —NH—$CH_2CH_2$—$OCH_3$, —NH—$CH_2CH_2CH_2$—$CO_2H$, and 1-pyrrolidin-2-one. In another embodiment of the present invention, $R^1$ is selected from the group consisting of hydrogen, bromo, —$CH_2CH_2CH_2$—$OCH_3$, —$CH_2CH_2CH_2$—OH, —CH═CH—$CH_2$—$OCH_3$, —CH═CH—$CH_2$—$CH_2OH$, —OH, —$OCH_3$, —O—$CH_2CH_2CH_2CH_2$—$CO_2H$, —O—$CH_2CH_2CH_2CH_2$—C(O)$NH_2$, —O—$CH_2CH_2CH_2CH_2$—$NH_2$, —O—$CH_2CH_2CH_2CH_2$—NH—C(O)—$CH_3$, —O—$CH_2CH_2CH_2CH_2$—NH—C(O)—O—C($CH_3$)$_3$, —O—$CH_2$—C(O)O—$CH_2CH_3$, —O—$CH_2CH_2CH_2CH_2$—C(O)O—$CH_2CH_3$, —NH—$CH_2CH_2$—$OCH_3$ and 1-pyrrolidin-2-one. In another embodiment of the present invention, $R^1$ is selected from the group consisting of hydrogen, bromo, —$CH_2CH_2CH_2$—$OCH_3$, —$CH_2CH_2CH_2$—OH, —CH═CH—$CH_2$—$OCH_3$ and —NH—$CH_2CH_2$—$OCH_3$. In another embodiment of the present invention, $R^1$ is hydrogen.

In an embodiment of the present invention

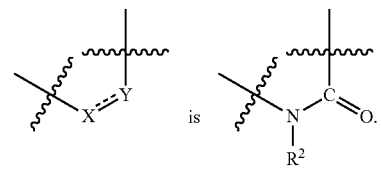

In another embodiment of the present invention,

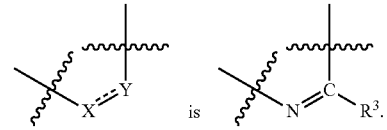

In another embodiment of the present invention,

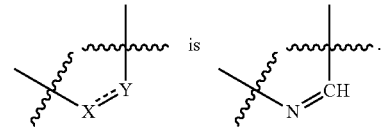

In another embodiment of the present invention,

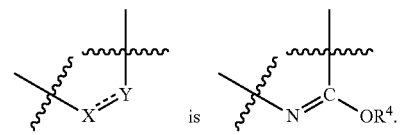

In an embodiment of the present invention, $R^2$ is selected from the group consisting of hydrogen, —($C_{1-4}$alkyl), —($C_{2-4}$alkyl)-O—($C_{1-4}$alkyl), —($C_{1-2}$alkyl)-$CO_2H$, —($C_{1-2}$alkyl)-C(O)O—($C_{1-4}$alkyl) and —($C_{1-4}$alkyl)-C(O)—$NR^LR^M$; wherein $R^L$ and $R^M$ are each independently selected from the group consisting of hydrogen and $C_{1-2}$alkyl. In another embodiment of the present invention, $R^2$ is selected from the group consisting of hydrogen, $C_{1-2}$alkyl, —($C_{2-4}$alkyl)-O—($C_{1-2}$alkyl) and —($C_{1-2}$alkyl)-C(O)$NH_2$. In an embodiment of the present invention, $R^2$ is selected from the group consisting of hydrogen and $C_{1-2}$alkyl.

In another embodiment of the present invention, $R^2$ is selected from the group consisting of hydrogen, methyl, —$CH_2CH_2CH_2$—$OCH_3$ and —$CH_2$—C(O)$NH_2$. In another embodiment of the present invention, $R^2$ is selected from the group consisting of hydrogen, methyl and —$CH_2CH_2CH_2$—$OCH_3$. In another embodiment of the present invention, $R^2$ is selected from the group consisting of hydrogen and methyl. In another embodiment of the present invention, $R^2$ is hydrogen.

In an embodiment of the present invention, $R^3$ is hydrogen. In another embodiment of the present invention, $R^3$ is —$OR^4$. In an embodiment of the present invention, $R^3$ is selected from the group consisting of hydrogen and —$OR^4$; wherein $R^4$ is selected from the group consisting of $C_{1-4}$alkyl. In another embodiment of the present invention, $R^3$ is —O—$C_{1-4}$alkyl. In another embodiment of the present invention, $R^3$ is selected from the group consisting of hydrogen and —$OR^4$; wherein $R^4$ is —$SO_2$-(fluorinated $C_{1-2}$alkyl). In another embodiment of the present invention, $R^3$ is selected from the group consisting hydrogen and —O—$SO_2$—$CF_3$.

In another embodiment of the present invention, $R^3$ is selected from the group consisting of hydrogen, —$OCH_3$, —O—$CH_2CH_2$—$OCH_3$, —O—$CH_2$—$CO_2H$, —O—$CH_2$—C(O)O—C($CH_3$)$_3$, —O—$CH_2CH_2CH_2CH_2CH_2$—$CO_2H$, —O—$CH_2CH_2CH_2CH_2CH_2$—C(O)$OCH_3$ and —O—$CH_2$—C(O)—NH—$CH_3$. In another embodiment of the present invention, $R^3$ is selected from the group consisting of hydrogen, —$OCH_3$, —O—$CH_2CH_2$—$OCH_3$, —O—$CH_2CH_2CH_2CH_2CH_2$—$CO_2H$, and —O—$CH_2$—C(O)—NH—$CH_3$. In another embodiment of the present invention, $R^3$ is selected from the group consisting of hydrogen, —$OCH_3$, —O—$CH_2CH_2$—$OCH_3$, and —O—$CH_2$—C(O)—NH—$CH_3$.

In an embodiment of the present invention, $R^4$ is selected from the group consisting of —$C_{1-6}$alkyl, -(hydroxy substituted $C_{2-4}$alkyl), —($C_{1-4}$alkyl)-$NR^JR^K$, —($C_{2-4}$alkyl)-O—($C_{1-4}$alkyl), —($C_{2-4}$alkyl)-O—($C_{1-4}$alkyl)-$CO_2H$, —($C_{2-4}$alkyl)-O—($C_{1-4}$alkyl)-C(O)—O—($C_{1-4}$alkyl), —($C_{2-4}$alkyl)-O—($C_{1-4}$alkyl)-C(O)—$NR^JR^K$, —($C_{1-6}$alkyl)-$CO_2H$, —($C_{1-6}$alkyl)-C(O)O—($C_{1-4}$alkyl), —($C_{1-4}$alkyl)-C(O)—$NR^JR^K$, —($C_{2-4}$alkyl)-$NR^J$—C(O)—($C_{1-4}$alkyl) and —$SO_2$-(fluorinated $C_{1-2}$alkyl); wherein $R^J$ and $R^K$ are each independently selected from the group consisting of hydrogen, $C_{2-6}$alkyl. In another embodiment of the present invention, $R^4$ is selected from the group consisting of —$C_{1-4}$alkyl, —($C_{2-2}$alkyl)-O—($C_{1-2}$alkyl), —($C_{2-6}$alkyl)-$CO_2H$, —($C_{1-6}$alkyl)-C(O)O—($C_{1-4}$alkyl) and —($C_{1-2}$alkyl)-C(O)—NH—($C_{1-2}$alkyl).

In an embodiment of the present invention, $R^5$ is selected from the group consisting of hydrogen and $C_{1-4}$alkyl. In an embodiment of the present invention, $R^5$ is selected from the group consisting of hydrogen and $C_{1-2}$alkyl. In another embodiment of the present invention, $R^5$ is hydrogen.

In an embodiment of the present invention, b is an integer from 0 to 1. In another embodiment of the present invention b is 1. In another embodiment of the present invention is 0.

In an embodiment of the present invention, $L^2$ is selected from the group consisting of —$CH_2$—, —$CH_2CH_2$— and —CH($CH_3$)—. In another embodiment of the present invention, $L^2$ is selected from the group consisting of —$CH_2$— and —CH($CH_3$)—.

In an embodiment of the present invention, $R^6$ is selected from the group consisting of azetidin-3-yl, pyrrolidin-3-yl, piperidin-4-yl, piperazin-1-yl, phenyl, pyrid-2-yl, pyrid-3-yl, pyrid-4-yl, thien-2-yl, thien-3-yl, furan-2-yl, furan-3-yl, cyclopropyl, cyclobutyl, cyclopentyl and cyclohexyl; wherein any of the $R^6$ ring structures is optionally substituted with one substituent selected from the group consisting of halogen, hydroxy, $C_{1-4}$alkyl, fluorinated $C_{1-4}$alkyl, $C_{1-4}$alkoxy, fluorinated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)—($C_{1-4}$alkyl), —C(O)-(fluorinated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)—($C_{1-4}$alkyl)-C(O)—$NR^PR^Q$, —$CO_2H$, —C(O)O—($C_{1-4}$alkyl), —C(=NH)—$NH_2$, —C(=N-Boc)-NH(Boc), —$NR^PR^Q$, —$NR^P$—C(O)—($C_{1-4}$alkyl), —$NR^Q$—$SO_2$—($C_{1-4}$alkyl), —$SO_2$—($C_{1-4}$alkyl), —$SO_2$-(fluorinated $C_{1-4}$alkyl), —$SO_2$—($C_{1-4}$alkyl)-C(O)O—($C_{1-4}$alkyl), —$SO_2$—$NR^PR^Q$ and —$SO_2$—($C_{1-4}$alkyl)-C(O)—$NR^PR^Q$; and wherein $R^P$ and $R^Q$ are each independently selected from the group consisting of hydrogen and $C_{1-4}$alkyl; and wherein $R^6$ is phenyl; the phenyl is further optionally substituted with an additional substituent selected from the group consisting of halogen, hydroxy, $C_{1-4}$alkyl, fluorinated $C_{1-4}$alkyl, $C_{1-4}$alkoxy and fluorinated $C_{1-4}$alkoxy.

In another embodiment of the present invention, $R^6$ is selected from the group consisting of azetidin-3-yl, pyrrolidin-3-yl, piperidin-4-yl, phenyl, pyrid-2-yl, pyrid-3-yl, and cyclohexyl; wherein any of the $R^6$ ring structures is optionally substituted with one substituent selected from the group consisting of halogen, $C_{1-4}$alkyl, fluorinated $C_{1-4}$alkyl, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)-(fluorinated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)—($C_{1-4}$alkyl)-C(O)—$NR^PR^Q$, —$CO_2H$, —C(O)O—($C_{1-4}$alkyl), —C(=NH)—$NH_2$, —C(=N-Boc)-NH(Boc), —$SO_2$—($C_{1-4}$alkyl), —$SO_2$-(fluorinated $C_{1-4}$alkyl) and —$SO_2$—($C_{1-4}$alkyl)-C(O)O—($C_{1-4}$alkyl); and wherein $R^P$ and $R^Q$ are each hydrogen; and wherein $R^6$ is phenyl; the phenyl is further optionally substituted with an additional halogen.

In another embodiment of the present invention, $R^6$ is selected from the group consisting of cyclohexyl, 4-(trifluoromethyl)-cyclohexyl, 4-(trifluoromethyl-sulfonyl)-cyclohexyl, 3-chloro-4-fluoro-phenyl, 3-fluoro-4-chloro-phenyl, 3-(trifluoromethyl)-phenyl, 4-(trifluoromethyl)-phenyl, 4-(methoxy-ethoxy)-phenyl, 4-(carboxy)-phenyl, 4-(methoxycarbonyl)-phenyl, 4-(t-butoxycarbonyl-methoxy)-phenyl, 4-(ethoxycarbonyl-n-propyloxy)-phenyl, 4-(carboxy-methoxy)-phenyl, 4-(carboxy-n-propyloxy)-phenyl, 4-(carboxy-methyl)-phenyl, 4-(methoxycarbonyl-methyl)-phenyl, 4-(aminocarbonyl)-phenyl, 4-(aminocarbonyl-methoxy)-phenyl, 4-(aminocarbonyl-n-propoxy)-phenyl, 4-(aminocarbonyl-methyl)-phenyl, 5-(trifluoromethyl)-pyrdi-2-yl, 5-(trifluoromethyl)-pyrdi-3-yl, 6-(trifluoromethyl)-pyrid-3-yl, 6-(methyl)-pyrid-3-yl, azetidin-3-yl, 1-(t-butoxycarbonyl)-azetidin-3-yl, S-(1-(t-butoxycarbonyl)-pyrrolidin-3-yl), R-(1-(t-butoxycarbonyl)-pyrrolidin-3-yl), S-(1-(trifluoromethyl-sulfonyl)-pyrrolidin-3-yl), R-(1-(trifluoromethyl-sulfonyl)-pyrrolidin-3-yl), piperidin-4-yl, 1-(1,1,1-trifluoroethyl)-piperidin-4-yl, 1-(ethoxycarbonyl)-piperidin-4-yl, 1-(methyl-sulfonyl)-piperidin-4-yl, 1-(ethyl-sulfonyl)-piperidin-4-yl, 1-(isopropyl-sulfonyl)-piperidin-4-yl, 1-(trifluoromethyl-sulfonyl)-piperidin-4-yl, 1-(1,1,1-trifluoroethyl-carbonyl)-piperidin-4-yl, 1-(carboxy-methyl)-piperidin-4-yl, 1-(carboxy-ethyl)-piperidin-4-yl, 1-(t-butoxycarbonyl-methyl)-piperidin-4-yl, 1-(t-butoxycarbonyl-ethyl)-piperidin-4-yl, 1-(carboxy-ethylcarbonyl)-piperidin-4-yl, 1-(carboxy-methylcarbonyl)-piperidin-4-yl, 1-(ethoxycarbonyl-methylcarbonyl)-piperidin-4-yl, 1-(ethoxycarbonyl-ethylcarbonyl)-piepridin-4-yl, 1-(aminocarbonyl-methylcarbonyl)-piperidin-4-yl, 1-(aminocarbonyl-ethylcarbonyl)-piperidin-4-yl, 1-(ethoxycarbonyl-methylsulfonyl)-piperidin-4-yl, 1-(ethoxycarbonyl-ethylsulfonyl)-piperidin-4-yl, 1-(amino-carboimido)-piepridin-4-yl and 1-(t-butoxycarbonyl-amino)-t-butoxycarbonyl-carboimido)-piperidin-4-yl.

In another embodiment of the present invention, $R^6$ is selected from the group consisting of cyclohexyl, 4-(trifluoromethyl)-cyclohexyl, 3-fluoro-4-chloro-phenyl, 3-(trifluoromethyl)-phenyl, 4-(trifluoromethyl)-phenyl, 4-(methoxyethoxy)-phenyl, 4-(methoxycarbonyl)-phenyl, 4-(t-butoxycarbonyl-methoxy)-phenyl, 4-(ethoxycarbonyl-n-propyloxy)-phenyl, 4-(methoxycarbonyl-methyl)-phenyl, 4-(aminocarbonyl-methoxy)-phenyl, 4-(aminocarbonyl-n-propoxy)-phenyl, 4-(aminocarbonyl-methyl)-phenyl, 5-(trifluoromethyl)-pyrdi-2-yl, 5-(trifluoromethyl)-pyrdi-3-yl, 6-(trifluoromethyl)-pyrid-3-yl, 6-(methyl)-pyrid-3-yl, S-(1-(trifluoromethyl-sulfonyl)-pyrrolidin-3-yl), R-(1-(trifluoromethyl-sulfonyl)-pyrrolidin-3-yl), 1-(1,1,1-trifluoroethyl)-piperidin-4-yl, 1-(ethoxycarbonyl)-piperidin-4-yl, 1-(methyl-sulfonyl)-piperidin-4-yl, 1-(ethyl-sulfonyl)-piperidin-4-yl, 1-(isopropyl-sulfonyl)-piperidin-4-yl, 1-(trifluoromethyl-sulfonyl)-piperidin-4-yl, 1-(1,1,1-trifluoroethyl-carbonyl)-piperidin-4-yl, 1-(t-butoxycarbonyl-methyl)-piperidin-4-yl, 1-(t-butoxycarbonyl-ethyl)-piperidin-4-yl, 1-(carboxy-ethylcarbonyl)-piperidin-4-yl, 1-(ethoxycarbonyl-methylcarbonyl)-piperidin-4-yl, 1-(ethoxycarbonyl-ethylcarbonyl)-piperidin-4-yl, 1-(aminocarbonyl-ethylcarbonyl)-piperidin-4-yl, 1-(ethoxycarbonyl-methylsulfonyl)-piperidin-4-yl, and 1-(t-butoxycarbonyl-amino)-t-butoxycarbonyl-carboimido)-piperidin-4-yl.

In another embodiment of the present invention, $R^6$ is selected from the group consisting of cyclohexyl, 4-(trifluoromethyl)-cyclohexyl, 3-fluoro-4-chloro-phenyl, 3-(trifluoromethyl)-phenyl, 4-(trifluoromethyl)-phenyl, 4-(methoxyethoxy)-phenyl, 4-(methoxycarbonyl)-phenyl, 4-(t-butoxycarbonyl-methoxy)-phenyl, 4-(ethoxycarbonyl-n-propyloxy)-phenyl, 4-(methoxycarbonyl-methyl)-phenyl, 4-(aminocarbonyl-methoxy)-phenyl, 4-(aminocarbonyl-methyl)-phenyl, 5-(trifluoromethyl)-pyrdi-2-yl, 5-(trifluoromethyl)-pyrdi-3-yl, 6-(trifluoromethyl)-pyrid-3-yl, S-(1-(trifluoromethyl-sulfonyl)-pyrrolidin-3-yl), 1-(1,1,1-trifluoroethyl)-piperidin-4-yl, 1-(ethoxycarbonyl)-piperidin-4-yl, 1-(methyl-sulfonyl)-piperidin-4-yl, 1-(ethyl-sulfonyl)-piperidin-4-yl, 1-(trifluoromethyl-sulfonyl)-piperidin-4-yl, 1-(1,1,1-trifluoroethyl-carbonyl)-piperidin-4-yl, 1-(t-butoxycarbonyl-methyl)-piperidin-4-yl, 1-(t-butoxycarbonyl-ethyl)-piperidin-4-yl, 1-(ethoxycarbonyl-methylcarbonyl)-piperidin-4-yl, 1-(ethoxycarbonyl-ethylcarbonyl)-piepridin-4-yl, 1-(ethoxycarbonyl-methylsulfonyl)-piperidin-4-yl, and 1-(t-butoxycarbonyl-amino)-t-butoxycarbonyl-carboimido)-piperidin-4-yl.

In another embodiment of the present invention, $R^6$ is selected from the group consisting of cyclohexyl, 3-fluoro-4-chloro-phenyl, 3-(trifluoromethyl)-phenyl, 4-(trifluoromethyl)-phenyl, 4-(methoxycarbonyl-methyl)-phenyl, 6-(trifluoromethyl)-pyrid-3-yl, 1-(1,1,1-trifluoroethyl)-piperidin-4-yl, 1-(ethoxycarbonyl)-piperidin-4-yl, 1-(ethyl-sulfonyl)-piperidin-4-yl, 1-(trifluoromethyl-sulfonyl)-piperidin-4-yl, 1-(1,1,1-trifluoroethyl-carbonyl)-piperidin-4-yl, 1-(t-butoxycarbonyl-methyl)-piperidin-4-yl, 1-(ethoxycarbonyl-methylcarbonyl)-piperidin-4-yl, 1-(ethoxycarbonyl-ethylcarbonyl)-piepridin-4-yl and 1-(ethoxycarbonyl-methylsulfonyl)-piperidin-4-yl. In another embodiment of the present invention, $R^6$ is 1-(trifluoromethyl-sulfonyl)-piperidin-4-yl.

In an embodiment of the present invention,

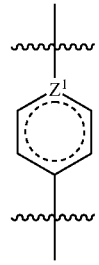

is selected from the group consisting of

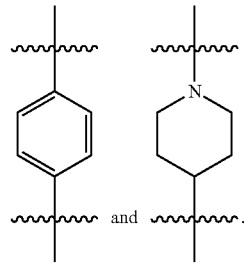 [SMILES: *c1ccc(*)cc1 ; *C1CCN(*)CC1]

In another embodiment of the present invention,

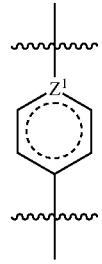

is selected from the group consisting of

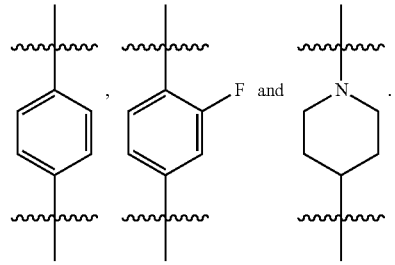

In another embodiment of the present invention,

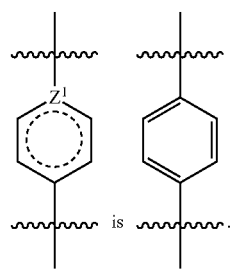

In another embodiment of the present invention,

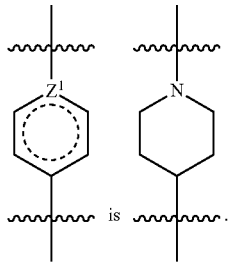 is

In an embodiment of the present invention, c is an integer from 0 to 1. In another embodiment of the present invention, c is 1. In another embodiment of the present invention, c is 0.

In an embodiment of the present invention, $L^3$ is selected from the group consisting of —$CH_2$—, —C(O)— and —$SO_2$—. In an embodiment of the present invention, $L^3$ is —$CH_2$—. In an embodiment of the present invention, $L^3$ is selected from the group consisting of —C(O)— and —$SO_2$—.

In an embodiment of the present invention, $R^7$ is selected from the group consisting of azetidin-3-yl, pyrrolidin-1-yl, piperidin-4-yl, phenyl, pyrid-2-yl, pyrid-3-yl, pyrid-4-yl, thien-2-yl, thein-3-yl, furan-2-yl, furan-3-yl, pyrimidin-2-yl, cyclopropyl, cyclobutyl, cyclopentyl and cyclohexyl; wherein any of the $R^7$ ring structures is optionally substituted with one substituent selected from the group consisting of halogen, hydroxy, $C_{1-4}$alkyl, fluorinated $C_{1-4}$alkyl, $C_{1-4}$alkoxy, fluorinated $C_{1-4}$alkoxy, —($C_{1-4}$alkyl)-O—($C_{1-4}$ alkyl), —($C_{1-4}$alkyl)-$CO_2H$, —($C_{1-4}$alkyl)-C(O)O—($C_{1-4}$ alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$ alkyl)-C(O)O—($C_{1-4}$alkyl), —O—($C_{1-4}$alkyl)-C(O)—$NR^PR^Q$, —C(O)—($C_{1-4}$alkyl), —C(O)-(fluorinated $C_{1-4}$alkyl), —C(O)—($C_{1-4}$alkyl)-$CO_2H$, —C(O)—($C_{1-4}$ alkyl)-C(O)O—($C_{1-4}$alkyl), —C(O)—$NR^PR^Q$, —C(O)—($C_{1-4}$alkyl)-C(O)—$NR^PR^Q$, —$CO_2H$, —C(O)O—($C_{1-4}$ alkyl), —C(=NH)—$NH_2$, —C(=N-Boc)-NH(Boc), —$NR^PR^Q$, —$NR^P$—C(O)—($C_{1-4}$alkyl), —$NR^Q$—$SO_2$—($C_{1-4}$alkyl), —$SO_2$—($C_{1-4}$alkyl), —$SO_2$-(fluorinated $C_{1-4}$alkyl), —$SO_2$—($C_{1-4}$alkyl)-C(O)O—($C_{1-4}$alkyl), —$SO_2$—$NR^PR^Q$ and —$SO_2$—($C_{1-4}$alkyl)-C(O)—$NR^PR^Q$; and wherein $R^P$ and $R^Q$ are each independently selected from the group consisting of hydrogen and $C_{1-4}$alkyl; and wherein $R^7$ is phenyl; the phenyl is further optionally substituted with an additional substituent selected from the group consisting of halogen, hydroxy, $C_{1-4}$alkyl, fluorinated $C_{1-4}$alkyl, $C_{1-4}$alkoxy and fluorinated $C_{1-4}$alkoxy.

In another embodiment of the present invention, $R^7$ is selected from the group consisting of cyclopropyl, phenyl, pyrrolidin-1-yl, pyrimidin-2-yl, pyrid-2-yl, furan-2-yl and thien-2-yl; wherein the phenyl, furanyl or thienyl is optionally substituted with a substituent selected from the group consisting of halogen, —$CO_2H$, —C(O)O—($C_{1-2}$alkyl). In another embodiment of the present invention, $R^7$ is selected from the group consisting of cyclopropyl, phenyl, 3-fluorophenyl, 3-carboxy-phenyl, 4-carboxy-phenyl, 4-(methoxycarbonyl)-phenyl, pyrrolidin-1-yl, pyrimidin-2-yl, pyrid-2-yl, 5-carboxy-furan-2-yl and 5-carboxy-thien-2-yl. In another embodiment of the present invention, $R^7$ is selected from the group consisting of cyclopropyl, phenyl, 3-fluorophenyl, 3-carboxy-phenyl, 4-carboxy-phenyl, 4-(methoxy-carbonyl)-phenyl, pyrrolidin-1-yl, pyrimidin-2-yl, pyrid-2-yl and 5-carboxy-thien-2-yl. In another embodiment of the present invention, $R^7$ is selected from the group consisting of cyclopropyl, phenyl, 3-fluorophenyl, 4-(methoxycarbonyl)-phenyl, pyrrolidin-1-yl, pyrimidin-2-yl and pyrid-2-yl. In another embodiment of the present invention, $R^7$ is selected from the group consisting of cyclopropyl, phenyl, 4-(methoxycarbonyl)-phenyl, pyrrolidin-1-yl, pyrimidin-2-yl and pyrid-2-yl.

In an embodiment of the present invention, $R^{13}$ is selected from the group consisting of hydrogen and —O—($C_{1-2}$ alkyl). In an embodiment of the present invention, $R^{13}$ is hydrogen.

In an embodiment of the present invention, $L^4$ is selected from the group consisting of —$CH_2$—, —$CH_2CH_2$— and —CH=CH—. In an embodiment of the present invention, $L^4$ is selected from the group consisting of —$CH_2$—, —$CH_2CH_2$—, —CH=CH—, cis-CH=CH— and trans-CH=CH—. In an embodiment of the present invention, $L^4$ is selected from the group consisting of —$CH_2CH_2$—, —CH=CH—, cis-CH=CH— and trans-CH=CH—.

In an embodiment of the present invention, d is an integer from 0 to 1. In another embodiment of the present invention, d is 1. In another embodiment of the present invention, d is 0.

In an embodiment of the present invention, each $R^8$ is independently selected from the group consisting of halogen, cyano, $C_{1-4}$alkyl, fluorinated $C_{1-2}$alkyl, $C_{1-4}$alkoxy and fluorinated $C_{1-2}$ alkoxy. In an embodiment of the present invention, $R^8$ is selected from the group consisting of halogen, $C_{1-2}$alkyl, fluorinated $C_{1-2}$alkyl and fluorinated $C_{1-2}$ alkoxy.

In an embodiment of the present invention, $R^8$ is selected from the group consisting of 3-fluoro, 3-chloro, 4-chloro, 4-methyl, 3-trifluoromethyl, 4-trifluoromethyl and 4-trifluoromethoxy. In an embodiment of the present invention, $R^8$ is selected from the group consisting of 3-fluoro, 3-chloro, 4-methyl, 3-trifluoromethyl, 4-trifluoromethyl and 4-trifluoromethoxy. In an embodiment of the present invention, $R^8$ is selected from the group consisting of 3-fluoro, 3-chloro and 3-trifluoromethyl.

In an embodiment of the present invention, $R^{14}$ is selected from the group consisting of hydrogen, halogen, —$C_{1-2}$ alkyl, —$NH_2$, —NH($C_{1-2}$alkyl) and —N($C_{1-2}$alkyl)$_2$. In another embodiment of the present invention, $R^{14}$ is selected from the group consisting of hydrogen, halogen and $C_{1-4}$alkyl. In another embodiment of the present invention, $R^{14}$ is hydrogen.

In an embodiment of the present invention,

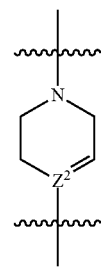

is selected from the group consisting of

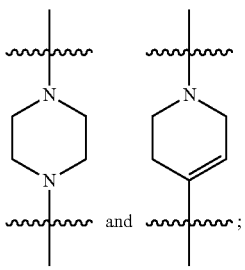 [SMILES: *N1CCN(*)CC1 ; *C1=CCN(*)CC1] and ;

wherein $Z^2$ is N and ---- represents a single bond or alternatively, $Z^2$ is C and "----" represents a double bond.

In an embodiment of the present invention, $R^9$ is selected from the group consisting of hydrogen, —C(O)O—($C_{1-4}$ alkyl), —C(O)—($C_{1-4}$alkyl), —C(O)-(fluorinated $C_{1-2}$ alkyl) and —$SO_2$-(fluorinated $C_{1-2}$alkyl). In another embodiment of the present invention, $R^9$ is selected from the group consisting of hydrogen, —C(O)O—($C_{1-4}$alkyl), —C(O)—($C_{1-2}$alkyl), —C(O)-(fluorinated $C_{1-2}$alkyl) and —$SO_2$-(fluorinated $C_{1-2}$alkyl).

In another embodiment of the present invention, $R^9$ is selected from the group consisting of hydrogen, —C(O)O-t-butyl, —C(O)-methyl, —C(O)—$CF_3$ and —$SO_2$—$CF_3$. In another embodiment of the present invention, $R^9$ is selected from the group consisting of —C(O)O-t-butyl, —C(O)—$CF_3$ and —$SO_2$—$CF_3$.

Additional embodiments of the present invention, include those wherein the substituents selected for one or more of the variables defined herein (e.g. $U^1$, $U^2$,

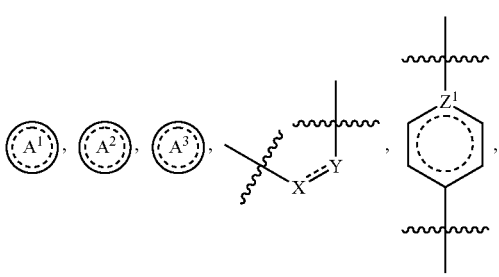

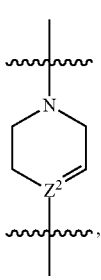, a, b, c, d, $L^1$, $L^2$, $L^3$, $L^4$, $Z^1$, $Z^2$, $R^0$, $R^1$, $R^2$, $R^3$, $R^4$, $R^5$, $R^6$, $R^7$, $R^8$, $R^9$, $R^{13}$, $R^{14}$, $R^{15}$, etc.) are independently selected to be any individual substituent or any subset of substituents selected from the complete list as defined herein. Additional embodiments of the present invention, include those wherein the substituents selected for one or more of the variables defined herein (e.g. 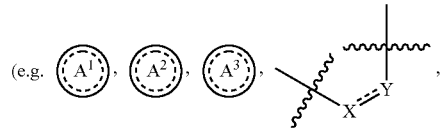

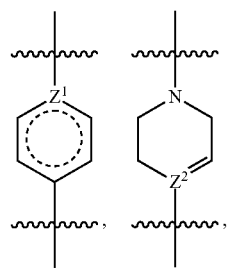, a, b, c, d, $L^1$, $L^2$, $L^3$, $L^4$, $Z^1$, $Z^2$, $R^0$, $R^1$, $R^2$, $R^3$, $R^4$, $R^5$, $R^6$, $R^7$, $R^8$, $R^9$, $R^{13}$, $R^{14}$, $R^{15}$, $U^1$, $U^2$, etc.) are independently selected to be individual substituent or subset of substituents selected from those exemplified in the Tables which follow herein.

In additional embodiments, the present invention is directed to any single compound or subset of compounds, independently selected from the representative compounds of formula (I), compounds of formula (II), compounds of formula (III) and compounds formula (IV), listed in the Tables which follow herein.

In the Tables which follow herein, unless otherwise noted, wherein a stereogenic center is present in the listed compound, the compound was prepared as a mixture of enantiomers. Where a stereogenic center is present, and the compound was prepared in an enantiomeric or diastereomeric excess, the S*- and R* designations are intended to indicate relative stereo-configuration (where the exact stereo-configuration of the stereogenic center has not been determined).

Representative compounds of formula (I) of the present invention are as listed in Tables (I-1), (I-2) and (I-3), below.

TABLE (I-1)

Representative Compounds of Formula (I)


| ID No. | A¹ | A² | $R^1$ | $R^2$ | $(L^2)_b$ | $R^6$ |
|---|---|---|---|---|---|---|
| 58 | 4-chloro-phenyl | 4-chloro-phenyl | H | H | —CH$_2$— | 4-(trifluoromethyl)-phenyl |
| 59 | 4-chloro-phenyl | 4-chloro-phenyl | H | H | b = 0 | 4-(trifluoromethyl)-phenyl |
| 61 | 4-chloro-phenyl | 4-chloro-phenyl | H | H | —CH$_2$— | 3-(trifluoromethyl)-phenyl |
| 70 | 4-chloro-phenyl | 4-chloro-phenyl | H | H | —CH$_2$— | 6-(trifluoromethyl)-pyrid-3-yl |
| 71 | 4-chloro-phenyl | 4-chloro-phenyl | H | H | b = 0 | cyclohexyl |
| 74 | 4-chloro-phenyl | 4-chloro-phenyl | H | H | —CH(CH$_3$)— | 3-trifluoromethyl-phenyl |
| 75 | 4-chloro-phenyl | 4-chloro-phenyl | H | H | b = 0 | 3-trifluoromethyl-phenyl |
| 76 | 4-chloro-phenyl | 4-chloro-phenyl | H | H | b = 0 | 3-chloro-4-fluoro-phenyl |
| 78 | 4-chloro-phenyl | 4-chloro-phenyl | H | H | —CH$_2$— | 5-trifluoromethyl-pyrid-2-yl |
| 79 | 4-chloro-phenyl | 4-chloro-phenyl | H | H | —CH$_2$— | 5-trifluoromethyl-pyrid-3-yl |
| 83 | 4-chloro-phenyl | 4-chloro-phenyl | H | H | b = 0 | 3-fluoro-4-chloro-phenyl |
| 85 | 4-chloro-phenyl | 4-chloro-phenyl | H | H | b = 0 | 4-(methoxy-carbonyl)-phenyl |
| 86 | 4-chloro-phenyl | 4-chloro-phenyl | H | H | b = 0 | 4-carboxy-phenyl |
| 87 | 4-chloro-phenyl | 4-chloro-phenyl | H | H | b = 0 | 4-(amino-carbonyl)-phenyl |
| 88 | 4-chloro-phenyl | 4-chloro-phenyl | H | H | b = 0 | 4-trifluoromethyl-cyclohexyl |
| 90 | 4-chloro-phenyl | 4-chloro-phenyl | H | —CH$_2$—C(O)NH$_2$ | b = 0 | 4-(trifluoromethyl-sulfonyl)-cyclohexyl |
| 93 | 4-chloro-phenyl | 4-chloro-phenyl | Br | H | b = 0 | 4-trifluoromethyl-phenyl |
| 94 | 4-chloro-phenyl | 4-chloro-phenyl | H | H | b = 0 | 4-(methoxy-ethoxy)-phenyl |
| 105 | 4-chloro-phenyl | 4-chloro-phenyl | H | H | b = 0 | 4-(t-butoxy-carbonyl-methoxy)-phenyl |
| 109 | 4-chloro-phenyl | 4-chloro-phenyl | H | H | b = 0 | 4-(carboxy-methoxy)-phenyl |
| 111 | 4-chloro-phenyl | 4-chloro-phenyl | H | H | b = 0 | 4-(amino-carbonyl-methoxy)-phenyl |
| 120 | 4-chloro-phenyl | 4-chloro-phenyl | H | H | b = 0 | 4-(ethoxy-carbonyl-n-propyloxy)-phenyl |
| 121 | 4-chloro-phenyl | 4-chloro-phenyl | H | H | b = 0 | 4-(carboxy-n-propyloxy)-phenyl |
| 123 | 4-chloro-phenyl | 4-chloro-phenyl | H | H | b = 0 | 4-(amino-carbonyl-n-propyloxy)-phenyl |
| 124 | 4-chloro-phenyl | 4-chloro-phenyl | H | H | b = 0 | 4-(methoxy-carbonyl-methyl)-phenyl |
| 125 | 4-chloro-phenyl | 4-chloro-phenyl | H | H | b = 0 | 4-(carboxy-methyl)-phenyl |
| 126 | 4-chloro-phenyl | 4-chloro-phenyl | H | H | b = 0 | 4-(amino-carbonyl-methyl)-phenyl |
| 134 | 4-chloro-phenyl | 4-chloro-phenyl | H | H | b = 0 | 6-methyl-pyrid-3-yl |

TABLE (I-2)

Representative Compounds of Formula (I)

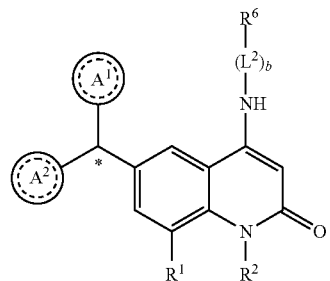

| ID No. | A¹ | A² | R¹ | R² | $(L^2)_b$ | R⁶ |
|---|---|---|---|---|---|---|
| 37 | 4-chloro-phenyl | thiazol-2-yl | H | H | b = 0 | 1-(ethoxy-carbonyl)-piperidin-4-yl |
| 39 | 4-chloro-phenyl | thiazol-2-yl | H | H | b = 0 | piperidin-4-yl |
| 40 | 4-chloro-phenyl | thiazol-2-yl | H | H | b = 0 | 1-(isopropyl-sulfonyl)-piperidin-4-yl |
| 41 | 4-chloro-phenyl | thiazol-2-yl | H | H | b = 0 | 1-(trifluoromethyl-sulfonyl)-piperidin-4-yl |
| 42 | 4-chloro-phenyl | thiazol-2-yl | H | H | —CH₂— | 1-(t-butoxy-carbonyl)-azetidin-3-yl |
| 43 | 4-chloro-phenyl | thiazol-2-yl | H | H | —CH₂— | azetidin-3-yl |
| 44 | 4-chloro-phenyl | 4-chloro-phenyl | H | H | b = 0 | 1-(trifluoromethyl-sulfonyl)-piperidin-4-yl |
| 45 | 4-chloro-phenyl | thiazol-2-yl | H | H | b = 0 | S-(1-t-butoxy-carbonyl-pyrrolidin-3-yl) |
| 46 | 4-chloro-phenyl | thiazol-2-yl | H | H | b = 0 | R-(1-t-butoxy-carbonyl-pyrrolidin-3-yl) |
| 47 | 4-chloro-phenyl | thiazol-2-yl | H | H | b = 0 | S-(1-(trifluoromethyl-sulfonyl)-pyrrolidin-3-yl) |
| 48 | 4-chloro-phenyl | thiazol-2-yl | H | H | b = 0 | R-(1-(trifluoromethyl-sulfonyl)-pyrrolidin-3-yl) |
| 49 | 4-chloro-phenyl | 4-chloro-phenyl | H | —CH₂— | b = 0 | 1-(trifluoromethyl-sulfonyl)-piperidin-4-yl |
| 52 | 4-chloro-phenyl | 4-fluoro-phenyl | H | H | b = 0 | 1-(trifluoromethyl-sulfonyl)-piperidin-4-yl |
| 53 | 4-chloro-phenyl | 3,4-dichloro-phenyl | H | H | b = 0 | 1-(trifluoromethyl-sulfonyl)-piperidin-4-yl |
| 54 | 4-chloro-phenyl | 4-methoxy-phenyl | H | H | b = 0 | 1-(trifluoromethyl-sulfonyl)-piperidin-4-yl |
| 55 | 4-chloro-phenyl | benzo[d][1,3]dioxol-5-yl | H | H | b = 0 | 1-(trifluoromethyl-sulfonyl)-piperidin-4-yl |
| 56 | 4-chloro-phenyl | 4-chloro-phenyl | H | H | b = 0 | 1-(ethyl-sulfonyl)-piperidin-4-yl |
| 62 | 4-chloro-phenyl | 4-trifluoro-methyl-phenyl | H | H | b = 0 | 1-(trifluoromethyl-sulfonyl)-piperidin-4-yl |
| 63 | 4-chloro-phenyl | 4-chloro-phenyl | H | H | b = 0 | 1-(methyl-sulfonyl)-piperidin-4-yl |
| 65 | 4-chloro-phenyl | benzo-thiazol-2-yl | H | H | b = 0 | 1-(trifluoromethyl-sulfonyl)-piperidin-4-yl |
| 66 | 4-chloro-phenyl | 4-hydroxy-phenyl | H | H | b = 0 | 1-(trifluoromethyl-sulfonyl)-piperidin-4-yl |

TABLE (I-2)-continued

Representative Compounds of Formula (I)

| | | | | | | |
|---|---|---|---|---|---|---|
| 69 | 4-chloro-phenyl | 4-chloro-phenyl | H | H | b = 0 | 1-(1,1,1-trifluoro-ethyl-carbonyl)-piperidin-4-yl |
| 72 | 4-chloro-phenyl | 6-chloro-pyrid-3-yl | H | H | b = 0 | 1-(trifluoromethyl-sulfonyl)-piperidin-4-yl |
| 77 | 4-chloro-phenyl | 4-chloro-phenyl | H | H | b = 0 | 1-(1,1,1-trifluoro-ethyl)-piperidin-4-yl |
| 89 | 4-chloro-phenyl | thiazol-2-yl | H | —CH$_3$ | b = 0 | 1-(trifluoromethyl-sulfonyl)-piperidin-4-yl |
| 92 | 4-chloro-phenyl | 4-chloro-phenyl | Br | H | b = 0 | 1-(trifluoromethyl-sulfonyl)-piperidin-4-yl |
| 95 | 4-chloro-phenyl | 4-chloro-phenyl | H | H | b = 0 | 1-(ethoxy-carbonyl-methyl-carbonyl)-piperidin-4-yl |
| 96 | 4-chloro-phenyl | 4-chloro-phenyl | H | H | b = 0 | 1-(carboxy-methyl-carbonyl)-piperidin-4-yl |
| 97 | 4-chloro-phenyl | 4-chloro-phenyl | H | H | b = 0 | 1-(ethoxy-carbonyl-ethyl-carbonyl)-piperidin-4-yl |
| 98 | 4-chloro-phenyl | 4-chloro-phenyl | H | H | b = 0 | 1-(carboxy-ethyl-carbonyl)-piperidin-4-yl |
| 99 | 4-chloro-phenyl | 4-chloro-phenyl | —NH-(1-CF$_3$—SO$_2$)-piper-idin-4-yl) | H | b = 0 | 1-(trifluoromethyl-sulfonyl)-piperidin-4-yl |
| 100 | 4-chloro-phenyl | 4-chloro-phenyl | —NH—CH$_2$CH$_2$—OCH$_3$ | H | b = 0 | 1-(trifluoromethyl-sulfonyl)-piperidin-4-yl |
| 101 | 4-chloro-phenyl | 4-(methoxy-ethyl-amino)-phenyl | —NH—CH$_2$CH$_2$—OCH$_3$ | H | b = 0 | 1-(trifluoromethyl-sulfonyl)-piperidin-4-yl |
| 102 | 4-chloro-phenyl | 4-chloro-phenyl | H | H | b = 0 | 1-(ethoxy-carbonyl-methyl-sulfonyl)-piperidin-4-yl |
| 103 | 4-chloro-phenyl | 4-chloro-phenyl | H | H | b = 0 | 1-(t-butoxy-carbonyl-methyl)-piperidin-4-yl |
| 104 | 4-chloro-phenyl | 4-chloro-phenyl | —NH-(n-propyl)-C(O)O—CH$_2$CH$_3$ | H | b = 0 | 1-(trifluoromethyl-sulfonyl)-piperidin-4-yl |
| 106 | 4-chloro-phenyl | 4-chloro-phenyl | H | H | b = 0 | 1-(amino-carbonyl-methyl-carbonyl)-piperidin-4-yl |
| 107 | 4-chloro-phenyl | 4-chloro-phenyl | 1-pyrrolidin-2-one | H | b = 0 | 1-(trifluoromethyl-sulfonyl)-piperidin-4-yl |
| 108 | 4-chloro-phenyl | 4-chloro-phenyl | —NH—CH$_2$CH$_2$CH$_2$—CO$_2$H | H | b = 0 | 1-(trifluoromethyl-sulfonyl)-piperidin-4-yl |
| 110 | 4-chloro-phenyl | 4-chloro-phenyl | H | —CH$_2$—CH$_2$—OCH$_3$ | b = 0 | 1-(trifluoromethyl-sulfonyl)-piperidin-4-yl |
| 112 | 4-chloro-phenyl | 4-chloro-phenyl | H | H | b = 0 | 1-(amino-carbonyl-ethyl-carbonyl)-piperidin-4-yl |
| 114 | 4-chloro-phenyl | 4-chloro-phenyl | H | H | b = 0 | 1-(t-butoxy-carbonyl-ethyl)-piperidin-4-yl |
| 115 | 4-chloro-phenyl | 4-chloro-phenyl | H | H | b = 0 | 1-(carboxy-ethyl)-piperidin-4-yl |
| 117 | 4-chloro-phenyl | 4-chloro-phenyl | H | H | b = 0 | 1-(carboxy-methyl)-piperidin-4-yl |
| 118 | 4-chloro-phenyl | 4-chloro-phenyl | H | H | b = 0 | 1-(amino-carboimido)-piperidin-4-yl |
| 119 | 4-chloro-phenyl | 4-chloro-phenyl | H | H | b = 0 | 1-((t-butoxy-carbonyl-amino)-t-butoxy-carbonyl-carboimido)-piperidin-4-yl |
| 139 | 4-chloro-phenyl | 4-chloro-phenyl | —NH—CH$_2$—CH$_2$—CH$_2$—CH$_3$ | CH$_3$ | b = 0 | 1-(trifluoromethyl-sulfonyl)-piperidin-4-yl |

TABLE (I-2)-continued

Representative Compounds of Formula (I)

| ID No. | | | | | | |
|---|---|---|---|---|---|---|
| 140 | 4-chloro-phenyl | 4-chloro-phenyl | —CH$_2$—CH$_2$—CH$_2$—OCH$_3$ | H | b = 0 | 1-(trifluoromethyl-sulfonyl)-piperidin-4-yl |
| 141 | 4-chloro-phenyl | 4-chloro-phenyl | —NH—CH$_2$—CH$_2$—CH$_2$—NH$_2$ | CH$_3$ | b = 0 | 1-(trifluoromethyl-sulfonyl)-piperidin-4-yl |

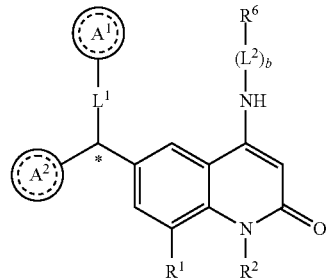

| ID No. | A$^1$ | A$^2$ | R$^1$ | R$^2$ | (L$^2$)$_b$ | R$^6$ |
|---|---|---|---|---|---|---|
| 135 | 4-chloro-phenyl | 4-fluoro-phenyl-CH$_2$— | H | H | b = 0 | 1-(trifluoromethyl-sulfonyl)-piperidin-4-yl |
| 136 | 4-chloro-phenyl | 4-chloro-phenyl-O— | H | H | b = 0 | 1-(trifluoromethyl-sulfonyl)-piperidin-4-yl |
| 137 | 4-chloro-phenyl | 4-phenyl-piperazin-1-yl- | H | H | b = 0 | 1-(trifluoromethyl-sulfonyl)-piperidin-4-yl |

TABLE (I-3)

Representative Compounds of Formula (I)

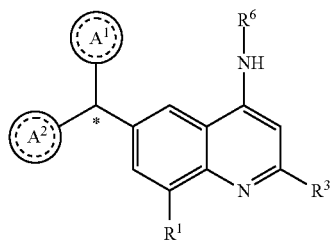

| ID No. | A$^1$ | A$^2$ | R$^1$ | R$^3$ | R$^6$ |
|---|---|---|---|---|---|
| 524 | 4-chloro-phenyl | 4-chloro-phenyl | bromo | H | 1-(trifluoromethyl-sulfonyl)-piperidin-4-yl |
| 525 | 4-chloro-phenyl | 4-chloro-phenyl | (1-CF$_3$—SO$_2$-piperidin-4-yl)-NH— | H | 1-(trifluoromethyl-sulfonyl)-piperidin-4-yl |
| 530 | 4-chloro-phenyl | 4-chloro-phenyl | H | —O—CH$_2$CH$_2$—OCH$_3$ | 1-(trifluoromethyl-sulfonyl)-piperidin-4-yl |
| 531 | 4-chloro-phenyl | 4-chloro-phenyl | H | —O—CH$_2$—C(O)O-t-butyl | 1-(trifluoromethyl-sulfonyl)-piperidin-4-yl |
| 532 | 4-chloro-phenyl | 4-chloro-phenyl | H | —O—CH$_2$—C(O)OH | 1-(trifluoromethyl-sulfonyl)-piperidin-4- |

TABLE (I-3)-continued

Representative Compounds of Formula (I)


| ID No. | A¹ | A² | R¹ | R³ | R⁶ |
|---|---|---|---|---|---|
| 533 | 4-chloro-phenyl | 4-chloro-phenyl | H | —O—CH₂—C(O)—NH—CH₃ | 1-(trifluoromethyl-sulfonyl)-piperidin-4-yl |
| 534 | 4-chloro-phenyl | 4-chloro-phenyl | H | —O-(n-pentyl)-C(O)—OCH₃ | 1-(trifluoromethyl-sulfonyl)-piperidin-4-yl |
| 535 | 4-chloro-phenyl | 4-chloro-phenyl | H | —O-(n-pentyl)-C(O)OH | 1-(trifluoromethyl-sulfonyl)-piperidin-4-yl |
| 536 | 4-chloro-phenyl | 4-chloro-phenyl | —OCH₃ | H | 1-(trifluoromethyl-sulfonyl)-piperidin-4-yl |
| 537 | 4-chloro-phenyl | 4-chloro-phenyl | —O—(CH₂)₄—CO₂H | H | 1-(trifluoromethyl-sulfonyl)-piperidin-4-yl |
| 538 | 4-chloro-phenyl | 4-chloro-phenyl | —O—CH₂—CH₂—CH₂—CH₂—C(O)—NH₂ | H | 1-(trifluoromethyl-sulfonyl)-piperidin-4-yl |
| 539 | 4-chloro-phenyl | 4-chloro-phenyl | —O—CH₂—CH₂—CH₂—CH₂—NH—C(O)O—C(CH₃)₃ | H | 1-(trifluoromethyl-sulfonyl)-piperidin-4-yl |
| 540 | 4-chloro-phenyl | 4-chloro-phenyl | —O—CH₂—CH₂—CH₂—CH₂—C(O)O—CH₂CH₃ | H | 1-(trifluoromethyl-sulfonyl)-piperidin-4-yl |
| 541 | 4-chloro-phenyl | 4-chloro-phenyl | —OH | H | 1-(trifluoromethyl-sulfonyl)-piperidin-4-yl |
| 542 | 4-chloro-phenyl | 4-chloro-phenyl | —O—CH₂—CH₂—CH₂—CH₂—NH₂ | H | 1-(trifluoromethyl-sulfonyl)-piperidin-4-yl |
| 543 | 4-chloro-phenyl | 4-chloro-phenyl | —O—CH₂—CH₂—CH₂—CH₂—NH—C(O)—CH₃ | H | 1-(trifluoromethyl-sulfonyl)-piperidin-4-yl |
| 544 | 4-chloro-phenyl | 4-chloro-phenyl | —O—CH₂—C(O)O—CH₂CH₃ | H | 1-(trifluoromethyl-sulfonyl)-piperidin-4-yl |
| 545 | 4-chloro-phenyl | 4-chloro-phenyl | —O—CH₂—CO₂H | H | 1-(trifluoromethyl-sulfonyl)-piperidin-4-yl |
| 546 | 4-chloro-phenyl | 4-chloro-phenyl | Br | —OCH₃ | 1-(trifluoromethyl-sulfonyl)-piperidin-4-yl |
| 547 | 4-chloro-phenyl | 4-chloro-phenyl | —CH=CH—CH₂—OCH₃ | —OCH₃ | 1-(trifluoromethyl-sulfonyl)-piperidin-4-yl |
| 548 | 4-chloro-phenyl | 4-chloro-phenyl | —CH₂—CH₂—CH₂—OCH₃ | —OCH₃ | 1-(trifluoromethyl-sulfonyl)-piperidin-4-yl |
| 549 | 4-chloro-phenyl | 4-chloro-phenyl | —CH=CH—CH₂OH | —OCH₃ | 1-(trifluoromethyl-sulfonyl)-piperidin-4-yl |
| 550 | 4-chloro-phenyl | 4-chloro-phenyl | —CH₂—CH₂—CH₂—OH | —OCH₃ | 1-(trifluoromethyl-sulfonyl)-piperidin-4-yl |

Representative compounds of formula (II) of the present invention are as listed in Tables (II-1) and (II-2), below.

TABLE (II-1)

Representative Compounds of Formula (II)

| ID No. | A¹ | A² | $(L^3)_c$ | R⁷ | (Sub) |
|---|---|---|---|---|---|
| 132 | 4-chloro-phenyl | 4-chloro-phenyl | —CH₂— | phenyl | H |
| 133 | 4-chloro-phenyl | 4-chloro-phenyl | c = 0 | phenyl | H |
| 138 | 4-chloro-phenyl | 4-chloro-phenyl | —C(O)— | pyrrolidin-1-yl | fluoro |

TABLE (II-2)

Representative Compounds of Formula (II)

| ID No. | A¹ | A² | $(L^3)_c$ | R⁷ |
|---|---|---|---|---|
| 57 | 4-chloro-phenyl | 4-chloro-phenyl | c = 0 | pyrimidin-2-yl |
| 60 | 4-chloro-phenyl | 4-chloro-phenyl | c = 0 | phenyl |
| 64 | 4-chloro-phenyl | 4-chloro-phenyl | —C(O)— | phenyl |
| 67 | 4-chloro-phenyl | 4-chloro-phenyl | —SO₂— | cyclopropyl |
| 68 | 4-chloro-phenyl | 4-chloro-phenyl | c = 0 | pyrdi-2-yl |
| 80 | 4-chloro-phenyl | 4-chloro-phenyl | —SO₂— | phenyl |
| 81 | 4-chloro-phenyl | 4-chloro-phenyl | —SO₂— | pyrrolidin-1-yl |
| 82 | 4-chloro-phenyl | 4-chloro-phenyl | —SO₂— | 3-fluoro-phenyl |
| 84 | 4-chloro-phenyl | 4-chloro-phenyl | —SO₂— | 3-carboxy-phenyl |
| 113 | 4-chloro-phenyl | 4-chloro-phenyl | —C(O)— | 4-(methoxy-carbonyl)-phenyl |
| 116 | 4-chloro-phenyl | 4-chloro-phenyl | —C(O)— | 4-carboxy-phenyl |
| 122 | 4-chloro-phenyl | 4-chloro-phenyl | —SO₂— | 4-carboxy-phenyl |
| 127 | 4-chloro-phenyl | 4-chloro-phenyl | —CH₂— | 4-carboxy-phenyl |
| 128 | 4-chloro-phenyl | 4-chloro-phenyl | —CH₂— | 5-carboxy-thein-2-yl |
| 129 | 4-chloro-phenyl | 4-chloro-phenyl | —CH₂— | 3-carboxy-phenyl |
| 130 | 4-chloro-phenyl | 4-chloro-phenyl | —SO₂— | 5-carboxy-thein-2-yl |
| 131 | 4-chloro-phenyl | 4-chloro-phenyl | —SO₂— | 5-carboxy-furan-2-yl |

Representative compounds of formula (III) of the present invention are as listed in Tables (III-1) and (III-2), below.

TABLE (III-1)

Representative Compounds of Formula (III)

| ID No. | A¹ | A² | R² | L⁴ | $(R^8)_d$ |
|---|---|---|---|---|---|
| 9 | 4-chloro-phenyl | thiazol-2-yl | —CH₃ | —CH₂CH₂— | 3-chloro |
| 11 | 4-chloro-phenyl | thiazol-2-yl | H | —CH₂CH₂— | 3-chloro |
| 15 | 4-chloro-phenyl | 4-chloro-phenyl | H | —CH=CH— | 3-fluoro |
| 16 | 4-chloro-phenyl | thien-3-yl | H | —CH=CH— | 3-fluoro |
| 18 | 4-chloro-phenyl | thien-3-yl | H | cis-CH=CH— | 3-trifluoromethyl |

TABLE (III-1)-continued

Representative Compounds of Formula (III)

| ID No. | A¹ | A² | R² | L⁴ | (R⁸)_d |
|---|---|---|---|---|---|
| 19 | 4-chloro-phenyl | thien-3-yl | H | trans-CH=CH— | 3-trifluoromethyl |
| 21 | 4-chloro-phenyl | thien-2-yl | H | —CH=CH— | d = 0 |
| 25 | 4-chloro-phenyl | thiazol-2-yl | H | —CH=CH— | d = 0 |
| 26 | 4-chloro-phenyl | thien-2-yl | H | —CH=CH— | 3-trifluoromethyl |
| 27 | 4-chloro-phenyl | thien-2-yl | H | —CH=CH— | 4-methyl |
| 28 | 4-chloro-phenyl | thien-2-yl | H | —CH=CH— | 4-trifluoromethyl |
| 29 | 4-chloro-phenyl | 5-chloro-thien-2-yl | H | —CH=CH— | 4-trifluoromethyl |
| 30 | 4-chloro-phenyl | 5-chloro-thien-2-yl | H | —CH=CH— | 3-fluoro |
| 31 | 4-chloro-phenyl | 5-chloro-thien-2-yl | H | —CH=CH— | d = 0 |
| 32 | 4-chloro-phenyl | phenyl | H | —CH=CH— | 3-fluoro |
| 33 | 4-chloro-phenyl | phenyl | H | —CH=CH— | 4-trifluoromethyl |
| 34 | 4-chloro-phenyl | phenyl | H | —CH=CH— | 4-chloro |
| 38 | 4-chloro-phenyl | thiazol-2-yl | H | —CH=CH— | 3-fluoro |
| 514 | 4-chloro-phenyl | 4-methoxy-phenyl | H | —CH=CH— | d = 0 |
| 515 | 4-chloro-phenyl | thiazol-2-yl | H | —CH₂— | 4-trifluoromethoxy |

TABLE (III-2)

Representative Compounds of Formula (III)

| ID No. | A¹ | A² | R³ | L⁴ | (R⁴)_d |
|---|---|---|---|---|---|
| 502 | 4-chloro-phenyl | 4-chloro-phenyl | H | —CH=CH— | d = 0 |
| 503 | 4-chloro-phenyl | 4-chloro-phenyl | H | E—CH=CH— | d = 0 |

TABLE (III-2)-continued

Representative Compounds of Formula (III)

| ID No. | A¹ | A² | R³ | L⁴ | (R⁴)_d |
|---|---|---|---|---|---|
| 505 | 4-methoxy-phenyl | thiazol-2-yl | H | —CH=CH— | d = 0 |
| 508 | 4-chloro-phenyl | thien-2-yl | H | —CH=CH— | d = 0 |
| 509 | 4-chloro-phenyl | thien-3-yl | H | —CH=CH— | d = 0 |
| 511 | 4-chloro-phenyl | thiazol-2-yl | H | —CH=CH— | d = 0 |
| 516 | 4-chloro-phenyl | thiazol-4-yl | H | —CH=CH— | d = 0 |
| 520 | 4-chloro-phenyl | thiazol-4-yl | H | —CH=CH— | d = 0 |
| 521 | 4-chloro-phenyl | 4-chloro-phenyl | H | —CH=CH— | 4-trifluoromethyl |

Representative compounds of formula (IV) of the present invention are as listed in Tables (IV-1) and (IV-2), below.

TABLE (IV-1)

Representative Compounds of Formula (IV)

| ID No. | A¹ | A² | | R⁹ |
|---|---|---|---|---|
| 13 | 4-chloro-phenyl | 4-chloro-phenyl | 1,2,3,6-tetrahydro-pyridin-4-yl | tert-butoxy-carbonyl |
| 14 | 4-chloro-phenyl | 4-chloro-phenyl | 1,2,3,6-tetrahydro-pyridin-4-yl | trifluoromethyl-carbonyl |
| 17 | 4-chloro-phenyl | 4-chloro-phenyl | 1,2,3,6-tetrahydro-pyridin-4-yl | trifluoromethyl-sulfonyl |
| 35 | 4-chloro-phenyl | thiazol-2-yl | piperazin-1-yl | trifluoromethyl-sulfonyl |

TABLE (IV-2)

Representative Compounds of Formula (IV)

| ID No. | A¹ | A² | R³ | | R⁹ |
|---|---|---|---|---|---|
| 513 | 4-chloro-phenyl | thiazol-2-yl | H | 1,2,3,6-tetrahydro-pyridin-4-yl | tert-butoxy-carbonyl- |
| 519 | 4-chloro-phenyl | 4-chloro-phenyl | —O—SO₂—CF₃ | 1,2,3,6-tetrahydro-pyridin-4-yl | trifluoromethyl-sulfonyl |
| 522 | 4-chloro-phenyl | thiazol-2-yl | —O—SO₂—CF₃ | piperazin-1-yl | methyl-carbonyl- |

Representative intermediates in the synthesis of the compounds of formula (I), compounds of formula (II), compounds of formula (III) and/or compounds of formula (IV) of the present invention are as listed in Table (INT) below.

TABLE INT

Representative Intermediates in the Synthesis of the Compounds of the Present Invention

| ID No. | A¹ | A² | (L²)_b | R⁶ |
|---|---|---|---|---|
| 50 | 4-chloro-phenyl | 4-fluoro-phenyl | b = 0 | 1-(trifluoromethyl-sulfonyl)-piperidin-4-yl |
| 51 | 4-chloro-phenyl | 4-methoxy-phenyl | b = 0 | 1-(trifluoromethyl-sulfonyl)-piperidin-4-yl |
| 73 | 4-chloro-phenyl | 4-chloro-phenyl | b = 0 | 1-(trifluoromethyl-sulfonyl)-piperidin-4-yl |

TABLE INT-continued

Representative Intermediates in the Synthesis of the
Compounds of the Present Invention

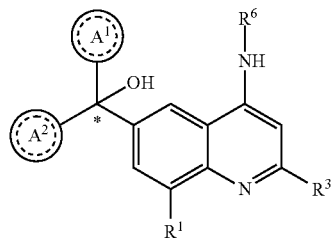

| ID No. | A¹ | A² | R¹ | R² | R³ |
|---|---|---|---|---|---|
| 529 | 4-chloro-phenyl | 4-chloro-phenyl | ethoxy-carbonyl-(n-propyl)-NH— | —O-t-butyl | 1-(trifluoro-methyl-sulfonyl)-piperidin-4-yl |

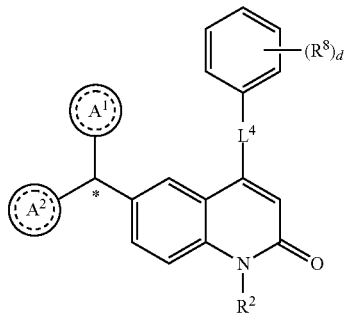

| ID No. | A¹ | A² | R₂ | L⁴ | (R⁸)_d |
|---|---|---|---|---|---|
| 8 | 4-chloro-phenyl | thiazol-2-yl | H | —CH₂CH₂— | 3-chloro |

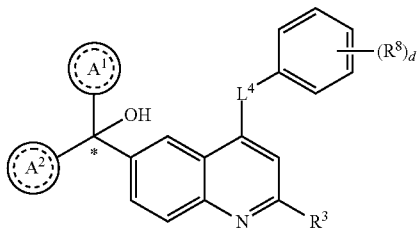

| ID No. | A¹ | A² | R³ | L⁴ | (R⁴)_d |
|---|---|---|---|---|---|
| 501 | 4-chloro-phenyl | 4-chloro-phenyl | H | —CH=CH— | d = 0 |
| 504 | 4-methoxy-phenyl | thiazol-2-yl | H | —CH=CH— | d = 0 |
| 506 | 4-chloro-phenyl | thien-2-yl | H | —CH=CH— | d = 0 |
| 507 | 4-chloro-phenyl | thien-3-yl | H | —CH=CH— | d = 0 |
| 510 | 4-chloro-phenyl | thiazol-2-yl | —O-t-butyl | —CH₂— | 4-trifluoro-methoxy |
| 512 | 4-chloro-phenyl | 4-methoxy-phenyl | —O-t-butyl | —CH=CH— | d = 0 |
| 517 | 4-chloro-phenyl | thiazol-4-yl | H | —CH=CH— | d = 0 |
| 518 | 4-chloro-phenyl | thien-3-yl | —O-t-butyl | —CH=CH— | 3-fluoro |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$alkyl" shall mean any straight or branched chain composition of between 1 and 4 carbon atoms (including methyl, ethyl, n-propyl, isopropyl, n-butyl, isobutyl and t-butyl).

One skilled in the art will recognize that the term "—($C_{X-Y}$alkyl)-" shall denote any $C_{X-Y}$alkyl straight or branched chain composition as defined above, wherein said $C_{X-Y}$alkyl straight or branched chain composition is divalent and is therefore bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CH_2F$, —$CH_2I$, —$CH_2Br$, —$CH_2Cl$, —$CF_3$, —$CCl_3$, —$CH_2$—$CF_3$, $CH_2$—$CCl_3$, —$CF_2$—$CF_2$—$CF_2$—$CF_3$, and the like. Similarly, the term "fluorinated $C_{1-4}$alkyl" shall mean any $C_{1-4}$alkyl group as defined above substituted with at least one fluoro atom, preferably one to three fluoro atoms. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{X-Y}$alkyl" shall mean any $C_{X-Y}$alkyl group as defined above, substituted with at least one hydroxy group, preferably one to two hydroxy groups, more preferably one hydroxy group; provided that when the "hydroxy substituted $C_{X-Y}$alkyl" is bound to a N or O atom of a substituent group as defined herein, then the hydroxy group(s) on the "hydroxy substituted $C_{X-Y}$alkyl" are not bound to C-1 carbon atom of the $C_{X-Y}$alkyl portion of the "hydroxy substituted $C_{X-Y}$alkyl" (i.e. the hydroxy group(s) are not bound to the carbon atom which is directly bound to the N or O atom of said substituent group). Suitable examples include but are not limited to —$CH_2OH$, —$CH_2CH_2OH$, —$CH(OH)CH_3$, —$CH_2CH_2CH_2OH$, —$CH_2CH(OH)CH_3$, —$CH_2CH_2CH_2CH_2OH$, —$C(CH_2CH_2OH)_2$—$CH_2CH_2OH$, and the like. In an embodiment, the $C_{X-Y}$alkyl is substituted with the hydroxy group(s) at terminal carbon atom(s).

As used herein, unless otherwise noted, the term "$C_{X-Y}$alkenyl" wherein X and Y are integers, shall mean a carbon chain composition of between X and Y carbon atoms wherein the carbon chain contains at least one, preferably one, double bond. For example, "$C_{3-4}$alkenyl" shall mean a 3 to 4 carbon chain composition containing at least one, preferably one, double bond. Suitable example include, but are not limited to —$CH_2$—$CH$=$CH_2$, —$CH$=$CH$—$CH_2$ and the like.

One skilled in the art will recognize that the term "—($C_{X-Y}$alkenyl)-" shall denote any $C_{X-Y}$alkenyl carbon chain composition as defined above, wherein said $C_{X-Y}$alkenyl is divalent and is therefore bound through two points of attachment, preferably through two terminal carbon atoms. For example, the term "—($C_{2-4}$alkenyl)-" shall mean any 2 to 4 carbon atom chain containing at least one, preferably one double bond. Suitable examples include, but are not limited to —$CH$=$CH$—, —$CH_2$—$CH$=$CH$—, —$CH$=$CH$—$CH_2$—, —$CH$=$CH$—$CH(CH_3)$— and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched chain carbon chain composition of between X and Y carbon atoms. For example, "$C_{1-4}$alkoxy" shall mean any oxygen ether radical of the above described straight or branched chain composition of between 1 and 4 carbon atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCH_2F$, —$OCH_2I$, —$OCH_2Br$, —$OCH_2Cl$, —$OCF_3$, —$OCCl_3$, —$OCH_2$—$CF_3$, —$OCH_2$—$CCl_3$, —$OCF_2$—$CF_2$—$CF_2$—$CF_3$, and the like. Similarly, the term "fluorinated $C_{1-4}$alkoxy" shall mean any $C_{1-4}$alkoxy group as defined above substituted with at least one fluoro atom, preferably one to three fluoro atoms. Suitable examples include but are not limited to —$OCF_3$, —$OCH_2$—$CF_3$, —$OCF_2$—$CF_2$—$CF_3$, and the like.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

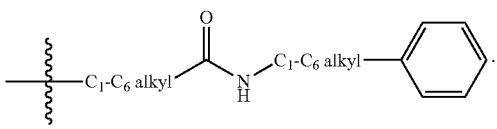

Abbreviations used in the specification, particularly the Schemes and Examples, are as follows:
AcOH=Acetic acid
BINAP (2,2'-Bis(diphenylphosphino)-1,1'-binaphthyl)
BLOQ=Below Limit of Quantitation
Boc$_2$O=Boc anhydride (i.e. di-tert-butyl dicarbonate)
BSA=Bovine Serum Albumin
cAMP=Cyclic Adenosine Monophosphate
CB1 or CB1R or CB$_1$R=Cannabinoid 1 Receptor
CB2=Cannabinoid 2 Receptor
CBz=Carboxybenzyl
CH(OEt)$_3$=Trimethoxymethane
DBU=1,8-Diazabicyclo[5.4.0]undec-7-ene
DCC=N,N'-Dicyclohexylcarbodiimide
DCE=1,1-Dichloroethane
DCM=Dichloromethane
DEAD=Diethylazodicarboxylate
DIPEA or DIEA or
Hunig's Base=Diisopropylethylamine
DME=Dimethoxyethane
DMEM=Dulbecco's Modified Eagle Medium
DMF=N,N-Dimethylformamide
DMSO=Dimethylsulfoxide
dppf=1,1'-Bis(diphenylphosphino)ferrocene
EDCI=1-Ethyl-3-(3-dimethylaminopropyl)carbodiimide
EDTA=Ethylene Diamine Tetraacetic Acid
Et$_3$N=Triethylamine
Et$_2$O=Diethyl ether
EtOAc=Ethyl acetate
EtOH=Ethanol
Et$_3$SiH=Triethylsilane
FBS=Fetal Bovine Serum
GPCR=G-coupled Receptor
HATU=O-(7-Azabenzotriazol-1-yl)-N,N,N'',N''-Tetramethyl Uronium Hexafluorophosphate
HBSS=Hank's Balanced Salt Solution
HBTU=N N,N,N',N'-Tetramethyl-O-(1H-benzotriazol-1-yl)uronium hexafluorophosphate
HDL=High Density Lipoprotein
HEPES=4-(2-Hydroxyethyl)-1-Piperazine Ethane Sulfonic Acid
HMPA=Hexamethylphosphoramide
HPLC=High Performance Liquid Chromatography
KOt-Bu or t-BuOK or
KOBu$^t$=Potassium t-butoxide
LADA=Latent Autoimmune Diabetes of Adults
LAH=Lithium aluminum hydride
LCMS=Liquid Chromatography-Mass Spectrometry
LDL=Low Density Lipoprotein
MCPBA or mCPBA=Meta-Chloroperoxybenzoic Acid
Meldrum's Acid=2,2-dimethyl-1,3-dioxane-4,6-dione
MeOH=Methanol
Mesyl=Methylsulfonyl
Mesyl Chloride=Methylsulfonyl chloride
MPLC=Medium Pressure Liquid Chromatography
MSA=Methanesulfonic Acid
MTBE=Methyl t-butyl ether
n-BuLi=n-Butyl Lithium
NaOt-Bu=Sodium t-butoxide
NASH=NonAlcoholic Steatohepatitis
NMR=Nuclear magnetic Resonance
NSB=Non-Specific Binding
—NPhth=Phthalimido-2-yl (i.e. Isoindo-2-yl-1,3-dione)
PBS=Phosphate Buffered Saline
Pd$_2$(Oac)$_2$=Palladium(II)acetate
Pd$_2$(dba)$_3$=Tris(dibenzylidene acetone)dipalladium(0)
Pd(dppf)Cl$_2$=[1,1'-Bis(diphenylphosphino) ferrocene]dichloropalladium(II)
Pd(PPh$_3$)$_4$=Tetrakistriphenylphosphine palladium (0)
(Ph)$_2$O or Ph$_2$O Phenyl Ether
P(o-tol)$_3$=Tri(o-tolyl)phosphine
PPh$_3$=Triphenyl phosphine
PPh$_3$Br$_2$=Triphenyl Phosphine Dibromide
RP-HPLC=Reverse Phase High Performance Liquid Chromatography
RT or rt=Room temperature
SPhos=Tert 2-Dicyclohexylphosphino-2',6'-dimethoxybiphenyl-Butoxycarbonyl
t-BOC or Boc=tert-Butoxycarbonyl
TEA=Triethylamine
TFA=Trifluoroacetic Acid
THF=Tetrahydrofuran
TLC=Thin Layer Chromatography
Tosyl=p-Toluenesulfonyl
Tris HCl or Tris-Cl Tris[hydroxymethyl]aminomethyl hydrochloride
Wilkinson's Catalyst=Chlorotris(triphenylphosphine)rhodium(I)
XANTPhos=4,5-Bis(diphenylphosphino)-9,9-dimethylxanthene
XPhos=2-Dicyclohexylphosphino-2',4',6'-triisopropylbiphenyl The compounds of the present invention are CB-1 inverse agonists useful for the treatment and/or prevention of metabolic disorders, including obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain. Preferably, the metabolic disorder is selected from the group consisting of obesity, Type II diabetes, and dyslipidemias. More preferably, the metabolic disorder is obesity or Type II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of one or more additional symptoms; and/or (d) delay or avoidance of the development or progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named. One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R'' wherein R'' is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($R$moles−$S$moles)/($R$moles+$S$moles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee=([\alpha-obs]/[\alpha-max])\times 100$.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Compounds of formula (I) wherein $R^0$ is

and wherein

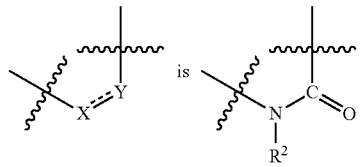

may be prepared according to the process outlined in Scheme (I-1), below. Preferably, in Scheme (I-1) below, $R^1$ is selected from the group consisting of hydrogen, halogen, $C_{1-4}$alkyl and —O—($C_{1-4}$alkyl).

Scheme (I-1)

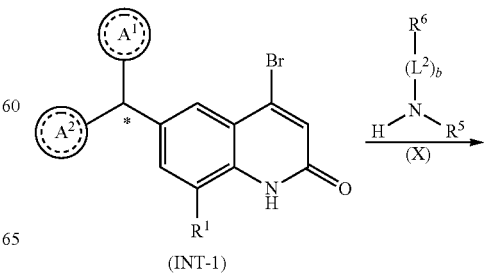

-continued

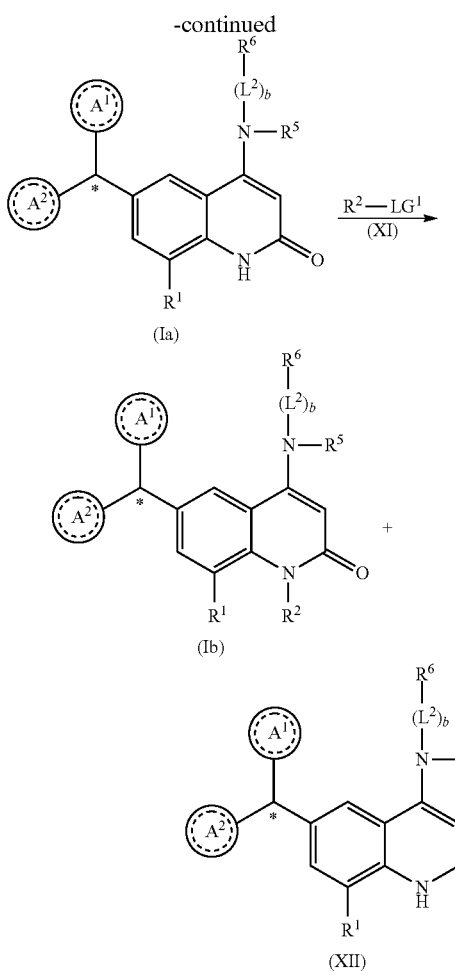

a suitably substituted compound of formula (X), as described in Scheme (I-1) above, to yield the corresponding compound of formula (Ib).

Compounds of formula (I) wherein R⁰ is

and wherein

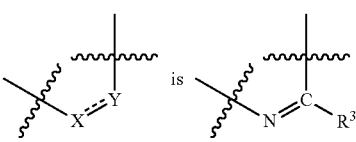  is and wherein R³ is hydrogen may be similarly prepared according to the process outlined in Scheme (I-1) above, by selecting a suitably substituted compound of formula (INT-4)

(INT-4)

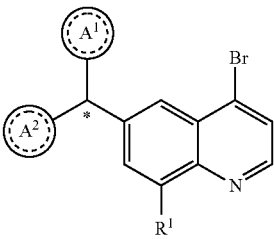

(a known compound or compound prepared for example, as described in Scheme C, which follows herein), substituting said compound of formula (INT-4) for the compound of formula (INT-1) in Scheme (I-1) above, and reacting as described therein (converting the compound of formula (INT-1) to the corresponding compound of formula (I)).

Compounds of formula (I) wherein R⁰ is

and wherein

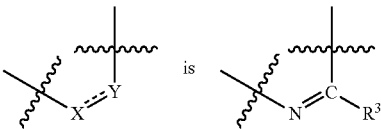 is wherein R³ is —OR⁴ may be prepared according to the process outlined in Scheme (I-2), below.

Accordingly, a suitably substituted compound of formula (INT-1), (a compound prepared for example, as described in Scheme A, which follows herein), is reacted with a suitably substituted compound of formula (X), a known compound or compound prepared by known methods; in the presence of a suitably selected catalyst such as Pd₂(dba)₃, Pd(OAc)₂, and the like; in the presence of a suitably selected ligand such as dppf, XantPhos, XPhos, and the like; in the presence of a suitably selected base such as Cs₂CO₃, K₂CO₃, K₃PO₄, and the like; in a suitably selected organic solvent such as 1,4-dioxane, toluene, DME, THF, and the like; to yield the corresponding compound of formula (Ia).

The compound of formula (Ia) is further, optionally reacted with a suitably substituted compound of formula (XI), wherein LG¹ is a suitably selected leaving group such as Cl, Br, I, tosylate, mesylate, and the like; in the presence of a suitably selected base such as Cs₂CO₃, K₂CO₃, NaH, and the like; in a suitably selected organic solvent such as acetonitrile, DMF, THF, and the like; to yield the corresponding compound of formula (Ib), in a mixture with the corresponding compound of formula (XII).

One skilled in the art will recognize that compounds of formula (Ib) may alternatively be prepared by reacting a suitably substituted compound of formula (INT-1) with a suitably substituted compound of formula (XI), as described in Scheme (I-1) above, to functionalize (with the desired R² group) the nitrogen atom at the 1-position of quinol-2-one core; and then further reacting the resulting compound with $R^3$ is hydrogen; and $R^1$ is $NR^E R^F$ may prepared according to the procedure as described in Scheme (I-3), below.

Scheme (I-2)

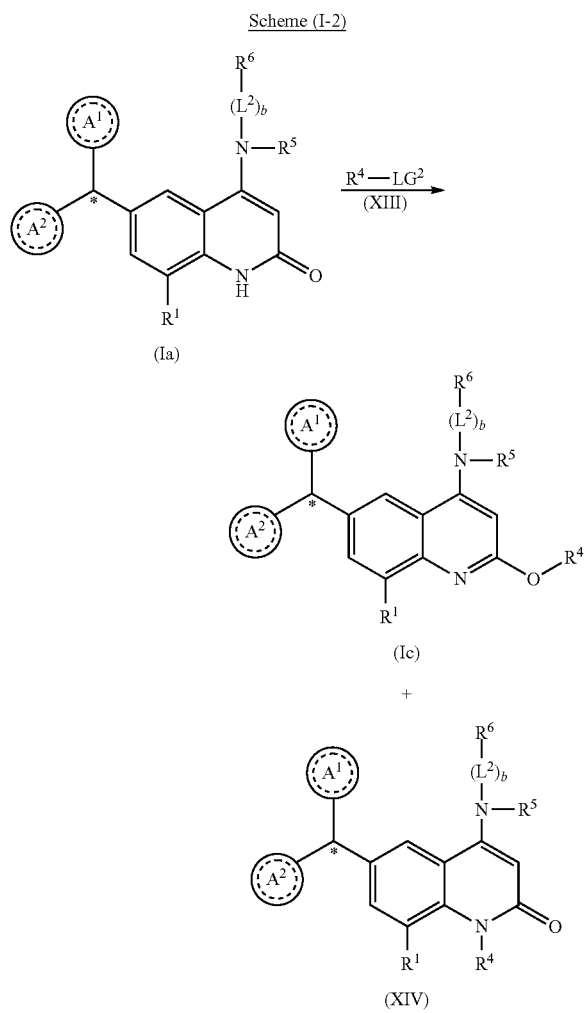

(Ia)

(Ic)

+

(XIV)

Accordingly, a suitably substituted compound of formula (Ia), prepared for example, as described in Scheme (I-1) above, is reacted with a suitably substituted compound of formula (XIII), wherein $LG^2$ is a suitably selected leaving group such as Br, Cl, I, mesylate, tosylate, and the like, a known compound or compound prepared by known methods; according to known methods (for example in the presence of a suitably selected base such as $Cs_2CO_3$, $K_2CO_3$, and the like; in a suitably selected solvent such as acetonitrile, DMF, THF, and the like), to yield the corresponding compound of formula (Ic), in a mixture with the corresponding compound of formula (XIV).

Compounds of formula (I) wherein $R^0$ is

;

wherein

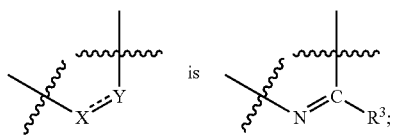

Scheme (I-3)

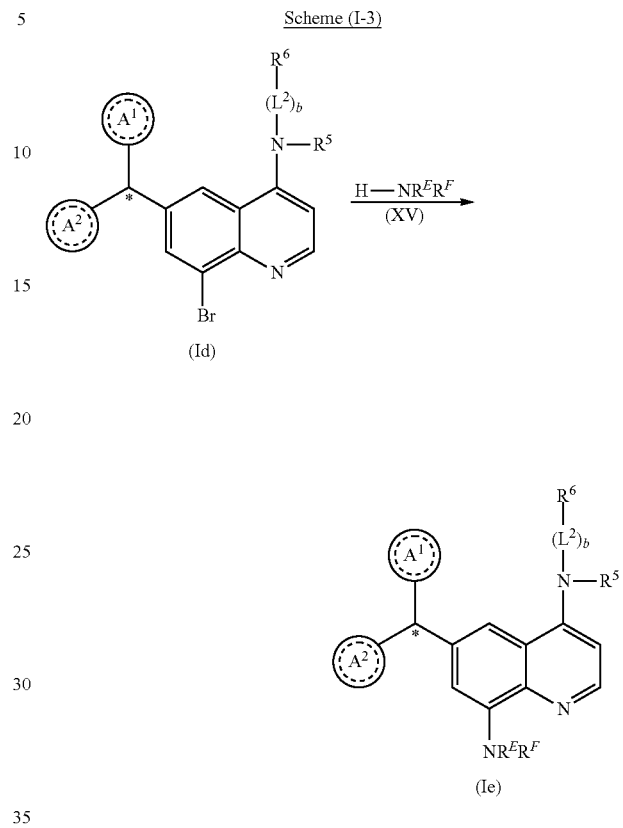

(Id)

(Ie)

Accordingly, a suitably substituted compound of formula (Id); prepared for example, as described herein (e.g. Scheme (I-1)) is reacted with a suitably substituted compound of formula (XV), a known compound or compound prepared by known methods; in the presence of a suitably selected catalyst such as $Pd_2(dba)_3$, $Pd(OAc)_2$, and the like; in the presence of a suitably selected ligand such as dppf, Xant-Phos, XPhos, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (Ie).

Compounds of formula (I) wherein $R^0$ is

;

wherein

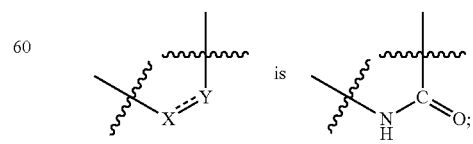

and $R^1$ is $NR^E R^F$ are preferably prepared according to the procedure as described in Scheme (I-4), below.

Scheme (I-4)

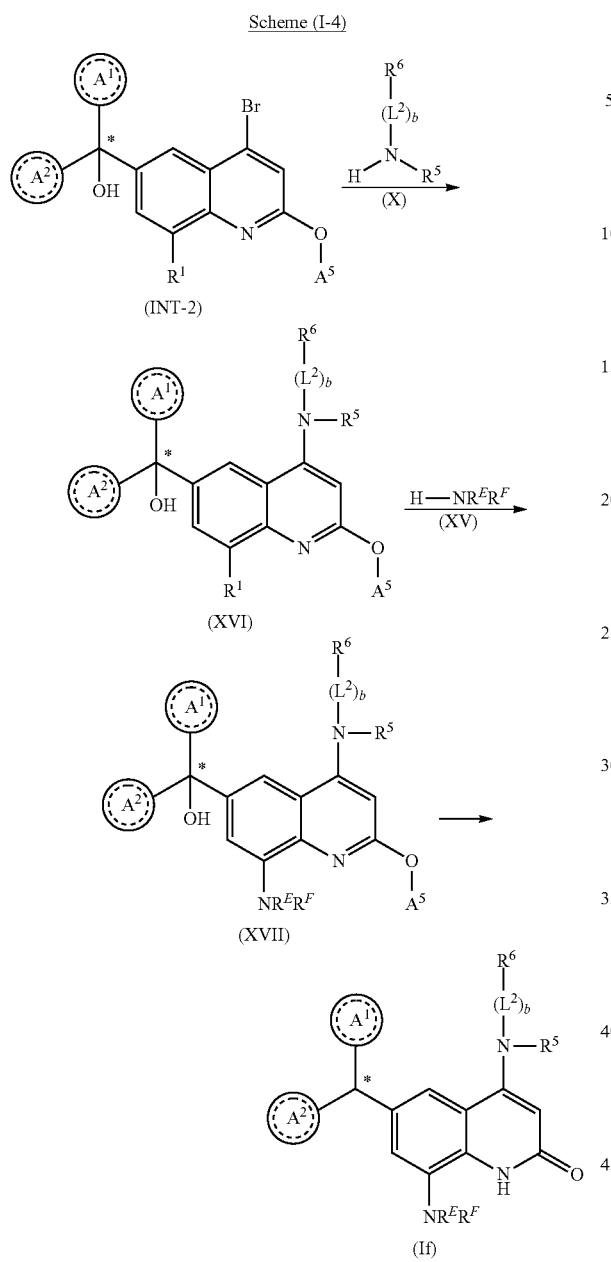

The compound of formula (XVI) is reacted with a suitably substituted compound of formula (XV), a known compound or compound prepared by known methods; in the presence of a suitably selected catalyst such as Pd$_2$(dba)$_3$, Pd(OAc)$_2$, and the like; in the presence of a suitably selected ligand such as dppf, XantPhos, XPhos, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XVII). Preferably, the compound of formula (XVI) is reacted with the compound of formula (XV) in the presence of Pd$_2$(dba)$_3$ in combination with XantPhos; to yield the corresponding compound of formula (XVII).

The compound of formula (XVII) is reacted with Et$_3$SiH in combination with TFA or SnCl$_2$ in combination with HCl or TiCl$_4$ in combination with Et$_3$SiH; in a suitably selected organic solvent such as DCM, DCE, and the like; to yield the corresponding compound of formula (If).

One skilled in the art will recognize that the compound of formula (If) may be further optionally reacted with a suitably substituted compound of formula (XI) and/or with a suitably substituted compound of formula (XIII) to further functionalize the compound of formula (If), as described herein; more particularly, to attach a desired R$^2$ and/or R$^4$ substituent group.

Compounds of formula (I) wherein R$^0$ is

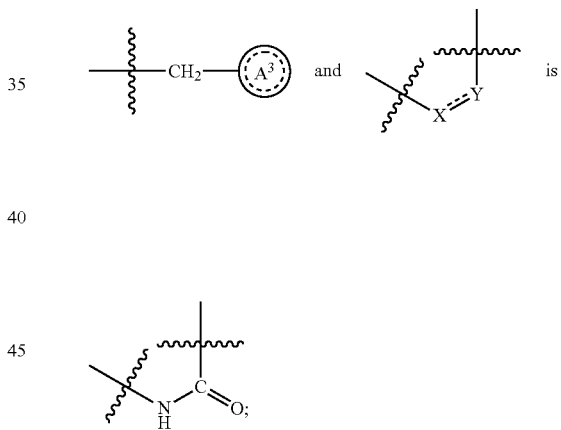

are preferably prepared according to the procedure as outlined in Scheme (I-5), below.

Accordingly, a suitably substituted compound of formula (INT-2) wherein R$^1$ is Br, and wherein A$^5$ is selected from C$_{1-4}$alkyl, preferably A$^1$ is methyl or t-butyl, prepared for example as described in Scheme B which follows herein, is reacted with a suitably substituted compound of formula (X), a known compound or compound prepared by known methods; in the presence of a suitably selected catalyst such as Pd$_2$(dba)$_3$, Pd(OAc)$_2$, and the like; in the presence of a suitably selected ligand such as dppf, XantPhos, XPhos, and the like in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XVI). Preferably, the compound of formula (INT-2) is reacted with the compound (X) in the presence of Pd$_2$(dba)$_3$ in combination with dppf; to yield the corresponding compound of formula (XVI).

Scheme (I-5)

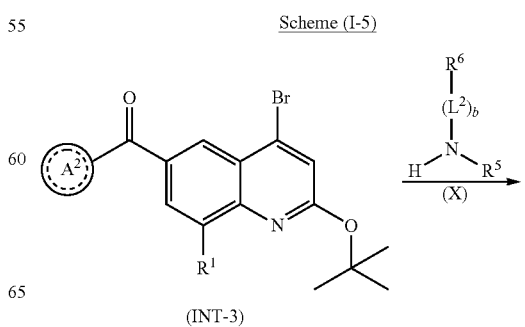

-continued

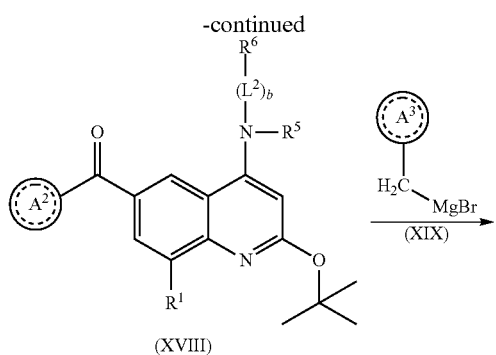

(XVIII)

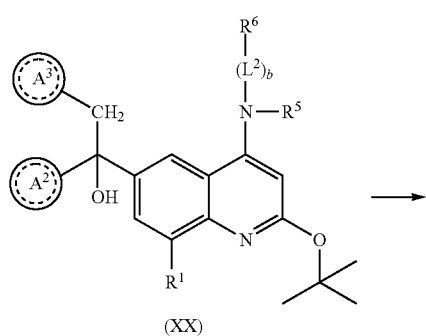

(XX)

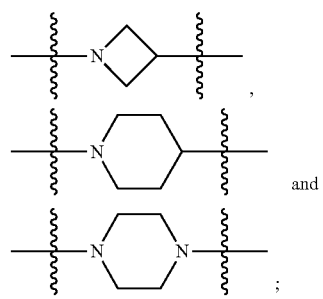

(XXI)

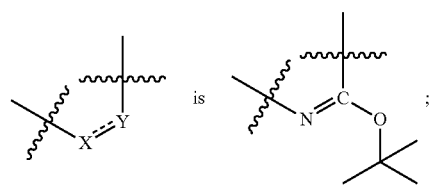

(Ig)

Accordingly, a suitably substituted compound of formula (INT-3), prepared for example as described in Scheme A which follows herein, is reacted with a suitably substituted compound of formula (X), a known compound or compound prepared according to known methods; in the presence of a suitably selected catalyst such as $Pd_2(dba)_3$, $Pd(OAc)_2$, and the like; in the presence of a suitably selected ligand such as dppf, XantPhos, XPhos, and the like in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XVIII).

The compound of formula (XVIII) is reacted with a suitably substituted compound of formula (XIX), a known compound or compound prepared by known methods, under Grignard conditions, in a suitably selected anhydrous organic solvent such as THF, diethyl ether, and the like; to yield the corresponding compound of formula (XX).

The compound of formula (XX) is reacted with a suitably selected acid such as TFA, HCl, p-toluene sulfonic acid, and the like, in a suitably selected solvent such as DCM, methanol, toluene, and the like; to yield the corresponding compound of formula (XXI).

The compound of formula (XXI) is reacted with $H_{2(g)}$ or a suitably selected source of hydrogen; in the presence of a suitably selected catalyst such as $PtO_2$, Wilkinson's catalyst, and the like; in a suitably selected solvent such as methanol, ethanol, and the like; to yield the corresponding compound of formula (Ig).

The compound of formula (Ig) may be further, optionally substituted with desired $R^1$, $R^2$ and/or $R^4$ substituent groups, according to the procedures as described herein.

Compounds of formula (I) wherein $R^0$ is

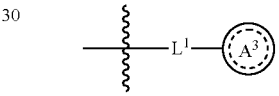

and wherein $L^1$ is selected from the group consisting of —O—, and wherein is may be prepared according to the procedure as described in Scheme (I-6), below.

Scheme (I-6)

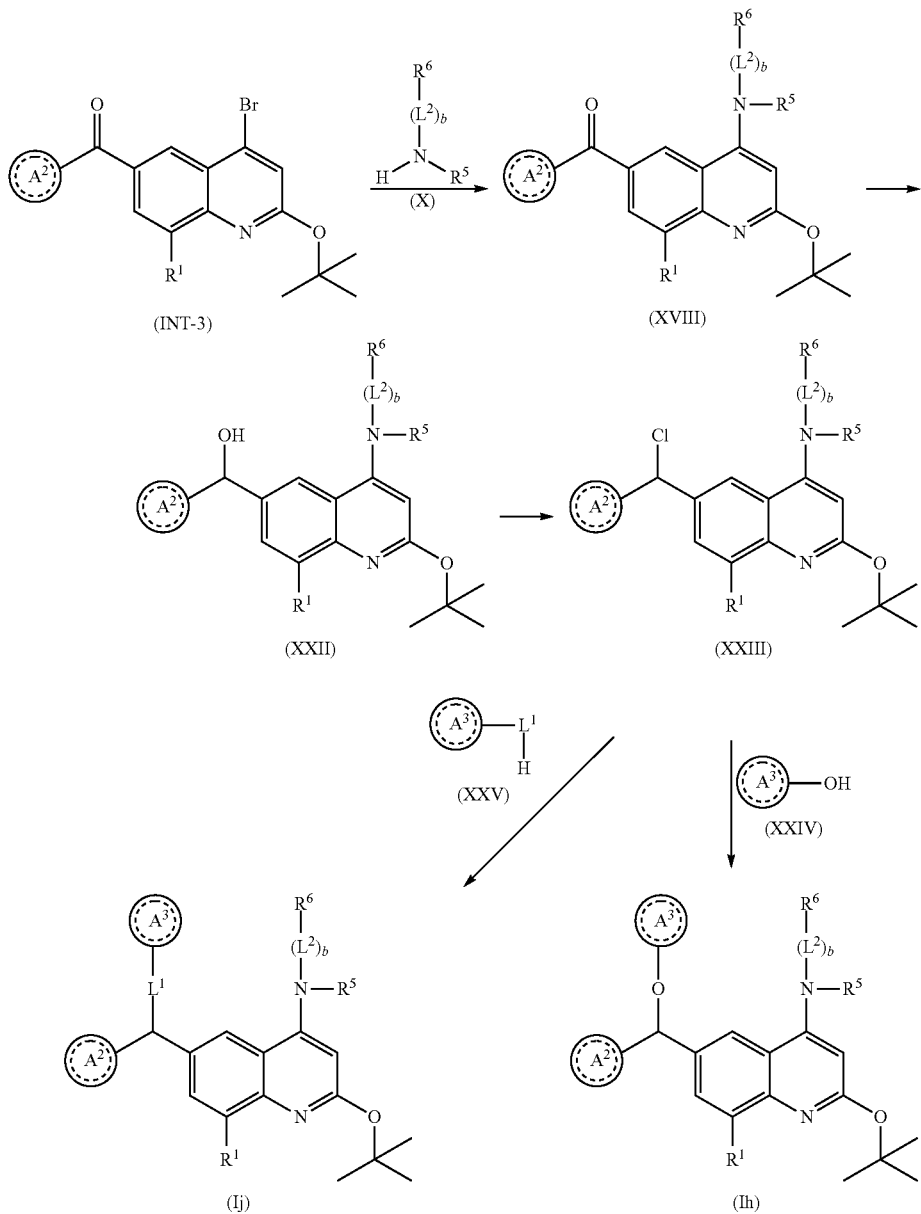

Accordingly, a suitably substituted compound of formula (INT-3), prepared for example as described in Scheme A, which follows herein, is reacted with a suitably substituted compound of formula (X), a known compound or compound prepared according to known methods; in the presence of a suitably selected coupling agent such as $Pd_2(dba)_3$, $Pd(OAc)_2$, and the like; in the presence of a suitably selected ligand such as dppf, XantPhos, XPhos, and the like in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XVIII).

The compound of formula (XVIII) is reacted with a suitably selected reducing agent such as $NaBH_4$, $LiBH_4$, and the like; in a suitably selected organic solvent such as methanol, THF, and the like; to yield the corresponding compound of formula (XXII).

The compound of formula (XXII) is reacted with a suitably selected chlorinating agent, such as $SOCl_2$, $CCl_4$ in combination with $PPh_3$, mesyl chloride, and the like; neat or in a suitably selected solvent such as DCM, and the like; to yield the corresponding compound of formula (XXIII).

The compound of formula (XXIII) is reacted with a suitably substituted compound of formula (XXIV), a known compound or compound prepared by known methods; in the presence of a suitably selected base such as $Cs_2CO_3$, $K_2CO_3$, $Na_2CO_3$, and the like; in a suitably selected solvent such as DMF, acetonitrile, DCM, THF, and the like; to yield the corresponding compound of formula (Ih).

Alternatively, the compound of formula (XXIII) is reacted with a suitably substituted compound of formula (XXV), wherein $L^1$ is selected from the group consisting of

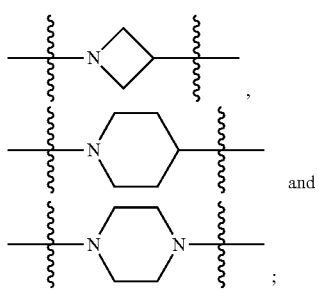

, a known compound or compound prepared by known methods, in the presence of a suitably selected organic base such as TEA, DIPEA, DBU, and the like; in a suitably selected solvent such as acetonitrile, DMF, and the like; to yield the corresponding compound of formula (Ij).

One skilled in the art will further recognize that the compound of formula (XXII) may alternatively be reacted with a suitably substituted compound of formula (XXIV) directly; under Mitsunobu conditions (for example in the presence of a mixture of DEAD and PPh$_3$, in THF); to yield the corresponding compound of formula (Ih).

Compounds of formula (I) wherein R$^0$ is

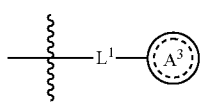

and wherein L$^1$ is selected from the group consisting of —O—,

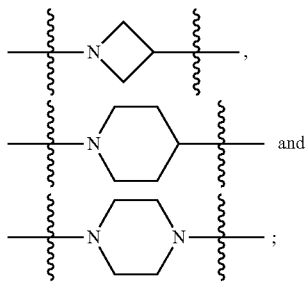

and wherein

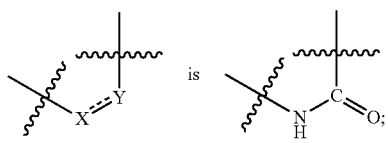

may be prepared from the corresponding compound of formula (Ij) or compound of formula (Ih) (prepared as described in Scheme (I-6) above) by reacting under acid hydrolysis conditions; more particularly, reacting with a suitably selected acid such as TFA, HCl, aqueous phosphoric acid, and the like; in a suitably selected solvent such as DCM, methanol, toluene, and the like.

One skilled in the art will further recognize that the compound of formula (Ih) and/or the compound of formula (Ij) (or the corresponding quinolone compounds) may be further, optionally substituted with desired R$^1$, R$^2$ and/or R$^4$ substituent groups, according to the procedures as described herein.

One skilled in the art will further recognize that compounds of formula (I) wherein R$^0$ is

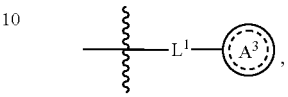

wherein

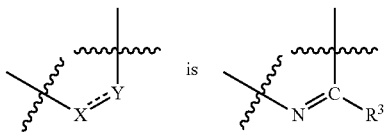

and wherein R$^3$ is hydrogen may be prepared by selecting a suitably substituted compound of formula (INT-6)

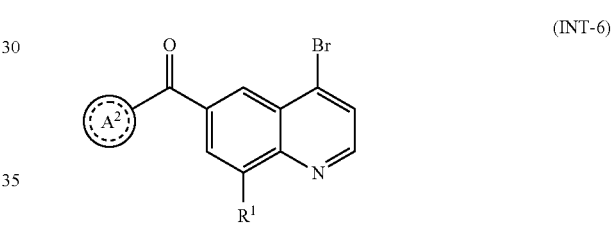

(INT-6)

prepared for example as described in Scheme which follows herein, and substituting said compound of formula (INT-6) for the compound of formula (INT-3) in Scheme (I-5) or Scheme (I-6) and reacting as described therein.

Additional substitutions and/or substituent transformations to yield the desired compound(s) of formula (I) may be effected according to the procedures as described herein (in the general synthesis schemes and examples) or according to methods known to those skilled in the art.

One skilled in the art will further recognize that compounds of formula (I) wherein R$^1$ is selected from the group consisting of —O—(C$_{1-4}$alkyl)-CO$_2$H, —O—(C$_{1-4}$alkyl)-C(O)O—(C$_{1-4}$alkyl), —O—(C$_{2-4}$alkyl)-NH$_2$, —O—(C$_{1-4}$alkyl)-C(O)—NH$_2$, —O(C$_{2-4}$alkyl)-NH—C(O)—(C$_{1-2}$alkyl) may be prepared from a suitably protected precursor to the compound of formula (I), for example, a suitably substituted compound of formula (XVIII), wherein R$^1$ is OH, by reacting with a suitably substituted compound of formula LG$^x$-(C$_{1-4}$alkyl)-CO$_2$(C$_{1-4}$alkyl), LG$^x$-(C$_{2-4}$alkyl)-NH—C(O)O—C(CH$_3$)$_3$), or LG$^x$-(C$_{2-4}$alkyl)-NPhth, wherein LG$^x$ is a suitably selected leaving group such as Br, Cl, I, mesylate, tosylate, and the like, a known compound or compound prepared by known methods; according to known methods (for example in the presence of a suitably selected base such as Cs$_2$CO$_3$, K$_2$CO$_3$, and the like; in a suitably selected solvent such as acetonitrile, DMF, THF, and the like), followed by appropriate functional group manipulations known to those skilled in the art, to yield the corresponding compound of formula (I).

One skilled in the art will further recognize that compounds of formula (I) wherein R¹ is selected from the group consisting of —(C$_{1-4}$alkyl)-O—(C$_{1-2}$alkyl), —(C$_{3-4}$alkenyl)-O—(C$_{1-2}$alkyl), —(C$_{3-4}$alkenyl)-OH, —C$_{1-4}$alkyl, —O—(C$_{1-4}$alkyl) may be prepared from a suitably protected precursor to the compound of formula (I), for example, a suitably substituted compound of formula (XVI) or a compound of formula (XVIII), wherein R¹ is Br, by reacting with a suitably substituted alkene, a known compound or compound prepared by known methods; according to known methods (for example in the presence of a suitably selected catalyst such as Pd(OAc)$_2$; in the presence of a suitably selected ligand such as P(o-tol)$_3$; in the presence of a suitably selected base such as DIEA; in a suitably selected solvent such as DMF), followed by appropriate functional group manipulations known to those skilled in the art, to yield the corresponding compound of formula (I).

Alternatively, compounds of formula (I) wherein R¹ is selected from the group consisting of —(C$_{1-4}$alkyl)-O—(C$_{1-2}$alkyl), —(C$_{3-4}$alkenyl)-O—(C$_{1-2}$alkyl), —(C$_{3-4}$alkenyl)-OH, —C$_{1-4}$alkyl, —O—(C$_{1-4}$alkyl) may be prepared from a suitably protected precursor to the compound of formula (I), for example, a suitably substituted compound of formula (XVI) or compound of formula (XVIII), wherein R¹ is Br, by reacting with a suitably substituted vinylboronate derivative, a known compound or compound prepared by known methods; according to known methods (for example in the presence of a suitably selected catalyst such as Pd(dppf)Cl$_2$; in the presence of a suitably selected base such as Cs$_2$CO$_3$, K$_2$CO$_3$, and the like; in a suitably selected solvent such as 1,4-dioxane, water, and the like), followed by appropriate functional group manipulations known to those skilled in the art, to yield the corresponding compound of formula (I).

Compounds of formula (II) wherein

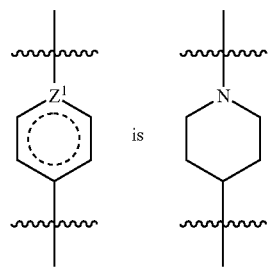

is and wherein

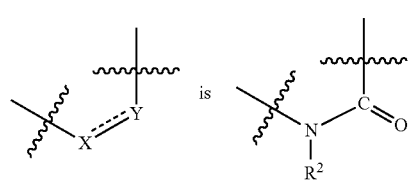

is may be prepared according to the process outlined in Scheme (II-1), below.

Scheme (II-1)

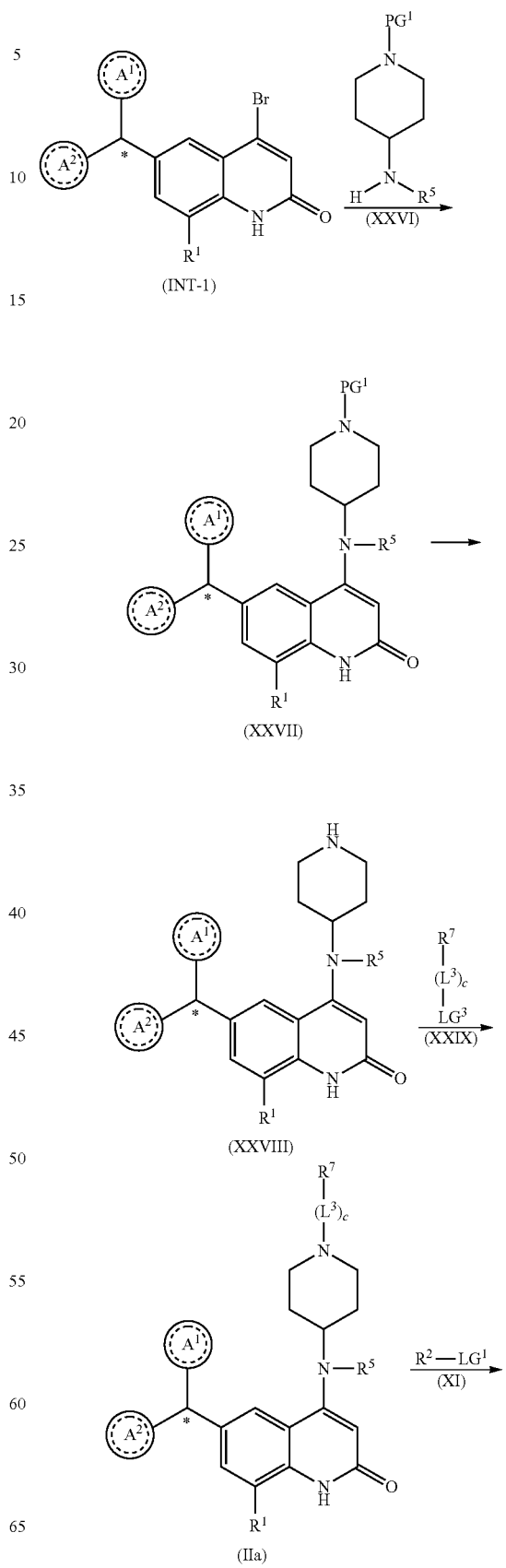

-continued

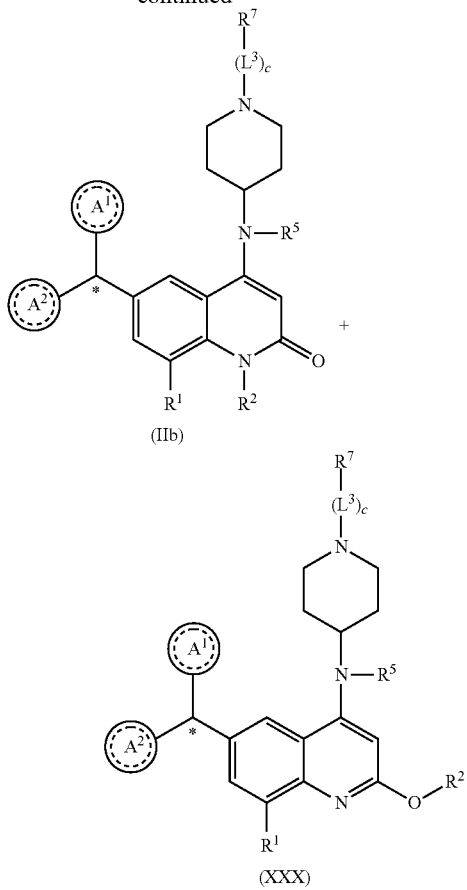

Accordingly, a suitably substituted compound of formula (INT-1), a known compound or compound prepared for example as described in Scheme A, which follows herein, is reacted with a suitably substituted compound of formula (XXVI), wherein $PG^1$ is a suitably selected nitrogen protecting group such as Boc, Cbz, ethoxy-carbonyl-, and the like, a known compound or compound prepared by known methods; in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (XXVII).

The compound of formula (XXVII) is de-protected according to known methods, to yield the corresponding compound of formula (XXVIII). For example, wherein $PG^1$ is Boc, the compound of formula (XXVII) is de-protected by reacting with a suitably selected acid such as HCl, TFA, and the like; alternatively, wherein $PG^1$ is ethoxy-carbonyl, the compound of formula (XXVII) is de-protected by reacting with HBr in a suitably selected solvent such as water, acetic acid, and the like.

The compound of formula (XXVIII) is reacted with a suitably selected compound of formula (XXIX), to yield the corresponding compound of formula (IIa).

In an example, the compound of formula (XXVIII) is reacted with a suitably substituted compound of formula (XXIX) wherein $L^3$ is selected from the group consisting of —$CH_2$—, —$CH(CH_3)$— and —$CH(CH_2CH_3)$—, and wherein $LG^3$ is a suitably selected leaving group such as Cl, Br, I, tosylate, mesylate, and the like; in the presence of a suitably selected base such as TEA, Hunig's base, $Na_2CO_3$, and the like; in a suitably selected solvent such as DMF, acetonitrile, DCM, and the like; to yield the corresponding compound of formula (IIa) wherein $L^3$ is the corresponding —$CH_2$—, —$CH(CH_3)$— or —$CH(CH_2CH_3)$—.

One skilled in the art will recognize that the compound of formula (IIa) wherein $L^3$ is selected from the group consisting of —$CH_2$—, —$CH(CH_3)$— and —$CH(CH_2CH_3)$— may alternatively be prepared by reacting the compound of formula (XXVIII) with a compound of the formula $R^7$—C (O)H or compound of formula $R^7$—C(O)—$CH_3$ or compound of formula $R^7$—C(O)—$CH_2CH_3$; in the presence of a suitably selected reducing agent such as $NaCNBH_3$, sodium triacetoxyborohydride, and the like; in a suitably selected organic solvent such as DCE, methanol, ethanol, and the like; to yield the corresponding compound of formula (IIa) wherein $L^3$ is the corresponding —$CH_2$—, —$CH(CH_3)$— or —$CH(CH_2CH_3)$—.

In another example, the compound of formula (XXVIII) is reacted with a suitably substituted compound of formula (XXIX) wherein $L^3$ is —C(O)— or —$SO_2$— and wherein $LG^3$ is for example, Cl; in the presence of a suitably selected tertiary organic base such as TEA, Hunig's base, and the like; in a suitably selected solvent such as DCM, THF, and the like; to yield the corresponding compound of formula (IIa) wherein $L^3$ is the corresponding —C(O)— or —$SO_2$—.

Preferably, wherein $R^7$-$L^3$ is $CF_3$—$SO_2$—, the compound of formula (XXVIII) is reacted with triflic anhydride, a known compound, in the presence of TEA, in methylene chloride; to yield the corresponding compound of formula (IIa) wherein $L^3$ is —$SO_2$—.

In another example, the compound of formula (XXVIII) is reacted with a suitably substituted compound of formula (XXIX) wherein $L^3$ is —C(O)— and wherein $LG^3$ is —OH; in the presence of a suitably selected peptide coupling agent such as DCC, HATU, HBTU, EDCI, and the like; optionally in the presence of a suitably selected base such as Hunig's base, TEA, and the like; in a suitably selected solvent such as DMF, DCM, and the like; to yield the corresponding compound of formula (IIa) wherein $L^3$ is —C(O)—.

In another example, wherein $L^3$ is absent (c is 0) and $R^7$ is selected from the group consisting of phenyl, pyrid-2-yl, pyrid-3-yl, pyrid-4-yl, thien-2-yl, thein-3-yl, furan-2-yl, furan-3-yl, pyrimidin-2-yl and pyrazin-2-yl; the compound of formula (XXVIII) is reacted with a suitably substituted compound of formula (XXIX) wherein $L^3$ is absent (i.e. c is 0) and wherein $LG^3$ is suitably selected group such as Cl, Br, I, triflate, and the like; in the presence of a suitably selected catalyst such as $Pd_2(dba)_3$, $Pd(OAc)_2$, and the like; in the presence of a suitably selected ligand such as BINAP, dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (IIa) wherein $L^3$ is absent (i.e. c is 0).

In another example, wherein $L^3$ is absent (c is 0) and $R^7$ is selected from the group consisting of cyclopropyl, cyclobutyl, cyclopentyl and cyclohexyl; the compound of formula (XXVIII) is reacted with a suitably substituted compound of formula (XXIX), wherein $L^3$ is absent (i.e. c is 0) and wherein $LG^3$ is suitably selected group such as Cl, Br, I, mesylate, tosylate, and the like; in the presence of a suitably selected base such as TEA, Hunig's base, $Na_2CO_3$, and the like; in a suitably selected solvent such as DMF, acetonitrile, DCM, and the like; to yield the corresponding compound of formula (IIa) wherein $L^3$ is absent (i.e. c is 0).

Alternatively, wherein $L^3$ is absent (c is 0) and $R^7$ is selected from the group consisting of cyclopropyl, cyclobutyl, cyclopentyl and cyclohexyl; the compound of formula (XXVIII) is reacted with cyclobutanone, cyclopentanone or cyclohexanone, respectively; in the presence of a suitably selected reducing agent such as $NaCNBH_3$, sodium triacetoxyborohydride, and the like; in a suitably selected organic solvent such as DCE, methanol, ethanol, and the like; to yield the corresponding compound of formula (IIa) wherein $L^3$ is absent (i.e. c is 0).

The compound of formula (IIa) is further, optionally, reacted with a suitably substituted compound of formula (XI), wherein $LG^1$ is a suitably selected leaving group such as Cl, Br, I, tosylate, mesylate, and the like; in the presence of a suitably selected base such as $Cs_2CO_3$, $K_2CO_3$, NaH, and the like; in a suitably selected organic solvent such as acetonitrile, DMF, THF, and the like; to yield the corresponding compound of formula (IIb), in a mixture with the corresponding compound of formula (XXX).

Compounds of formula (II) wherein

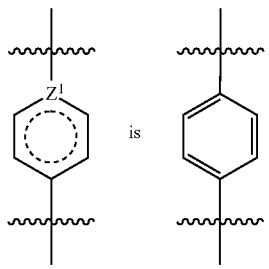

and wherein

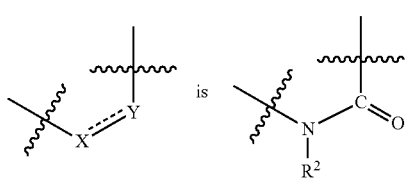

and may be prepared according to the process outlined in Scheme (II-2), below.

Scheme (II-2)

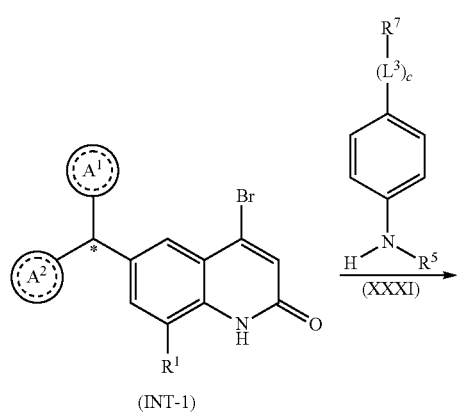

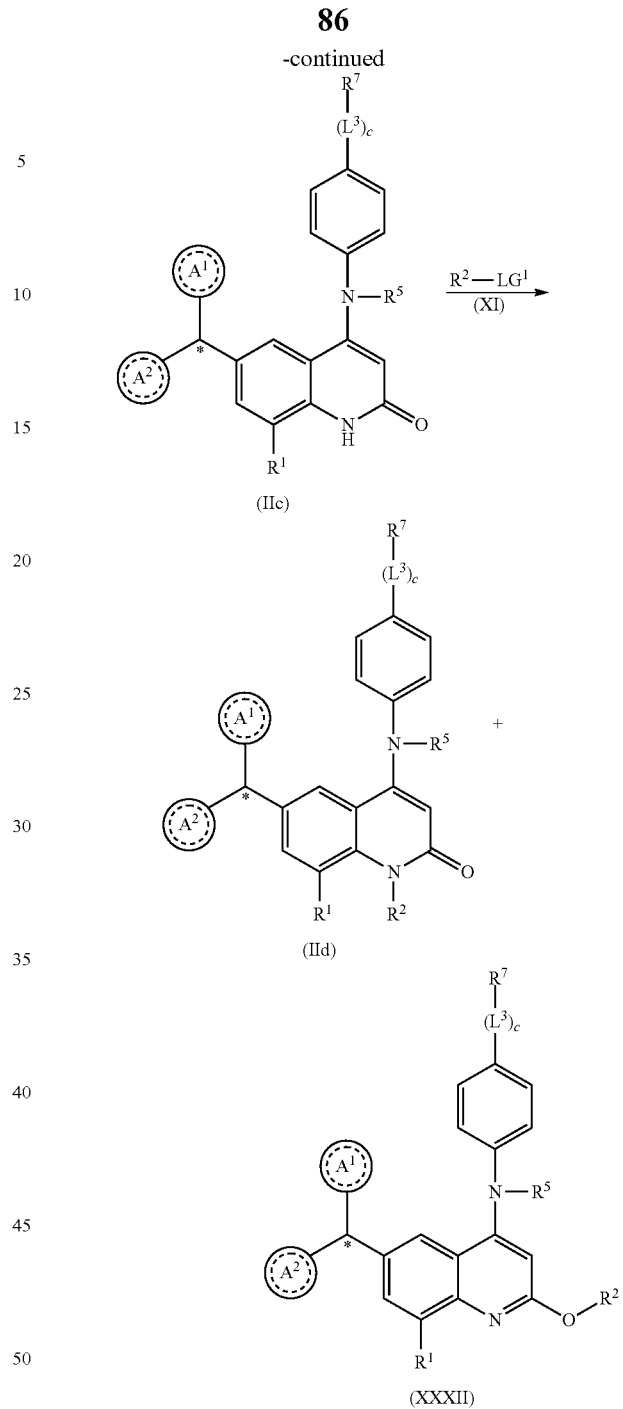

Accordingly, a suitably substituted compound of formula (INT-1), a known compound or compound prepared for example as described in Scheme A, which follows herein, is reacted with a suitably substituted compound of formula (XXXI), a known compound or compound prepared by known methods; in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (IIc).

One skilled in the art will recognize that the compound of formula (IIc) may be further, optionally reacted with a suitably substituted compound of formula (XI), as described in Scheme (II-1) above (i.e. by substituting the compound of formula (IIc) for the compound of formula (IIa) in Scheme (II-1) above), to yield the corresponding compound of formula (IId), in a mixture with the corresponding compound of formula (XXXII).

One skilled in the art will further recognize that compounds of formula (II) wherein

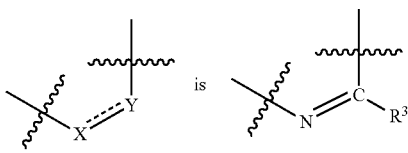

is and wherein R³ is hydrogen may be similarly prepared according to the processes outlined in Scheme (II-1) and Scheme (II-2) above, by selecting a suitably substituted compound of formula (INT-4)

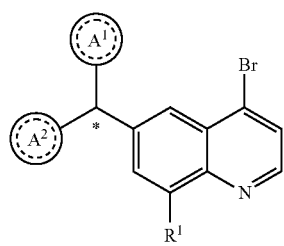

(INT-4)

a compound prepared for example, as described in Scheme C, which follows herein, and substituting said compound of formula (INT-4) for the compound of formula (INT-1) in Scheme (II-1) or Scheme (II-2) above, and reacting as described therein.

Compounds of formula (II) wherein

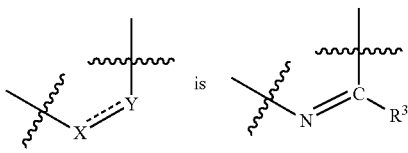

is and wherein R³ is —OR⁴, may be prepared according to the process described in Scheme (II-3) below.

Scheme (II-3)

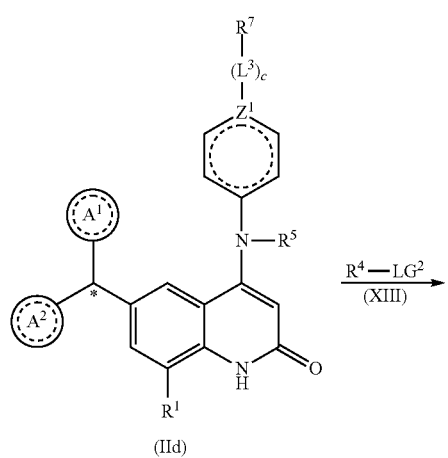

(IId)

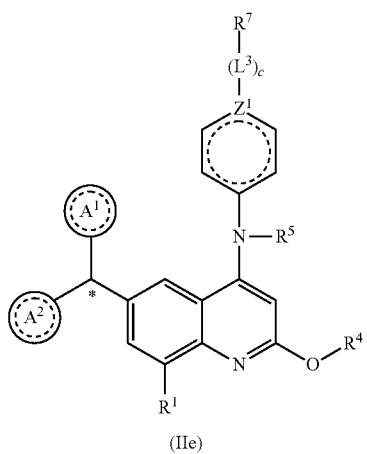

(IIe)

+

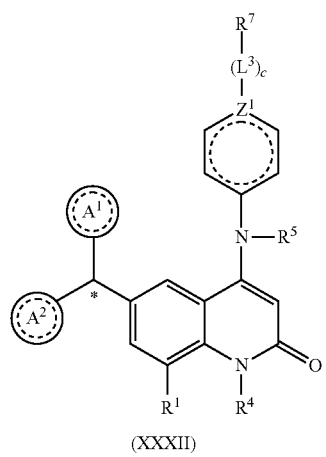

(XXXII)

Accordingly, a suitably substituted compound of formula (IId) wherein R¹ is other than hydroxy, prepared for example as described in Scheme (II-1) or Scheme (II-2) above, is reacted with a suitably substituted compound of formula (XIII), wherein LG² is a suitably selected leaving group such as Br, Cl, I, mesylate, tosylate, and the like, a known compound or compound prepared by known methods; according to known methods (for example in the presence of a suitably selected base such as $Cs_2CO_3$, $K_2CO_3$, and the like; in a suitably selected solvent such as acetonitrile, DMF, THF, and the like), to yield the corresponding compound of formula (IIe), in a mixture with the corresponding compound of formula (XXXII).

Compounds of formula (II) wherein

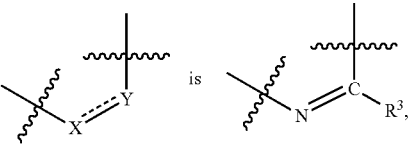

is wherein R³ is hydrogen, and wherein R¹ is selected from the group consisting of $NR^E R^F$ may be prepared by selecting a suitably substituted compound of formula (IIf)

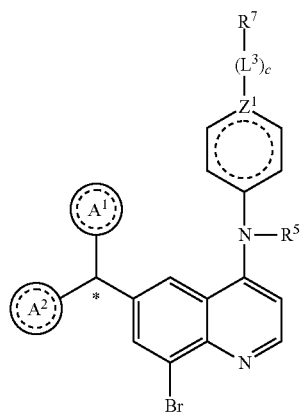

(IIf)

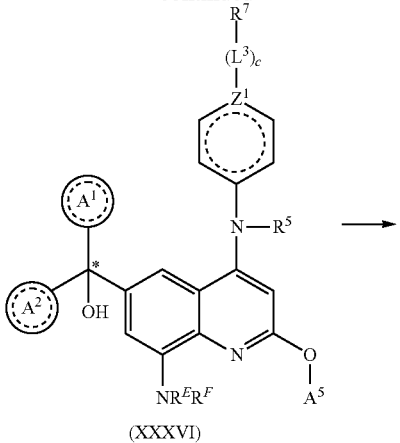

(XXXVI)

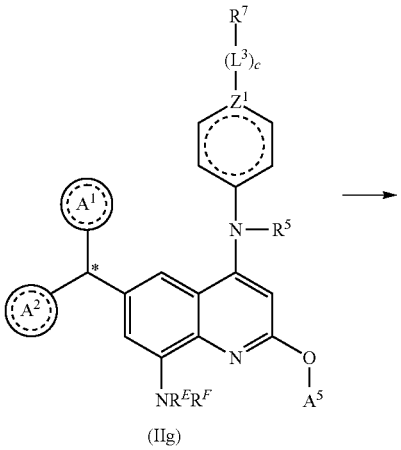

(IIg)

prepared for example as described in Scheme (II-1) or Scheme (II-2) above; substituting said compound of formula (IIf) for the compound of formula (Id) in Scheme (I-3) above, and reacting with a suitably substituted compound of formula (XV), as described therein.

Compounds of formula (II) wherein

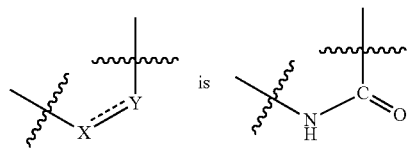

and wherein $R^1$ is selected from the group consisting of $NR^ER^F$ are preferably prepared according to the procedure as described in Scheme (II-4), below.

Scheme (II-4)

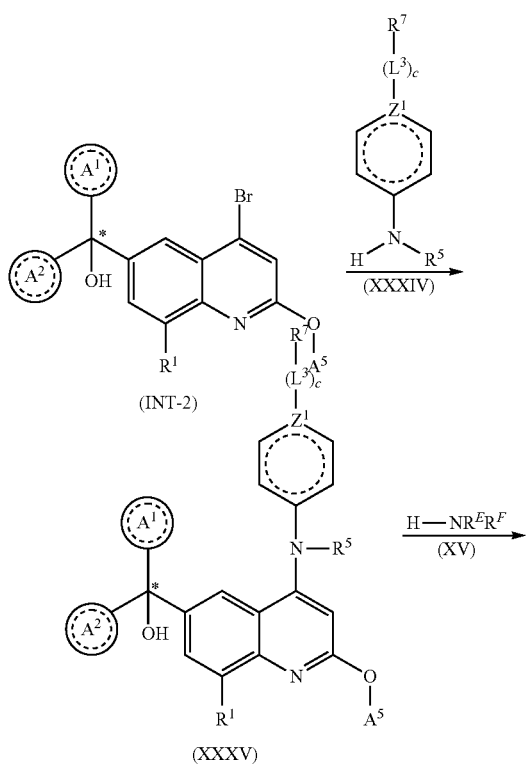

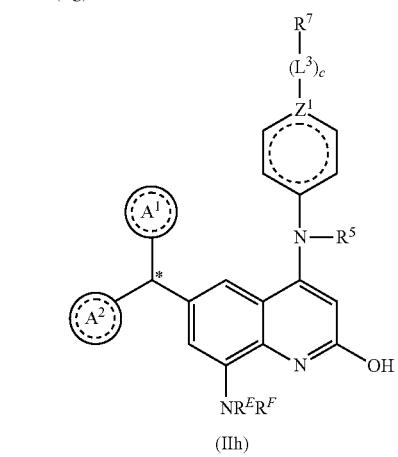

(IIh)

Accordingly, a suitably substituted compound of formula (INT-2) wherein $R^1$ is Br, and wherein $A^5$ is selected from the group consisting of $C_{1-4}$alkyl, preferably methyl or t-butyl, prepared for example as described in Scheme B, which follows herein, is reacted with a suitably substituted compound of formula (XXXIV), a known compound or compound prepared by known methods; in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (XXXV).

The compound of formula (XXXV) is reacted with a suitably substituted compound of formula (XV), a known compound or compound prepared by known methods; in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XXXVI). Preferably, the compound of formula (XXXV) is reacted with the compound of formula (XV) in the presence of $Pd_2(dba)_3$ in combination with XantPhos; to yield the corresponding compound of formula (XXXVI).

The compound of formula (XXXVI) is reacted with $Et_3SiH$ in combination with TFA or $SnCl_2$ in combination with HCl or $TiCl_4$ in combination with $Et_3SiH$; in a suitably selected organic solvent such as DCM, DCE, and the like; to yield the corresponding compound of formula (IIg).

The compound of formula (IIg) is reacted under acid hydrolysis conditions, for example with a suitably selected acid such as HCl, TFA, aqueous phosphoric acid, and the like; in a suitably selected organic solvent such as DCM, methanol, toluene, and the like; to yield the corresponding compound of formula (IIh).

One skilled in the art will further recognize that compounds of formula (II) wherein $R^1$ is selected from the group consisting of —O—($C_{1-4}$alkyl)-$CO_2H$, —O—($C_{1-4}$alkyl)-C(O)O—($C_{1-4}$alkyl), —O—($C_{1-4}$alkyl)-$NH_2$, —O—($C_{1-4}$alkyl)-C(O)—$NH_2$, —O($C_{1-4}$alkyl)-NH—C(O)—($C_{1-2}$alkyl) may be prepared from a suitably protected precursor to the compound of formula (II), for example, a suitably substituted compound of formula (XXXV), wherein $R^1$ is OH, by reacting with a suitably substituted compound of formula $LG^x$-($C_{1-4}$alkyl)-$CO_2$($C_{1-4}$alkyl), $LG^x$-($C_{2-4}$alkyl)-NH—C(O)O—C($CH_3$)$_3$), or $LG^x$-($C_{2-4}$alkyl)-NPhth wherein $LG^x$ is a suitably selected leaving group such as Br, Cl, I, mesylate, tosylate, and the like, a known compound or compound prepared by known methods; according to known methods (for example in the presence of a suitably selected base such as $Cs_2CO_3$, $K_2CO_3$, and the like; in a suitably selected solvent such as acetonitrile, DMF, THF, and the like), followed by appropriate functional group manipulations known to those skilled in the art, to yield the corresponding compound of formula (II).

One skilled in the art will further recognize that compounds of formula (II) wherein $R^1$ is selected from the group consisting of —($C_{1-4}$alkyl)-O—($C_{1-2}$alkyl), —($C_{3-4}$alkenyl)-O—($C_{1-2}$alkyl), —($C_{3-4}$alkenyl)-OH, —$C_{1-4}$alkyl, —O—($C_{1-4}$alkyl) may be prepared from a suitably protected precursor to the compound of formula (II), for example, a suitably substituted compound of formula (XXXV), wherein $R^1$ is Br, by reacting with a suitably substituted alkene, a known compound or compound prepared by known methods; according to known methods (for example in the presence of a suitably selected catalyst such as $Pd(OAc)_2$; in the presence of a suitably selected ligand such as P(o-tol)$_3$; in the presence of a suitably selected base such as DIEA; in a suitably selected solvent such as DMF), followed by appropriate functional group manipulations known to those skilled in the art, to yield the corresponding compound of formula (II).

Alternatively, compounds of formula (II) wherein $R^1$ is selected from the group consisting of —($C_{1-4}$alkyl)-O—($C_{1-2}$ alkyl), —($C_{3-4}$alkenyl)-O—($C_{1-2}$alkyl), —($C_{3-4}$alkenyl)-OH, —$C_{1-4}$alkyl, —O—($C_{1-4}$alkyl) may be prepared from a suitably protected precursor to the compound of formula (II), for example, a suitably substituted compound of formula (XXXV), wherein $R^1$ is Br, by reacting with a suitably substituted vinylboronate derivative, a known compound or compound prepared by known methods; according to known methods (for example in the presence of a suitably selected catalyst such as $Pd(dppf)Cl_2$; in the presence of a suitably selected base such as $Cs_2CO_3$, $K_2CO_3$, and the like; in a suitably selected solvent such as 1,4-dioxane, water, and the like), followed by appropriate functional group manipulations known to those skilled in the art, to yield the corresponding compound of formula (II).

Compounds of formula (III) wherein

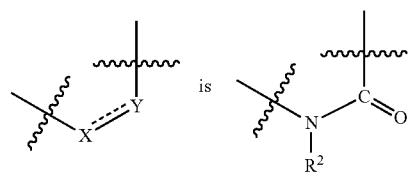

is and wherein $L^4$ is —CH=CH— may be prepared according to the procedure as outlined in Scheme (III-1), below.

Scheme (III-1)

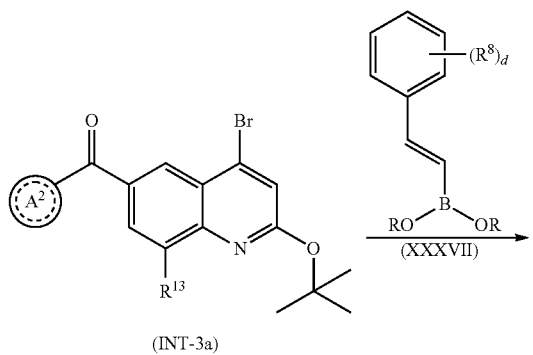

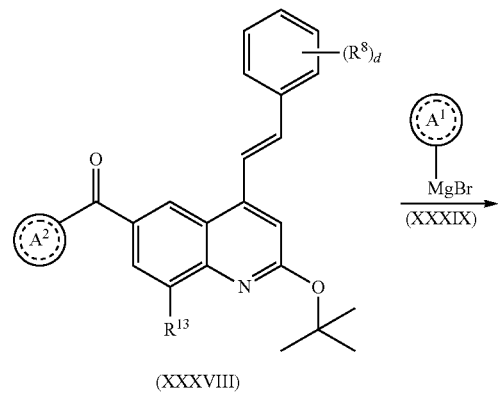

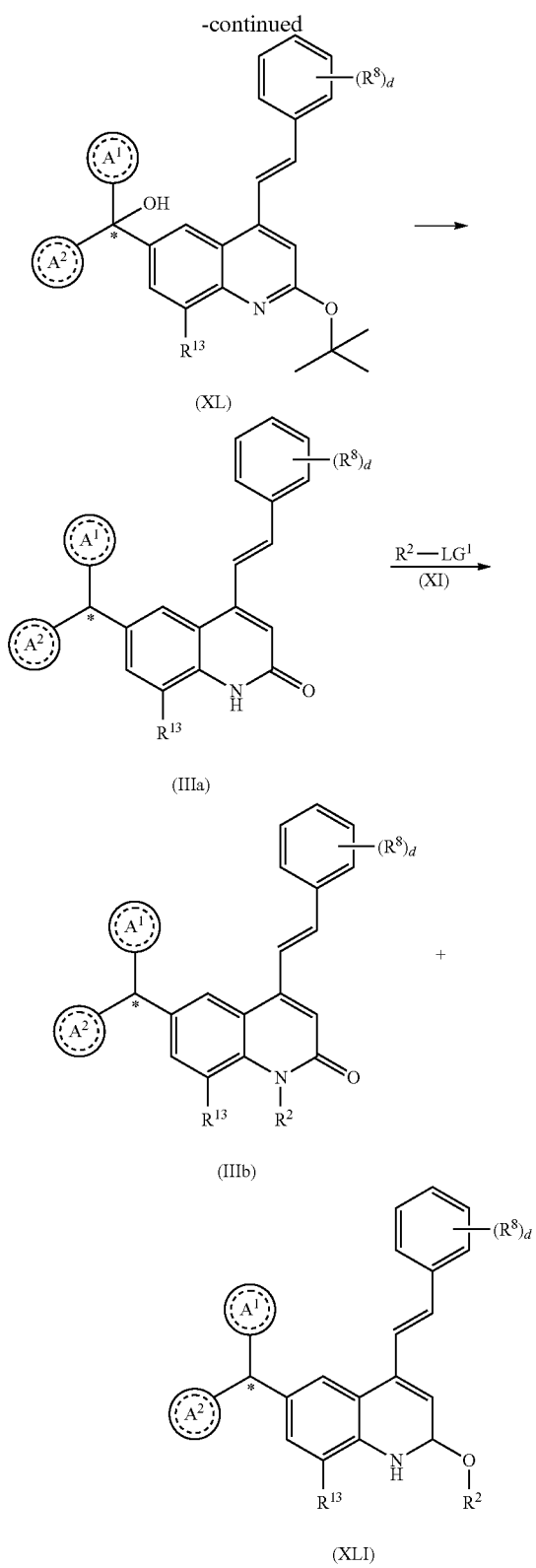

(XL)

(IIIa)

(IIIb)

(XLI)

Accordingly, a suitably substituted compound of formula (INT-3a) (a compound of formula (INT-3) wherein $R^1$ is selected from the group consisting of hydrogen and —O—$C_{1-4}$alkyl), prepared for example as described in Scheme A, is reacted with a suitably substituted compound of formula (XXXVII) (i.e. a suitably selected boronic acid or boronic ester), a known compound or compound prepared by known methods, to yield the corresponding compound of formula (XXXVIII).

In an example, the compound of formula (INT-3a) is reacted with the compound of formula (XXXVII), wherein both R groups are the same and are hydrogen (i.e. a suitably selected boronic acid); in the presence of a suitably selected catalyst such as Pd(OAc)$_2$, Pd(PPh$_3$)$_4$, Pd$_2$(dba)$_3$.CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XXXVIII).

In another example, the compound of formula (INT-3a) is reacted with a suitably substituted compound of formula (XXXVII) wherein both R groups are the same and are $C_{1-2}$alkyl, or are taken together with the oxygen atoms to which they are bound to form

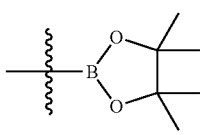

(i.e. a suitably selected boronic ester); in the presence of a suitably selected catalyst such as Pd(OAc)$_2$, Pd(PPh$_3$)$_4$, Pd$_2$(dba)$_3$.CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XXXVIII).

The compound of formula (XXXVIII) is reacted with a suitably substituted compound of formula (XXXIX), a known compound or compound prepared by known methods, under Grignard conditions (i.e. in a suitably selected anhydrous solvent such as diethyl ether, THF, and the like), to yield the corresponding compound of formula (XL).

The compound of formula (XL) is reacted with Et$_3$SiH in combination with TFA or SnCl$_2$ in combination with HCl or TiCl$_4$ in combination with Et$_3$SiH; in a suitably selected organic solvent such as DCM, DCE, and the like; to yield the corresponding compound of formula (IIIa).

The compound of formula (IIIa) is further, optionally, reacted with a suitably substituted compound of formula (XI), wherein $LG^1$ is a suitably selected leaving group such as Cl, Br, I, tosylate, mesylate, and the like; in the presence of a suitably selected base such as Cs$_2$CO$_3$, K$_2$CO$_3$, NaH, and the like; in a suitably selected organic solvent such as acetonitrile, DMF, THF, and the like; to yield the corresponding compound of formula (IIIb), in a mixture with the corresponding compound of formula (XLI).

One skilled in the art will recognize that compounds of formula (III) wherein

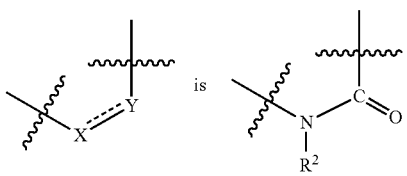

is and wherein L⁴ is —CH=CH— may alternatively be prepared by reacting a suitably substituted compound of formula (INT-1a)

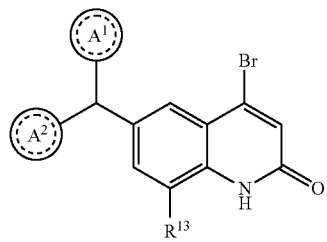

(INT-1a)

(a compound of formula (INT-1) wherein $R^1$ is selected from the group consisting of hydrogen and —O—$C_{1-4}$alkyl (i.e. wherein $R^1$ is limited to the subset of substituents as in $R^{13}$)), prepared for example as describe in Scheme A which follows herein, with a suitably substituted compound of formula (XXXVII), as described in Scheme (III-1) above; to yield the corresponding compound of formula (III) wherein

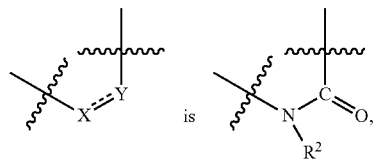

wherein $R^2$ is hydrogen and wherein L⁴ is —H=CH=CH—; and then further, optionally reacted with a suitably substituted compound of formula (XI), as described in Scheme (III-1) above.

Compounds of formula (III) wherein

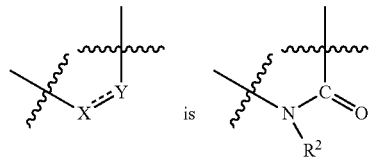

and wherein L⁴ is —$CH_2$— may be prepared according to the procedure as outlined in Scheme (III-2), below.

Scheme (III-2)

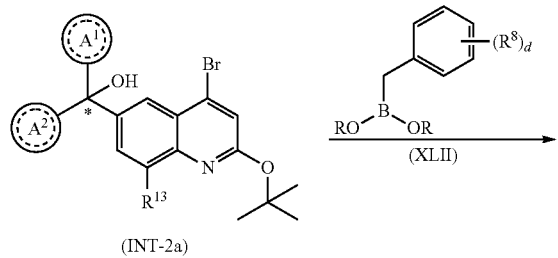

Accordingly, a suitably substituted compound of formula (INT-2a), (a compound of formula (INT-2) wherein $R^1$ is selected from the group consisting of hydrogen and —O—$C_{1-4}$alkyl (i.e. wherein $R^1$ is limited to the subset of substituents as in $R^{13}$)), prepared for example as described in Scheme B above, is reacted with a suitably substituted compound of formula (XLII), to yield the corresponding compound of formula (XLIII).

In an example, the compound of formula (INT-2a) is reacted with the compound of formula (XLII), wherein both R groups are the same and are hydrogen (i.e. a suitably selected boronic acid); in the presence of a suitably selected coupling agent such as Pd(OAc)$_2$, Pd(PPh$_3$)$_4$, Pd$_2$(dba)$_3$·CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XLIII).

In another example, the compound of formula (INT-2a) is reacted with a suitably substituted compound of formula (XLII) wherein both R groups are the same and are $C_{1-2}$alkyl, or are taken together with the oxygen atoms to which they are bound to form

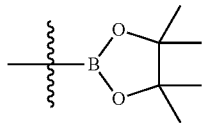 [SMILES: *B1OC(C)(C)C(C)(C)O1]

(i.e. a suitably selected boronic ester); in the presence of a suitably selected catalyst such as $Pd(OAc)_2$, $Pd(PPh_3)_4$, $Pd_2(dba)_3 \cdot CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XLIII).

The compound of formula (XLIII) is reacted with $Et_3SiH$ in combination with TFA or $SnCl_2$ in combination with HCl or $TiCl_4$ in combination with $Et_3SiH$; in a suitably selected organic solvent such as DCM, DCE, and the like; to yield the corresponding compound of formula (IIIc).

One skilled in the art will recognize that the compound of formula (IIIc) may be substituted for the compound of formula (IIIa) in Scheme (II-1), above and then reacted with a suitably substituted compound of formula (XI), wherein $LG^1$ is a suitably selected leaving group such as Cl, Br, I, tosylate, mesylate, and the like; as described therein (in the presence of a suitably selected base such as $Cs_2CO_3$, $K_2CO_3$, NaH, and the like; in a suitably selected organic solvent such as acetonitrile, DMF, THF, and the like); to yield the corresponding compound of formula (IIId), in a mixture with the corresponding compound of formula (XLIV).

Compounds of formula (III) wherein

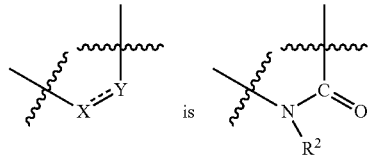

and wherein $L^4$ is $-CH_2CH_2-$ may be prepared according to the procedure as outlined in Scheme (III-3), below.

Scheme (III-3)

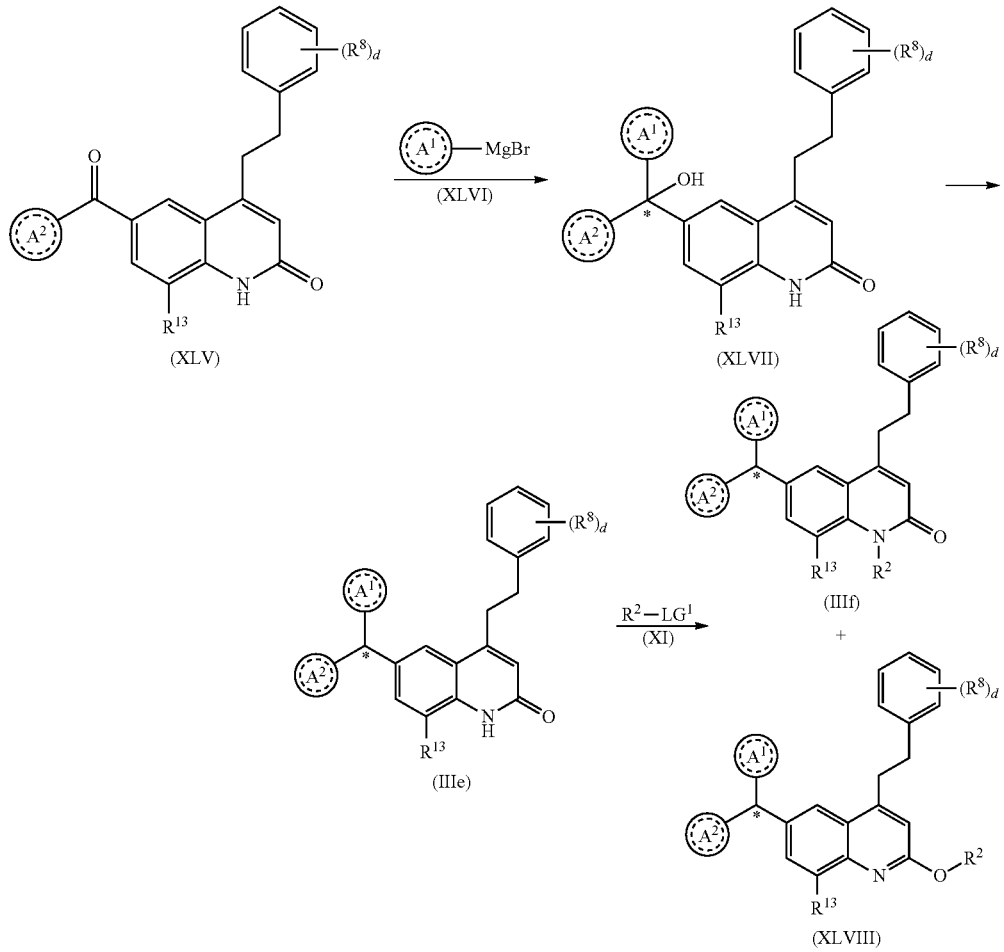

Accordingly, a suitably substituted compound of formula (XLV), a known compound or compound prepared by known methods (e.g. ANGIBAUD, P. R., et al., PCT Publication WO2002/051835 A1, published 4 Jul., 2002), is reacted with a suitably substituted compound of formula (XLVI), a known compound or compound prepared by known methods, under Grignard conditions; to yield the corresponding compound of formula (XLVII).

The compound of formula (XLVII) is reacted with $Et_3SiH$ in combination with TFA or $SnCl_2$ in combination with HCl or $TiCl_4$ in combination with $Et_3SiH$; in a suitably selected organic solvent such as DCM, DCE, and the like; to yield the corresponding compound of formula (IIIe).

The compound of formula (IIIe) is further optionally reacted with a suitably substituted compound of formula (XI), wherein $LG^1$ is a suitably selected leaving group such as Cl, Br, I, tosylate, mesylate, and the like; as described therein (in the presence of a suitably selected base such as $Cs_2CO_3$, $K_2CO_3$, NaH, and the like; in a suitably selected organic solvent such as acetonitrile, DMF, THF, and the like); to yield the corresponding compound of formula (IIIf), in a mixture with the corresponding compound of formula (XLVIII).

Compounds of formula (III) wherein

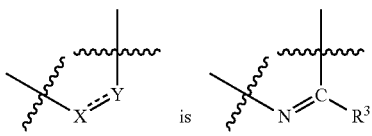

wherein $R^3$ is —$OR^4$ may be prepared according to the process outlined in Scheme (III-4), below.

Scheme (III-4)

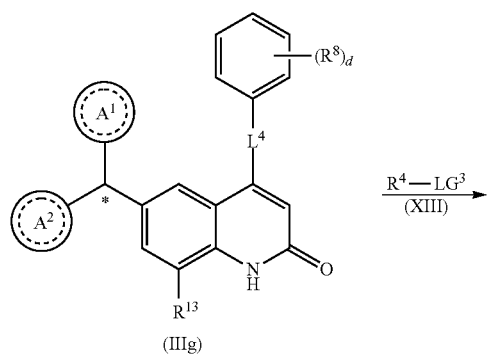

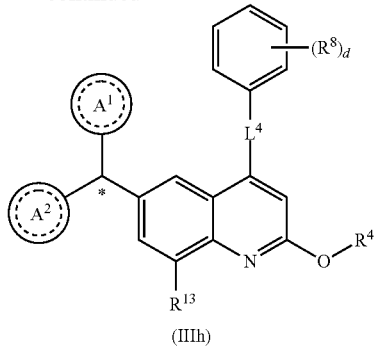

+

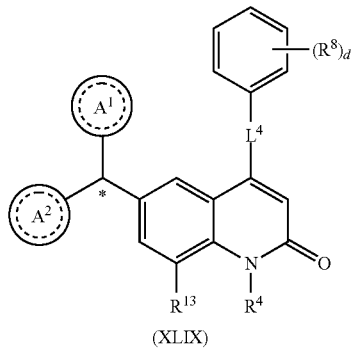

Accordingly, a suitably substituted compound of formula (IIIg), prepared for example as described in Scheme (III-1), Scheme (III-2) or Scheme (III-3) above, is reacted with a suitably substituted compound of formula (XIII), wherein $LG^2$ is a suitably selected leaving group such as Br, Cl, I, mesylate, tosylate, and the like, a known compound or compound prepared by known methods; according to known methods (for example in the presence of a suitably selected base such as $Cs_2CO_3$, $K_2CO_3$, and the like; in a suitably selected solvent such as acetonitrile, DMF, THF, and the like), to yield the corresponding compound of formula (IIIh), in a mixture with the corresponding compound of formula (XLIX).

Compounds of formula (III) wherein

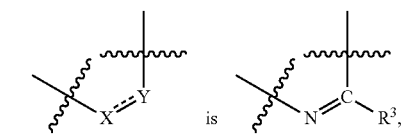

wherein $R^3$ is hydrogen and $L^4$ is —CH=CH— may be similarly prepared according to the procedures as described above, by selecting and substituting a suitably substituted compound of formula (INT-6a)

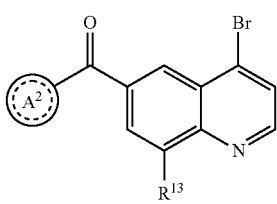

(a compound of formula (INT-6) wherein $R^1$ is selected from the group consisting of hydrogen and —O—$C_{1-4}$alkyl (i.e. wherein $R^1$ is limited to the subset of substituents as in $R^{13}$)), for the compound of formula (INT-3a), in Scheme (II-1) and reacting as therein described.

Compounds of formula (III), wherein

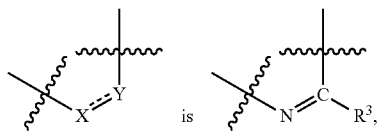

is and wherein $R^3$ is hydrogen and wherein $L^4$ is —$CH_2CH_2$— may be similarly prepared according to the procedures as described above, by selecting and substituting a suitably substituted compound of formula (LX)

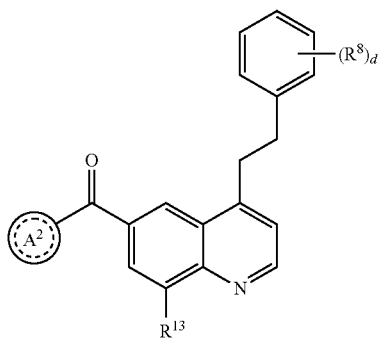

(LX)

a compound prepared for example, as described in ANGIBAUD, P. R., et al., PCT Publication WO2002/051835 A1, published 4 Jul., 2002, and reacting as described in Scheme (III-3), above.

Compounds of formula (III) wherein

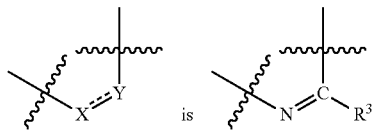

is and wherein $R^3$ is hydrogen and wherein $L^4$ is —$CH_2$— may be similarly prepared according to the procedures as described above, by selecting and substituting a suitably substituted compound of formula (INT-5a)

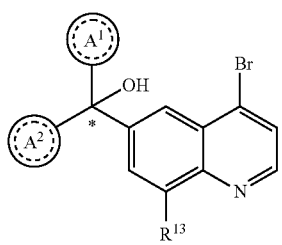

(INT-5a)

(a compound of formula (INT-5a) wherein R is selected from the group consisting of hydrogen and —O—$C_{1-4}$ alkyl), prepared for example as described in Scheme C, for the compound of formula (INT-2a), in Scheme (III-2), and reacting as therein described.

Compounds of formula (IV) wherein

is and wherein

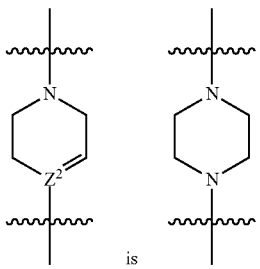

is may be prepared according to the process outlined in Scheme (IV-1), below.

Scheme (IV-1)

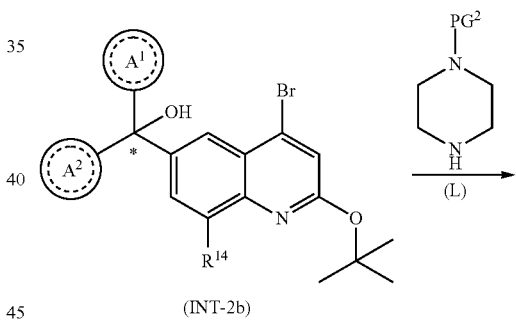

(INT-2b)

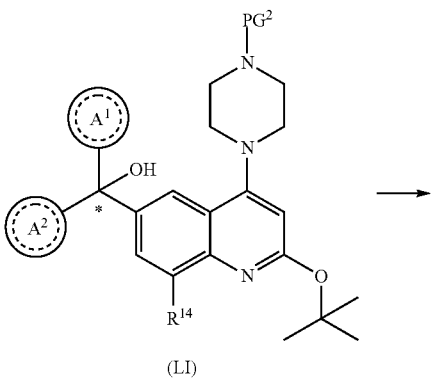

(LI)

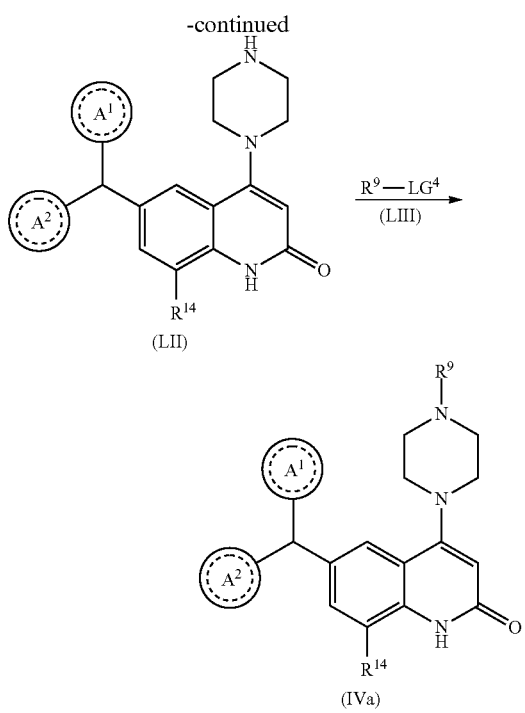

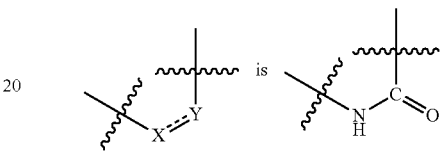

In another example, wherein $R^9$ is —C(O)—($C_{1-4}$alkyl), the compound of formula (LII) is reacted with a suitably substituted compound of formula (LIII), wherein $LG^3$ is —OH; in the presence of a suitably selected peptide coupling agent such as DCC, HATU, HBTU, EDCI, and the like; optionally in the presence of a suitably selected base such as Hunig's base, TEA, and the like; in a suitably selected solvent such as DMF, DCM, and the like; to yield the corresponding compound of formula (IVa).

Preferably, wherein $R^9$ is $CF_3$—$SO_2$—, the compound of formula (LII) is reacted with triflic anhydride, a known compound, in the presence of TEA, in methylene chloride; to yield the corresponding compound of formula (IVa).

Compounds of formula (IV) wherein

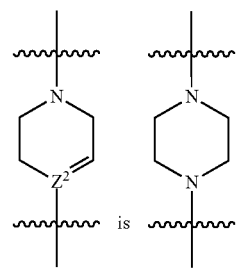

and wherein

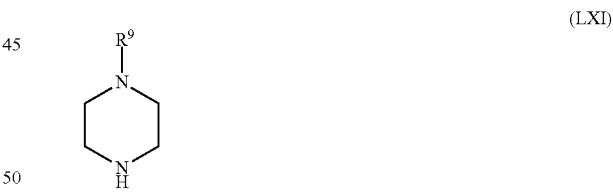

Accordingly, a suitably substituted compound of formula (INT-2b), (a compound of formula (INT-2) wherein $R^1$ is selected from the group consisting of hydrogen, hydroxy, halogen, $C_{1-4}$alkyl, —O—$C_{1-4}$alkyl, —$NH_2$, —NH($C_{1-4}$alkyl) and —N($C_{1-4}$alkyl)$_2$), prepared for example as described in Scheme B, is reacted with a suitably substituted compound of formula (L), wherein $PG^1$ is a suitably selected nitrogen protecting group such as Boc, Cbz, ethoxy-carbonyl-, and the like, a known compound or compound prepared by known methods; in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (LI).

The compound of formula (LI) is de-protected according to known methods, to yield the corresponding compound of formula (LII). For example, wherein $PG^1$ is Boc, the compound of formula (LI) is de-protected by reacting with a suitably selected acid such as HCl, TFA, and the like; alternatively, wherein $PG^1$ is ethoxy-carbonyl, the compound of formula (LI) is de-protected by reacting with HBr in a suitably selected solvent such as water, acetic acid, and the like.

The compound of formula (LII) is reacted with a suitably selected compound of formula (LIII), to yield the corresponding compound of formula (IVa).

In an example, wherein $R^9$ is selected from the group consisting of —C(O)O—($C_{1-4}$alkyl), —C(O)—($C_{1-4}$alkyl), —C(O)-(halogenated $C_{1-4}$alkyl) and —$SO_2$-(halogenated $C_{1-4}$alkyl), the compound of formula (LII) is reacted with a suitably substituted compound of formula (LIII), wherein $LG^4$ is, for example, Cl; in the presence of a suitably selected tertiary organic base such as TEA, Hunig's base, and the like; in a suitably selected solvent such as DCM, THF, and the like; to yield the corresponding compound of formula (IVa).

may alternatively be prepared according to the process outlined in Scheme (IV-1) above, by selecting an substituting a suitably substituted compound of formula (LXI)

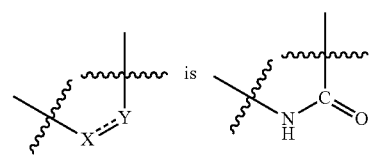

for the compound of formula (L) and reacting as described therein (i.e. reacting under palladium-catalyzed cross-coupling conditions to yield an intermediate, which is then further reacted to remove the —OH and -t-butyl groups).

Compounds of formula (IV) wherein and wherein

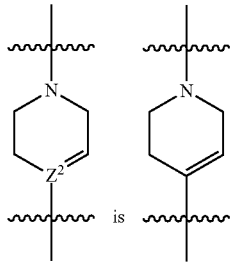

is may be prepared according to the process outlined in Scheme (IV-3), below.

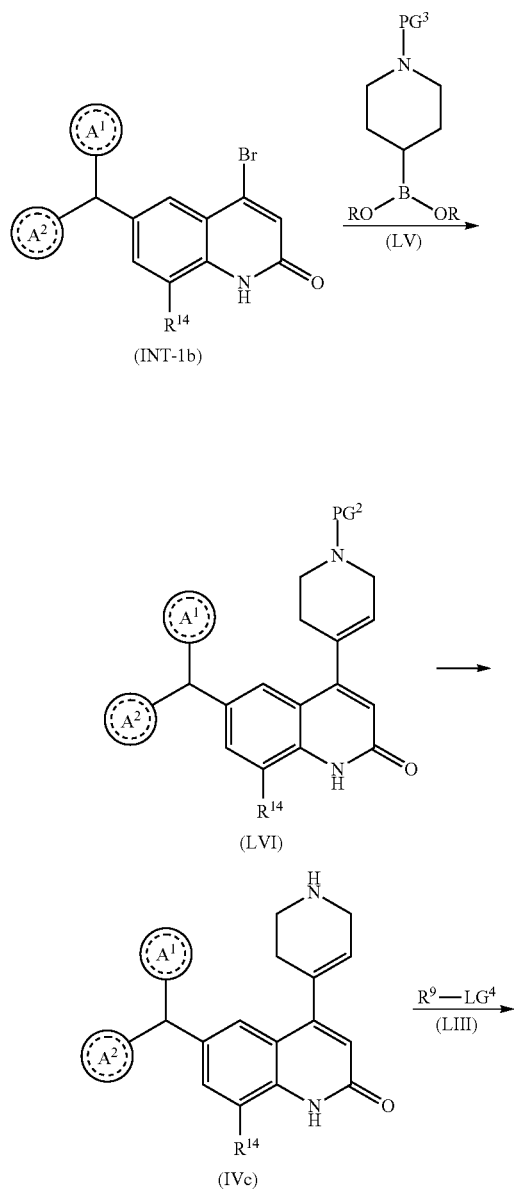

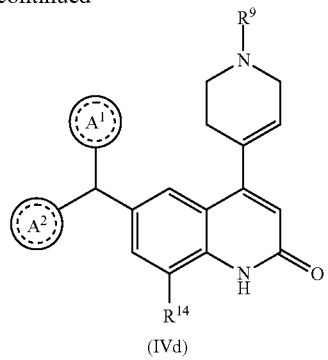

(IVd)

Accordingly, a suitably substituted compound of formula (INT-1b), (a compound of formula (INT-1) wherein $R^1$ is selected from the group consisting of hydrogen, hydroxy, halogen, $C_{1-4}$alkyl, —O—$C_{1-4}$alkyl, —$NH_2$, —NH($C_{1-4}$ alkyl) and —N($C_{1-4}$alkyl)$_2$), prepared for example as described in Scheme A, is reacted with a suitably substituted compound of formula (LV) (i.e. a suitably substituted boronic acid or boronic ester), and wherein $PG^3$ is a suitably selected nitrogen protecting group such as Boc, Cbz, ethoxycarbonyl-, and the like, to yield the corresponding compound of formula (LVI).

In an example, the compound of formula (INT-1b) is reacted with the compound of formula (LV), wherein both R groups are the same and are hydrogen (i.e. a suitably selected boronic acid); in the presence of a suitably selected catalyst such as Pd(OAc)$_2$, Pd(PPh$_3$)$_4$, Pd$_2$(dba)$_3$.CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (LVI).

In another example, the compound of formula (INT-1b) is reacted with a suitably substituted compound of formula (LV) wherein both R groups are the same and are $C_{1-2}$alkyl, or are taken together with the oxygen atoms to which they are bound to form $$\text{\{structure: pinacol boronate ester\}}$$

(i.e. a suitably selected boronic ester); in the presence of a suitably selected catalyst such as Pd(OAc)$_2$, Pd(PPh$_3$)$_4$, Pd$_2$(dba)$_3$.CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (LVI).

The compound of formula (LVI) is de-protected according to known methods, to yield the corresponding compound of formula (IVc). For example, wherein $PG^3$ is Boc, the compound of formula (LVI) is de-protected by reacting with a suitably selected acid such as HCl, TFA, and the like; alternatively, wherein $PG^3$ is ethoxy-carbonyl, the compound of formula (LVI) is de-protected by reacting with HBr in a suitably selected solvent such as water, acetic acid, and the like. (One skilled in the art will recognize that the compound of formula (IVc) corresponds to the compound of formula (IV) wherein

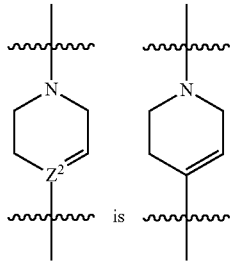

and wherein $R^9$ is hydrogen.)

The compound of formula (IVc) is reacted with a suitably selected compound of formula (LIII), to yield the corresponding compound of formula (IVd).

In an example, wherein $R^9$ is selected from the group consisting of —C(O)O—($C_{1-4}$alkyl), —C(O)—($C_{1-4}$alkyl), —C(O)-(halogenated $C_{1-4}$alkyl) and —SO$_2$-(halogenated $C_{1-4}$alkyl), the compound of formula (IVc) is reacted with a suitably substituted compound of formula (LIII), wherein $LG^4$ is, for example, Cl; in the presence of a suitably selected tertiary organic base such as TEA, Hunig's base, and the like; in a suitably selected solvent such as DCM, THF, and the like; to yield the corresponding compound of formula (IVd).

In another example, wherein $R^9$ is —C(O)—($C_{1-4}$alkyl), the compound of formula (IVc) is reacted with a suitably substituted compound of formula (LIII), wherein $LG^3$ is —OH; in the presence of a suitably selected peptide coupling agent such as DCC, HATU, HBTU, EDCI, and the like; optionally in the presence of a suitably selected base such as Hunig's base, TEA, and the like; in a suitably selected solvent such as DMF, DCM, and the like; to yield the corresponding compound of formula (IVd).

Preferably, wherein $R^9$ is $CF_3$—$SO_2$—, the compound of formula (IVc) is reacted with triflic anhydride, a known compound, in the presence of TEA, in methylene chloride; to yield the corresponding compound of formula (IVd).

The compound formula (IVd) is further, optionally, reacted with a suitably substituted compound of formula (XI), wherein $LG^1$ is a suitably selected leaving group such as Cl, Br, I, tosylate, mesylate, and the like; in the presence of a suitably selected base such as $Cs_2CO_3$, $K_2CO_3$, NaH, and the like; in a suitably selected organic solvent such as acetonitrile, DMF, THF, and the like; to yield the corresponding compound of formula (IVe), in a mixture with the corresponding compound of formula (LVII).

Compounds of formula (IV) wherein

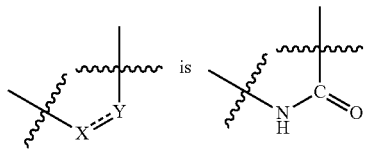

and wherein

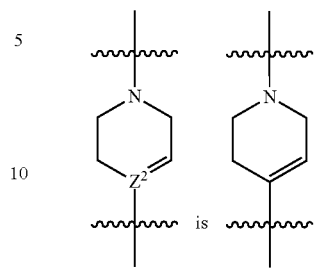

may alternatively be prepared according to the process outlined in Scheme (IV-2) above, by selecting an substituting a suitably substituted compound of formula (LXII)

(LXII)

for the compound of formula (L) and reacting as described therein (i.e. reacting under palladium-catalyzed cross-coupling conditions).

Compounds of formula (IV) wherein

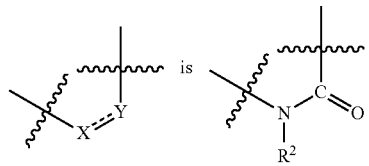

may be prepared as described in Scheme (IV-3), below.

Scheme (IV-3)

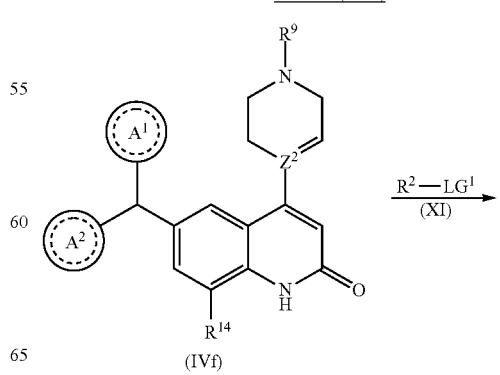

-continued

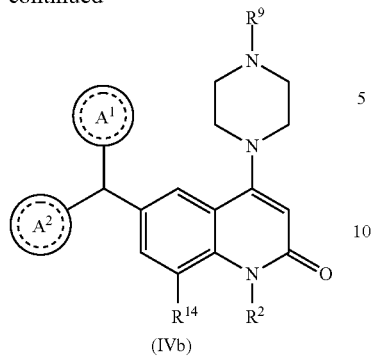

(IVb)

+

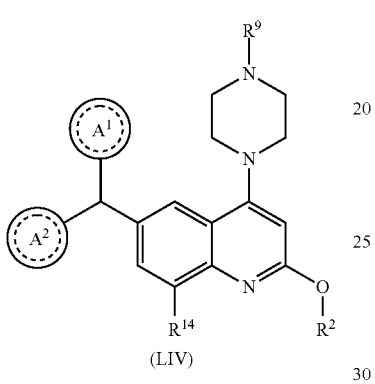

(LIV)

Accordingly, a suitably substituted compound of formula (IVf) wherein $R^{14}$ is hydrogen, is reacted with a suitably substituted compound of formula (XI), wherein $LG^1$ is a suitably selected leaving group such as Cl, Br, I, tosylate, mesylate, and the like; in the presence of a suitably selected base such as $Cs_2CO_3$, $K_2CO_3$, NaH, and the like; in a suitably selected organic solvent such as acetonitrile, DMF, THF, and the like; to yield the corresponding compound of formula (IVb), in a mixture with the corresponding compound of formula (LIV).

Compounds of formula (IV) wherein

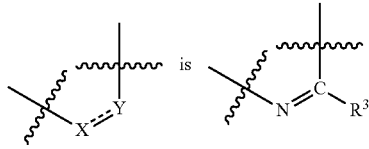

wherein $R^3$ is —$OR^4$, may be prepared according to the procedure described in Scheme (IV-4), below.

Scheme (IV-3)

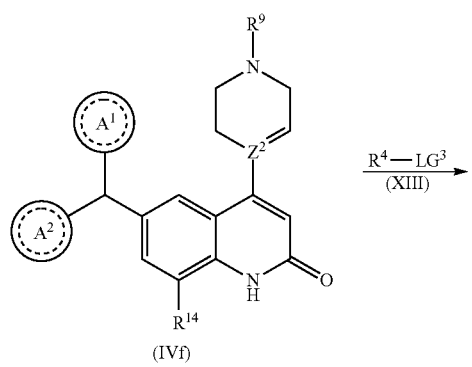

-continued

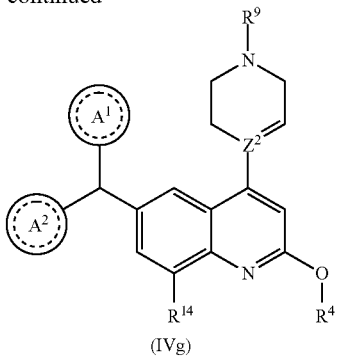

(IVg)

+

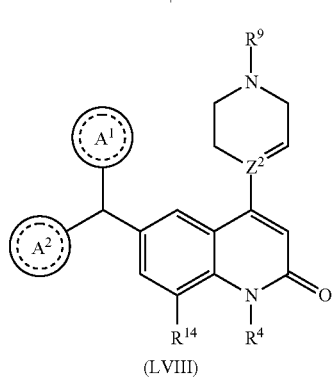

(LVIII)

Accordingly, a suitably substituted compound of formula (IVf), prepared for example, as described herein, is reacted with a suitably substituted compound of formula (XIII), wherein $LG^2$ is a suitably selected leaving group such as Br, Cl, I, mesylate, tosylate, and the like, a known compound or compound prepared by known methods; according to known methods (for example in the presence of a suitably selected base such as $Cs_2CO_3$, $K_2CO_3$, and the like; in a suitably selected solvent such as acetonitrile, DMF, THF, and the like), to yield the corresponding compound of formula (IVg), in a mixture with the corresponding compound of formula (LVIII).

Compounds of formula (IV) wherein

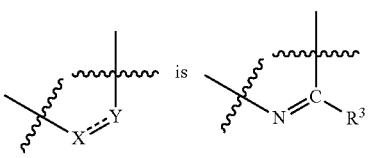

and wherein $R^3$ is hydrogen and wherein

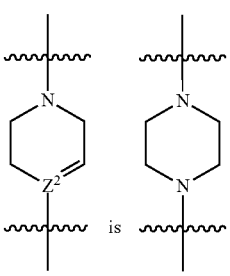

may be similarly prepared according to the procedures as described above, by selecting and substituting a suitably substituted compound of formula (INT-5b)

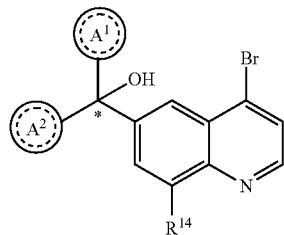

(INT-5b)

(a compound of formula (INT-5) wherein $R^1$ is selected from the group consisting of hydrogen, halogen, —OH, —$C_{1-4}$alkyl, —O—($C_{1-4}$alkyl), —$NH_2$, —$NH(C_{1-4}$alkyl) and —$N(C_{1-4}$alkyl)$_2$), prepared for example as described in Scheme C, for the compound of formula (INT-2b), in Scheme (IV-1), and reacting as therein described.

Compounds of formula (III) wherein

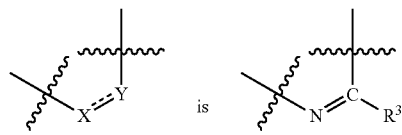

and wherein $R^3$ is hydrogen and wherein

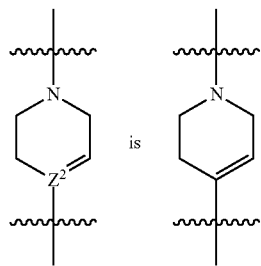

may be similarly prepared according to the procedures as described above, by selecting and substituting a suitably substituted compound of formula (INT-4b)

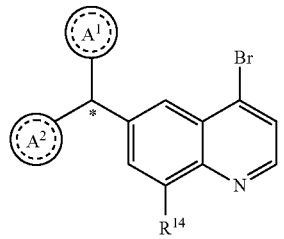

(INT-4b)

(a compound of formula (INT-4) wherein $R^1$ is selected from the group consisting of hydrogen, halogen, —OH, —$C_{1-4}$alkyl, —O—($C_{1-4}$alkyl), —$NH_2$, —$NH(C_{1-4}$alkyl) and —$N(C_{1-4}$alkyl)$_2$), prepared for example as described in Scheme C, for the compound of formula (INT-1b), in Scheme (IV-2), and reacting as therein described.

One skilled in the art will recognize that in the synthesis of the compounds of formula (I), the compounds of formula (II), the compounds of formula (III) and the compounds of formula (IV) of the present invention, additional substitutions and/or substituent transformations may be effected according to the procedures as described herein (in the general synthesis schemes and examples) or according to methods known to those skilled in the art, to yield additional desired compounds of the present invention. One skilled in the art will further recognize that the reaction steps and processes described herein may be adapted and/or applied to the synthesis of any of the compounds of the present invention.

Compounds of formula (INT-1), compounds of formula (INT-2) and compounds of formula (INT-3) may be prepared according to the procedure as outlined in Scheme A, below.

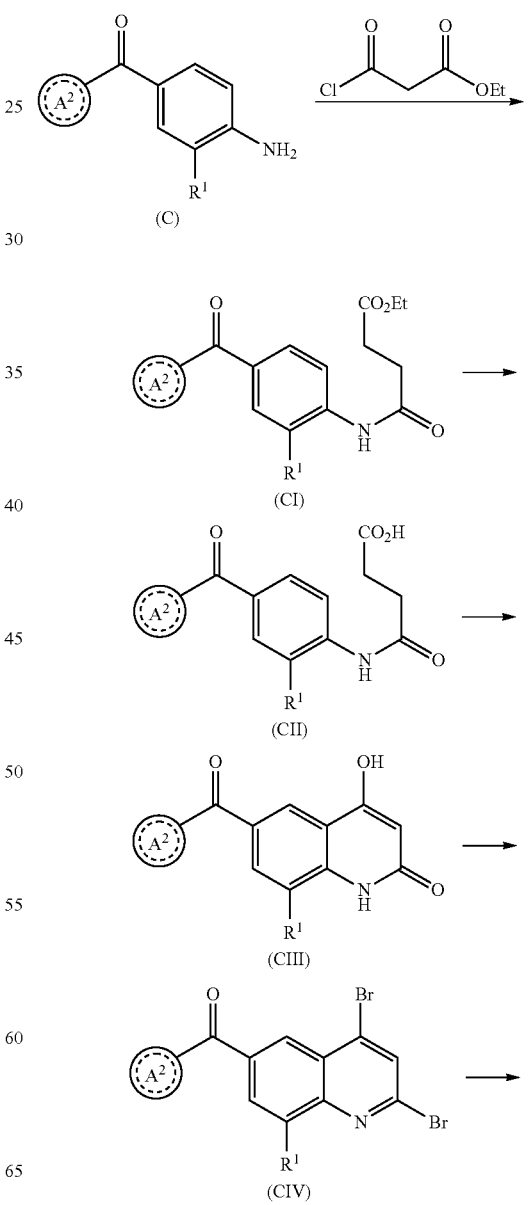

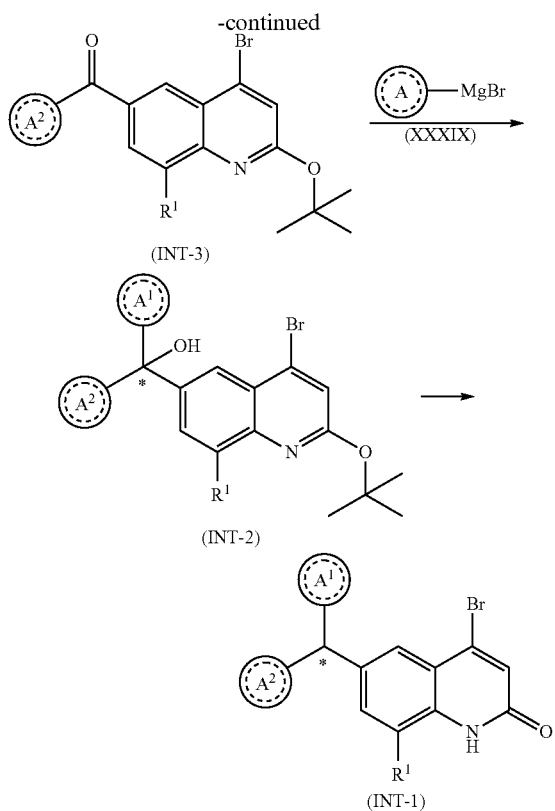

(INT-3)

(INT-2)

(INT-1)

Accordingly, a suitably compound of formula (C), wherein $R^1$ is selected from the group consisting of hydrogen, halogen (preferably bromo), —$C_{1-4}$alkyl and —O—($C_{1-4}$alkyl), a known compound or compound prepared by known methods, is reacted with ethyl 3-chloro-3-oxopropanoate, a known compound; in the presence of a suitably selected organic base such as TEA, DIPEA, pyridine, and the like; in a suitably selected organic solvent such as DCM, THF, 1,4-dioxane, and the like; to yield the corresponding compound of formula (CI).

The compound of formula (CI) is reacted with a suitably selected base such as LiOH, NaOH, and the like; in a suitably selected solvent or mixture of solvents such as 1,4-dioxane/water, THF/water, ethanol/water, and the like; to yield the corresponding compound of formula (CII).

The compound of formula (CII) is subjected to ring closure, by reacting with $CH_3SO_3H$; in the presence of $P_2O_5$; optionally, in a suitably selected solvent such as toluene, benzene, chlorobenzene, and the like; to yield the corresponding compound of formula (CIII).

The compound of formula (CIII) is reacted with a suitably selected brominating agent such as $PBr_3$, $POBr_3$, $PPh_3Br_2$, and the like; neat or in a suitably selected solvent such as toluene, benzene, DMF, and the like; to yield the corresponding compound of formula (CIV).

The compound of formula (CIV) is reacted with a suitably selected reagent such as KOt-Bu, NaOt-Bu, and the like; in a suitably selected organic solvent such as toluene, THF, 1,4-dioxane, o-dichlorobenzene and the like; to yield the corresponding compound of formula (INT-3).

The compound of formula (INT-3) is reacted with a suitably substituted compound of formula (XXXIX), a known compound or compound prepared by known methods, under Grignard conditions, more particularly, in the presence in a suitably selected anhydrous organic solvent such as diethyl ether, THF, and the like; to yield the corresponding compound of formula (INT-2).

The compound of formula (INT-2) is reacted with $Et_3SiH$ in combination with TFA, or $SnCl_2$ in combination with HCl, or $TiCl_4$ in combination with $Et_3SiH$; in a suitably selected organic solvent such as DCM, DCE, and the like; to yield the corresponding compound of formula (INT-1).

One skilled in the art will recognize that the compound of formula (CIV) may alternatively be reacted with a suitably selected sodium or potassium $C_{1-4}$alkoxide, such as for example, $NaOCH_3$ or $NaOCH_2CH_3$, to yield the corresponding compound of formula (INT-3) wherein the —O-t-butyl group at the 2-position of the quinoline core is replaced with the corresponding —O—$C_{1-4}$alkyl, for example —$OCH_3$ or —$OCH_2CH_3$ The resulting compound is then reacted with a suitably substituted compound of formula (XXXIX), a known compound or compound prepared by known methods, under Grignard conditions, as described above; and then de-protected by reacting with a suitably selected acid such as HCl, HBr, and the like.

Compounds of formula (INT-2) wherein $R^1$ is wherein $R^1$ is selected from the group consisting of hydrogen, halogen (preferably bromo), —$C_{1-4}$alkyl and —O—($C_{1-4}$alkyl), may alternatively be prepared according to the procedure as outlined in Scheme B, below.

Scheme B

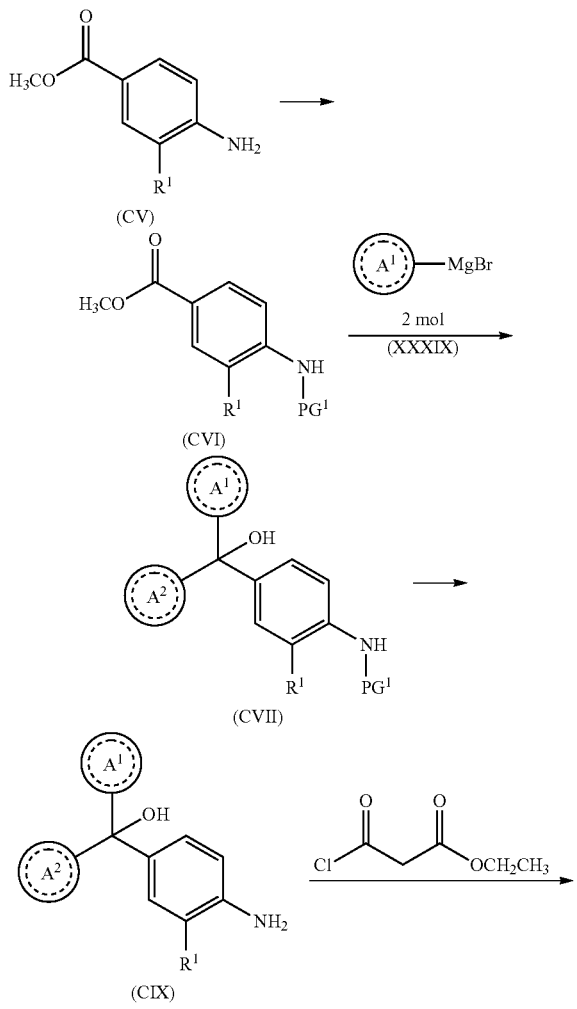

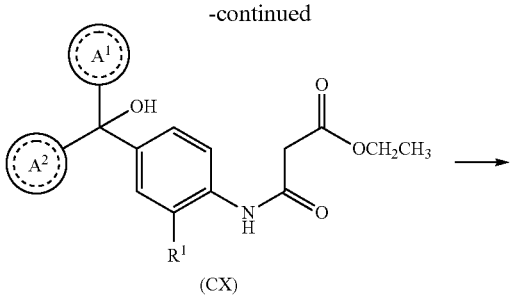

(CX)

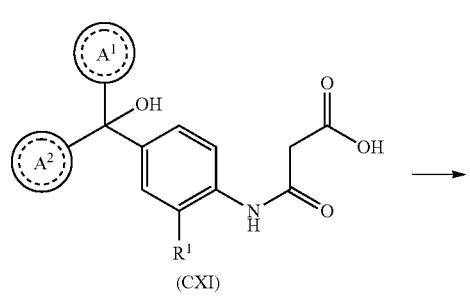

(CXI)

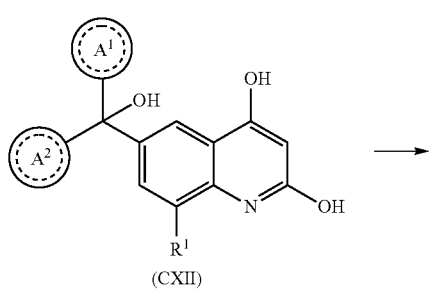

(CXII)

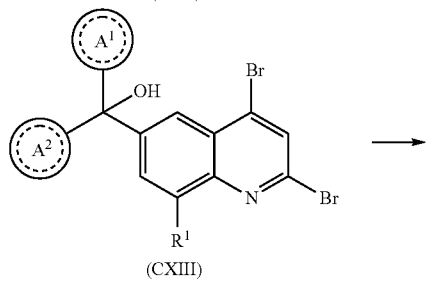

(CXIII)

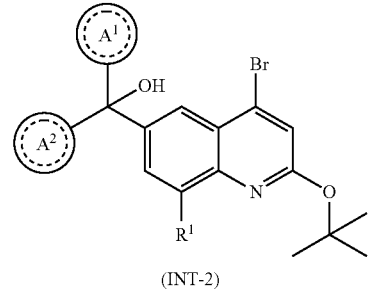

(INT-2)

Accordingly, a suitably substituted compound of formula (CV), a known compound or compound prepared by known methods is protected at the terminal amine group according to known methods, to yield the corresponding compound of formula (CVI), wherein PG¹ is a suitably selected nitrogen protecting group such as Boc, Cbz, and the like. For example, wherein PG¹ is Boc, the methyl 4-amino-3-bromobenzoate is reacted with Boc-anhydride, in the presence of TEA, in THF.

The compound of formula (CVI) is reacted with at least two moles of a suitably substituted compound of formula (XXXIX), a known compound or compound prepared by known methods, under Grignard conditions; in a suitably selected anhydrous organic solvent such as diethyl ether, THF, and the like; to yield the corresponding compound of formula (CVII) wherein

and are the same.

The compound of formula (CVII) is de-protected according to known methods, to yield the corresponding compound of formula (CIX). For example, wherein PG¹ is Boc, the compound of formula (CVII) is de-protected by reacting with a suitably selected acid such as TFA, and the like; in a suitably selected organic solvent such as 1,4-dioxane, and the like.

The compound of formula (CIX) is reacted with ethyl 3-chloro-3-oxopropanoate, a known compound; in the presence of a suitably selected organic base such as TEA, DIPEA, pyridine, and the like; in a suitably selected organic solvent such as DCM, THF, 1,4-dioxane, and the like; to yield the corresponding compound of formula (CX).

The compound of formula (CX) is reacted with a suitably selected base such as LiOH, NaOH, and the like; in a suitably selected solvent or mixture of solvents such as 1,4-dioxane/water, THF/water, ethanol/water, and the like; to yield the corresponding compound of formula (CXI).

The compound of formula (CXI) is subjected to ring closure, by reacting with $CH_3SO_3H$; in the presence of $P_2O_5$; in a suitably selected solvent such as toluene, benzene, chlorobenzene, and the like; to yield the corresponding compound of formula (CXII).

The compound of formula (CXII) is reacted with a suitably selected brominating agent such as $PBr_3$, $POBr_3$, $PPh_3Br_2$, and the like; neat or in a suitably selected solvent such as toluene, benzene, DMF, and the like; to yield the corresponding compound of formula (CXIII).

The compound of formula (CXIII) is reacted with a suitably selected reagent such as KOt-Bu, NaOt-Bu, and the like; in a suitably selected organic solvent such as toluene, THF, 1,4-dioxane, o-dichlorobenzene and the like; to yield the corresponding compound of formula (INT-2).

Compounds of formula (INT-4) and (INT-5), wherein R¹ is selected from the group consisting of hydrogen, halogen (preferably bromo), —$C_{1-4}$alkyl and —O—($C_{1-4}$alkyl), and wherein

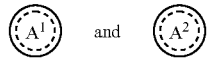

and are the same, may be prepared according to the procedure as outlined in Scheme C, below.

Scheme C

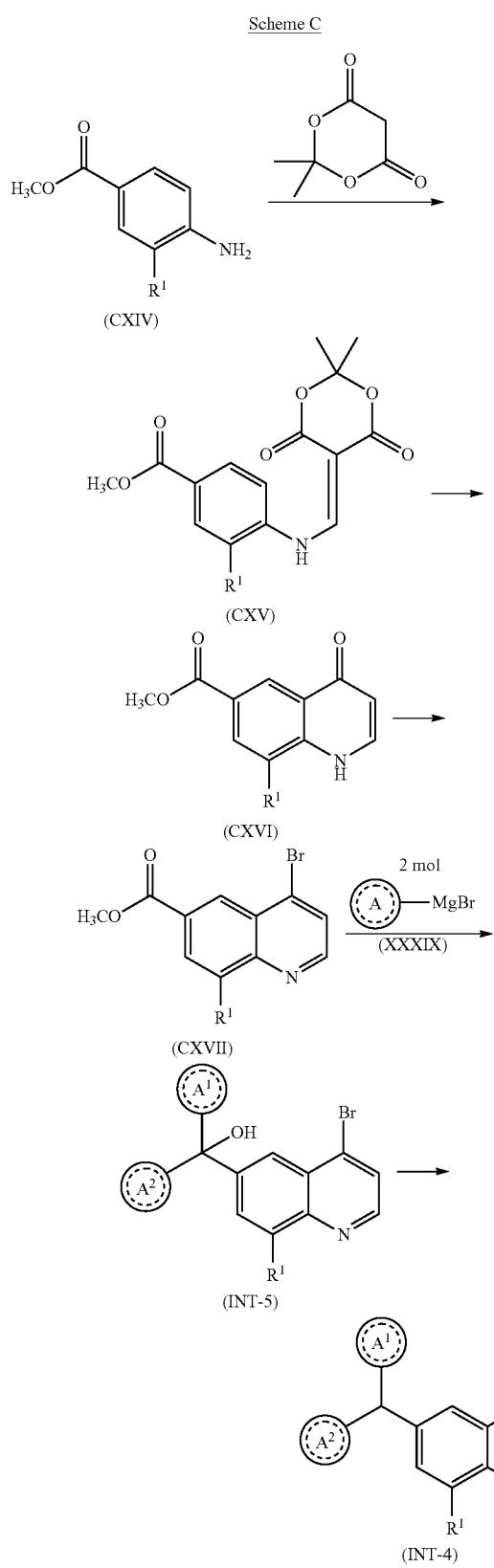

4,6-dione, a known compound; in the presence of a suitably selected reagent such as CH(OEt)₃, DMF-dimethylacetal, and the like; neat or in a suitably selected solvent such as ethanol, isopropanol, and the like; preferably at an elevated temperature in the range of from about 75° C. to about 120° C., for example, at about 100° C.; to yield the corresponding compound of formula (CXV).

The compound of formula (CXV) is subjected to ring-closure, by reacting in DOWTHERM™; to yield the corresponding compound of formula (CXVI).

The compound of formula (CXVI) is reacted with a suitably selected brominating agent such as PBr₃, POBr₃, PPh₃Br₂, and the like; neat or in a suitably selected solvent such as toluene, benzene, DMF, and the like; to yield the corresponding compound of formula (CXVII).

The compound of formula (CXVII) is reacted with at least two moles of a suitably substituted compound of formula (XXXIX), a known compound or compound prepared by known methods, under Grignard conditions; in a suitably selected anhydrous organic solvent such as diethyl ether, THF, and the like; to yield the corresponding compound of formula (INT-5), wherein

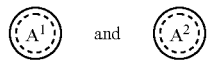

are the same.

The compound of formula (INT-5) is reacted with Et₃SiH in combination with TFA, or SnCl₂ in combination with HCl or TiCl₄ in combination with Et₃SiH; in a suitably selected organic solvent such as DCM, DCE, and the like; to yield the corresponding compound of formula (INT-4).

Compounds of formula (INT-4) wherein

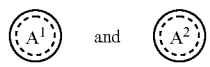

are different may be prepared according to the procedure as described in Scheme D, below.

Scheme D

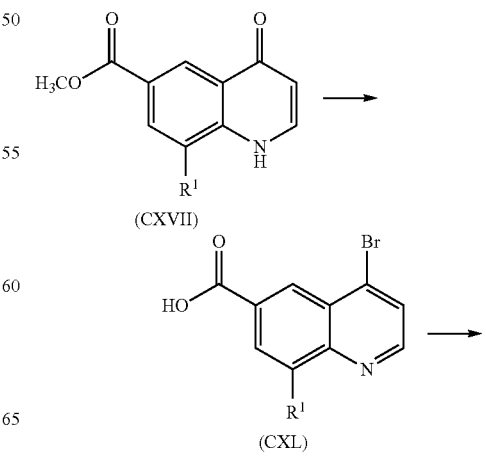

Accordingly, a suitably substituted compound of formula (CXIV), a known compound or compound prepared by known methods, is reacted with 2,2-dimethyl-1,3-dioxane-

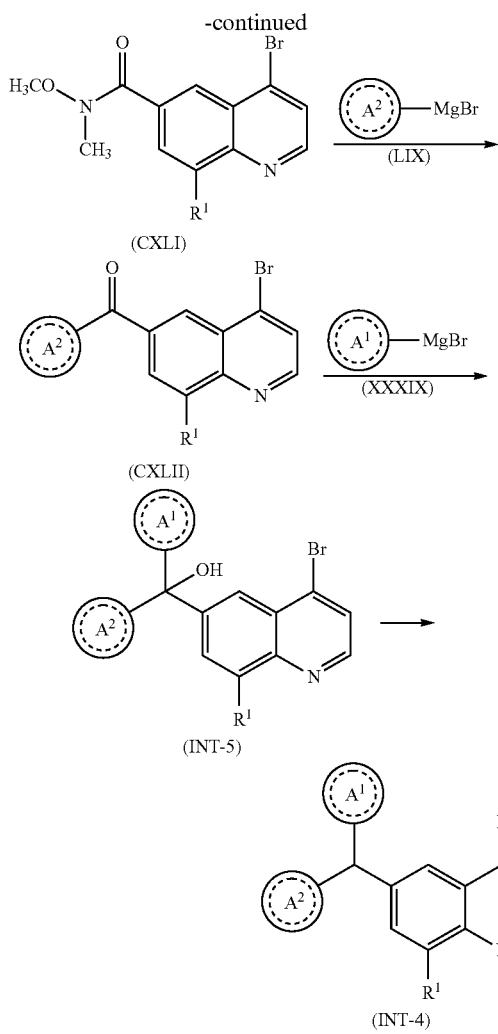

(CXLI)

(CXLII)

(INT-5)

(INT-4)

Accordingly, a suitably substituted compound of formula (CXVII), prepared for example as described in Scheme C above, is hydrolyzed by reacting with a suitably selected base such as LiOH, NaOH, and the like; in a suitably selected solvent or mixture of solvents such as 1,4-dioxane/water, THF/water, ethanol/water, and the like; to yield the corresponding compound of formula (CXL).

The compound of formula (CXL), is reacted with N,O-dimethylhydroxylamine (also known as Weinreb amide), under peptide coupling conditions, as would be known to those skilled in the art; to yield the corresponding compound of formula (CXLI).

The compound of formula (CXLI) is reacted with a suitably substituted compound of formula (LIX), a known compound or compound prepared by known methods, under Grignard conditions; in a suitably selected anhydrous organic solvent such as diethyl ether, THF, and the like; to yield the corresponding compound of formula (CXLII).

The compound of formula (CXLII) is reacted with a suitably substituted compound of formula (XXXIX), a known compound or compound prepared by known methods, under Grignard conditions; in a suitably selected anhydrous organic solvent such as diethyl ether, THF, and the like; to yield the corresponding compound of formula (INT-5).

The compound of formula (INT-5) is reacted with Et$_3$SiH in combination with TFA, or SnCl$_2$ in combination with HCl or TiCl$_4$ in combination with Et$_3$SiH; in a suitably selected organic solvent such as DCM, DCE, and the like; to yield the corresponding compound of formula (INT-4).

One skilled in the art will recognize that in the process as described in Scheme D above, the

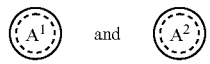

groups may be incorporated into the desired compound in either order. Accordingly, the compound of formula (CXLI) may alternatively be reacted first with a suitably substituted compound of formula (XXXIX) and the resulting intermediate then reacted with a suitably substituted compound of formula (LIX), as described above, to yield the corresponding compound of formula (INT-5).

One skilled in the art will recognize that compounds of formula (INT-4) (INT-5) and/or (INT-6) may alternatively be prepared by substituting a suitably substituted compound of formula (CXVIII)

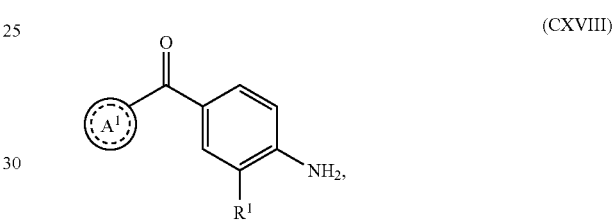

(CXVIII)

for the compound of formula (CXIV); and reacting said compound of formula (CXVIII) as described in Scheme C above, more particularly reacting sequentially with (a) 2,2-dimethyl-1,3-dioxane-4,6-dione, (b) under ring-closure conditions, (c) with a suitably selected brominating agent (to yield the corresponding compound of formula (INT-6), (d) with about one mole of a suitably selected compound of formula (XXXIX) or about one mole of a suitably selected compound of formula (LIX) (as appropriate to yield the desired intermediate compound), and (e) with for example, with Et$_3$SiH in combination with TFA (to yield the corresponding compound of formula (INT-4) or compound of formula (INT-5)).

Compounds of formula (INT-4) wherein R$^1$ is hydrogen, halogen (preferably bromo), C$_{1-4}$alkyl and —O—(C$_{1-4}$ alkyl), may alternatively be prepared similarly to the process outlined in Scheme C above. More particularly, a suitably substituted compound of formula (CXIX)

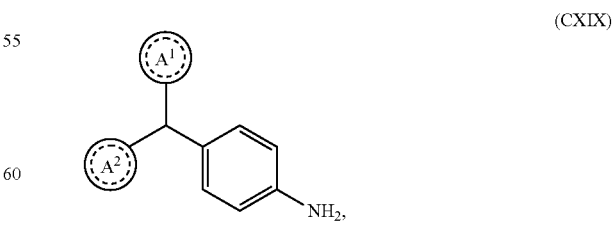

(CXIX)

is substituted for the compound of formula (CXIV) in Scheme C above and reacted sequentially as follows: (a) with 2,2-dimethyl-1,3-dioxane-4,6-dione, (b) under ring-closure conditions; (c) with a brominating agent; and (d)

with for example, with Et₃SiH in combination with TFA, as described in Scheme C above.

One skilled in the art will further recognize that compounds of formula (INT-1) may alternatively be prepared from the corresponding compound of formula (INT-4), as described in Scheme E, below.

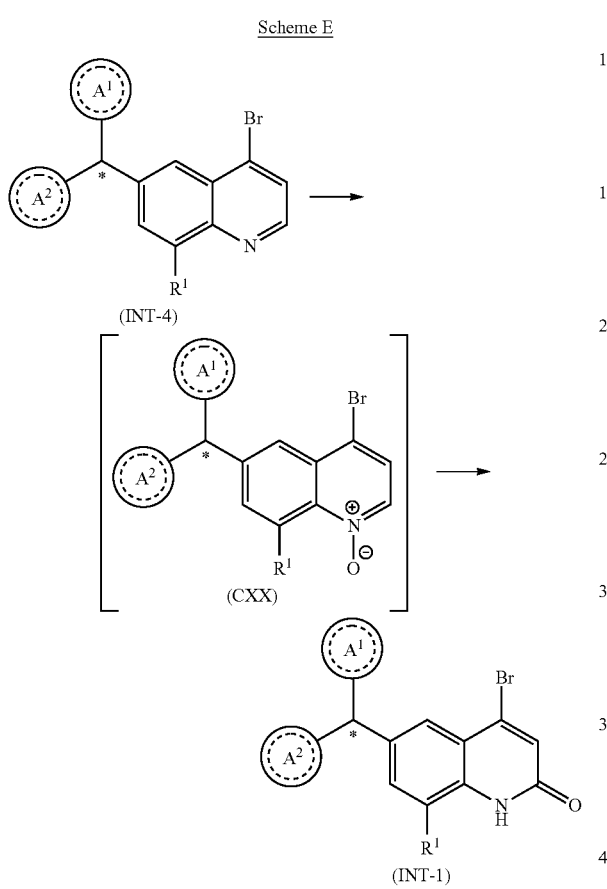

Accordingly, a suitably substituted compound of formula (INT-4), prepared for example as described in Scheme C above, may be further optionally reacted with a suitably selected oxidizing agent such as MCPBA, and the like; in a suitably selected organic solvent such as DCM, chloroform, and the like; to yield the corresponding compound of formula (CXX), which compound is not isolated.

The compound of formula (CXX) is reacted with a suitably selected reagent such as tosyl chloride, mesyl chloride, and the like; in the presence of a suitably selected base such as K₂CO₃, Na₂CO₃, and the like; in a suitably selected organic solvent such as DCM, chloroform, and the like; to yield the corresponding compound of formula (INT-1).

Compounds of formula (INT-4) wherein

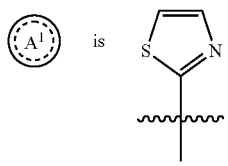

and R¹ is hydrogen are preferably prepared according to the process outlined in Scheme F, below.

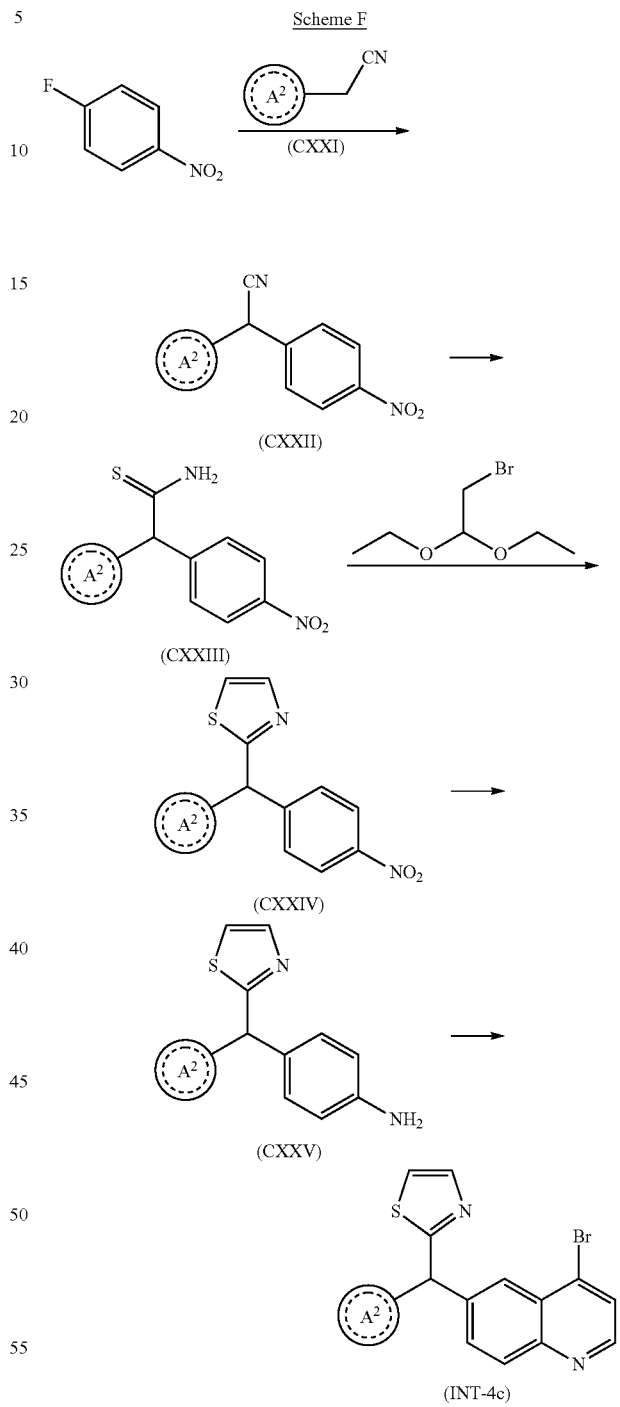

Accordingly, 1-fluoro-4-nitrobenzene, a known compound, is reacted with a suitably substituted compound of formula (CXXI), a known compound or compound prepared by known methods; in the presence of a suitably selected reagent such as KOt-Bu, NaOt-Bu, and the like; in a suitably selected solvent such as a mixture of isopropanol/THF, and the like; to yield the corresponding compound of formula (CXXII).

The compound of formula (CXXII) is reacted with a suitably selected reagent such as P$_2$S$_5$, and the like; in a suitably selected solvent such as toluene, ethanol, and the like; preferably at an elevated temperature in the range of from about 60° C. to about 120° C., for example, at about 110° C.; to yield the corresponding compound of formula (CXXII The compound of formula (CXXIII) is reacted with 2-bromo-1,1-diethoxyethane, a known compound in the presence of acetic acid; in a suitably selected solvent such as water, ethanol, and the like; to yield the corresponding compound of formula (CXXIV).

The compound of formula (CXXIV) is reacted with a suitably selected reagent such as SnCl$_2$ in the presence of HCl; in a suitably selected solvent such as methanol, and the like; to yield the corresponding compound of formula (CXXV).

The compound of formula (CXXV) is then reacted as described in Scheme C above, to yield the desired intermediate compound. More particularly, the compound of formula (CXXV) is substituted for the compound of formula (CXIV) in Scheme C above, and reacted sequentially with: (a) with 2,2-dimethyl-1,3-dioxane-4,6-dione, (b) a under ring closure conditions, for example DOWTHERM™, and (c) a suitably selected brominating agent; to yield the corresponding compound of formula (INT-4c).

The boronic acid compounds of the formula Q-B(OR)$_2$, hereinafter referred to as compounds of formula (CXXX), wherein Q is selected from the group consisting of

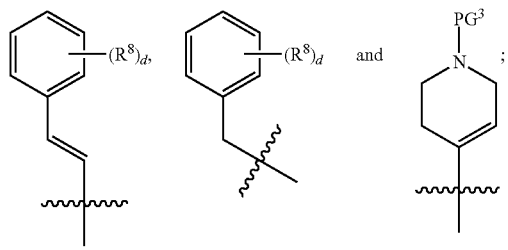

and wherein each R is the same and are selected from the group consisting of hydrogen and C$_{1-4}$alkyl; or are taken together with the oxygen atoms to which they are bound to form

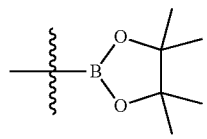 [SMILES: *B1OC(C)(C)C(C)(C)O1]

are intermediates used in the synthesis of the compounds of formula (I) of the present invention (i.e. the boronic acids of formula (CXXX) including compounds of formula (XXXVII), compounds of formula (XLII) and compounds of formula (LV)).

Compounds of formula (CXXX) are known compound or compounds that may be prepared according to methods as would be readily recognized by those skilled in the art. In an example, boronic acid compounds of the formula (CXXX) wherein Q is

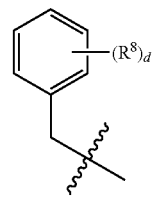

and wherein each R is the same and is selected from the group consisting of hydrogen and C$_{1-4}$alkyl, may be prepared according to the process described in Scheme G below.

Scheme G

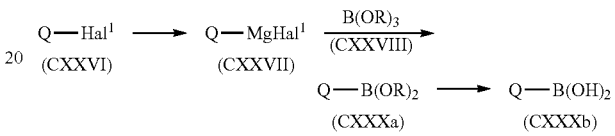

Accordingly, a suitably substituted compound of formula (CXXVI), wherein Hal$^1$ is selected from the group consisting of Cl, Br and I, a known compound or compound prepared by known methods is converted to the corresponding Grignard reagent (e.g. by reacting with Mg, according to known methods); to yield the corresponding compound of formula (CXXVII). The compound of formula (CXXVII) is then reacted with a suitably selected compound of formula (CXXVIII), wherein each R is the same and is C$_{1-4}$alkyl, a known compound or compound prepared by known methods; to yield the corresponding boronic acid compound of formula (CXXXa). The compound of formula (CXXXa) is further optionally reacted under acid hydrolysis condition, known to those skilled in the art, to yield the corresponding compound of formula (CXXXb).

In another example, compounds of formula (CXXX) wherein the two R groups are taken together with the oxygen atoms to which they are bound to form

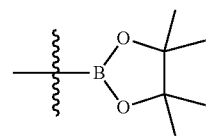 [SMILES: *B1OC(C)(C)C(C)(C)O1]

may be prepared according to the process described in Scheme H below.

Scheme H

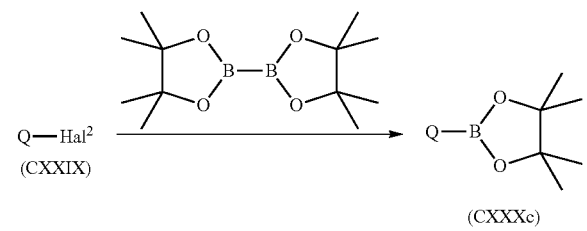

Accordingly, a suitably substituted compound of formula (CXXIX), wherein Hal² is selected from the group consisting of Br and I, a known compound or compound prepared by known methods, is reacted with bis(pinacolato)diboron (also known as 4,4,4',4',5,5,5',5'-octamethyl-2,2'-bi(1,3,2-dioxaborolane)), a known compound, according to known methods (e.g. reacting with $Pd_2(dba)_3$, in the presence of $PPh_3$ and a suitably selected base such as $Cs_2CO_3$), to yield the corresponding compound of formula (CXXXc).

One skilled in the art will recognize that in any of the processes described herein, the

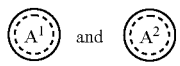

and rings (as substituent groups or in reagents containing said substituent groups) may be interchanged, and the synthesis completed as described, to yield the corresponding desired compound.

One skilled in the art will further recognize that additional substitutions and/or substituent transformations (to yield the desired intermediates or compound(s) of the present invention) may be effected according to the procedures as described herein (in the general synthesis schemes and examples) or according to methods known to those skilled in the art.

The present invention further comprises pharmaceutical compositions containing one or more compounds of formula (A) and/or one or more compounds of formula (B) and/or one or more compounds of formula (I) and/or one or more compounds of formula (II) and/or one or more compounds of formula (III) and/or one or more compounds of formula (IV) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.5 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may contain suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of metabolic disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.01 to about 50.0 mg/kg of body weight per day, or any amount or range therein. More preferably, from about 0.05 to about 15.0 mg/kg of body weight per day, or any amount or range therein. More preferably, from about 0.07 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Synthesis Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE A

Synthesis of Intermediate (4-bromo-2-(tert-butoxy)quinolin-6-yl)(4-chlorophenyl)methanone

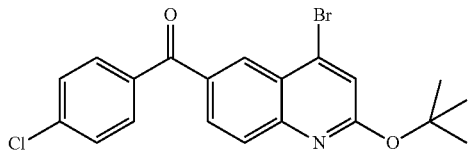 [SMILES: CC(C)(C)Oc1cc(Br)c2cc(C(=O)c3ccc(Cl)cc3)ccc2n1]

STEP 1: (4-chlorophenyl)(4-nitrophenyl)methanone

A 2-L 4-neck flask equipped with a thermocouple controller, a mechanical stirrer, a condenser, and a nitrogen inlet/outlet adapter was charged with DCE (480.8 mL), chlorobenzene (1) (90.4 mL, 888.5 mmol) and 4-nitrobenzoylchloride (111.4 g, 600.3 mmol), and the resulting mixture stirred and warmed to 40° C. Aluminum trichloride (97.0 g, 720.4 mmol) was added portionwise over 1 h and then the reaction was heated to 60° C. and stirred for 10 h. The reaction was cooled to 20° C., poured into ice-water (2 L) and stirred for 10 min. The resulting aqueous mixture was extracted with DCM (600 mL×2). The combined organic extracts were was washed with deionized water (1 L×3). The solvent was concentrated at 40° C. to remove DCM and then at 66° C. to yield a pale to slight yellowish solid, which was dissolved in hot EtOH (500 mL) at 76° C., stirred for 30 min, and then gradually cooled to 4° C. over 1 h. The resulting solid was collected by filtration to yield (4-chlorophenyl)(4-nitrophenyl)methanone as a slightly yellowish crystalline solid. (ES, m/z) 262 (M+H)$^+$, 284, 286 (M+Na)$^+$

STEP 2. (4-aminophenyl)(4-chlorophenyl)methanone

A 3-L 3-neck flask equipped with a thermocouple controller, a mechanical stirrer, a condenser, and a nitrogen inlet/outlet adapter was charged with (4-chlorophenyl)(4-nitrophenyl)methanone (132.0 g, 504.5 mmol), concentrated aqueous HCl (693.3 mL, 8.1 mol), and SnCl$_2$ (313.3 g, 1.62 mol). The yellowish suspension was carefully heated to 36° C. with fast agitation (1000 rmp). The electric power to the heating mantle was turned off at 36° C. A moderate exotherm was observed, which gradually increased to 77° C. over 1 h with gas evolution to form a foamy suspension. The electric power was turned on at 77° C. again and gradually heated to 100° C. over 30 min and refluxed for 2 h. The reaction was cooled to 10° C., slowly poured into a mixture of ice (1 L) and 33% NaOH (1 L, 8.25 M) with fast stirring in an ice-water bath. The resulting yellowish slurry (pH=2-3) was adjusted to pH=9-10 with 50% NaOH. The resulting solid was collected by filtration and washed with deionized water (100 mL). The filtration cake was dried under air-suction at 20° C. overnight and then in a vacuum oven at 60° C. for 24 h to yield a yellowish solid. The yellowish solid (322 g) was suspended in deionized water (2 L) and extracted with EtOAc (2 L×3). The combined organic phases were washed with brine (1 L/each). The solvent was concentrated at 60° C. to yield (4-aminophenyl)(4-chlorophenyl)methanone as a slightly yellowish crystalline solid. (ES, m/z) 232, 234 (M+H)$^+$

STEP 3: ethyl 3-((4-(4-chlorobenzoyl)phenyl)amino)-3-oxopropanoate

A 5-L 4-neck flask equipped with a thermocouple controller, a mechanical stirrer, a condenser, and a nitrogen inlet/outlet adapter was charged with (4-aminophenyl)(4-chlorophenyl)methanone (86.6 g, 370.1 mmol), DCM (2.61 L), and Et$_3$N (70.3 mL, 499.6 mmol). After the solution was cooled to 5° C. in an ice-bath, ethyl 3-chloro-3-oxopropanoate (64.5 mL, 407.1 mmol) was added dropwise over 60 min. The resulting mixture was stirred at 0° C. for 1 h. Additional ethyl 3-chloro-3-oxopropanoate (12.9 mL) was added dropwise and the mixture was stirred at 0° C. for an additional 2 h. The reaction was cooled to 0° C. and ice-water (2 L) was added, followed by solid K$_2$CO$_3$ (60 g) until the solution was basic (pH=9~10). After phase separation, the organic layer was concentrated at 40° C. (to remove DCM) and then at 60° C. (to remove ex Et$_3$N) to yield ethyl 3-((4-(4-chlorobenzoyl)phenyl)amino)-3-oxopropanoate as a slightly yellowish solid, which was used in the next step without further purification. (ES, m/z) 346, 348 (M+H)$^+$

STEP 4: 3-((4-(4-chlorobenzoyl)phenyl)amino)-3-oxopropanoic acid

A 3-L 4-neck flask equipped with a thermocouple controller, a mechanical stirrer, a dropping funnel, and a nitrogen inlet/outlet adapter was charged with ethyl 3-((4-(4-chlorobenzoyl)phenyl)amino)-3-oxopropanoate (128.0 g, 370.2 mmol), EtOH (1.29 L), and KOH (27.7 g, 1444.2 mmol). The resulting mixture was stirred at 20° C. for 24 h. Additional KOH (1.12 g, 0.04 eq.) was added and the reaction was stirred for an additional 6 h. The resulting yellowish thick slurry was dissolved in deionized water (1.2 L) and then poured into a 12-L 4-neck flask equipped with an overhead stirrer that contained ice-water (6 L) in an ice-water bath. The aqueous pH was adjusted to pH 2-3 using 2 N aqueous HCl solution with fast stirring at 8-10° C. for 20 min. The solid in the resulting milky slurry was collected by filtration, washed with deionized water (100 mL), dried under air-suction for 20 h and then in a vacuum oven at 60° C. under hi-vacuum (20 mmHg) for 72 h to yield 3-((4-(4-chlorobenzoyl)phenyl)amino)-3-oxopropanoic acid as a yellowish solid, which was used in the next step without further purification. (ES, m/z) 318, 320 (M+H)$^+$

STEP 5: 6-(4-chlorobenzoyl)-4-hydroxyquinolin-2(1H)-one

A 2-L 4-neck flask equipped with a thermocouple controller, a mechanical stirrer, and a nitrogen inlet/outlet adapter was charged with CH$_3$SO$_2$OH (236.0 mL, 3.60 mol), P$_2$O$_5$ (34.6 g, 241.1 mmol) was added and the mixture was vigorously stirred at 80° C. for 90 min. Solid 3-((4-(4-chlorobenzoyl)phenyl)amino)-3-oxopropanoic acid (111.0 g, 321.4 mmol) was added portionwise over 3 min at 80° C., and the resulting mixture was stirred at 80° C. for 2 h. The hot mixture was poured slowly into ice-water (5 L) and vigorously agitated for 1 h. The resulting solid was collected by filtration, washed with deionized water (2 L×2), and dried by air-suction for 20 h to yield a slightly yellowish solid. The solid was suspended in acetone (990 mL) at 53° C. and sonicated for 30 min. The resulting yellowish slurry was stirred at 20° C. for 10 min. The solid was collected by filtration, washed with acetone (50 mL), dried by air-suction for 1 h and then under high vacuum (22 mmHg) at 60° C. for 20 h to yield 6-(4-chlorobenzoyl)-4-hydroxyquinolin-2 (1H)-one as a light beige-yellowish solid. Elemental analysis: Calculated for $C_{16}H_{10}ClNO_5$+0.1 $H_2O$+0.21 $CH_3COCH_3$; MW=313.72. Theoretical: C, 63.67; H, 3.68; Cl, 11.30; N, 4.46; % $H_2O$, 0.60; Measured: C, 63.58; H, 3.23; Cl, 11.53; N, 4.64; % $H_2O$, 0.53

STEP 6: (4-chlorophenyl)(2,4-dibromoquinolin-6-yl)methanone

To a suspension of 6-(4-chlorobenzoyl)-4-hydroxyquinolin-2(1H)-one (7 g) in toluene (120 mL) was added phosphorus oxybromide (3 eq., 20 g) and the resulting mixture was refluxed until LCMS indicated consumption of starting material. After cooling in an ice bath, the reaction mixture was carefully hydrolyzed by addition of ice/water (200 mL) and neutralized using 6 N solution of NaOH. The precipitates were collected by filtration, washed with water (3×100 ml) and dried under vacuum to yield (4-chlorophenyl)(2,4-dibromoquinolin-6-yl)methanone. (ES, m/z) 426, 428 $(M+H)^+$ STEP 7: (4-bromo-2-(tert-butoxy)quinolin-6-yl)(4-chlorophenyl)methanone A mixture of (4-chlorophenyl)(2,4-dibromoquinolin-6-yl) methanone (5 g) and $KOBu^t$ (1.1 eq. 12.93 mmol) in dry toluene (60 mL) was heated at 70° C. for 2 hr. and then cooled to room temperature. The reaction was diluted with EtOAc and water. The aqueous layer was extracted with ethyl acetate. The organics were combined and then washed with water, concentrated and subjected to chromatography (5-15% EtOAc/hexanes silica column) to yield (4-bromo-2-(tert-butoxy)quinolin-6-yl)(4-chlorophenyl)methanone.
$^1$H NMR (DMSO-$d_6$) δ: 8.35 (s, 1H), 8.07 (d, J=8.8 Hz, 1H), 7.92 (d, J=8.6 Hz, 1H), 7.79-7.88 (m, J=8.3 Hz, 2H), 7.63-7.74 (m, J=8.1 Hz, 2H), 7.45 (s, 1H), 1.69 (s, 9H).

Example 1

Compound #41

6-((4-chlorophenyl)(thiazol-2-yl)methyl)-4-((1-((trifluoromethyl)sulfonyl)piperidin-4-yl)amino)quinolin-2(1H)-one

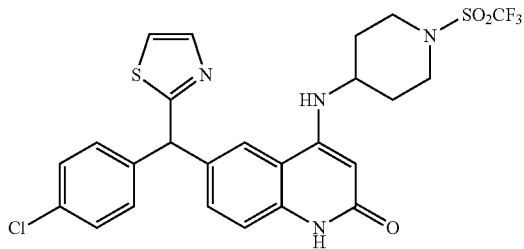

STEP 1: (4-bromo-2-tert-butoxyquinolin-6-yl)(4-chlorophenyl)(thiazol-2-yl)methanol Into a 50-mL 3-necked round-bottom flask purged and maintained with an inert atmosphere of nitrogen, was placed a solution of thiazole (255 mg, 3.00 mmol, 2.00 equip) in tetrahydrofuran (15 mL). To the resulting mixture was then added n-BuLi (1 mL, 1.70 equip, 2.5 M) dropwise with stirring at −78° C. The resulting solution was stirred for 50 min at −78° C. To the resulting mixture was added a solution of (4-bromo-2-tert-butoxyquinolin-6-yl) (4-chlorophenyl) methanone (630 mg, 1.50 mmol, 1.00 equip) in tetrahydrofuran (5 mL) dropwise with stirring at −78° C. The resulting solution was allowed to react, with stirring, for an additional 40 min at −78° C. The resulting solution was stirred for 30 min at 0° C. The reaction was then quenched by the addition of water. The resulting solution was extracted with ethyl acetate (3×50 mL) and the organic layers combined. The resulting mixture was washed with water (2×50 mL) and brine (1×50 mL). The resulting mixture was dried over anhydrous sodium sulfate. The residue was applied onto a silica gel column with ethyl acetate:petroleum ether (1:4) to yield (4-bromo-2-tert-butoxyquinolin-6-yl)(4-chlorophenyl) (thiazol-2-yl)methanol as a white solid. (ES, m/z): $[M+H]^+$ 505

STEP 2: 4-bromo-6-((4-chlorophenyl)(thiazol-2-yl) methyl)quinolin-2-ol

Into a 250-mL round-bottom flask, was placed [4-bromo-2-(tert-butoxy)quinolin-6-yl](4-chlorophenyl)1,3-thiazol-2-ylmethanol (5.5 g, 10.92 mmol, 1.00 equip), AcOH (78 mL), hydrogen chloride (13 mL), and $SnCl_2$.2 $H_2O$ (7.4 g, 32.80 mmol, 3.00 equip). The resulting solution was stirred for 40 min at 100° C. The resulting mixture was concentrated under vacuum. The resulting solution was diluted with water (200 mL). The resulting solution was extracted with DCM (3×200 mL) and the organic layers combined. The resulting mixture was washed with water (2×200 mL). The resulting mixture was dried over anhydrous sodium sulfate. The residue was applied onto a silica gel column with dichloromethane: methanol (10:1) to yield 4-bromo-6-[(4-chlorophenyl)(1,3-thiazol-2-yl)methyl]quinolin-2-ol as a white solid. (ES, m/z): $[M+H]^+$ 433

STEP 3: 6-((4-chlorophenyl)(thiazol-2-yl)methyl)-4-((1-((trifluoromethyl)sulfonyl)piperidin-4-yl)amino) quinolin-2(1H)-one Into a 20-mL vial purged and maintained with an inert atmosphere of nitrogen, was placed 4-bromo-6-[(4-chlorophenyl)(1,3-thiazol-2-yl)methyl]quinolin-2-ol (648 mg, 1.50 mmol, 1.00 equip), $Cs_2CO_3$ (978 mg, 2.00 equip), 1-(trifluoromethane)sulfonylpiperidin-4-amine hydrochloride (138 mg, 0.51 mmol, 0.10 equip), 1,4-dioxane (20 ml), $Pd_2(dba)_3$ (155.25 mg, 0.10 equip), DPPF (293.62 mg, 0.53 mmol, 0.35 equip), t-BuOK (420 mg, 3.75 mmol, 2.5 equip). The resulting solution was stirred overnight at 100° C. The resulting solution was extracted with ethyl acetate (3×50 mL) and the organic layers combined. The resulting mixture was washed with water (2×50 mL) and brine (1×50 mL). The resulting mixture was dried over anhydrous sodium sulfate and concentrated under vacuum. The residue was applied onto a silica gel column with dichloromethane/methanol (10:1) to yield 6-((4-chlorophenyl)(thiazol-2-yl) methyl)-4-((1-((trifluoromethyl)sulfonyl)piperidin-4-yl) amino)quinolin-2(1H)-one as a yellow solid.

(ES, m/z): [M+H]⁺ 583; ¹H-NMR (300 MHz, DMSO-d₆) δ 10.829 (s, 1H), 8.056 (s, 1H), 7.827 (d, J=3.3 Hz, 1H), 7.698 (d, J=3.0 Hz, 1H), 7.304-7.436 (m, 5H), 7.223 (d, J=8.7 Hz, 1H), 6.571 (d, J=7.5 Hz, 1H), 5.915 (s, 1H), 5.502 (s, 1H), 3.881 (d, J=12.6 Hz, 2H), 3.765 (br, 1H), 3.417-3.457 (2H), 2.102 (d, J=12.6 Hz, 2H), 1.601-1.638 (m, 2H)

Example 2

Compound #44

6-(bis(4-chlorophenyl)methyl)-4-(1-(trifluoromethylsulfonyl)piperidin-4-ylamino)quinolin-2(1H)-one

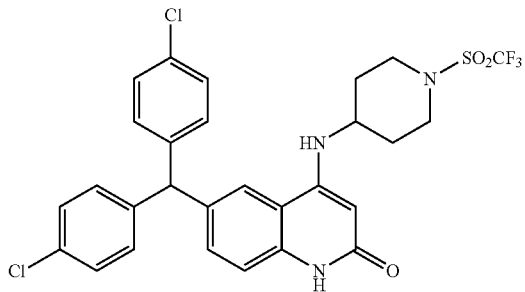

STEP 1: (4-bromo-2-tert-butoxyquinolin-6-yl)bis(4-chlorophenyl)methanol

Into a 250-mL 3-necked round-bottom flask purged and maintained with an inert atmosphere of nitrogen, was placed a solution of (4-bromo-2-tert-butoxyquinolin-6-yl)(4-chlorophenyl)methanone (4 g, 9.55 mmol, 1.00 equip) in tetrahydrofuran (65 mL). To the resulting mixture was then added (4-chlorophenyl)magnesium bromide (8.2 mL, 1.30 equip, 1 M) dropwise with stirring at 0° C. The resulting solution was stirred for 2 h at 0° C. The reaction was then quenched by the addition of water. The resulting solution was extracted with ethyl acetate (3×150 mL) and the organic layers combined. The resulting mixture was washed with water (2×100 mL) of water and brine (1×100 mL). The resulting mixture was dried over anhydrous sodium sulfate. The residue was applied onto a silica gel column with ethyl acetate:petroleum ether (1:4) to yield (4-bromo-2-tert-butoxyquinolin-6-yl)bis(4-chlorophenyl)methanol as white solid. (ES, m/z): [M+H]⁺532

STEP 2: 4-bromo-6-((4-chlorophenyl)(thiazol-2-yl)methyl)quinolin-2-ol

Into a 100-mL round-bottom flask, was placed a solution of [4-bromo-2-(tert-butoxy)quinolin-6-yl]bis(4-chlorophenyl)methanol (1.5 g, 2.82 mmol, 1.00 equip) in dichloromethane (55 mL), Et₃SiH (1.3 g, 4.00 equip), and trifluoroacetic acid (8 g, 70.77 mmol, 25.00 equip). The resulting solution was stirred overnight at room temperature. The pH value of the solution was adjusted to 7-8 with sodium bicarbonate. The resulting solution was extracted with DCM (3×50 ml) and the organic layers combined. The resulting mixture was washed with water (2×50 mL). The resulting mixture was washed with brine (1×50 mL). The resulting mixture was dried over anhydrous sodium sulfate and concentrated to yield 6-[bis(4-chlorophenyl)methyl]-4-bromoquinolin-2-ol as a white solid. (ES, m/z): [M+H]⁺433

STEP 3: 6-(bis(4-chlorophenyl)methyl)-4-(1-(trifluoromethylsulfonyl)piperidin-4-ylamino)quinolin-2-ol Into a 100-mL round bottom flask purged and maintained with an inert atmosphere of nitrogen, was placed 6-[bis(4-chlorophenyl)methyl]-4-bromoquinolin-2-ol (3.4 g, 7.40 mmol, 1.00 equip), 1-(trifluoromethane)sulfonylpiperidin-4-amine hydrochloride (3.4 g, 12.65 mmol, 1.70 equip), Pd(dba)₃ (680 mg, 0.10 equip), dppf (1.44 g, 2.60 mmol, 0.35 equip), Cs₂CO₃ (6.05 g, 2.50 equip), KOt-Bu (1.5 g, 1.80 equip), and 1,4-dioxane (35 mL). The resulting solution was stirred overnight at 100° C. The reaction was then quenched by the addition of water (100 mL). The resulting solution was extracted with ethyl acetate (3×150 mL) and the organic layers combined. The resulting mixture was washed with water (2×100 mL) and brine (1×100 mL). The resulting mixture was dried over anhydrous sodium sulfate and concentrated under vacuum. The residue was applied onto a silica gel column with dichloromethane/methanol (10:1). The resulting residue was purified by re-crystallization from CH₃CN to yield 6-[bis(4-chlorophenyl)methyl]-4-[[1-(trifluoromethane)sulfonylpiperidin-4-yl]amino]quinolin-2-ol as a white.

(ES, m/z): [M+H]⁺ 610; ¹H-NMR (300 MHz, DMSO-d₆) δ 10.786 (s, 1H), 7.930 (s, 1H), 7.390-7.418 (m, 4H), 7.128-7.222 (m, 6H), 6.542 (d, J=7.8 Hz, 1H), 5.629 (s, 1H), 5.490 (s, 1H), 3.872 (d, J=13.2 Hz, 2H), 3.373 (br, 1H), 3.411-3.452 (m, 2H), 2.069-2.107 (m, 2H), 1.556-1.663 (m, 2H)

Example 3

Compound #59

6-(bis(4-chlorophenyl)methyl)-4-((4-(trifluoromethyl)phenyl)amino)quinolin-2(1H)-one

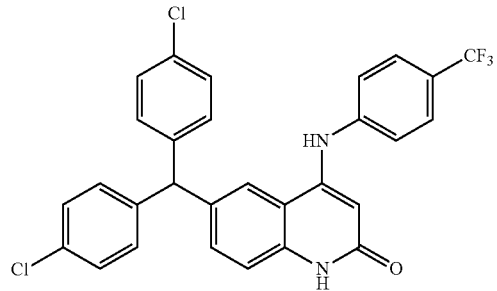 [SMILES: O=c1cc(Nc2ccc(C(F)(F)F)cc2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 4-(trifluoromethyl)aniline (78.9 mg, 0.49 mmol, 1.50 equip), Pd₂(dba)₃ (30 mg, 0.03 mmol, 0.10 equip), dppf (63.4 mg, 0.11 mmol, 0.35 equip), Cs₂CO₃ (266 mg, 0.82 mmol, 2.50 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with dichloromethane/methanol (20:1). The resulting residue was recrystallized from ethyl acetate:petroleum ether in the ratio of 1:10 to yield 6-[bis(4-chlorophenyl)methyl]-4-[[4-(trifluoromethyl)phenyl]amino]quinolin-2-ol as a light yellow solid.

LCMS (ES, m/z) 539 [M+H]+; 1H-NMR (300 MHz, DMSO-$d_6$) δ 11.277 (s, 1H), 8.871 (s, 1H), 7.886 (s, 1H), 7.715 (d, J=8.4 Hz, 2H), 7.443-7.384 (m, 6H), 7.291 (s, 2H), 7.162 (d, J=6.0 Hz, 4H), 5.995 (s, 1H), 5.700 (brs, 1H)

Example 4

Compound #60

6-[bis(4-chlorophenyl)methyl]-4-[(1-phenylpiperidin-4-yl)amino]quinolin-2-ol

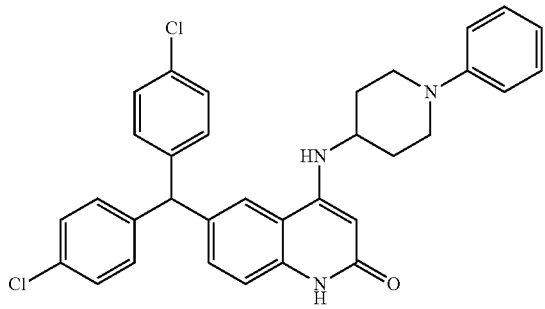 [SMILES: O=c1cc(NC2CCN(c3ccccc3)CC2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 1-phenylpiperidin-4-amine (86 mg, 0.49 mmol, 1.49 equip), Pd$_2$(dba)$_3$ (30 mg, 0.03 mmol, 0.10 equip), dppf (63.4 mg, 0.11 mmol, 0.35 equip), Cs$_2$CO$_3$ (266 mg, 0.82 mmol, 2.50 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with dichloromethane/methanol (20:1). The resulting residue was recrystallized from ethyl acetate:petroleum ether in the ratio of 1:10 to yield 6-[bis(4-chlorophenyl)methyl]-4-[(1-phenylpiperidin-4-yl)amino]quinolin-2-ol as an off-white solid.

LCMS (ES, m/z) 554 [M+H]+; 1H-NMR (300 MHz, DMSO-$d_6$) δ10.713 (s, 1H), 7.946 (s, 1H), 7.372 (d, J=8.1 Hz, 4H), 7.229-7.103 (m, 8H), 6.957 (d, J=8.1 Hz, 2H), 6.756-6.708 (m, 1H), 6.471 (d, J=7.8 Hz, 1H), 5.588 (s, 1H), 5.421 (s, 1H), 3.776 (d, J=12.6 Hz, 2H), 3.604-3.586 (br, 1H), 2.929-2.848 (m, 2H), 1.975 (d, J=9.3 Hz, 4H), 1.694-1.624 (m, 2H)

Example 5

Compound #61

6-(bis(4-chlorophenyl)methyl)-4-((3-(trifluoromethyl)benzyl)amino)quinolin-2(1H)-one

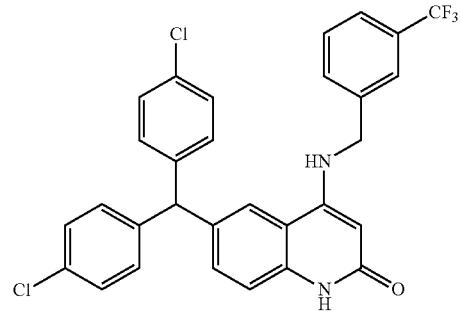 [SMILES: O=c1cc(NCc2cccc(C(F)(F)F)c2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), [3-(trifluoromethyl)phenyl]methanamine (85.78 mg, 0.49 mmol, 1.50 equip), Pd$_2$(dba)$_3$ (30 mg, 0.03 mmol, 0.10 equip), dppf (63.4 mg, 0.11 mmol, 0.35 equip), Cs$_2$CO$_3$ (266 mg, 0.82 mmol, 2.50 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with dichloromethane/methanol (20:1). The resulting residue was recrystallized from ethyl acetate:petroleum ether in the ratio of 1:10 to yield 6-(bis(4-chlorophenyl)methyl)-4-((3-(trifluoromethyl)benzyl)amino)quinolin-2(1H)-one as an off-white solid.

(ES, m/z) 553 [M+H]+; 1H-NMR (300 MHz, DMSO-$d_6$) δ10.786 (s, 1H), 7.927 (s, 1H), 7.723 (s, 1H), 7.632-7.597 (m, 4H), 4.319 (d, J=8.4 Hz, 4H), 7.211-7.184 (m, 6H), 5.673 (s, 1H), 5.164 (s, 1H), 4.533 (d, J=5.1 Hz, 2H)

Example 6

Compound #70

6-(bis(4-chlorophenyl)methyl)-4-(((6-(trifluoromethyl)pyridin-3-yl)methyl)amino)quinolin-2(1H)-one

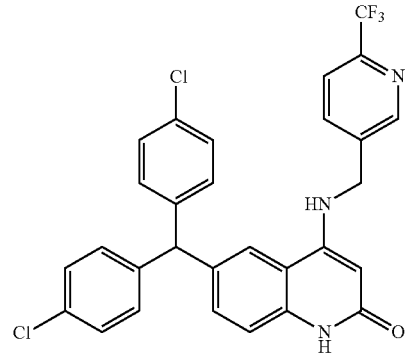 [SMILES: O=c1cc(NCc2ccc(C(F)(F)F)nc2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), [6-(trifluoromethyl)pyridin-3-yl]methanamine (86 mg, 0.49 mmol, 1.49 equip), $Pd_2(dba)_3$ (30 mg, 0.03 mmol, 0.10 equip), dppf (63.4 mg, 0.11 mmol, 0.35 equip), $Cs_2CO_3$ (266 mg, 0.82 mmol, 2.50 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with dichloromethane/methanol (20:1). The resulting residue was recrystallized from ethyl acetate: petroleum ether in the ratio of 1:10 to yield 6-(bis(4-chlorophenyl)methyl)-4-(((6-(trifluoromethyl)pyridin-3-yl)methyl)amino)quinolin-2(1H)-one as an off-white solid.

(ES, m/z) 554 [M+H]$^+$; $^1$H-NMR (300 MHz, DMSO-$D_6$) δ10.808 (s, 1H), 8.767 (s, 1H), 7.980 (d, J=8.1 Hz, 1H), 7.889-7.818 (m, 2H), 7.777-7.543 (m, 1H), 7.477-7.385 (m, 4H), 7.324-7.152 (m, 6H), 5.643 (s, 1H), 5.261 (s, 1H), 4.569 (s, 2H)

Example 7

Compound #71

6-(bis(4-chlorophenyl)methyl)-4-(cyclohexylamino)quinolin-2(1H)-one

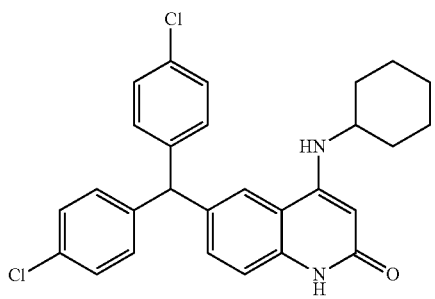 [SMILES: O=c1cc(NC2CCCCC2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 1,4-dioxane (3 mL), cyclohexanamine (48.5 mg, 0.49 mmol, 1.50 equip), $Pd_2(dba)_3$ (30 mg, 0.03 mmol, 0.10 equip), dppf (63.4 mg, 0.11 mmol, 0.35 equip), and $Cs_2CO_3$ (266 mg, 0.82 mmol, 2.50 equip). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with dichloromethane/methanol (20:1). The resulting residue was recrystallized from ethyl acetate:petroleum ether in the ratio of 1:10 to yield 6-(bis(4-chlorophenyl)methyl)-4-(cyclohexylamino)quinolin-2(1H)-one as an off-white solid.

(ES, m/z) 477 [M+H]$^+$; $^1$H-NMR (300 MHz, DMSO-$D_6$) δ10.681 (s, 1H), 7.958 (s, 1H), 7.380 (d, J=8.4 Hz, 4H), 7.181-7.077 (m, 6H), 6.392 (d, J=7.8 Hz, 1H), 5.601 (s, 1H), 5.291 (s, 1H), 1.969-1.938 (m, 2H), 1.761-1.621 (m, 3H), 1.391-1.217 (m, 6H)

Example 8

Compound #72

6-[(4-chlorophenyl)(6-chloropyridin-3-yl)methyl]-4-[[1-(trifluoromethane)sulfonylpiperidin-4-yl]amino]-1,2-dihydroquinolin-2-one

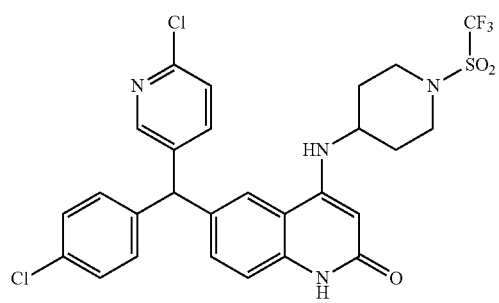 [SMILES: O=c1cc(NC2CCN(S(=O)(=O)C(F)(F)F)CC2)c2cc(C(c3ccc(Cl)cc3)c3ccc(Cl)nc3)ccc2[nH]1]

STEP 1: 2-(tert-butoxy)-6-[(4-chlorophenyl)carbonyl]-N-[1-(trifluoromethane)sulfonylpiperidin-4-yl]quinolin-4-amine Into a 500-mL flask purged and maintained with an inert atmosphere of nitrogen, was placed a solution of 4-bromo-2-(tert-butoxy)-6-[(4-chlorophenyl)carbonyl]quinoline (20 g, 47.77 mmol, 1.00 equip) in 1,4-dioxane (200 ml), 1-(trifluoromethane)sulfonylpiperidin-4-amine hydrochloride (22 g, 81.88 mmol, 1.70 equip), $Pd_2(dba)_3$ (4.92 g, 0.10 equip), dppf (9.2 g, 16.60 mmol, 0.35 equip), $Cs_2CO_3$ (38.8 g, 119.08 mmol, 2.50 equip), and KOt-Bu (9.6 g, 85.55 mmol, 1.80 equip). The resulting solution was stirred for 2 hr at 100° C. The reaction was then quenched by the addition of water (200 mL). The resulting solution was extracted with ethyl acetate (3×500 mL) and the organic layers combined. The resulting mixture was washed with water (2×300 mL) and brine (1×300 mL). The resulting mixture was dried over anhydrous sodium sulfate and concentrated under vacuum. The residue was applied onto a silica gel column with dichloromethane/methanol (20:1) to yield 2-(tert-butoxy)-6-[(4-chlorophenyl)carbonyl]-N-[1-(trifluoromethane)sulfonylpiperidin-4-yl]quinolin-4-amine as a yellow solid. LCMS (ES, m/z) 570 [M+H]$^+$ STEP 2: (2-(tert-butoxy)-4-((1-((trifluoromethyl)sulfonyl)piperidin-4-yl)amino)quinolin-6-yl)(4-chlorophenyl)(6-chloropyridin-3-yl)methanol Into a 25-mL 3-necked round-bottom flask purged and maintained with an inert atmosphere of nitrogen, was placed a solution of 5-bromo-2-chloropyridine (250 mg, 1.30 mmol, 3.00 equip) in tetrahydrofuran (10 mL). To the resulting mixture was then added n-BuLi (1.1 mL, 2.50 equip, 1M) dropwise with stirring at −78° C. The resulting solution was stirred for 0.5 h at −78° C. To this was added a solution of 2-(tert-butoxy)-6-[(4-chlorophenyl)carbonyl]-N-[1-(trifluoromethane)sulfonylpiperidin-4-yl]quinolin-4-amine (250 mg, 0.44 mmol, 1.00 equip) in tetrahydrofuran (5 mL) dropwise with stirring at −78° C. The resulting solution was allowed to react, with stirring, for an additional 0.5 h at −78° C. The resulting solution was allowed to react, with stirring, for an additional 2 h at room temperature. The reaction was then quenched by the addition of water (30 mL). The resulting solution was extracted with ethyl acetate (3×50 mL) and the organic layers combined. The resulting mixture was washed with water (2×30 mL) and brine (1×30 mL). The resulting mixture was dried over anhydrous sodium sulfate and concentrated under vacuum. The resulting residue was used in the next step without further purification. LCMS (ES, m/z) 683 [M+H]$^+$ STEP 3: 6-[(4-chlorophenyl)(6-chloropyridin-3-yl) methyl]-4-[[1-(trifluoromethane)sulfonylpiperidin-4-yl]amino]-1,2-dihydroquinolin-2-one Into a 25-mL 3-necked round-bottom flask purged and maintained with an inert atmosphere of nitrogen, was placed [2-(tert-butoxy)-4-[[1-(trifluoromethane)sulfonylpiperidin-4-yl]amino]quinolin-6-yl](4-chlorophenyl)(6-chloropyridin-3-yl)methanol (350 mg, 0.51 mmol, 1.00 equip), SnCl$_2$ (380 mg, 2.00 mmol, 4.00 equip), hydrogen chloride (1 mL, 37%), and AcOH (10 mL). The resulting solution was stirred for 1 h at 100° C. The pH value of the solution was adjusted to 8-9 with sodium bicarbonate. The resulting solution was extracted with ethyl acetate (3×100 mL) and the organic layers combined. The resulting mixture was washed with water (2×50 mL) and brine (1×50 mL). The resulting mixture was dried over anhydrous sodium sulfate and concentrated under vacuum. The residue was applied onto a silica gel column with DCM:MeOH (20:1). The product was recrystallized from ethyl acetate:n-hexane in the ratio of 1:5 to yield 6-[(4-chlorophenyl)(6-chloropyridin-3-yl)methyl]-4-[[1-(trifluoromethane)sulfonylpiperidin-4-yl]amino]-1,2-dihydroquinolin-2-one as a light-yellow solid.

(ES, m/z) 611 [M+H]$^+$; $^1$H-NMR (300 MHz, DMSO-D$_6$) δ10.791 (s, 1H), 8.225 (s, 1H), 7.900 (s, 1H), 7.607-7.572 (m, 1H), 7.500-7.472 (m, 1H), 7.419-7.391 (m, 2H), 7.223-7.139 (m, 4H), 6.528-6.502 (m, 1H), 5.686 (s, 1H), 5.479 (s, 1H), 3.877-3.832 (m, 2H), 3.721 (br, 1H), 3.434-3.395 (m, 2H), 2.094-2.053 (m, 2H), 1.638-1.531 (m, 2H).

Example 9

Compound #53

6-[(4-chlorophenyl)(3,4-dichlorophenyl)methyl]-4-[[1-(trifluoromethane)sulfonylpiperidin-4-yl]amino]-1,2-dihydroquinolin-2-one STEP 1: (2-tert-butoxy-4-(1-(trifluoromethylsulfonyl)piperidin-4-ylamino)quinolin-6-yl)(4-chlorophenyl)(3,4-dichlorophenyl)methanol Into a 25-mL round-bottom flask, was placed a solution of 2-(tert-butoxy)-6-[(4-chlorophenyl)carbonyl]-N-[1-(trifluoromethane)sulfonylpiperidin-4-yl]quinolin-4-amine (150 mg, 0.26 mmol, 1.00 equip) in tetrahydrofuran (15 ml). To the resulting mixture was then added (3,4-dichlorophenyl) magnesium bromide (2 mL, 8.00 equip) dropwise with stirring at 0° C. The resulting solution was stirred overnight at room temperature. The reaction was then quenched by the addition of water (30 mL). The resulting solution was extracted with ethyl acetate (3×50 mL) and the organic layers combined. The resulting mixture was washed with water (2×50 mL). The resulting mixture was washed with brine (1×50 mL). The resulting mixture was dried over sodium sulfate and concentrated under vacuum to yield (2-tert-butoxy-4-(1-(trifluoromethylsulfonyl)piperidin-4-ylamino)quinolin-6-yl)(4-chlorophenyl)(3,4-dichlorophenyl)methanol as a yellow oil. (ES, m/z) 718 [M+H]

STEP 2: 6-[(4-chlorophenyl)(3,4-dichlorophenyl) methyl]-4-[[1-(trifluoromethane)sulfonylpiperidin-4-yl]amino]-1,2-dihydroquinolin-2-one Into a 25-mL round-bottom flask, was placed a solution of [2-(tert-butoxy)-4-[[1-(trifluoromethane)sulfonylpiperidin-4-yl]amino]quinolin-6-yl](4-chlorophenyl)(3,4-dichlorophenyl)methanol (200 mg, 0.28 mmol, 1.00 equip) in dichloromethane (15 ml), Et$_3$SiH (130 mg, 1.12 mmol, 4.02 equip), and trifluoroacetic acid (850 mg, 7.52 mmol, 26.96 equip). The resulting solution was stirred overnight at room temperature. The pH value of the solution was adjusted to 8-9 with sodium bicarbonate. The resulting solution was extracted with ethyl acetate (3×50 mL) and the organic layers combined. The resulting mixture was washed with water (2×50 mL). The resulting mixture was washed with brine (1×50 mL). The resulting mixture was dried over sodium sulfate and concentrated under vacuum. The residue was applied onto a silica gel column with dichloromethane/methanol (30:1) to yield 6-[(4-chlorophenyl)(3,4-dichlorophenyl)methyl]-4-[[1-(trifluoromethane)sulfonylpiperidin-4-yl]amino]-1,2-dihydroquinolin-2-one as a white solid.

(ES, m/z) 646 [M+H]$^+$; $^1$H-NMR (300 MHz, DMSO-D$_6$) δ10.790 (s, 1H), 7.900 (s, 1H), 7.591 (d, J=8.4 Hz, 1H), 7.348-7.414 (m, 3H), 7.084-7.215 (m, 5H), 6.526 (d, J=7.5 Hz, 1H), 5.649 (s, 1H), 5.475 (s, 1H), 3.829-3.873 (m, 2H), 3.731 (br, 1H), 3.347-3.433 (m, 2H), 2.052-2.089 (m, 2H), 1.534-1.639 (m, 2H)

Example 10

Compound #54

6-((4-chlorophenyl)(4-methoxyphenyl)methyl)-4-((1-((trifluoromethyl)sulfonyl)piperidin-4-yl)amino) quinolin-2(1H)-one

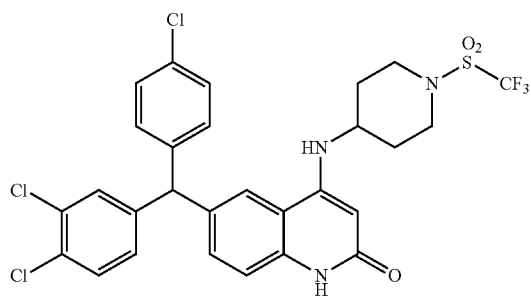 [SMILES: O=c1cc(NC2CCN(S(=O)(=O)C(F)(F)F)CC2)c2cc(C(c3ccc(Cl)cc3)c3ccc(Cl)c(Cl)c3)ccc2[nH]1]

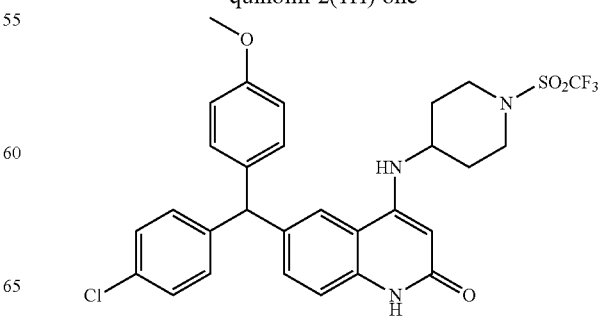

STEP 1: (2-tert-butoxy-4-(1-(trifluoromethylsulfonyl)piperidin-4-ylamino)quinolin-6-yl)(4-chlorophenyl)(4-methoxyphenyl)methanol Into a 25-mL round-bottom flask, was placed a solution of 2-(tert-butoxy)-6-[(4-chlorophenyl)carbonyl]-N-[1-(trifluoromethane)sulfonylpiperidin-4-yl]quinolin-4-amine (300 g, 526.29 mmol, 1.00 equip) in tetrahydrofuran (15 ml). To the resulting mixture was then added (4-methoxyphenyl)magnesium bromide (2 mL, 4.00 equip) dropwise with stirring at 0° C. The resulting solution was stirred overnight at room temperature. The reaction was then quenched by the addition of water (30 mL). The resulting solution was extracted with ethyl acetate (3×50 mL) and the organic layers combined. The resulting mixture was washed with water (2×50 mL). The resulting mixture was washed with saturated brine (1×50 mL). The resulting mixture was dried over sodium sulfate and concentrated under vacuum to yield [2-(tert-butoxy)-4-[[1-(trifluoromethane)sulfonylpiperidin-4-yl]amino]quinolin-6-yl](4-chlorophenyl)(4-methoxyphenyl)methanol as a yellow solid. (ES, m/z): [M+H]+ 678

STEP 2: 6-((4-chlorophenyl)(4-methoxyphenyl)methyl)-4-((1-((trifluoromethyl)sulfonyl)piperidin-4-yl)amino)quinolin-2(1H)-one Into a 25-mL round-bottom flask, was placed a solution of [2-(tert-butoxy)-4-[[1-(trifluoromethane)sulfonylpiperidin-4-yl]amino]quinolin-6-yl](4-chlorophenyl)(4-methoxyphenyl)methanol (200 mg, 0.29 mmol, 1.00 equip) in dichloromethane (15 ml), Et₃SiH (840 mg, 25.00 equip), and trifluoroacetic acid (137 mg, 1.21 mmol, 4.00 equip). The resulting solution was stirred overnight at room temperature. The pH value of the solution was adjusted to 8-9 with NaHCO₃ (sat.). The resulting solution was extracted with ethyl acetate (3×50 mL) and the organic layers combined. The resulting mixture was washed with water (2×50 mL). The resulting mixture was washed with brine (1×50 mL). The resulting mixture was dried over sodium sulfate and concentrated under vacuum. The residue was applied onto a silica gel column with dichloromethane/methanol (30:1) to yield 6-((4-chlorophenyl)(4-methoxyphenyl)methyl)-4-((1-((trifluoromethyl)sulfonyl)piperidin-4-yl)amino)quinolin-2(1H)-one as a white solid.

(ES, m/z): [M+H]+606; ¹H-NMR (300 MHz, DMSO-D₆) δ10.756 (s, 1H), 7.914 (s, 1H), 7.372 (d, J=8.4 Hz, 2H), 7.194-7.007 (m, 6H), 6.887 (d, J=8.7 Hz, 2H), 6.536 (d, J=7.2 Hz, 1H), 5.538 (s, 1H), 5.470 (s, 1H), 3.878-3.837 (m, 2H), 3.600-3.800 (m, 4H), 3.439-3.351 (m, 2H), 2.094-2.056 (m, 2H), 1.614-1.582 (m, 2H)

Example 11

Compound #51

6-[(4-chlorophenyl)(hydroxy)(4-methoxyphenyl)methyl]-4-[[1-(trifluoromethane)sulfonylpiperidin-4-yl]amino]-1,2-dihydroquinolin-2-one

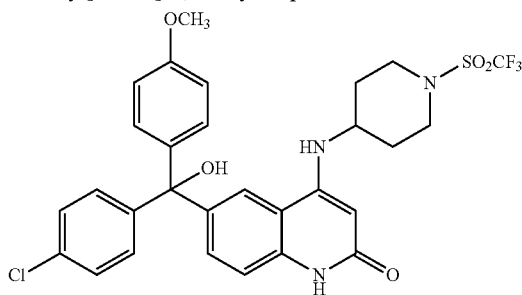

Into a 25-mL round-bottom flask, was placed a solution of [2-(tert-butoxy)-4-[[1-(trifluoromethane)sulfonylpiperidin-4-yl]amino]quinolin-6-yl](4-chlorophenyl)(4-methoxyphenyl)methanol (400 mg, 0.59 mmol, 1.00 equip) in dichloromethane (10 ml), and trifluoroacetic acid (1 mL, 10.00 equip). The resulting solution was stirred overnight at room temperature. The reaction was then quenched by the addition of water (30 mL). The resulting solution was extracted with ethyl acetate (3×50 mL) and the organic layers combined. The resulting mixture was washed with water (2×50 mL). The resulting mixture was washed with brine (1×50 mL). The resulting mixture was dried over sodium sulfate and concentrated under vacuum. The residue was applied onto a silica gel column with dichloromethane/methanol (30:1) to yield 6-[(4-chlorophenyl)(hydroxy)(4-methoxyphenyl)methyl]-4-[[1-(trifluoromethane)sulfonylpiperidin-4-yl]amino]-1,2-dihydroquinolin-2-one as a white solid.

(ES, m/z) 622 [M+H]+; ¹H-NMR (300 MHz, DMSO-D₆) δ10.741 (s, 1H), 8.111 (s, 1H), 7.348-7.377 (m, 2H), 7.217-7.246 (d, J=9.3 Hz, 2H), 7.003-7.117 (m, 4H), 6.867 (d, J=8.7 Hz, 2H), 6.582 (d, J=8.1 Hz, 1H), 6.409 (s, 1H), 5.472 (s, 1H), 3.843 (d, J=12.6 Hz, 2H), 3.700-3.820 (m, 1H), 3.735 (s, 3H), 3.388-3.429 (m, 2H), 2.040 (d, J=12.6 Hz, 2H), 1.589-1.700 (m, 2H)

Example 12

Compound #57

6-(bis(4-chlorophenyl)methyl)-4-((1-(pyrimidin-2-yl)piperidin-4-yl)amino)quinolin-2(1H)-one

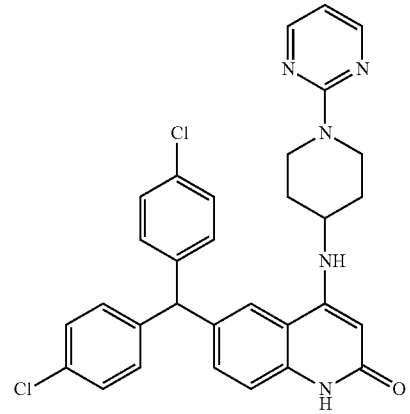 [SMILES: O=c1cc(NC2CCN(c3ncccn3)CC2)c2cc(C(c3ccc(Cl)cc3)c3ccc(Cl)cc3)ccc2[nH]1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 1-(pyrimidin-2-yl)piperidin-4-amine dihydrochloride (122.5 mg, 0.49 mmol, 1.49 equip), Pd₂(dba)₃ (30 mg, 0.03 mmol, 0.10 equip), dppf (63.4 mg, 0.11 mmol, 0.35 equip), Cs₂CO₃ (266 mg, 0.82 mmol, 2.50 equip), KOt-Bu (73 mg, 0.65 mmol, 2.00 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield 6-[bis(4-chlorophenyl)methyl]-4-[[1-(pyrimidin-2-yl)piperidin-4-yl]amino]quinolin-2-ol as a white solid.

(ES, m/z) 556 [M+H]+; 1H-NMR (300 MHz, DMSO-D6) δ10.746 (s, 1H), 8.385 (d, J=4.5 Hz, 2H), 7.925 (s, 1H), 7.375-7.403 (m, 4H), 7.212-7.117 (m, 6H), 6.642-6.611 (m, 1H), 6.454 (d, J=7.8 Hz, 1H), 5.598 (s, 1H), 5.484 (s, 1H), 4.715-4.671 (m, 2H), 3.755 (br, 1H), 3.126-3.043 (m, 2H), 2.020-1.983 (d, J=11.1 Hz, 2H), 1.539-1.470 (m, 2H)

Example 13

Compound #56

6-(bis(4-chlorophenyl)methyl)-4-((1-(ethylsulfonyl) piperidin-4-yl)amino)quinolin-2(1H)-one

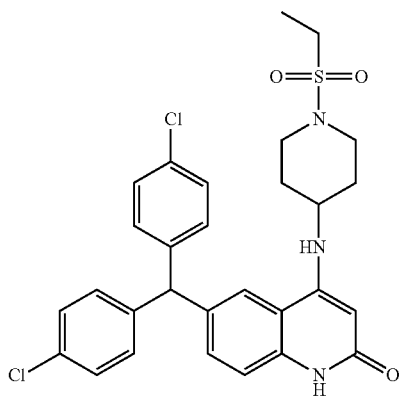 [SMILES: CCS(=O)(=O)N1CCC(Nc2cc(=O)[nH]c3ccc(C(c4ccc(Cl)cc4)c4ccc(Cl)cc4)cc23)CC1]

Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 1-(ethanesulfonyl)piperidin-4-amine (94.12 mg, 0.49 mmol, 1.50 equip), Pd2(dba)3 (30 mg, 0.03 mmol, 0.10 equip), dppf (63.4 mg, 0.11 mmol, 0.35 equip), Cs2CO3 (266 mg, 0.82 mmol, 2.50 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield 6-[bis(4-chlorophenyl)methyl]-4-[[1-(ethanesulfonyl)piperidin-4-yl]amino]quinolin-2-ol as an off-white solid.

(ES, m/z) 570 [M+H]+; 1H-NMR (300 MHz, DMSO-D6) δ10.740 (s, 1H), 7.934 (s, 1H), 7.389 5 (d, J=8.4 Hz, 4H), 7.200-7.099 (m, 6H), 6.499 (d, J=7.5 Hz, 6H), 5.614 (s, 1H), 5.417 (s, 1H), 3.672-3.588 (m, 3H), 3.109-2.963 (m, 4H), 2.019-1.985 (m, 2H), 1.616-1.539 (m, 2H), 1.253 (t, J=7.5 Hz, 3H)

Example 14

Compound #77

6-(bis(4-chlorophenyl)methyl)-4-((1-(2,2,2-trifluoroethyl)piperidin-4-yl)amino)quinolin-2(1H)-one

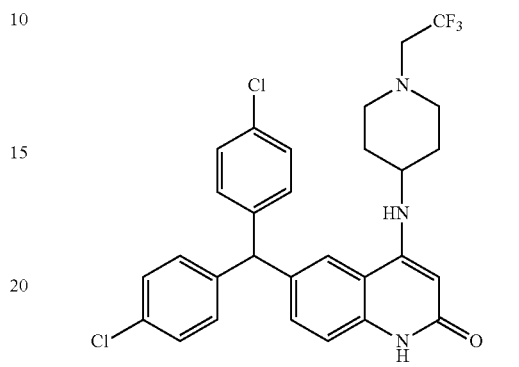

STEP 1: tert-butyl N-[1-(2,2,2-trifluoroethyl)piperidin-4-yl]carbamate

Into a 50-mL 3-necked round-bottom flask, was placed tert-butyl N-(piperidin-4-yl)carbamate (2 g, 9.99 mmol, 1.00 equip), tetrahydrofuran (20 mL), To this was added sodium hydride (480 mg, 20.00 mmol, 2.00 equip) at 0° C. The resulting solution was stirred for 0.5 h at 0° C., and 2,2,2-trifluoroethyl trifluoromethanesulfonate (2.784 g, 11.99 mmol, 1.20 equip) was added. The resulting solution was stirred for 2 h at 0° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum to yield tert-butyl N-[1-(2,2,2-trifluoroethyl)piperidin-4-yl]carbamate as yellow oil. LCMS (ES, m/z) 283 [M+H]+

STEP 2: 1-(2,2,2-trifluoroethyl)piperidin-4-amine 2,2,2-trifluoroacetate

Into a 50-mL round-bottom flask, was placed tert-butyl N-[1-(2,2,2-trifluoroethyl)piperidin-4-yl]carbamate (2.0 g, 7.08 mmol, 1.00 equip), dichloromethane (20 mL), and CF3COOH (4 mL). The resulting solution was stirred overnight at room temperature. The resulting mixture was concentrated under vacuum to yield 1-(2,2,2-trifluoroethyl) piperidin-4-amine 2,2,2-trifluoroacetate as a yellow oil. (ES, m/z) 183 [M+H]+

STEP 3: 6-[bis(4-chlorophenyl)methyl]-4-[[1-(2,2,2-trifluoroethyl)piperidin-4-yl]amino]quinolin-2-ol Into a 8-mL round-bottom flask purged and maintained with an inert atmosphere of nitrogen, was placed 6-[bis(4-chlorophenyl)methyl]-4-bromoquinolin-2-ol (200 mg, 0.44 mmol, 1.00 equip), 1,4-dioxane (5 mL), 1-(2,2,2-trifluoroethyl)piperidin-4-amine 2,2,2-trifluoroacetate (193 mg, 0.65 mmol, 1.50 equip), Pd2(dba)3 (40 mg, 0.04 mmol, 0.10 equip), dppf (84.5 mg, 0.15 mmol, 0.35 equip), Cs2CO3 (355 mg, 1.09 mmol, 2.50 equip), and KOt-Bu (97.6 mg, 0.87 mmol, 2.00 equip). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were removed by filtration. The filtrate was concentrated under vacuum. The residue was applied onto a silica gel column with dichloromethane/methanol (20:1). The resulting residue was recrystallized from ethyl acetate: petroleum ether in the ratio of 1:10 to yield 6-[bis(4-chlorophenyl)methyl]-4-[[1-(2,2,2-trifluoroethyl)piperidin-4-yl]amino]quinolin-2-ol as a white solid.

(ES, m/z) 560 [M+H]$^+$, $^1$H-NMR (400 MHz, DMSO-D$_6$) δ10.712 (s, 1H), 7.929 (s, 1H), 7.388 (d, J=8.4 Hz, 4H), 7.189-7.106 (m, 6H), 6.404 (d, J=7.6 Hz, 1H), 5.612 (s, 1H), 5.343 (s, 1H), 3.290 (br, 1H), 3.219-3.142 (m, 2H), 2.950-2.922 (m, 2H), 2.470-2.500 (m, 2H), 1.912-1.884 (m, 2H), 1.635-1.583 (m, 2H)

Example 15

Compound #66

6-((4-chlorophenyl)(4-hydroxyphenyl)methyl)-4-((1-((trifluoromethyl)sulfonyl)piperidin-4-yl)amino)quinolin-2(1H)-one

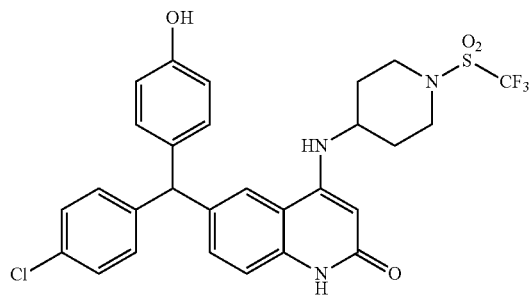 [SMILES: O=c1cc(NC2CCN(S(=O)(=O)C(F)(F)F)CC2)c2cc(C(c3ccc(O)cc3)c3ccc(Cl)cc3)ccc2[nH]1]

Into a 25-mL round-bottom flask, was placed a solution of 6-[(4-chlorophenyl)(4-methoxyphenyl)methyl]-4-[[1-(trifluoromethane)sulfonylpiperidin-4-yl]amino]-1,2-dihydroquinolin-2-one (120 mg, 0.20 mmol, 1.00 equip) in dichloromethane (10 ml), and BBr$_3$ (60 g, 1.20 equip) was added. The resulting solution was stirred overnight at room temperature. The pH value of the solution was adjusted to 8-9 with sodium bicarbonate. The resulting solution was extracted with ethyl acetate (3×50 mL) and the organic layers combined. The resulting mixture was washed with water (2×50 mL) and with brine (1×50 mL). The resulting mixture was dried over sodium sulfate and concentrated under vacuum. The residue was applied onto a silica gel column with dichloromethane/methanol (20:1) to yield 6-[(4-chlorophenyl)(4-hydroxyphenyl)methyl]-4-[[1-(trifluoromethane)sulfonylpiperidin-4-yl]amino]-1,2-dihydroquinolin-2-one as a yellow solid.

(ES, m/z) 592 [M+H]$^+$, $^1$H-NMR (300 MHz, DMSO-D$_6$) δ10.734 (s, 1H), 9.312 (s, 1H), 7.894 (s, 1H), 7.352 (d, J=8.7 Hz, 2H), 7.180-7.082 (m, 4H), 6.887 (d, J=8.4 Hz, 2H), 6.693 (d, J=8.4 Hz, 2H), 6.525 (d, J=7.5 Hz, 1H), 5.466 (s, 2H), 3.874-3.723 (m, 3H), 3.430-3.389 (m, 2H), 2.086-2.047 (m, 2H), 1.647-1.540 (m, 2H)

Example 16

Compound #81

6-(bis(4-chlorophenyl)methyl)-4-((1-(pyrrolidin-1-ylsulfonyl)piperidin-4-yl)amino)quinolin-2(1H)-one

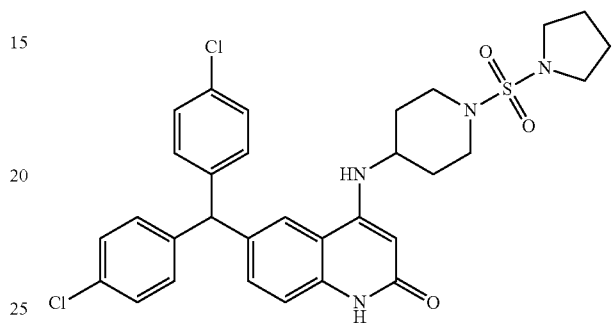

STEP 1: tert-butyl 4-([6-[bis(4-chlorophenyl)methyl]-2-hydroxyquinolin-4-yl]amino)piperidine-1-carboxylate Into a 50-mL round-bottom flask purged and maintained with an inert atmosphere of nitrogen, was placed 6-[bis(4-chlorophenyl)methyl]-4-bromoquinolin-2-ol (500 mg, 1.09 mmol, 1.00 equip), tert-butyl 4-aminopiperidine-1-carboxylate (326.8 mg, 1.63 mmol, 1.50 equip), Pd$_2$(dba)$_3$ (99.8 mg, 0.11 mmol, 0.10 equip), dppf (211 mg, 0.38 mmol, 0.35 equip), Cs$_2$CO$_3$ (882.35 mg, 2.71 mmol, 2.50 equip), and 1,4-dioxane (10 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield tert-butyl 4-([6-[bis(4-chlorophenyl)methyl]-2-hydroxyquinolin-4-yl]amino)piperidine-1-carboxylate as an off-white solid. (ES, m/z) 578 [M+H]$^+$ STEP 2: 6-[bis(4-chlorophenyl)methyl]-4-[(piperidin-4-yl)amino]quinolin-2-ol Into a 25-mL round-bottom flask, was placed tert-butyl 4-([6-[bis(4-chlorophenyl)methyl]-2-hydroxyquinolin-4-yl]amino)piperidine-1-carboxylate (570 mg, 0.99 mmol, 1.00 equip), dichloromethane (8 mL), and CF$_3$COOH (2 mL). The resulting solution was stirred for 2 h at room temperature. The resulting mixture was concentrated under vacuum. The resulting residue was recrystallized from ethyl acetate: petroleum ether in the ratio of 1:10 to yield 6-[bis(4-chlorophenyl)methyl]-4-[(piperidin-4-yl)amino]quinolin-2-ol as an off-white solid. LCMS-(ES, m/z) 478 [M+H]$^+$

STEP 3: 6-[bis(4-chlorophenyl)methyl]-4-[[1-(pyrrolidine-1-sulfonyl)piperidin-4-yl]amino]quinolin-2-ol Into a 8-mL round-bottom flask, was placed 6-[bis(4-chlorophenyl)methyl]-4-[(piperidin-4-yl)amino]quinolin-2-ol (70 mg, 0.15 mmol, 1.00 equip), dichloromethane (3 mL), pyrrolidine-1-sulfonyl chloride (37.2 mg, 0.22 mmol, 1.50 equip), and triethylamine (44.6 mg, 0.44 mmol, 3.01 equip). The resulting solution was stirred for 2 h at room temperature. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield 6-[bis(4-chlorophenyl)methyl]-4-[[1-(pyrrolidine-1-sulfonyl)piperidin-4-yl]amino]quinolin-2-ol as an off-white solid.

LCMS (ES, m/z) 611 [M+H]$^+$, $^1$H-NMR (300 MHz, DMSO-D$_6$) δ10.736 (s, 1H), 7.937 (s, 1H), 7.378 (d, J=8.4 Hz, 4H), 7.094-7.196 (m, 6H), 6.485 (d, J=7.5 Hz, 1H), 5.604 (s, 1H), 5.422 (s, 1H), 3.586-3.628 (m, 3H), 3.214 (t, J=6.6 Hz, 4H), 2.938-3.014 (m, 2H), 1.973 (d, J=11.4 Hz), 1.847 (t, J=6.6 Hz, 4H), 1.510-1.615 (m, 2H)

Example 17

Compound #64

4-((1-benzoylpiperidin-4-yl)amino)-6-(bis(4-chlorophenyl)methyl)quinolin-2(1H)-one

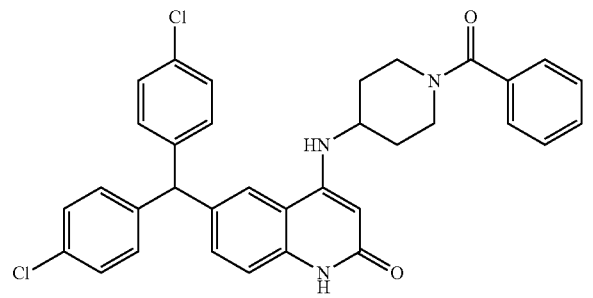 [SMILES: O=C(c1ccccc1)N1CCC(Nc2cc(=O)[nH]c3ccc(C(c4ccc(Cl)cc4)c4ccc(Cl)cc4)cc23)CC1]

STEP 1: tert-butyl N-(1-benzoylpiperidin-4-yl)carbamate

Into a 50-mL round-bottom flask, was placed tert-butyl N-(piperidin-4-yl)carbamate (2 g, 9.99 mmol, 1.20 equip), dichloromethane (20 mL) and triethylamine (2.53 g, 25.00 mmol, 3.00 equip). To the resulting mixture was then slowly added benzoyl chloride (1.17 g, 8.32 mmol, 1.00 equip). The resulting solution was stirred for 2 h at room temperature. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum to yield tert-butyl N-(1-benzoylpiperidin-4-yl)carbamate as a white solid. (ES, m/z) 305 [M+H]$^+$

STEP 2: 1-benzoylpiperidin-4-amine; trifluoroacetic acid salt

Into a 50-mL round-bottom flask, was placed tert-butyl N-(1-benzoylpiperidin-4-yl)carbamate (2.6 g, 8.54 mmol, 1.00 equip), dichloromethane (20 mL), and CF$_3$COOH (5 mL). The resulting solution was stirred overnight at room temperature. The resulting mixture was concentrated under vacuum to yield 1-benzoylpiperidin-4-amine, trifluoroacetic acid salt as a yellow oil. LCMS (ES, m/z) 205 [M+H]$^+$

STEP 3: 4-[(1-benzoylpiperidin-4-yl)aminol-6-[bis(4-chlorophenyl)methyl]]quinolin-2-ol Into a 8-mL round-bottom flask purged and maintained with an inert atmosphere of nitrogen, was placed 6-[bis(4-chlorophenyl)methyl]-4-bromoquinolin-2-ol (150 mg, 0.33 mmol, 1.00 equip), 1-benzoylpiperidin-4-amine hydrochloride (118 mg, 0.49 mmol, 1.50 equip), Pd$_2$(dba)$_3$ (30.0 mg, 0.03 mmol, 0.10 equip), dppf (63.4 mg, 0.11 mmol, 0.35 equip), Cs$_2$CO$_3$ (266 mg, 0.82 mmol, 2.50 equip), KOt-Bu (73 mg, 0.65 mmol, 2.00 equip), and 1,4-dioxane (3 mL). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were removed by filtration. The filtrate was concentrated under vacuum. The residue was applied onto a silica gel column with dichloromethane/methanol (20:1). The resulting residue was recrystallized from ethyl acetate:petroleum ether in the ratio of 1:10 to yield 4-[(1-benzoylpiperidin-4-yl)amino]-6-[bis(4-chlorophenyl)methyl]quinolin-2-ol as an off-white solid.

LCMS (ES, m/z) 582 [M+H]$^+$, $^1$H-NMR (300 MHz, DMSO-D$_6$) δ10.744 (s, 1H), 7.937 (s, 1H), 7.486-7.465 (m, 3H), 7.414-7.377 (m, 6H), 7.210-7.109 (m, 6H), 6.472 (d, J=7.5 Hz, 1H), 5.619 (s, 1H), 5.465 (s, 1H), 4.495 (br, 1H), 3.738 (br, 1H), 3.612 (brs, 1H), 3.230 (br, 1H), 2.985 (br, 1H), 2.006-1.925 (m, 1H), 1.600-1.450 (br, 1H)

Example 18

Compound #136

6-[4-chlorophenoxy(4-chlorophenyl)methyl]-4-[[1-(trifluoromethane)sulfonylpiperidin-4-yl]amino]-1,2-dihydroquinolin-2-one

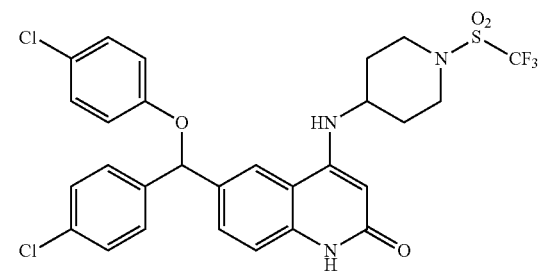 [SMILES: O=c1cc(NC2CCN(S(=O)(=O)C(F)(F)F)CC2)c2cc(C(Oc3ccc(Cl)cc3)c3ccc(Cl)cc3)ccc2[nH]1]

STEP 1: [2-(tert-butoxy)-4-[[1-(trifluoromethane)sulfonylpiperidin-4-yl]amino]quinolin-6-yl](4-chlorophenyl)methanol Into a 100-mL round-bottom flask, was placed a solution of 2-(tert-butoxy)-6-[(4-chlorophenyl)carbonyl]-N-[1-(trifluoromethane)sulfonylpiperidin-4-yl]quinolin-4-amine (1.14 g, 2.00 mmol, 1.00 equip) in methanol (40 ml), and NaBH₄ (60 mg, 1.59 mmol, 1.50 equip) was added. The resulting solution was stirred for 2 h at room temperature. The reaction was then quenched by the addition of water (50 mL). The resulting solution was extracted with ethyl acetate (3×100 mL) and the organic layers combined. The resulting mixture was washed with water (2×50 mL). The resulting mixture was washed with brine (1×50 mL). The resulting mixture was dried over sodium sulfate and concentrated under vacuum to yield [2-(tert-butoxy)-4-[[1-(trifluoromethane)sulfonylpiperidin-4-yl]amino]quinolin-6-yl](4-chlorophenyl)methanol as a light yellow solid. LCMS (ES, m/z) 572 [M+H]⁺

STEP 2: 2-(tert-butoxy)-6-((4-chlorophenoxy)(4-chlorophenyl)methyl)-N-(1-((trifluoromethyl)sulfonyl)piperidin-4-yl)quinolin-4-amine Into a 25-mL round-bottom flask, was placed a solution of [2-(tert-butoxy)-4-[[1-(trifluoromethane)sulfonylpiperidin-4-yl]amino]quinolin-6-yl](4-chlorophenyl)methanol (250 mg, 0.44 mmol, 1.00 equip) in dichloromethane (6 ml), 4-chlorophenol (60 mg, 0.47 mmol, 1.10 equip), PPh₃ (150 mg, 1.30 equip), and DEAD (100 mg, 0.57 mmol, 1.30 equip). The resulting solution was stirred for 3 h at room temperature. The reaction was then quenched by the addition of water (30 mL). The resulting solution was extracted with ethyl acetate (3×50 mL) and the organic layers combined. The resulting mixture was washed with water (2×30 mL). The resulting mixture was washed with brine (1×30 mL). The resulting mixture was dried over sodium sulfate and concentrated under vacuum and the resulting residue was used in the next step directly. LCMS (ES, m/z) 682 [M+H]⁺

STEP 3: 6-[4-chlorophenoxy(4-chlorophenyl)methyl]-4-[[1-(trifluoromethane)sulfonylpiperidin-4-yl]amino]-1,2-dihydroquinolin-2-one Into a 25-mL round-bottom flask, was placed 2-(tert-butoxy)-6-[4-chlorophenoxy(4-chlorophenyl)methyl]-N-[1-(trifluoromethane)sulfonylpiperidin-4-yl]quinolin-4-amine (250 mg, 0.37 mmol, 1.00 equip), dichloromethane (10 mL), and trifluoroacetic acid (1 mL). The resulting solution was stirred overnight at room temperature. The resulting solution was extracted with ethyl acetate (3×50 mL) and the organic layers combined. The resulting mixture was washed with water (2×30 mL). The resulting mixture was washed with saturated brine (1×30 mL). The resulting mixture was dried over sodium sulfate and concentrated under vacuum. The residue was applied onto a silica gel column with dichloromethane/methanol (20:1) to yield 6-[4-chlorophenoxy(4-chlorophenyl)methyl]-4-[[1-(trifluoromethane)sulfonylpiperidin-4-yl]amino]-1,2-dihydroquinolin-2-one as a white solid.

LCMS (ES, m/z) 626 [M+H]⁺, H-NMR (300 MHz, DMSO) δ 10.749 (s, 1H), 8.069 (s, 1H), 7.443-7.379 (m, 5H), 7.239-7.210 (m, 2H), 7.143-7.114 (m, 1H), 6.973-6.945 (m, 2H), 6.557-6.531 (m, 1H), 6.384 (s, 1H), 5.417 (s, 1H), 3.838-3.788 (m, 2H), 3.684 (br, 1H), 3.460-3.360 (m, 2H), 2.034-1.918 (m, 2H), 1.587-1.549 (m, 2H).

Example 19

Compound #135

6-(1-(4-chlorophenyl)-2-(4-fluorophenyl)ethyl)-4-((1-((trifluoromethyl)sulfonyl)piperidin-4-yl)amino)quinolin-2(1H)-one

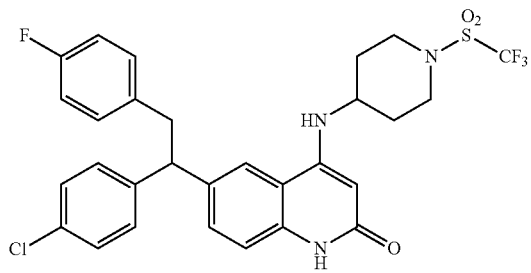 [SMILES: O=c1cc(NC2CCN(S(=O)(=O)C(F)(F)F)CC2)c2cc(C(Cc3ccc(F)cc3)c3ccc(Cl)cc3)ccc2[nH]1]

STEP 1: 1-(2-(tert-butoxy)-4-((1-((trifluoromethyl)sulfonyl)piperidin-4-yl)amino)quinolin-6-yl)-1-(4-chlorophenyl)-2-(4-fluorophenyl)ethanol Into a 25-mL round-bottom flask, was placed a solution of 2-(tert-butoxy)-6-[(4-chlorophenyl)carbonyl]-N-[1-(trifluoromethane)sulfonylpiperidin-4-yl]quinolin-4-amine (150 mg, 0.26 mmol, 1.00 equip) in tetrahydrofuran (10 ml). To the resulting mixture was then added [(4-fluorophenyl)methyl]magnesium bromide (2 mL, 8.00 equip) dropwise with stirring at 0° C. The resulting solution was stirred overnight at room temperature. The reaction was then quenched by the addition of water (30 mL). The resulting solution was extracted with ethyl acetate (3×50 mL) and the organic layers combined. The resulting mixture was washed with water (2×50 mL) and brine (1×50 mL). The resulting mixture was dried over sodium sulfate and concentrated under vacuum. The resulting residue was used in the next step without further purification. LCMS (ES, m/z) 680 [M+H]⁺

STEP 2: (E)-6-(1-(4-chlorophenyl)-2-(4-fluorophenyl)vinyl)-4-((1-((trifluoromethyl)sulfonyl)piperidin-4-yl)amino)quinolin-2(1H)-one Into a 25-mL round-bottom flask, was placed a solution of 1-[2-(tert-butoxy)-4-[[1-(trifluoromethane)sulfonylpiperidin-4-yl]amino]quinolin-6-yl]-1-(4-chlorophenyl)-2-(4-fluorophenyl)ethan-1-ol (150 mg, 0.22 mmol, 1.00 equip) in dichloromethane (15 ml), Et₃SiH (100 mg, 4.00 equip), and trifluoroacetic acid (600 mg, 5.31 mmol, 25.00 equip). The resulting solution was stirred for 3 h at room temperature. The pH value of the solution was adjusted to 8-9 with sodium bicarbonate. The resulting solution was extracted with ethyl acetate (3×50 mL) and the organic layers combined. The resulting mixture was washed with water (2×50 mL) and brine (1×50 mL). The resulting mixture was dried over sodium sulfate and concentrated under vacuum. The residue was applied onto a silica gel column with dichloromethane/methanol (30:1) to yield a white solid. LCMS (ES, m/z) 606 [M+H]⁺

STEP 3: 6-(1-(4-chlorophenyl)-2-(4-fluorophenyl)ethyl)-4-((1-((trifluoromethyl)sulfonyl)piperidin-4-yl)amino)quinolin-2(1H)-one In an evacuated 25-mL round-bottom flask was placed a solution of 6-[(E)-1-(4-chlorophenyl)-2-(4-fluorophenyl)

ethenyl]-4-[[1-(trifluoromethane)sulfonylpiperidin-4-yl] amino]-1,2-dihydroquinolin-2-one (150 mg, 0.25 mmol, 1.00 equip) in methanol (15 ml), PtO₂ (150 mg), and the flask was charged with an atmosphere of H₂. The resulting solution was stirred overnight at room temperature. The solids were filtered out. The residue was applied onto a silica gel column with dichloromethane/methanol (20:1) to yield 6-[1-(4-chlorophenyl)-2-(4-fluorophenyl)ethyl]-4-[[1-(trifluoromethane)sulfonylpiperidin-4-yl]amino]-1,2-dihydroquinolin-2-one as a white solid.

LCMS (ES, m/z) 608 [M+H]⁺, H-NMR (400 MHz, DMSO) δ10.704 (s, 1H), 7.920 (s, 1H), 7.437 (d, J=8.4 Hz, 1H), 7.390-7.270 (m, 4H), 7.198-7.119 (m, 3H), 7.023-6.980 (m, 2H), 6.520 (d, J=7.6 Hz, 1H), 5.457 (s, 1H), 4.337-4.298 (m, 1H), 3.907-3.876 (m, 2H), 3.762 (br, 1H), 3.475-3.306 (m, 4H), 2.134-2.104 (m, 2H), 1.655-1.626 (m, 2H).

Example 20

Compound #49

6-[bis(4-chlorophenyl)methyl]-1-methyl-4-[[1-(trifluoromethane)sulfonylpiperidin-4-yl]amino]-1,2-dihydroquinolin-2-one

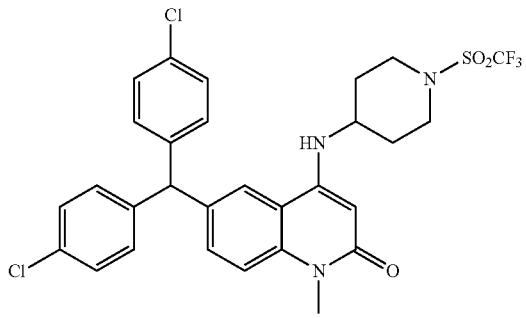

STEP 1: 6-[bis(4-chlorophenyl)methyl]-4-bromo-1-methyl-1,2-dihydroquinolin-2-one Into a 50-mL round-bottom flask, was placed a solution of 6-[bis(4-chlorophenyl)methyl]-4-bromo-1,2-dihydroquinolin-2-one (700 mg, 1.52 mmol, 1.00 equip) in N,N-dimethylformamide (15 mL), potassium carbonate (630 mg, 4.56 mmol, 3.00 equip), and CH₃I (0.33 g, 1.50 equip). The resulting solution was stirred for 1 h at room temperature. The reaction was then quenched by the addition of water (30 mL). The resulting solution was extracted with ethyl acetate (3×50 mL) and the organic layers combined. The resulting mixture was washed with water (2×50 mL) and saturated brine (1×50 mL). The resulting mixture was concentrated under vacuum. The residue was applied onto a silica gel column with ethyl acetate/petroleum ether (1:10) to yield 6-[bis(4-chlorophenyl)methyl]-4-bromo-1-methyl-1,2-dihydroquinolin-2-one as a yellow solid. (ES, m/z): [M+H]⁺ 474

STEP 2: 6-(bis(4-chlorophenyl)methyl)-1-methyl-4-((1-(((trifluoromethyl)sulfonyl)piperidin-4-yl)amino)quinolin-2(1H)-one Into a 20-mL vial purged and maintained with an inert atmosphere of nitrogen, was placed a solution of 6-[bis(4-chlorophenyl)methyl]-4-bromo-1-methyl-1,2-dihydroquinolin-2-one (120 mg, 0.25 mmol, 1.00 equip) in 1,4-dioxane (2 ml), 1-(trifluoromethane)sulfonylpiperidin-4-amine hydrochloride (114 mg, 0.42 mmol, 1.70 equip), Pd(dba)₃ (23 mg, 0.10 equip), dppf (48 mg, 0.09 mmol, 0.35 equip), Cs₂CO₃ (204 mg, 0.63 mmol, 2.50 equip), and KOt-Bu (50 mg, 0.45 mmol, 1.80 equip). The resulting solution was stirred overnight at 100° C. The reaction was then quenched by the addition of water (20 mL). The resulting solution was extracted with ethyl acetate (3×50 mL) and the organic layers combined. The resulting mixture was washed with water (2×50 mL) and brine (1×50 mL). The resulting mixture was dried over anhydrous sodium sulfate and concentrated under vacuum. The residue was applied onto a silica gel column with dichloromethane/methanol (20:1). The resulting residue was recrystallized from ethyl acetate:n-hexane in the ratio of 1:5 to yield 6-[bis(4-chlorophenyl)methyl]-1-methyl-4-[[1-(trifluoromethane)sulfonylpiperidin-4-yl]amino]-1,2-dihydroquinolin-2-one as an off-white solid.

(ES, m/z): [M+H]⁺ 624; ¹H-NMR (300 MHz, DMSO-D₆) δ8.017 (s, 1H), 7.380-7.407 (m, 5H), 7.119-7.226 (m, 5H), 6.584 (d, J=7.5 Hz, 1H), 5.661-5.670 (m, 2H), 3.837-3.880 (m, 2H), 3.761 (br, 1H), 3.557 (s, 3H), 3.440-3.475 (m, 2H), 2.078 (d, J=12.3 Hz, 2H), 1.545-1.653 (m, 2H)

Example 21

Compound #90

2-(6-(bis(4-chlorophenyl)methyl)-2-oxo-4-((1-((trifluoromethyl)sulfonyl)piperidin-4-yl)amino)quinolin-1 (2H)-yl)acetamide

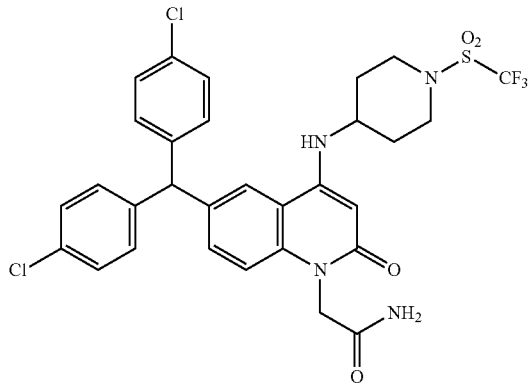 [SMILES: NC(=O)Cn1c(=O)cc(NC2CCN(S(=O)(=O)C(F)(F)F)CC2)c2cc(C(c3ccc(Cl)cc3)c3ccc(Cl)cc3)ccc21]

STEP 1: 2-[6-[bis(4-chlorophenyl)methyl]-4-bromo-2-oxo-1,2-dihydroquinolin-1-yl]acetamide Into a 25-mL round-bottom flask, was placed 6-[bis(4-chlorophenyl)methyl]-4-bromo-1,2-dihydroquinolin-2-one (300 mg, 0.65 mmol, 1.00 equip), N,N-dimethylformamide (10 mL, 0.14 mmol, 0.21 equip) and sodium hydride (52.3 mg, 1.31 mmol, 2.00 equip, 60%). To the resulting mixture was then added 2-bromoacetamide (108 mg, 0.78 mmol, 1.20 equip). The resulting solution was stirred for 2 h at room temperature. The reaction was then quenched by the addition of water (200 mL). The resulting solution was extracted with ethyl acetate (3×100 mL) and the organic layers combined and dried over sodium sulfate. The solids were filtered out. The filtrate was concentrated under vacuum. The residue was applied onto a silica gel column with DCM:MeOH (20:1) to yield 2-[6-[bis(4-chlorophenyl)methyl]-4-bromo-2-oxo-1,2-dihydroquinolin-1-yl]acetamide as a white solid. LCMS (ES, m/z) 517 [M+H]+

STEP 2: 2-[6-[bis(4-chlorophenyl)methyl]-2-oxo-4-[[1-(trifluoromethane)sulfonylpiperidin-4-yl]amino]-1,2-dihydroquinolin-1-yl]acetamide Into a 8-mL round-bottom flask purged and maintained with an inert atmosphere of nitrogen, was placed 2-[6-[bis(4-chlorophenyl)methyl]-4-bromo-2-oxo-1,2-dihydroquinolin-1-yl]acetamide (160 mg, 0.31 mmol, 1.00 equip), 1,4-dioxane (3 mL), 1-(trifluoromethane)sulfonylpiperidin-4-amine hydrochloride (124.6 mg, 0.46 mmol, 1.50 equip), Pd$_2$(dba)$_3$ (28.4 mg, 0.03 mmol, 0.10 equip), dppf (60 mg, 0.11 mmol, 0.35 equip), Cs$_2$CO$_3$ (253 mg, 0.78 mmol, 2.51 equip), and t-BuOK (69.5 mg, 0.62 mmol, 2.00 equip). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield 2-[6-[bis(4-chlorophenyl)methyl]-2-oxo-4-[[1-(trifluoromethane)sulfonylpiperidin-4-yl]amino]-1,2-dihydroquinolin-1-yl]acetamide as a gray solid.
LCMS (ES, m/z) 667 [M+H]+

Example 22

Compound #89

4-bromo-6-((4-chlorophenyl)(thiazol-2-yl)methyl)-1-methylquinolin-2(1H)-one

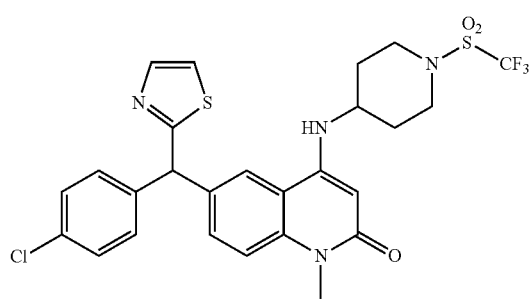 [SMILES: Cn1c(=O)cc(NC2CCN(S(=O)(=O)C(F)(F)F)CC2)c2cc(C(c3ccc(Cl)cc3)c3nccs3)ccc21]

STEP 1: 4-bromo-6-[(4-chlorophenyl)(1,3-thiazol-2-yl)methyl]-1-methyl-1,2-dihydroquinolin-2-one Into a 25-mL round-bottom flask, was placed 4-bromo-6-[(4-chlorophenyl)(1,3-thiazol-2-yl)methyl]-1,2-dihydroquinolin-2-one (370 mg, 0.86 mmol, 1.00 equip), potassium carbonate (355 mg, 2.57 mmol, 3.00 equip), and N,N-dimethylformamide (10 mL). To the resulting mixture was then added CH$_3$I (182 mg, 1.28 mmol, 1.50 equip) dropwise with stirring. The resulting solution was stirred for 2 h at room temperature. The reaction was then quenched by the addition of water (200 mL). The resulting solution was extracted with ethyl acetate (3×100 mL) and the organic layers combined and concentrated. The residue was applied onto a silica gel column with ethyl acetate/petroleum ether (1:1) to yield 4-bromo-6-[(4-chlorophenyl)(1,3-thiazol-2-yl)methyl]-1-methyl-1,2-dihydroquinolin-2-one as a yellow solid. LCMS (ES, m/z) 447 [M+H]+

STEP 2: 6-[(4-chlorophenyl)(1,3-thiazol-2-yl)methyl]-1-methyl-4-[[1-(trifluoromethane)sulfonylpiperidin-4-yl]amino]-1,2-dihydroquinolin-2-one Into a 8-mL round-bottom flask purged and maintained with an inert atmosphere of nitrogen, was placed 4-bromo-6-[(4-chlorophenyl)(1,3-thiazol-2-yl)methyl]-1-methyl-1,2-dihydroquinolin-2-one (200 mg, 0.45 mmol, 1.00 equip), 1,4-dioxane (3 mL), 1-(trifluoromethane)sulfonylpiperidin-4-amine hydrochloride (180 mg, 0.67 mmol, 1.49 equip), Pd$_2$(dba)$_3$ (41 mg, 0.04 mmol, 0.10 equip), dppf (87 mg, 0.16 mmol, 0.35 equip), Cs$_2$CO$_3$ (365 mg, 1.12 mmol, 2.50 equip), and t-BuOK (100 mg, 0.88 mmol, 1.96 equip). The resulting solution was stirred overnight at 100° C. The reaction was then quenched by the addition of water (100 mL). The resulting solution was extracted with ethyl acetate (3×50 mL) and the organic layers combined and dried over anhydrous sodium sulfate. The solids were filtered out. The filtrate was concentrated under vacuum. The residue was applied onto a silica gel column with dichloromethane/methanol (20:1). The resulting residue was recrystallized from ethyl acetate:petroleum ether in the ratio of 1:10 to yield 6-[(4-chlorophenyl)(1,3-thiazol-2-yl)methyl]-1-methyl-4-[[1-(trifluoromethane)sulfonylpiperidin-4-yl]amino]-1,2-dihydroquinolin-2-one as an off-white solid.
LCMS (ES, m/z) 597 [M+H]+; $^1$H-NMR (300 MHz, DMSO-D$_6$) δ8.111 (s, 1H), 7.814 (d, J=3.3 Hz, 1H), 7.685 (d, J=3.3 Hz, 4H), 7.469-7.395 (m, 4H), 7.305 (d, J=8.7 Hz, 2H), 6.564 (d, J=7.8 Hz, 1H), 5.951 (s, 1H), 5.649 (s, 1H), 3.877-3.685 (m, 3H), 3.547 (s, 3H), 3.469-3.396 (m, 2H), 2.101-2.062 (m, 2H), 1.654-1.537 (m, 2H)

Example 23

Compound #97

4-[4-([6-[bis(4-chlorophenyl)methyl]-2-hydroxyquinolin-4-yl]amino)piperidin-1-yl]-4-oxobutanoate

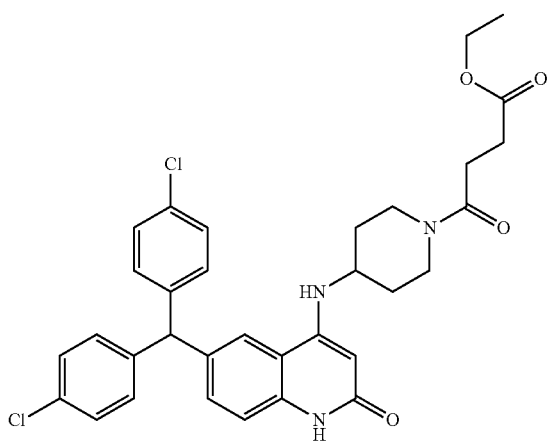 [SMILES: CCOC(=O)CCC(=O)N1CCC(Nc2cc(=O)[nH]c3ccc(C(c4ccc(Cl)cc4)c4ccc(Cl)cc4)cc23)CC1]

Into a 25-mL sealed tube purged and maintained with an inert atmosphere of nitrogen, was placed 6-[bis(4-chlorophenyl)methyl]-4-bromoquinolin-2-ol (300 mg, 0.65 mmol, 1.00 equip, 99%), ethyl 4-(4-aminopiperidin-1-yl)-4-oxobutanoate (295.1 mg, 0.97 mmol, 1.50 equip), Pd$_2$(dba)$_3$ (60 mg, 0.06 mmol, 0.10 equip, 99%), dppf (126.7 mg, 0.23 mmol, 0.35 equip, 99%), Cs$_2$CO$_3$ (532.7 mg, 1.62 mmol, 2.50 equip, 99%), t-BuOK (146.4 mg, 1.29 mmol, 2.00 equip, 99%), and 1,4-dioxane (9 mL). The resulting solution was stirred overnight at 100° C. in an oil bath. The resulting solution was diluted with water (80 mL). The resulting solution was extracted with ethyl acetate (3×80 mL) and the organic layers combined. The resulting mixture was washed with water (1×80 mL) and brine (1×80 mL). The resulting mixture was dried over anhydrous sodium sulfate. The solids were filtered out. The resulting mixture was concentrated under vacuum. The resulting residue was purified by Prep-HPLC with the following conditions: Column, Sunfire Prep C$_{18}$ OBD 5 μm, 19×150 mm; mobile phase, Phase A: water (0.05% NH$_4$HCO$_3$), Phase B:CH$_3$CN (20% CH$_3$CN up to 80% in 8 min, up to 100% for 0.1 min, hold 100% in 1.9 min, down to 20% in 0.1 min, hold 20% in 1.9 min); Detector, UV 220 & 254 nm to yield ethyl 4-[4-([6-[bis(4-chlorophenyl) methyl]-2-hydroxyquinolin-4-yl]amino)piperidin-1-yl]-4-oxobutanoate as a white solid.

LCMS (ES, m/z) 606 [M+H]$^+$

Example 24

Compound #98

4-(4-((6-(bis(4-chlorophenyl)methyl)-2-oxo-1,2-dihydroquinolin-4-yl)amino)piperidin-1-yl)-4-oxobutanoic acid

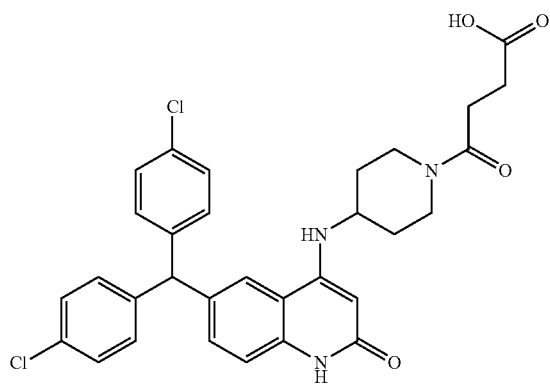 [SMILES: O=C(O)CCC(=O)N1CCC(Nc2cc(=O)[nH]c3ccc(C(c4ccc(Cl)cc4)c4ccc(Cl)cc4)cc23)CC1]

Into a 25-mL round-bottom flask, was placed ethyl 4-[4-([6-[bis(4-chlorophenyl)methyl]-2-hydroxyquinolin-4-yl] amino)piperidin-1-yl]-4-oxobutanoate (60 g, 96.94 mmol, 1.00 equip, 98%), ethanol (15 mL), and sodium hydroxide (3 mL). The resulting solution was stirred for 4 h at room temperature. The resulting mixture was concentrated and acidified to pH3-4 with 1 N HCl. The solids were collected by filtration. The resulting residue was purified by recrystallization from methanol to yield 4-[4-([6-[bis(4-chlorophenyl)methyl]-2-oxo-1,2-dihydroquinolin-4-yl]amino) piperidin-1-yl]-4-oxobutanoic acid as a white solid.

LCMS (ES, m/z) 578 [M+H]$^+$

Example 25

Compound #106

3-(4-((6-(bis(4-chlorophenyl)methyl)-2-oxo-1,2-dihydroquinolin-4-yl)amino)piperidin-1-yl)-3-oxopropanamide

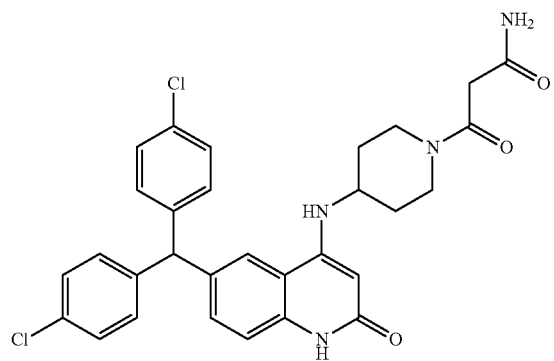 [SMILES: NC(=O)CC(=O)N1CCC(Nc2cc(=O)[nH]c3ccc(C(c4ccc(Cl)cc4)c4ccc(Cl)cc4)cc23)CC1]

Into a 8-mL vial, was placed 3-[4-([6-[bis(4-chlorophenyl)methyl]-2-hydroxyquinolin-4-yl]amino)piperidin-1-yl]-3-oxopropanoic acid (20 mg, 0.03 mmol, 1.00 equip, 98%), NH$_4$Cl (9.48 mg, 0.18 mmol, 5.00 equip), DIEA (45.7 mg, 0.35 mmol, 10.00 equip, 99%), HATU (20.2 mg, 0.05 mmol, 1.50 equip, 99%), and N,N-dimethylformamide (3 mL). The resulting solution was stirred overnight at room temperature. The resulting solution was diluted with water (20 mL). The resulting solution was extracted with ethyl acetate (3×20 mL) and the organic layers combined. The resulting mixture was washed with water (1×20 mL) and brine (1×20 mL). The resulting mixture was dried over anhydrous sodium sulfate. The solids were filtered out. The residue was applied onto a silica gel column with dichloromethane/methanol (10:1) to yield 3-[4-([6-[bis(4-chlorophenyl)methyl]-2-hydroxyquinolin-4-yl]amino)piperidin-1-yl]-3-oxopropanamide as a white solid.

LCMS (ES, m/z) 563 [M+H]$^+$

Example 26

Compound #105 tert-butyl 2-(4-((6-(bis(4-chlorophenyl)methyl)-2-oxo-1,2-dihydroquinolin-4-yl)amino)phenoxy)acetate

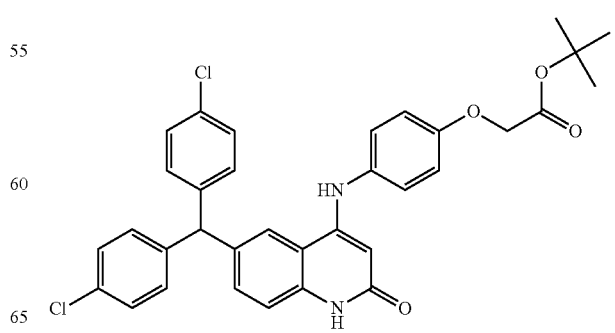

STEP 1: tert-butyl 2-(4-nitrophenoxy)acetate

Into a 100-mL round-bottom flask purged and maintained with an inert atmosphere of nitrogen, was placed 4-nitrophenol (1 g, 7.12 mmol, 1.00 equip, 99%), tert-butyl 2-bromoacetate (1.68 g, 8.53 mmol, 1.00 equip), potassium carbonate (1.49 g, 10.60 mmol, 1.50 equip, 99%), and tetrahydrofuran (50 mL). The resulting solution was stirred for 4 h at 70° C. in an oil bath. The resulting solution was diluted with water (150 mL). The resulting solution was extracted with ethyl acetate (3×100 mL) and the organic layers combined. The resulting mixture was washed with water (1×100 mL) and brine (1×100 mL). The resulting mixture was dried over anhydrous sodium sulfate. The solids were filtered out. The filtrate was concentrated under vacuum. The residue was applied onto a silica gel column with ethyl acetate/petroleum ether (1:20) to yield tert-butyl 2-(4-nitrophenoxy)acetate as a yellow solid.

STEP 2: tert-butyl 2-(4-aminophenoxy)acetate

Into a 100-mL round-bottom flask, was placed tert-butyl 2-(4-nitrophenoxy)acetate (2 g, 7.74 mmol, 1.00 equip, 98%), Palladium on carbon (200 mg), and methanol (50 mL). To the above hydrogen was introduced. The resulting solution was stirred for 18 h at room temperature. The solids were filtered out. The resulting mixture was concentrated under vacuum. The residue was applied onto a silica gel column with ethyl acetate/petroleum ether (1:10) to yield tert-butyl 2-(4-aminophenoxy)acetate as a reddish oil.

STEP 3 tert-butyl 2-(4-((6-(bis(4-chlorophenyl) methyl)-2-oxo-1,2-dihydroquinolin-4-yl)amino)phenoxy)acetate Into a 25-mL round-bottom flask purged and maintained with an inert atmosphere of nitrogen, was placed 6-[bis(4-chlorophenyl)methyl]-4-bromoquinolin-2-ol (300 mg, 0.65 mmol, 1.00 equip), tert-butyl 2-(4-aminophenoxy)acetate (220.8 mg, 0.98 mmol, 1.50 equip, 99%), Pd$_2$(dba)$_3$ (60 mg, 0.06 mmol, 0.10 equip, 99%), dppf (126.7 mg, 0.23 mmol, 0.35 equip, 99%), Cs$_2$CO$_3$ (532.7 mg, 1.62 mmol, 2.50 equip, 99%), and 1,4-dioxane (9 mL). The resulting solution was stirred overnight at 100° C. in an oil bath. The resulting solution was diluted with water (60 mL). The resulting solution was extracted with ethyl acetate (3×60 mL) and the organic layers combined. The resulting mixture was washed with water (1×60 mL) and brine (1×60 mL). The resulting mixture was dried over anhydrous sodium sulfate. The solids were filtered out. The resulting mixture was concentrated under vacuum. The residue was applied onto a silica gel column with dichloromethane/methanol (30:1). The resulting residue was recrystallized from EtOAc:n-hexane in the ratio of 1:20 to yield tert-butyl 2-(4-((6-(bis(4-chlorophenyl) methyl)-2-oxo-1,2-dihydroquinolin-4-yl)amino)phenoxy) acetate as a white solid.

LCMS (ES, m/z) 601 [M+H]$^+$; $^1$H-NMR (300 MHz, DMSO-D$_6$) δ10.922 (s, 1H), 8.442 (s, 1H), 7.985 (s, 1H), 7.407-7.379 (m, 4H), 7.469-7.395 (m, 4H), 7.7.227-7.159 (m, 8H), 6.7.966 (d, J=12 Hz, 1H), 5.646 (s, 1H), 5.366 (s, 1H), 4.665 (s, 2H), 1.433 (s, 9H)

Example 27

Compound #109

2-(4-((6-(bis(4-chlorophenyl)methyl)-2-oxo-1,2-dihydroquinolin-4-yl)amino)phenoxy)acetic acid

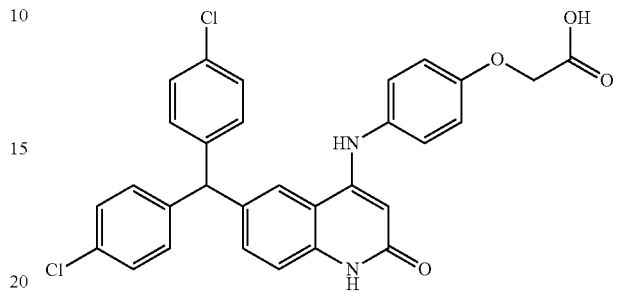

Into a 100-mL round-bottom flask, was placed tert-butyl 2-[4-([6-[bis(4-chlorophenyl)methyl]-2-oxo-1,2-dihydroquinolin-4-yl]amino)phenoxy]acetate (200 mg, 0.33 mmol, 1.00 equip, 98%), trifluoroacetic acid (379 mg, 3.32 mmol, 10.00 equip), and dichloromethane (20 mL). The resulting solution was stirred for 3 h at room temperature. The resulting mixture was concentrated under vacuum. The resulting residue was purified by re-crystallization from methanol to yield 2-[4-([6-[bis(4-chlorophenyl)methyl]-2-oxo-1,2-dihydroquinolin-4-yl]amino)phenoxy]acetic acid as an off-white solid.

LCMS (ES, m/z) 545 [M+H]$^+$

Example 28

Compound #111

2-(4-((6-(bis(4-chlorophenyl)methyl)-2-oxo-1,2-dihydroquinolin-4-yl)amino)phenoxy)acetamide

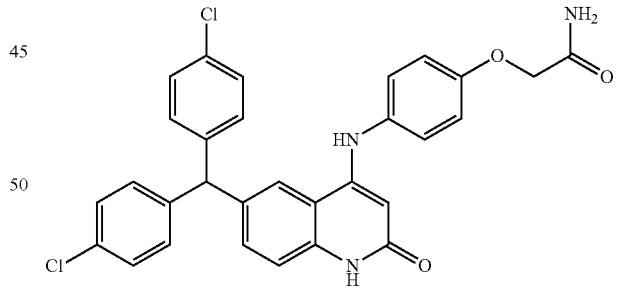

Into a 25-mL round-bottom flask, was placed 2-[4-([6-[bis(4-chlorophenyl)methyl]-2-hydroxyquinolin-4-yl] amino)phenoxy]acetic acid (30 g, 53.90 mmol, 1.00 equip, 98%), NH$_4$Cl (14.72 mg, 0.27 mmol, 5.00 equip, 98%), DIPEA (71 mg, 0.54 mmol, 10.00 equip, 98%), HATU (31.37 mg, 0.08 mmol, 1.50 equip, 98%), and N,N-dimethylformamide (5 mL). The resulting solution was stirred overnight at room temperature. The resulting solution was diluted with water (50 mL). The resulting solution was extracted with ethyl acetate (3×50 mL) and the organic layers combined. The resulting mixture was washed with water (1×50 mL) and brine (1×50 mL). The resulting mixture was dried over anhydrous sodium sulfate. The solids were filtered out. The resulting mixture was concentrated under vacuum. The resulting residue was recrystallized from ethyl acetate:n-hexane in a ratio of 1:20 to yield 2-[4-([6-[bis(4-chlorophenyl)methyl]-2-hydroxyquinolin-4-yl]amino)phenoxy]acetamide as an off-white solid.

LCMS (ES, m/z) 544 [M+H]$^+$

Example 29

Compound #122

4-((4-((6-(bis(4-chlorophenyl)methyl)-2-oxo-1,2-dihydroquinolin-4-yl)amino)piperidin-1-yl)sulfonyl)benzoic acid

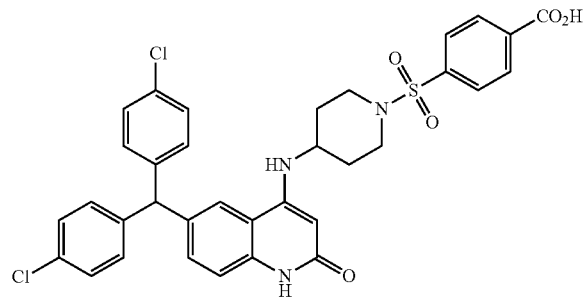 [SMILES: O=C(O)c1ccc(S(=O)(=O)N2CCC(Nc3cc(=O)[nH]c4ccc(C(c5ccc(Cl)cc5)c5ccc(Cl)cc5)cc34)CC2)cc1]

Into a 25-mL round-bottom flask, was placed 6-[bis(4-chlorophenyl)methyl]-4-[(piperidin-4-yl)amino]-1,2-dihydroquinolin-2-one (150 mg, 0.31 mmol, 1.00 equip, 98%), 4-(chlorosulfonyl)benzoic acid (103.77 mg, 0.47 mmol, 1.50 equip), triethylamine (98.28 mg, 0.95 mmol, 3.00 equip, 98%), dichloromethane (3 g, 35.32 mmol, 114.96 equip). The resulting solution was stirred overnight at room temperature. The resulting mixture was concentrated under vacuum. The resulting residue was purified by Prep-HPLC with the following conditions: Column, Sunfire Prep C$_{18}$ OBD 5 um, 19×150 mm; mobile phase, Phase A: water (0.05% NH$_4$HCO$_3$), Phase B:CH$_3$CN (20% CH$_3$CN up to 65% in 8 min, up to 100% in 0.1 min, hold 100% for 1.9 min, down to 20% in 0.1 min, hold 20% for 1.9 min); Detector, UV 220 & 254 nm to yield 4-[4-([6-[bis(4-chlorophenyl)methyl]-2-oxo-1,2-dihydroquinolin-4-yl]amino)piperidine-1-sulfonyl]benzoic acid as an off-white solid.

LCMS (ES, m/z) 662 [M+H]$^+$

Example 30

Compound #129

3-((4-((6-(bis(4-chlorophenyl)methyl)-2-oxo-1,2-dihydroquinolin-4-yl)amino)piperidin-1-yl)methyl)benzoic acid

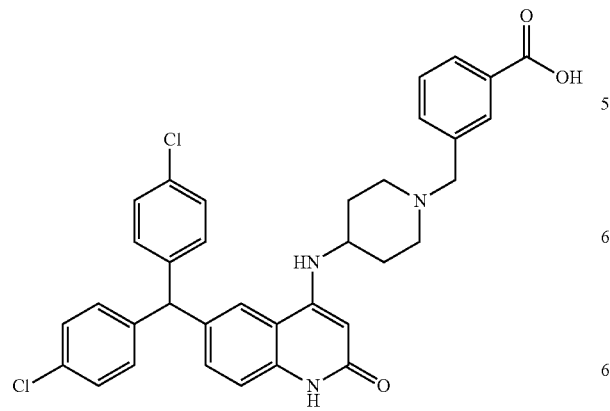

STEP 1: methyl 3-[[4-([6-[bis(4-chlorophenyl)methyl]-2-hydroxyquinolin-4-yl]amino)piperidin-1-yl]methyl]benzoate Into a 25-mL round-bottom flask, was placed 6-[bis(4-chlorophenyl)methyl]-4-[(piperidin-4-yl)amino]quinolin-2-ol (100 mg, 0.21 mmol, 1.00 equip), methyl 3-formylbenzoate (68 mg, 0.41 mmol, 2.00 equip), methanol (10 mL), NaBH$_3$CN (66 mg, 1.03 mmol, 5.00 equip), and acetic acid (0.1 mL). The resulting solution was stirred overnight at 25° C. The resulting mixture was concentrated under vacuum. The residue was applied onto a silica gel column with dichloromethane/methanol (20:1) to yield methyl 3-[[4-([6-[bis(4-chlorophenyl)methyl]-2-hydroxyquinolin-4-yl]amino)piperidin-1-yl]methyl]benzoate as a yellow solid.

LCMS (ES, m/z) 626 [M+H]

STEP 2: 3-[[4-([6-[bis(4-chlorophenyl)methyl]-2-hydroxyquinolin-4-yl]amino)piperidin-1-yl]methyl]benzoic acid Into a 100-mL round-bottom flask, was placed methyl 3-[[4-([6-[bis(4-chlorophenyl)methyl]-2-hydroxyquinolin-4-yl]amino)piperidin-1-yl]methyl]benzoate (80 mg, 0.13 mmol, 1.00 equip), methanol (20 mL), and 1M sodium hydroxide (20 mL). The resulting solution was stirred overnight at 30° C. The resulting mixture was concentrated under vacuum. The pH value of the solution was adjusted to 5-6 with 10% HCl. The solids were collected by filtration to yield 3-[[4-([6-[bis(4-chlorophenyl)methyl]-2-hydroxyquinolin-4-yl]amino)piperidin-1-yl]methyl]benzoic acid as a white solid.

LCMS (ES, m/z) 612 [M+H]

Example 31

Compound #130

5-[4-([6-[bis(4-chlorophenyl)methyl]-2-hydroxyquinolin-4-yl]amino)piperidine-1-sulfonyl]thiophene-2-carboxylic acid, trifluoroacetic acid salt

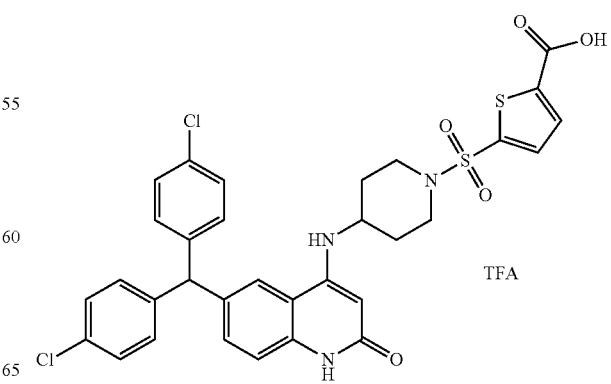

161

STEP 1: methyl 5-[4-([6-[bis(4-chlorophenyl) methyl]-2-hydroxyquinolin-4-yl]amino)piperidine-1-sulfonyl]thiophene-2-carboxylate Into a 50-mL round-bottom flask, was placed 6-[bis(4-chlorophenyl)methyl]-4-[(piperidin-4-yl)amino]quinolin-2-ol (150 mg, 0.31 mmol, 1.00 equip), dichloromethane (20 mL), triethylamine (0.5 mL), and methyl 5-(chlorosulfonyl) thiophene-2-carboxylate (76 mg, 0.32 mmol, 1.00 equip). The resulting solution was stirred for 1 h at 25° C. The resulting mixture was concentrated under vacuum. The residue was applied onto a silica gel column with dichloromethane/methanol (20:1) to yield methyl 5-[4-([6-[bis(4-chlorophenyl)methyl]-2-hydroxyquinolin-4-yl]amino)piperidine-1-sulfonyl]thiophene-2-carboxylate as a yellow solid. LCMS (ES, m/z) 682 [M+H]+

STEP 2: 5-[4-([6-[bis(4-chlorophenyl)methyl]-2-hydroxyquinolin-4-yl]amino)piperidine-1-sulfonyl] thiophene-2-carboxylic acid, trifluoroacetic acid salt Into a 100-mL round-bottom flask, was placed methyl 5-[4-([6-[bis(4-chlorophenyl)methyl]-2-hydroxyquinolin-4-yl]amino)piperidine-1-sulfonyl]thiophene-2-carboxylate (100 mg, 0.15 mmol, 1.00 equip), methanol (20 mL), and 1M sodium hydroxide (20 mL). The resulting solution was stirred overnight at 50° C. The resulting mixture was concentrated under vacuum. The pH value of the solution was adjusted to 5-6 with 10% HCl. The solids were collected by filtration. The resulting residue was purified by Prep-HPLC with the following conditions: water with 0.05% TFA and MeOH (60% MeOH up to 85% in 10 min, hold 95% for 1 min, down to 60% in 1 min) to yield 5-[4-([6-[bis(4-chlorophenyl)methyl]-2-hydroxyquinolin-4-yl]amino)piperidine-1-sulfonyl]thiophene-2-carboxylic acid; trifluoroacetic acid salt as an off-white solid.

LCMS (ES, m/z) 668 [M+H]

Example 32

Compound #549

(2E)-3-[6-[bis(4-chlorophenyl)methyl]-2-methoxy-4-[[1-(trifluoromethane)sulfonylpiperidin-4-yl]amino] quinolin-8-yl]prop-2-en-1-ol

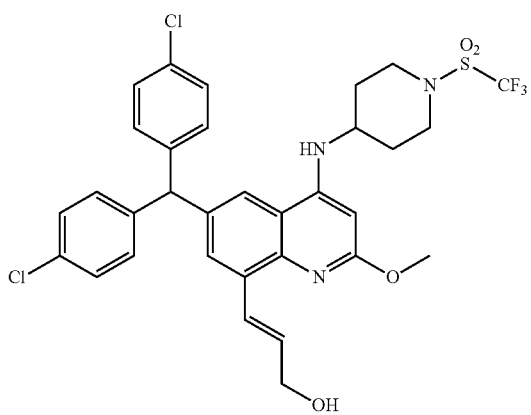 [SMILES: COc1cc(NC2CCN(S(=O)(=O)C(F)(F)F)CC2)c2cc(C(c3ccc(Cl)cc3)c3ccc(Cl)cc3)cc(/C=C/CO)c2n1]

162

STEP 1: 4-amino-3-bromo-N-methoxy-N-methylbenzamide

Into a 1-L round-bottom flask, was placed a solution of 4-amino-3-bromobenzoic acid (50 g, 231.45 mmol, 1.00 equip) in N,N-dimethylformamide (500 mL), TEA (128 mL, 4.00 equip), HATU (106 g, 278.78 mmol, 1.20 equip), and methoxy(methyl)amine hydrochloride (45 g, 461.33 mmol, 2.00 equip). The resulting solution was stirred overnight at room temperature. The resulting solution was diluted with water (1 L). The resulting solution was extracted with ethyl acetate (1 L) and the organic layers combined and dried over anhydrous sodium sulfate. The solids were filtered out. The resulting mixture was concentrated under vacuum. The residue was applied onto a silica gel column with ethyl acetate/petroleum ether (1:2) to yield 4-amino-3-bromo-N-methoxy-N-methylbenzamide as a yellow solid. LCMS (ES, m/z) 259 [M+H]

STEP 2: tert-butyl N-[2-bromo-4-[methoxy(methyl) carbamoyl]phenyl]carbamate

Into a 2-L round-bottom flask purged and maintained with an inert atmosphere of nitrogen, was placed a solution of 4-amino-3-bromo-N-methoxy-N-methylbenzamide (59 g, 227.71 mmol, 1.00 equip) in 1,4-dioxane (1500 mL), and Boc$_2$O (351 g, 1.61 mol, 7.00 equip). The resulting solution was stirred overnight at 100° C. The resulting mixture was concentrated under vacuum. The residue was suspended in saturated sodium chloride (200 mL). The resulting solution was extracted with ethyl acetate (2×300 mL) and the organic layers combined and dried over anhydrous sodium sulfate. The solids were filtered out. The filtrate was concentrated under vacuum. The residue was applied onto a silica gel column with ethyl acetate/petroleum ether (1:2) to yield tert-butyl N-[2-bromo-4-[methoxy(methyl)carbamoyl]phenyl]carbamate as a yellow solid. LCMS (ES, m/z) 359 [M+H]

STEP 3: tert-butyl N-[2-bromo-4-[(4-chlorophenyl) carbonyl]phenyl]carbamate

Into a 1-L round-bottom flask purged and maintained with an inert atmosphere of nitrogen, was placed a solution of tert-butyl N-[2-bromo-4-[methoxy(methyl)carbamoyl]phenyl]carbamate (30 g, 83.52 mmol, 1.00 equip) in tetrahydrofuran (400 mL). To the resulting mixture was then added (4-chlorophenyl)magnesium bromide (250 mL, 3.00 equip, 1M) dropwise with stirring at 0° C. The resulting solution was stirred overnight at room temperature. The resulting solution was diluted with saturated sodium chloride (200 mL). The resulting solution was extracted with ethyl acetate (400 mL) and the organic layers combined and dried over anhydrous sodium sulfate. The solids were filtered out. The resulting mixture was concentrated under vacuum. The resulting residue was recrystallized from ethyl acetate:petroleum ether in a ratio of 1:20. The solids were collected by filtration. The mother liquor was concentrated under vacuum. The residue was applied onto a silica gel column with ethyl acetate/petroleum ether (1:10) to yield additional tert-butyl N-[2-bromo-4-[(4-chlorophenyl)carbonyl]phenyl] carbamate as a light yellow solid.

LCMS (ES, m/z) 410 [M+H]+

STEP 4: 2-bromo-4-[(4-chlorophenyl)carbonyl]aniline

Into a 500-mL round-bottom flask, was placed a solution of tert-butyl N-[2-bromo-4-[(4-chlorophenyl)carbonyl]phenyl]carbamate (20 g, 48.70 mmol, 1.00 equip) in dichloromethane (300 mL). To the resulting mixture was then added trifluoroacetic acid (38 mL, 10.00 equip) dropwise with stirring. The resulting solution was stirred overnight at room temperature. The reaction was then quenched by the addition of saturated sodium bicarbonate (500 mL). The resulting solution was extracted with DCM (500 mL) and the organic layers combined and dried over anhydrous sodium sulfate. The solids were filtered out. The resulting mixture was concentrated under vacuum. The resulting residue was recrystallized from ethyl acetate:petroleum ether in the ratio of 1:15 to yield 2-bromo-4-[(4-chlorophenyl)carbonyl]aniline as a light yellow solid. LCMS (ES, m/z) 310 [M+H]$^+$

STEP 5: 2-([2-bromo-4-[(4-chlorophenyl)carbonyl] phenyl]carbamoyl)acetic acid Into a 1-mL round-bottom flask, was placed a solution of 2-bromo-4-[(4-chlorophenyl)carbonyl]aniline (28.62 g, 92.15 mmol, 1.00 equip) in toluene (400 mL), and 2,2-dimethyl-1,3-dioxane-4,6-dione (25.92 g, 179.84 mmol, 2.00 equip). The resulting solution was stirred overnight at 88° C. The solution was cooled to room temperature and the solids were collected by filtration to yield 2-([2-bromo-4-[(4-chlorophenyl)carbonyl]phenyl]carbamoyl)acetic acid as a yellow solid. LCMS (ES, m/z) 396 [M+H]$^+$

STEP 6: 8-bromo-6-[(4-chlorophenyl)carbonyl]-4-hydroxy-1,2-dihydroquinolin-2-one Into a 250-mL 3-necked round-bottom flask, was placed $P_2O_5$ (8.95 g, 63.03 mmol, 1.00 equip), and MSA (80.55 g). The resulting solution was stirred for 1 h at 80° C. and then the temperature was raised to 99° C. To the resulting mixture was then added 2-([2-bromo-4-[(4-chlorophenyl)carbonyl] phenyl]carbamoyl) acetic acid (25 g, 63.03 mmol, 1.00 equip) in several batches. The resulting solution was stirred for 3 h at 99° C. The resulting solution was cooled to room temperature and added dropwise into saturated sodium chloride (500 mL). The solids were collected by filtration and then dissolved in ethyl acetate (200 mL). And the undissolved solids were collected by filtration to yield 8-bromo-6-[(4-chlorophenyl)carbonyl]-4-hydroxy-1,2-dihydroquinolin-2-one as a yellow solid. The filtrate was concentrated under vacuum and was applied onto a silica gel column with ethyl acetate first and then dichloromethane/methanol (8:2) to yield additional 8-bromo-6-[(4-chlorophenyl)carbonyl]-4-hydroxy-1,2-dihydroquinolin-2-one as a yellow solid. LCMS (ES, m/z) 378 [M+H]$^+$

STEP 7: 2,4,8-tribromo-6-[(4-chlorophenyl)carbonyl]quinoline

Into a 500-mL round-bottom flask, was placed a solution of 8-bromo-6-[(4-chlorophenyl)carbonyl]-4-hydroxy-1,2-dihydroquinolin-2-one (9 g, 23.77 mmol, 1.00 equip) in 1,4-dioxane (100 mL), and phosphoroyl tribromide (20.7 g, 72.20 mmol, 3.00 equip). The resulting solution was stirred for 12 h at 92° C. The reaction was cooled to room temperature and then quenched by the addition of water/ice (200 mL). The solids were collected by filtration. The solid was washed with methanol (100 mL) and petroleum ether (100 mL). The remaining solid was dissolved with ethyl acetate (2 L) and the resulting mixture filtered and the ethyl acetate phase isolated. The resulting mixture was concentrated under vacuum. The resulting residue was recrystallized from ethyl acetate:petroleum ether in the ratio of 1:10 to yield 2,4,8-tribromo-6-[(4-chlorophenyl)carbonyl]quinoline as a gray solid. LCMS (ES, m/z) 506 [M+H]$^+$

STEP 8: 4,8-dibromo-6-[(4-chlorophenyl)carbonyl]-2-methoxyquinoline

Into a 100-mL round-bottom flask, was placed 2,4,8-tribromo-6-[(4-chlorophenyl)carbonyl]quinoline (2 g, 3.97 mmol, 1.00 equip), toluene (20 mL), and tetrahydrofuran (2 mL). To the resulting mixture was then added NaOCH$_3$ (642 mg, 11.89 mmol, 3.00 equip). The resulting solution was stirred for 2 h at 66° C. Then another batch of NaOCH$_3$ (642 mg, 11.89 mmol, 3.00 equip) was added to the solution. The resulting solution was allowed to react, with stirring, for an additional 2 h at 66° C. And then a final batch of NaOCH$_3$ (642 mg, 11.89 mmol, 3.00 equip) was added to the solution. The resulting solution was allowed to react, with stirring, for an additional 2 h at 66° C. The reaction was then quenched by the addition of saturated sodium bicarbonate (200 mL). The resulting solution was extracted with DCM (2×100 mL) and the organic layers combined and dried over anhydrous sodium sulfate. The solids were filtered out. The resulting mixture was concentrated under vacuum to yield 4,8-dibromo-6-[(4-chlorophenyl)carbonyl]-2-methoxyquinoline as a yellow solid. LCMS (ES, m/z) 456 [M+H]$^+$

STEP 9: bis(4-chlorophenyl)(4,8-dibromo-2-methoxyquinolin-6-yl)methanol

Into a 100-mL round-bottom flask, was placed a solution of 4,8-dibromo-6-[(4-chlorophenyl)carbonyl]-2-methoxyquinoline (1.5 g, 3.29 mmol, 1.00 equip) in tetrahydrofuran (30 mL). To the resulting mixture was then added (4-chlorophenyl)magnesium bromide (9.87 mL, 3.00 equip, 1M) dropwise with stirring at 0° C. The resulting solution was stirred for 3 h at room temperature. The reaction was then quenched by the addition of saturated sodium bicarbonate (100 mL). The solids were filtered out and washed with ethyl acetate (100 mL), and the ethyl acetate was combined with the filtrate. The resulting solution was extracted with ethyl acetate (100 mL) and the organic layers combined and dried over anhydrous sodium sulfate. The solids were filtered out. The resulting mixture was concentrated under vacuum. The residue was applied onto a silica gel column with ethyl acetate/petroleum ether (1:9) to yield bis(4-chlorophenyl)(4,8-dibromo-2-methoxyquinolin-6-yl)methanol as a yellow solid. LCMS (ES, m/z) 568 [M+H]$^+$

STEP 10: (8-bromo-2-methoxy-4-[[1-(trifluoromethane)sulfonylpiperidin-4-yl]amino]quinolin-6-yl)bis(4-chlorophenyl)methanol Into a 50-mL round-bottom flask, was placed bis(4-chlorophenyl)(4,8-dibromo-2-methoxyquinolin-6-yl)methanol (1.3 g, 2.29 mmol, 1.00 equip), dppf (216 mg, 0.39 mmol, 0.17 equip), Pd$_2$(dba)$_3$.CHCl$_3$ (114 mg, 0.11 mmol, 0.05 equip), Cs$_2$CO$_3$ (2.99 g, 9.18 mmol, 4.00 equip), 1,4-dioxane (10 mL), and 1-(trifluoromethane)sulfonylpiperidin-4-amine hydrochloride (1.23 g, 4.58 mmol, 2.00 equip). The resulting solution was stirred overnight at 84° C. The resulting solution was diluted with saturated sodium bicarbonate (100 mL). The resulting solution was extracted with ethyl acetate (2×100 mL) and the organic layers combined and dried over anhydrous sodium sulfate. The solids were filtered out. The resulting mixture was concentrated under vacuum. The residue was applied onto a silica gel column with ethyl acetate/petroleum ether (1:9) to yield (8-bromo-2-methoxy-4-[[1-(trifluoromethane)sulfonylpiperidin-4-yl]amino]quinolin-6-yl)bis(4-chlorophenyl)methanol as a yellow solid. LCMS (ES, m/z) 720 [M+H]+

STEP 11: (2E)-3-[6-[bis(4-chlorophenyl)(hydroxy)methyl]-2-methoxy-4-[[1-(trifluoromethane)sulfonylpiperidin-4-yl]amino]quinolin-8-yl]prop-2-en-1-yl acetate Into a 50-mL round-bottom flask, was placed (8-bromo-2-methoxy-4-[[1-(trifluoromethane)sulfonylpiperidin-4-yl]amino]quinolin-6-yl)bis(4-chlorophenyl)methanol (900 mg, 1.25 mmol, 1.00 equip), Pd(OAc)$_2$ (56 mg, 0.25 mmol, 0.20 equip), P(o-tol)$_3$ (152 mg, 0.50 mmol, 0.40 equip), DIEA (1.61 g, 12.46 mmol, 10.00 equip), N,N-dimethylformamide (10 mL), and prop-2-en-1-yl acetate (1.25 g, 12.49 mmol, 10.00 equip). The resulting solution was stirred for 3 days at 129° C. under nitrogen. The resulting solution was diluted with saturated sodium bicarbonate (50 mL). The resulting solution was extracted with ethyl acetate (2×100 mL) and the organic layers combined and dried over anhydrous sodium sulfate. The solids were filtered out. The resulting mixture was concentrated under vacuum. The residue was applied onto a silica gel column with ethyl acetate/petroleum ether (1:4) to yield (2E)-3-[6-[bis(4-chlorophenyl)(hydroxy)methyl]-2-methoxy-4-[[1-(trifluoromethane)sulfonylpiperidin-4-yl]amino]quinolin-8-yl]prop-2-en-1-yl acetate as a yellow solid. LCMS (ES, m/z) 738 [M+H]+

STEP 12: (2E)-3-[6-[bis(4-chlorophenyl)methyl]-2-methoxy-4-[[1-(trifluoromethane)sulfonylpiperidin-4-yl]amino]quinolin-8-yl]prop-2-en-1-yl acetate Into a 100-mL round-bottom flask, was placed a solution of (2E)-3-[6-[bis(4-chlorophenyl)(hydroxy)methyl]-2-methoxy-4-[[1-(trifluoromethane)sulfonylpiperidin-4-yl]amino]quinolin-8-yl]prop-2-en-1-yl acetate (270 mg, 0.37 mmol, 1.00 equip) in dichloromethane (mL) and nitrogen was bubbled into the solution for 30 min. To the resulting mixture was then added Et$_3$SiH (5.90 mL, 100.00 equip) dropwise with stirring. To this was added trifluoroacetic acid (0.56 mL, 20.00 equip) dropwise with stirring. The resulting solution was stirred for 3 h at room temperature. The reaction was then quenched by the addition of saturated sodium bicarbonate (50 mL). The resulting solution was extracted with DCM (2×50 mL) and the organic layers combined and dried over anhydrous sodium sulfate. The solids were collected by filtration. The resulting mixture was concentrated under vacuum. The residue was applied onto a silica gel column with dichloromethane/methanol (9:1) to yield (2E)-3-[6-[bis(4-chlorophenyl)methyl]-2-methoxy-4-[[1-(trifluoromethane)sulfonylpiperidin-4-yl]amino]quinolin-8-yl]prop-2-en-1-yl acetate as a yellow solid. LCMS (ES, m/z) 722 [M+H]+

STEP 13: (2E)-3-[6-[bis(4-chlorophenyl)methyl]-2-methoxy-4-[[1-(trifluoromethane)sulfonylpiperidin-4-yl]amino]quinolin-8-yl]prop-2-en-1-ol Into a 50-mL round-bottom flask, was placed (2E)-3-[6-[bis(4-chlorophenyl)methyl]-2-methoxy-4-[[1-(trifluoromethane)sulfonylpiperidin-4-yl]amino]quinolin-8-yl]prop-2-en-1-yl acetate (230 mg, 0.32 mmol, 1.00 equip), sodium hydroxide (88 mg, 2.20 mmol, 2.00 equip), methanol (3 mL), water (2 mL), and tetrahydrofuran (1 mL). The resulting solution was stirred for 3 h at room temperature. The resulting solution was diluted with saturated sodium chloride (20 mL). The resulting solution was extracted with ethyl acetate (50 mL) and the organic layers combined and dried over anhydrous sodium sulfate. The solids were removed by filtration. The resulting mixture was concentrated under vacuum. The resulting residue was purified by Prep-HPLC with the following conditions (waters 2767-1): Column, X-Bridge Prep C18, 5 um, 19×100 mm; mobile phase, Phase A, water with 0.05% NH$_4$HCO$_3$, Phase B, CH$_3$CN (35% CH$_3$CN up to 95% in 12 min); Detector, UV 254 to yield (2E)-3-[6-[bis(4-chlorophenyl)methyl]-2-methoxy-4-[[1-(trifluoromethane)sulfonylpiperidin-4-yl]amino]quinolin-8-yl]prop-2-en-1-ol as an off-white solid.

LCMS (ES, m/z) 680 [M+H]+; $^1$H-NMR: (400 MHz, DMSO-D$_6$) δ: 7.969 (s, 1H), 7.561-7.389 (m, 6H), 7.177 (d, J=8.4 Hz, 4H), 6.656 (d, J=7.8 Hz, 1H), 6.383-6.329 (m, 1H), 6.062 (s, 1H), 5.700 (s, 1H), 4.833-4.796 (m, 1H), 4.153-4.121 (m, 2H), 3.915-3.838 (m, 6H), 3.436-3.321 (m, 2H), 2.105-2.069 (m, 2H), 1.621-1.588 (m, 2H).

Example 33

Compound #546

6-(bis(4-chlorophenyl)methyl)-8-bromo-2-methoxy-N-(1-(((trifluoromethyl)sulfonyl)piperidin-4-yl)quinolin-4-amine

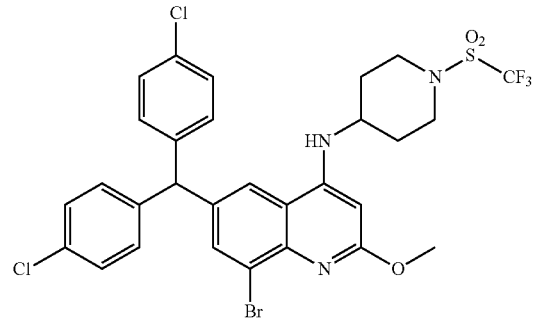 [SMILES: COc1cc(NC2CCN(S(=O)(=O)C(F)(F)F)CC2)c2cc(C(c3ccc(Cl)cc3)c3ccc(Cl)cc3)cc(Br)c2n1]

Into a 100-mL round-bottom flask, was placed (8-bromo-2-methoxy-4-[[1-(trifluoromethane)sulfonylpiperidin-4-yl]amino]quinolin-6-yl)bis(4-chlorophenyl)methanol (300 mg, 0.42 mmol, 1.00 equip), dichloromethane (50 mL), Et$_3$SiH (0.3 mL), and trifluoroacetic acid (0.9 mL). The resulting solution was stirred overnight at 25° C. The resulting mixture was concentrated under vacuum. The residue was applied onto a silica gel column with ethyl acetate/petroleum ether (1:10) to yield 6-[bis(4-chlorophenyl)methyl]-8-bromo-2-methoxy-N-[1-(trifluoromethane)sulfonylpiperidin-4-yl]quinolin-4-amine as a yellow solid.

LCMS (ES, m/z) 704 [M+H]+; $^1$H-NMR (400 MHz, DMSO-D$_6$) δ: 8.103 (s, 1H), 7.551 (s, 1H), 7.412 (d, J=6.3 Hz, 4H), 7.165 (d, J=6.3 Hz, 2H), 6.812 (d, J=8.0 Hz, 1H), 6.117 (s, 1H), 5.731 (s, 1H), 3.992 (s, 3H), 3.938-3.803 (m, 3H), 3.424-3.362 (m, 2H), 2.100-2.072 (m, 2H), 1.639-1.548 (m, 2H).

Example 34

Compound #547

6-(bis(4-chlorophenyl)methyl)-2-methoxy-8-(3-methoxyprop-1-en-1-yl)-N-(1-(((trifluoromethyl)sulfonyl)piperidin-4-yl)quinolin-4-amine

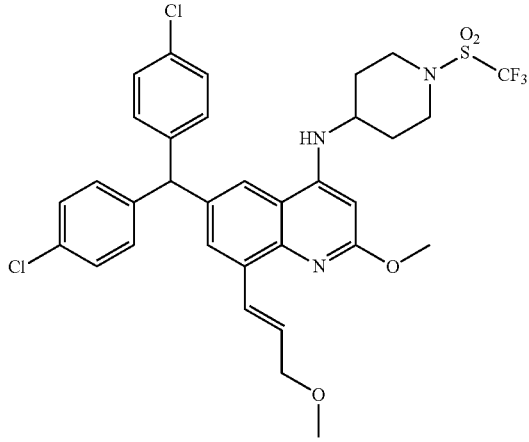 [SMILES: COC/C=C/c1cc(C(c2ccc(Cl)cc2)c2ccc(Cl)cc2)cc2c(NC3CCN(S(=O)(=O)C(F)(F)F)CC3)cc(OC)nc12]

Into a 10-mL round-bottom flask purged and maintained with an inert atmosphere of nitrogen, was placed 6-[bis(4-chlorophenyl)methyl]-8-bromo-2-methoxy-N-[1-(trifluoromethane)sulfonylpiperidin-4-yl]quinolin-4-amine (50 mg, 0.07 mmol, 1.00 equip), 2-[(1E)-3-methoxyprop-1-en-1-yl]-4,4,5,5-tetramethyl-1,3,2-dioxaborolane (16 mg, 0.08 mmol, 1.10 equip), Pd(dppf)Cl$_2$ (5 mg), potassium carbonate (30 mg, 0.22 mmol, 3.00 equip), 1,4-dioxane (2 mL), and water (0.5 mL). The resulting solution was stirred overnight at 80° C. The solids were filtered out. The resulting mixture was concentrated under vacuum. The residue was applied onto a silica gel column with ethyl acetate:petroleum ether (1:4) to yield 6-[bis(4-chlorophenyl)methyl]-2-methoxy-8-[(1E)-3-methoxyprop-1-en-1-yl]-N-[1-(trifluoromethane)sulfonylpiperidin-4-yl]quinolin-4-amine as a white solid.

LCMS (ES, m/z) 694 [M+H]$^+$, $^1$H-NMR (400 MHz, DMSO-D$_6$) δ: 7.922 (s, 1H), 7.509-7.419 (m, 2H), 7.433 (d, J=8.4 Hz, 4H), 7.117 (d, J=8.4 Hz, 4H), 6.650-6.600 (m, 1H), 6.380-6.260 (m, 1H), 6.002 (s, 1H), 5.629 (s, 1H), 4.012-4.009 (m, 2H), 3.845-3.772 (m, 6H), 3.340-3.328 (m, 2H), 3.215 (s, 3H), 2.080-1.980 (m, 2H), 1.650-1.520 (m, 2H).

Example 35

Compound #548

6-[bis(4-chlorophenyl)methyl]-2-methoxy-8-(3-methoxypropyl)-N-[1-(trifluoromethane)sulfonylpiperidin-4-yl]quinolin-4-amine

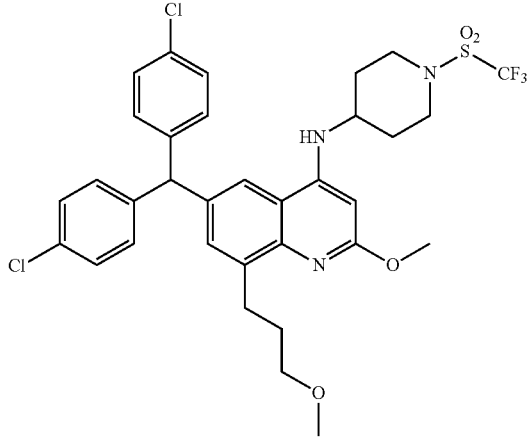 [SMILES: COCCCc1cc(C(c2ccc(Cl)cc2)c2ccc(Cl)cc2)cc2c(NC3CCN(S(=O)(=O)C(F)(F)F)CC3)cc(OC)nc12]

Into a 100-mL round-bottom flask, was placed 6-[bis(4-chlorophenyl)methyl]-2-methoxy-8-[(1E)-3-methoxyprop-1-en-1-yl]-N-[1-(trifluoromethane)sulfonylpiperidin-4-yl]quinolin-4-amine (100 mg, 0.14 mmol, 1.00 equip), methanol (20 mL), PtO$_2$ (5 mg), and the flask was charged with H$_2$. The resulting solution was stirred overnight at 25° C. The solids were filtered out. The resulting mixture was concentrated under vacuum. The residue was applied onto a silica gel column with ethyl acetate:petroleum ether (1:4) to yield 6-[bis(4-chlorophenyl)methyl]-2-methoxy-8-(3-methoxypropyl)-N-[1-(trifluoromethane)sulfonylpiperidin-4-yl]quinolin-4-amine as a light yellow solid.

LCMS (ES, m/z) 696 [M+H]$^+$, $^1$H-NMR (400 MHz, DMSO-D$_6$) δ: 7.912 (d, J=0.8 Hz, 1H), 7.390 (d, J=8.2 Hz, 4H), 7.142 (d, J=8.2 Hz, 4H), 7.705 (s, 1H), 6.606 (d, J=8.0 Hz, 1H), 6.034 (s, 1H), 5.661 (s, 1H), 3.883 (s, 3H), 3.842-3.747 (m, 3H), 3.429-3.397 (m, 2H), 3.290-3.194 (m, 2H), 3.118 (s, 3H), 2.991-2.955 (m, 2H), 2.094-2.067 (m, 2H), 1.873-1.804 (m, 2H), 1.658-1.624 (m, 2H)

Example 36

Compound #140

6-(bis(4-chlorophenyl)methyl)-8-(3-methoxypropyl)-4-((1-(((trifluoromethyl)sulfonyl)piperidin-4-yl)amino)quinolin-2(1H)-one

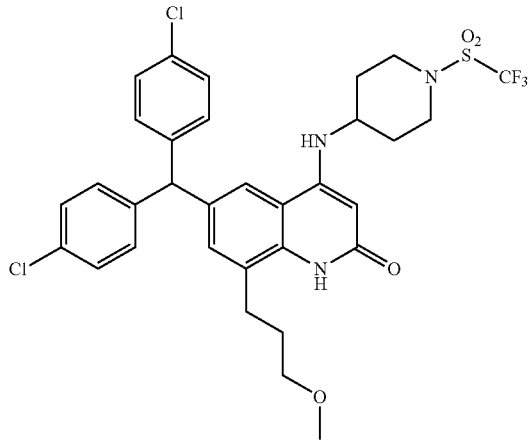 [SMILES: COCCCc1cc(C(c2ccc(Cl)cc2)c2ccc(Cl)cc2)cc2c(NC3CCN(S(=O)(=O)C(F)(F)F)CC3)cc(=O)[nH]c12]

Into a 10-mL round-bottom flask, was placed 6-[bis(4-chlorophenyl)methyl]-2-methoxy-8-(3-methoxypropyl)-N-[1-(trifluoromethane)sulfonylpiperidin-4-yl]quinolin-4-amine (8 mg, 0.01 mmol, 1.00 equip), 1,4-dioxane (2 mL), and 4N hydrogen chloride (2 mL). The resulting solution was stirred overnight at 100° C. The resulting mixture was concentrated under vacuum. The residue was applied onto a silica gel column with ethyl acetate:petroleum ether (1:2) to yield 6-(bis(4-chlorophenyl)methyl)-8-(3-methoxypropyl)-4-((1-((trifluoromethyl)sulfonyl)piperidin-4-yl)amino)quinolin-2(1H)-one as a white solid.

LCMS (ES, m/z) 682 [M+H]$^+$; $^1$H-NMR (300 MHz, DMSO-D$_6$) δ: 9.819 (s, 1H), 7.730 (s, 1H), 7.319 (d, J=8.4 Hz, 4H), 7.056 (d, J=8.4 Hz, 4H), 6.862 (s, 1H), 6.457 (d, J=10.5 Hz, 1H), 5.527 (s, 1H), 5.431 (s, 1H), 3.850-3.762 (m, 3H), 3.324-3.261 (m, 2H), 3.132-3.054 (m, 5H), 2.750-2.698 (m, 2H), 2.050-1.980 (m, 2H), 1.588-1.544 (m, 4H).

Example 37

Compound #100 and #101

6-(bis(4-chlorophenyl)methyl)-8-((2-methoxyethyl)amino)-4-((1-((trifluoromethyl)sulfonyl)piperidin-4-yl)amino)quinolin-2(1H)-one and 6-((4-chlorophenyl)(4-((2-methoxyethyl)amino)phenyl)methyl)-8-((2-methoxyethyl)amino)-4-((1-((trifluoromethyl)sulfonyl)piperidin-4-yl)amino)quinolin-2(1H)-one

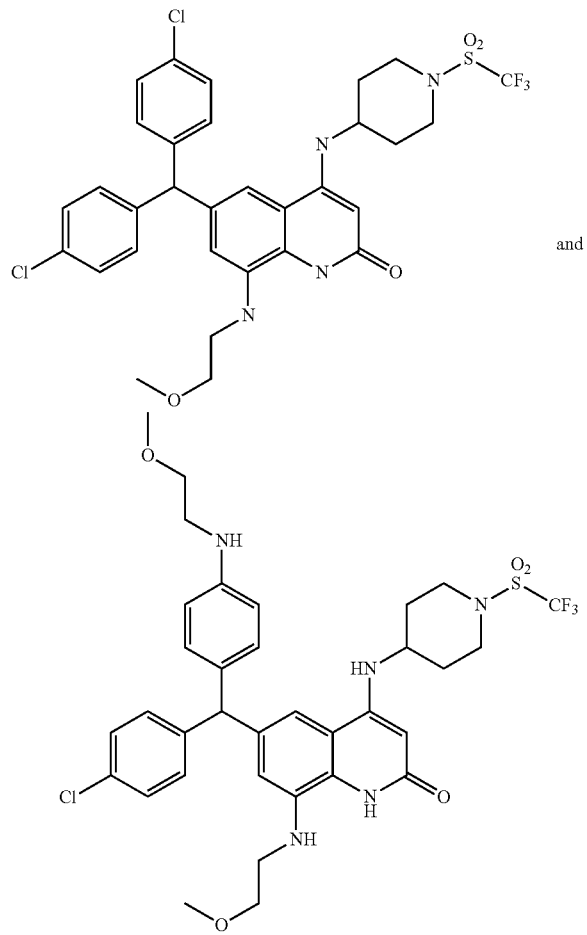

and

STEP 1: 4,8-dibromo-2-(tert-butoxy)-6-[(4-chlorophenyl)carbonyl]quinoline

Into a 100-mL round-bottom flask purged and maintained with an inert atmosphere of nitrogen, was placed a solution of 2,4,8-tribromo-6-[(4-chlorophenyl)carbonyl]quinoline (1.0 g, 1.98 mmol, 1.00 equip) in toluene (30 mL), and KOt-Bu (2.18 mL, 1.10 equip). The resulting solution was stirred for 1.5 h at 65° C. The resulting solution was diluted with saturated sodium chloride (50 mL). The resulting solution was extracted with ethyl acetate (2×100 mL) and the organic layers combined and dried over anhydrous sodium sulfate. The solids were filtered out. The resulting mixture was concentrated under vacuum. The residue was applied onto a silica gel column with ethyl acetate/petroleum ether (5:95) to yield 4,8-dibromo-2-(tert-butoxy)-6-[(4-chlorophenyl)carbonyl]quinoline as a yellow solid. LCMS (ES, m/z) 498 [M+H]$^+$ STEP 2: bis(4-chlorophenyl)[4,8-dibromo-2-(tert-butoxy)quinolin-6-yl]methanol Into a 100-mL round-bottom flask purged and maintained with an inert atmosphere of nitrogen, was placed a solution of 4,8-dibromo-2-(tert-butoxy)-6-[(4-chlorophenyl)carbonyl]quinoline (440 mg, 0.88 mmol, 1.00 equip) in tetrahydrofuran (30 mL). To the resulting mixture was then added (4-chlorophenyl)magnesium bromide (2.67 mL, 3.00 equip, 1M) dropwise with stirring at 0° C. The resulting solution was stirred for 3 h at room temperature. The reaction was then quenched by the addition of saturated sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The residue was applied onto a silica gel column with ethyl acetate/petroleum ether (1:9) to yield bis(4-chlorophenyl)[4,8-dibromo-2-(tert-butoxy)quinolin-6-yl]methanol as a yellow solid. LCMS (ES, m/z) 610 [M+H]$^+$ STEP 3: [8-bromo-2-(tert-butoxy)-4-[[1-(trifluoromethane)sulfonylpiperidin-4-yl]amino]quinolin-6-yl]bis(4-chlorophenyl)methanol Into a 25-mL round-bottom flask, was placed a solution of 1-(trifluoromethane)sulfonylpiperidin-4-amine hydrochloride (244 mg, 0.91 mmol, 1.05 equip) in 1,4-dioxane (13 mL), bis(4-chlorophenyl)[4,8-dibromo-2-(tert-butoxy)quinolin-6-yl]methanol (530 mg, 0.87 mmol, 1.00 equip), Pd$_2$(dba)$_3$·CHCl$_3$ (46 mg, 0.04 mmol, 0.05 equip), dppf (83 mg, 0.15 mmol, 0.17 equip), and Cs$_2$CO$_3$ (851 mg, 2.61 mmol, 3.00 equip). The resulting solution was stirred overnight at 85° C. The reaction was cooled to room temperature and then quenched by the addition of saturated sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The residue was applied onto a silica gel column with ethyl acetate/petroleum ether (1:9) to yield [8-bromo-2-(tert-butoxy)-4-[[1-(trifluoromethane)sulfonylpiperidin-4-yl]amino]quinolin-6-yl]bis(4-chlorophenyl)methanol as a yellow solid. LCMS (ES, m/z) 762 [M+H]$^+$ STEP 4: (2-(tert-butoxy)-8-((2-methoxyethyl)amino)-4-((1-((trifluoromethyl)sulfonyl)piperidin-4-yl)amino)quinolin-6-yl)bis(4-chlorophenyl)methanol and (2-(tert-butoxy)-8-((2-methoxyethyl)amino)-4-((1-((trifluoromethyl)sulfonyl)piperidin-4-yl)amino)quinolin-6-yl)(4-chlorophenyl)(4-((2-methoxyethyl)amino)phenyl)methanol A mixture of (8-bromo-2-(tert-butoxy)-4-((1-((trifluoromethyl)sulfonyl)piperidin-4-yl)amino) quinolin-6-yl)bis(4-chlorophenyl)methanol (58 mg, 0.0762 mmol), 2-methoxyethanamine, Pd$_2$(dba)$_3$ (6.98 mg, 0.0076 mmol), XPhos (15.98 mg, 0.0335 mmol), and Cs$_2$CO$_3$ (74.45 mg, 0.229 mmol) in 1,4-dioxane (0.7 mL) was heated to 100° C. for 5 hr under the Ar$_2$. The reaction was diluted with EtOAc and water. The aqueous layer was extracted with EtOAc. The combined organics were concentrated and purified by silica column (15% EtOAc/hexanes) to yield (2-(tert-butoxy)-8-((2-methoxyethyl)amino)-4-((1-((trifluoromethyl)sulfonyl)piperidin-4-yl)amino)quinolin-6-yl)bis(4-chlorophenyl)methanol and (25-35% EtOAc/hexanes) (2-(tert-butoxy)-8-((2-methoxyethyl)amino)-4-((1-((trifluoromethyl)sulfonyl)piperidin-4-yl)amino)quinolin-6-yl)(4-chlorophenyl)(4-((2-methoxyethyl)amino)phenyl)methanol. (M+H)+: 755, 757, respectively.

STEP 5: 6-(bis(4-chlorophenyl)methyl)-8-((2-methoxyethyl)amino)-4-((1-((trifluoromethyl)sulfonyl)piperidin-4-yl)amino)quinolin-2(1H)-one To solution of (2-(tert-butoxy)-8-((2-methoxyethyl)amino)-4-((1-((trifluoromethyl) sulfonyl)piperidin-4-yl)amino)quinolin-6-yl)bis(4-chlorophenyl)methanol (12 mg, 0.0159 mmol) and triethylsilane (0.0152 mL, 0.0953 mmol) in CH$_2$Cl$_2$ (1 mL) was added slowly TFA (0.03 mL, 0.392 mmol). The resulting mixture was stirred for 4 hr at room temperature. The reaction was diluted with CH$_2$Cl$_2$ and washed with Na$_2$CO$_3$ to make the aqueous layer basic. The organics were washed with water, dried over anhydrous Na$_2$SO$_4$ and concentrated. The resulting residue was triturated from Et$_2$O/hexanes (1:3) to yield 6-(bis(4-chlorophenyl)methyl)-8-((2-methoxyethyl)amino)-4-((1-((trifluoromethyl)sulfonyl)piperidin-4-yl)amino)quinolin-2(1H)-one.
(M+H)+: 683, 685. $^1$H NMR (CDCl$_3$): 11.59 (br. s., 1H), 7.21-7.36 (m, 4H), 7.03 (d, J=8.1 Hz, 4H), 6.45 (s, 1H), 6.47 (s, 1H), 5.61 (s, 2H), 5.49 (s, 1H), 4.54 (d, J=6.6 Hz, 1H), 3.97 (m, 2H), 3.51-3.70 (m, 3H), 3.36 (s, 3H), 3.11-3.31 (m, 4H), 2.25 (m, 2H), 1.53-1.74 (m, 2H)

6-((4-chlorophenyl)(4-((2-methoxyethyl)amino)phenyl)methyl)-8-((2-methoxyethyl)amino)-4-((1-((trifluoromethyl)sulfonyl)piperidin-4-yl)amino)quinolin-2(1H)-one was similarly prepared by reacting (2-(tert-butoxy)-8-((2-methoxyethyl)amino)-4-((1-((trifluoromethyl)sulfonyl)piperidin-4-yl)amino)quinolin-6-yl)(4-chlorophenyl)(4-((2-methoxyethyl)amino)phenyl)methanol (prepared as described in Step 4 above) according to the procedure as described in Step 5 above.
(ES, m/z) [M+H]+: 722. $^1$H NMR (CDCl$_3$) δ:11.25 (br. s., 1H), 7.24-7.38 (m, 3H), 7.15-7.24 (m, 2H), 6.95-7.09 (m, 3H), 6.48-6.60 (m, 3H), 5.47 (s, 1H), 5.28 (br. s., 1H), 4.86 (d, J=6.1 Hz, 1H), 4.10 (br. s., 1H), 3.90 (m, 2H), 3.59 (m, 5H), 3.38 (s, 3H), 3.32 (s, 3H), 3.21 (m, 2H), 3.25 (m, 4H), 2.17 (m, 2H), 1.66 (m, 2H)

Example 38

Compound #141

8-((4-aminobutyl)amino)-6-(bis(4-chlorophenyl)methyl)-4-((1-((trifluoromethyl)sulfonyl)piperidin-4-yl)amino)quinolin-2(1H)-one

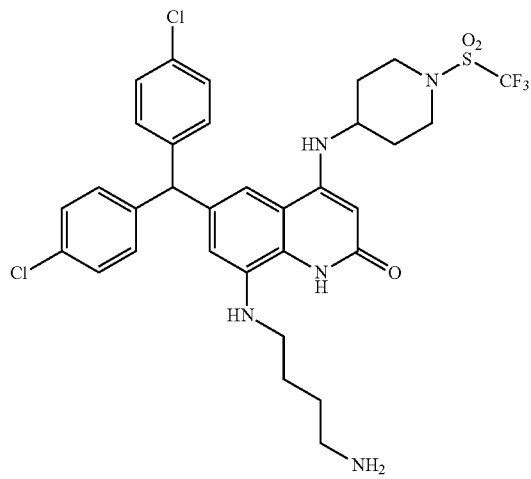 [SMILES: NCCCCNc1cc(C(c2ccc(Cl)cc2)c2ccc(Cl)cc2)cc2c(NC3CCN(S(=O)(=O)C(F)(F)F)CC3)cc(=O)[nH]c12]

STEP 1: tert-butyl N-[4-([6-[bis(4-chlorophenyl)(hydroxy)methyl]-2-(tert-butoxy)-4-[[1-(trifluoromethane)sulfonylpiperidin-4-yl]amino]quinolin-8-yl]amino)butyl]carbamate Into a 25-mL round-bottom flask purged and maintained with an inert atmosphere of nitrogen, was placed a solution of [8-bromo-2-(tert-butoxy)-4-[[1-(trifluoromethane)sulfonylpiperidin-4-yl]amino]quinolin-6-yl]bis(4-chlorophenyl)methanol (200 mg, 0.26 mmol, 1.00 equip) in 1,4-dioxane (2 mL), tert-butyl N-(4-aminobutyl)carbamate (98 mg, 0.52 mmol, 2.00 equip), Pd$_2$(dba)$_3$.CHCl$_3$ (13 mg, 0.01 mmol, 0.05 equip), Cs$_2$CO$_3$ (254 mg, 0.78 mmol, 3.00 equip), and XANTPHOS (25 mg, 0.04 mmol, 0.17 equip). The resulting solution was stirred overnight at 89° C. The reaction was then quenched by the addition of saturated sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The residue was applied onto a silica gel column with ethyl acetate/petroleum ether (1:6) to yield tert-butyl N-[4-([6-[bis(4-chlorophenyl)(hydroxy)methyl]-2-(tert-butoxy)-4-[[1-(trifluoromethane)sulfonylpiperidin-4-yl]amino]quinolin-8-yl]amino)butyl]carbamate as a yellow solid. LCMS (ES, m/z) 868 [M+H]+

STEP 2: 8-[(4-aminobutyl)amino]-6-[bis(4-chlorophenyl)methyl]-4-[[1-(trifluoromethane)sulfonylpiperidin-4-yl]amino]-1,2-dihydroquinolin-2-one TFA salt Into a 50-mL round-bottom flask, was placed tert-butyl N-[4-([6-[bis(4-chlorophenyl)(hydroxy)methyl]-2-(tert-butoxy)-4-[[1-(trifluoromethane)sulfonylpiperidin-4-yl]amino]quinolin-8-yl]amino)butyl]carbamate (200 mg, 0.23 mmol, 1.00 equip) and dichloromethane (10 mL). The solution was bubbled with nitrogen for 30 min to remove air. To this solution was added Et$_3$SiH (3.66 mL, 100.00 equip). To the resulting mixture was then added trifluoroacetic acid (0.351 mL, 20.00 equip) dropwise with stirring in 5 min. The resulting solution was stirred for 2 h at room temperature. To this was added trifluoroacetic acid (0.351 mL, 20.00 equip) dropwise with stirring in 5 min. The resulting solution was allowed to react, with stirring, for an additional 5.5 h at room temperature. The resulting solution was diluted with saturated sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The resulting residue was purified by Prep-HPLC with the following conditions (Waters2767-1): Column, X-Bridge Prep C18, 5 um, 19×100 mm; mobile phase, Phase A: water with 0.05% TFA Phase B: CH$_3$CN (35% CH$_3$CN up to 95% in 12 min); Detector, UV 254 to yield 8-[(4-aminobutyl)amino]-6-[bis(4-chlorophenyl)methyl]-4-[[1-(trifluoromethane)sulfonylpiperidin-4-yl]amino]-1,2-dihydroquinolin-2-one TFA salt as a white solid.
LCMS (ES, m/z) 696 [M+H]+; $^1$H-NMR (400 MHz, CD$_3$OD) δ: 7.226-7.190 (m, 5H), 7.021 (d, J=8.4 Hz, 4H), 6.410 (s, 1H), 5.562 (s, 1H), 5.514 (s, 1H), 3.889-3.857 (m, 2H), 3.676-3.622 (m, 1H), 3.264-3.217 (m, 2H), 3.032-2.973 (m, 2H), 2.858-2.799 (m, 2H), 2.073-2.041 (m, 2H), 1.648-1.528 (m, 6H).

Example 39

Compound #139

6-[bis(4-chlorophenyl)methyl]-8-(butylamino)-1-methyl-4-[[1-(trifluoromethane)sulfonylpiperidin-4-yl]amino]-1,2-dihydroquinolin-2-one

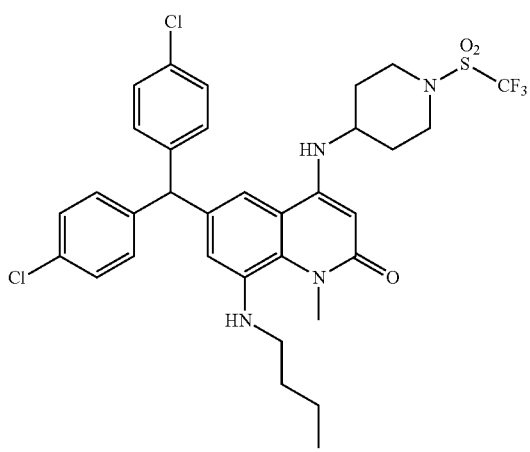 [SMILES: CCCCNc1cc(C(c2ccc(Cl)cc2)c2ccc(Cl)cc2)cc2c(NC3CCN(S(=O)(=O)C(F)(F)F)CC3)cc(=O)n(C)c12]

STEP 1: 6-[bis(4-chlorophenyl)methyl]-4,8-dibromoquinolin-2-ol

Into a 100-mL round-bottom flask, was placed bis(4-chlorophenyl)[4,8-dibromo-2-(tert-butoxy)quinolin-6-yl]methanol (500 mg, 0.82 mmol, 1.00 equip), dichloromethane (50 mL), triethylsilane (1 mL), and trifluoroacetic acid (2 mL). The resulting solution was stirred overnight at 25° C. The resulting solution was diluted with DCM (100 mL). The resulting mixture was washed with saturated sodium bicarbonate (3×100 mL) and dried over anhydrous sodium sulfate. The solids were filtered out. The resulting mixture was concentrated under vacuum to yield 6-[bis(4-chlorophenyl)methyl]-4,8-dibromoquinolin-2-ol as a yellow solid. LCMS (ES, m/z) 538 [M+H]$^+$ STEP 2: 6-[bis(4-chlorophenyl)methyl]-4,8-dibromo-1-methyl-1,2-dihydroquinolin-2-one Into a 25-mL round-bottom flask, was placed 6-[bis(4-chlorophenyl)methyl]-4,8-dibromoquinolin-2-ol (360 mg, 0.67 mmol, 1.00 equip), N,N-dimethylformamide (15 mL), Cs$_2$CO$_3$ (654 mg, 2.01 mmol, 3.00 equip), and CH$_3$I (190 mg, 1.34 mmol, 2.00 equip). The resulting solution was stirred overnight at 80° C. The resulting solution was diluted with water (80 mL). The solids were collected by filtration to yield 6-[bis(4-chlorophenyl)methyl]-4,8-dibromo-1-methyl-1,2-dihydroquinolin-2-one as a yellow solid. LCMS (ES, m/z) 552 [M+H]$^+$ STEP 3: 6-[bis(4-chlorophenyl)methyl]-8-bromo-1-methyl-4-[[1-(trifluoromethane)sulfonylpiperidin-4-yl]amino]-1,2-dihydroquinolin-2-one Into a 10-mL round-bottom flask purged and maintained with an inert atmosphere of nitrogen, was placed 6-[bis(4-chlorophenyl)methyl]-4,8-dibromo-1-methyl-1,2-dihydroquinolin-2-one (80 mg, 0.14 mmol, 1.00 equip), 1-(trifluoromethane)sulfonylpiperidin-4-amine hydrochloride (40 mg, 0.15 mmol, 1.05 equip), Pd$_2$(dba)$_3$ (8 mg, 0.01 mmol, 0.05 equip), dppf (14 mg, 0.03 mmol, 0.17 equip), Cs$_2$CO$_3$ (142 mg, 0.44 mmol, 3.00 equip), and 1,4-dioxane (5 mL). The resulting solution was stirred overnight at 75° C. The solids were filtered out. The resulting mixture was concentrated under vacuum. The residue was applied onto a silica gel column with ethyl acetate:petroleum ether (1:10) to yield 6-[bis(4-chlorophenyl)methyl]-8-bromo-1-methyl-4-[[1-(trifluoromethane)sulfonylpiperidin-4-yl]amino]-1,2-dihydroquinolin-2-one as a yellow solid. LCMS (ES, m/z) 704 [M+H]$^+$ STEP 4: 6-[bis(4-chlorophenyl)methyl]-8-(butylamino)-1-methyl-4-[[1-(trifluoromethane)sulfonylpiperidin-4-yl]amino]-1,2-dihydroquinolin-2-one Into a 10-mL round-bottom flask purged and maintained with an inert atmosphere of nitrogen, was placed 6-[bis(4-chlorophenyl)methyl]-8-bromo-1-methyl-4-[[1-(trifluoromethane)sulfonylpiperidin-4-yl]amino]-1,2-dihydroquinolin-2-one (100 mg, 0.14 mmol, 1.00 equip), butan-1-amine (20 mg, 0.27 mmol, 2.00 equip), Pd$_2$(dba)$_3$ (7 mg, 0.01 mmol, 0.05 equip), XANTPHOS (12 mg, 0.02 mmol, 0.15 equip), Cs$_2$CO$_3$ (138 mg, 0.42 mmol, 3.00 equip), 1,4-dioxane (3 mL). The resulting solution was stirred overnight at 75° C. The solids were filtered out. The resulting mixture was concentrated under vacuum. The residue was applied onto a silica gel column with dichloromethane/methanol (20:1) to yield 6-[bis(4-chlorophenyl)methyl]-8-(butylamino)-1-methyl-4-[[1-(trifluoromethane)sulfonylpiperidin-4-yl]amino]-1,2-dihydroquinolin-2-one as a light yellow solid.
LCMS (ES, m/z) 695 [M+H]$^+$

Example 40

Compound #524

6-(bis(4-chlorophenyl)methyl)-8-bromo-N-(1-((trifluoromethyl)sulfonyl)piperidin-4-yl)quinolin-4-amine

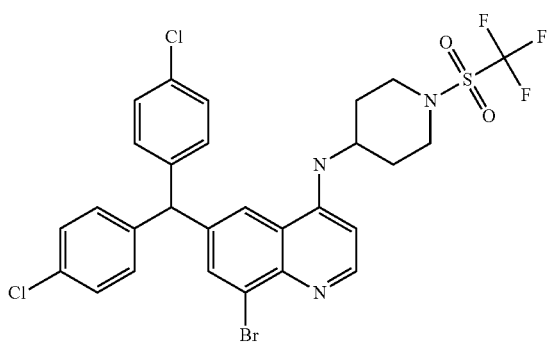 [SMILES: O=S(=O)(N1CCC(Nc2ccnc3c(Br)cc(C(c4ccc(Cl)cc4)c4ccc(Cl)cc4)cc23)CC1)C(F)(F)F]

STEP 1: methyl 3-bromo-4-(((2,2-dimethyl-4,6-dioxo-1,3-dioxan-5-ylidene)methyl)amino)benzoate To a suspension of methyl 4-amino-3-bromobenzoate (2 g, 8.69 mmol) in isopropanol (10 mL) was added Meldrum's acid (1.63 g, 11 mmol) and triethyl orthoformate (5.26 mL, 31.6 mmol). The resulting mixture was heated at 100° C. for 4 hr and cooled to room temperature. The resulting precipitates were filtered off and washed with 10% Et₂O/hexanes to yield methyl 3-bromo-4-(((2,2-dimethyl-4,6-dioxo-1,3-dioxan-5-ylidene)methyl)amino)benzoate. (M+Na)⁺: 408.

STEP 2: methyl 8-bromo-4-oxo-1,4-dihydroquinoline-6-carboxylate

To a flask with DOWTHERM (35 mL) at 210° C. was added methyl 3-bromo-4-(((2,2-dimethyl-4,6-dioxo-1,3-dioxan-5-ylidene)methyl)amino)benzoate (3.3 g, 8.59 mmol) in portions. The resulting solution was heated for 20 min and cooled down to room temperature. Solids were precipitated from the solution. To the reaction mixture was then added hexanes and the precipitate filtered. The solids were washed thoroughly with Et₂O and hexanes and dried under vacuum to yield methyl 8-bromo-4-oxo-1,4-dihydroquinoline-6-carboxylate. (M+H)⁺: 282, 284

STEP 3: methyl 4,8-dibromoquinoline-6-carboxylate

To a suspension of methyl 8-bromo-4-oxo-1,4-dihydroquinoline-6-carboxylate (272 mg, 0.964 mmol) in DMF (5 mL) at room temperature was added slowly phosphorous tribromide (0.1 mL, 1.06 mmol). The resulting mixture was stirred under argon for 30 min. The reaction mixture was made basic by the addition of solid NaHCO₃ until the pH was greater than 10, and then the reaction mixture was diluted with water and the solid collected by filtration. The product was washed with several portion of water and dried to yield methyl 4,8-dibromoquinoline-6-carboxylate. (M+H)⁺: 344, 346, 348.

STEP 4: bis(4-chlorophenyl)(4,8-dibromoquinolin-6-yl)methanol

A solution of (4-chlorophenyl)magnesium bromide (2.02 mL, 1.0 M in THF) was dropwise added to a suspension of methyl 4,8-dibromoquinoline-6-carboxylate (0.2 g, 0.58 mmol) in THF (5 mL) at room temperature. The resulting mixture was slowly dissolved and became a clear solution after 30 min. During this period of time, cooling was needed, when the temperature of the reaction mixture rose above room temperature. After 2 hr, the reaction was quenched with ice water and saturated NH₄Cl followed by EtOAc. The aqueous layer was extracted with EtOAc. The combined organics were concentrated and purified by silica column (25-30% EtOAc/hexanes) chromatography to yield bis(4-chlorophenyl)(4,8-dibromoquinolin-6-yl)methanol. (M+H)⁺: 536, 540, 541

STEP 5: 6-(bis(4-chlorophenyl)methyl)-4,8-dibromoquinoline

To solution of bis(4-chlorophenyl)(4,8-dibromoquinolin-6-yl)methanol (175 mg, 0.325 mmol) and triethylsilane (0.208 mL, 1.3 mmol) in CH₂Cl₂ was added slowly TFA (0.35 mL, 4.57 mmol). The resulting mixture was stirred for 4 hr at room temperature. The reaction was diluted with CH₂Cl₂ and washed with Na₂CO₃ to make the aqueous layer basic. The organics were concentrated and purified by silica column (15% EtOAc/hexanes) chromatography to yield 6-(bis(4-chlorophenyl)methyl)-4,8-dibromoquinoline. (M+H)⁺: 520, 523, 528.

STEP 6: 6-(bis(4-chlorophenyl)methyl)-8-bromo-N-(1-((trifluoromethyl)sulfonyl)piperidin-4-yl)quinolin-4-amine A mixture of 6-(bis(4-chlorophenyl)methyl)-4,8-dibromoquinoline (40 mg, 0.0766 mmol), 1-((trifluoromethyl)sulfonyl)piperidin-4-amine (22.6 mg, 0.0843 mmol), Pd₂(dba)₃ (3.5 mg, 0.00383 mmol), dppf (7.2 mg, 0.013 mmol), Cs₂CO₃ (62.4 mg, 0.192 mmol) and 1,4-dioxane (0.9 mL) was heated under argon to 95° C. overnight. The reaction was diluted with EtOAc and water. The aqueous layer was extracted with EtOAc. The combined organics were concentrated and purified by silica column (45% EtOAc/hexanes) chromatography to yield 6-(bis(4-chlorophenyl)methyl)-8-bromo-N-(1-((trifluoromethyl)sulfonyl)piperidin-4-yl)quinolin-4-amine.

(M+H)⁺: 674, 676; ¹H NMR (CDCl₃): δ 8.64 (d, J=5.14 Hz, 1H), 7.73 (s, 1H), 7.40 (s, 1H), 7.30 (d, J=8.31 Hz, 4H), 7.03 (d, J=8.31 Hz, 4H), 6.49 (d, J=5.38 Hz, 1H), 5.63 (s, 1H), 4.78 (d, J=6.60 Hz, 1H), 4.01 (m, 2H), 3.64-3.81 (m, 1H), 3.18-3.38 (m, 2H), 2.28 (m, 2H), 1.61-1.77 (m, 2H)

Example 41

Compound #92

6-(bis(4-chlorophenyl)methyl)-8-bromo-4-((1-((trifluoromethyl)sulfonyl)piperidin-4-yl)amino)quinolin-2(1H)-one

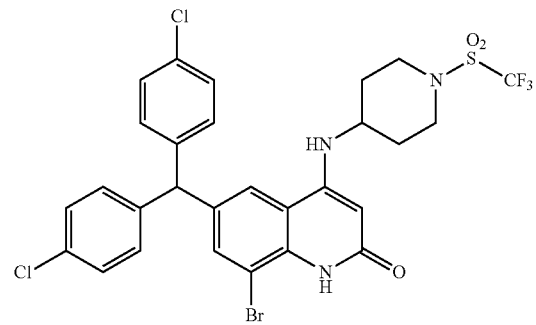 [SMILES: O=c1cc(NC2CCN(S(=O)(=O)C(F)(F)F)CC2)c2cc(C(c3ccc(Cl)cc3)c3ccc(Cl)cc3)cc(Br)c2[nH]1]

A mixture of 6-(bis(4-chlorophenyl)methyl)-4,8-dibromoquinolin-2(1H)-one (48 mg, 0.0892 mmol), 1-((trifluoromethyl)sulfonyl)piperidin-4-amine (26.4 mg, 0.0981 mmol), Pd₂(dba)₃ (8.2 mg, 0.00892 mmol), dppf (14.8 mg, 0.0268 mmol), Cs₂CO₃ (72.7 mg, 0.223 mmol) and 1,4-dioxane (0.9 mL) was heated under argon to 95° C. overnight. The reaction was diluted with EtOAc and water. The aqueous layer was extracted with EtOAc. The combined organics were concentrated and purified by silica column (40-50% EtOAc/hexanes) chromatography to yield 6-(bis(4-chlorophenyl)methyl)-8-bromo-4-((1-((trifluoromethyl)sulfonyl)piperidin-4-yl)amino)quinolin-2(1H)-one.

(ES, m/z) 688, 690 [M+H]⁺. ¹H NMR (CDCl₃) δ: 8.57 (br. s., 1H), 7.38 (s, 1H), 7.31 (d, J=8.6 Hz, 4H), 7.13 (s, 1H), 7.00 (d, J=8.6 Hz, 4H), 5.63 (s, 1H), 5.55 (s, 1H), 4.52 (d, J=6.6 Hz, 1H), 4.01 (m, 2H), 3.49-3.65 (m, 1H), 3.21 (m, 2H), 2.26 (m, 2H), 1.60-1.71 (m, 2H)

Example 42

Compound #536

6-[bis(4-chlorophenyl)methyl]-8-methoxy-N-[1-(trifluoromethane)sulfonylpiperidin-4-yl]quinolin-4-amine

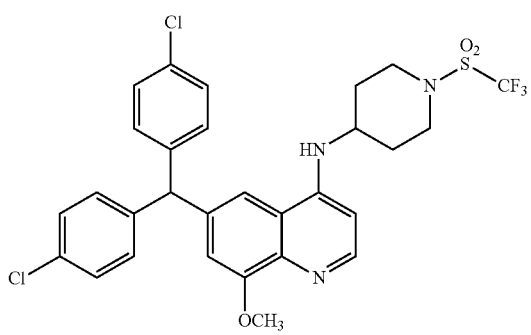 [SMILES: COc1cc(C(c2ccc(Cl)cc2)c2ccc(Cl)cc2)cc2c(NC3CCN(S(=O)(=O)C(F)(F)F)CC3)ccnc12]

STEP 1: methyl 4-[[(2,2-dimethyl-4,6-dioxo-1,3-dioxan-5-ylidene)methyl]amino]-3-methoxybenzoate Into a 250-mL round-bottom flask, was placed methyl 4-amino-3-methoxybenzoate (10 g, 55.19 mmol, 1.00 equip), 2,2-dimethyl-1,3-dioxane-4,6-dione (9.5 g, 65.91 mmol, 1.20 equip), $(CH_3O)_3CH$ (100 mL). The resulting solution was stirred overnight at 100° C. The reaction mixture was cooled with a water/ice bath. The solids were collected by filtration to yield methyl 4-[[(2,2-dimethyl-4,6-dioxo-1,3-dioxan-5-ylidene)methyl]amino]-3-methoxybenzoate as a light yellow solid. LCMS (ES, m/z) 336 [M+H]

STEP 2: methyl 8-methoxy-4-oxo-1,4-dihydroquinoline-6-carboxylate

Into a 500-mL round-bottom flask, was placed methyl 5-[[(2,2-dimethyl-4,6-dioxo-1,3-dioxan-5-ylidene)methyl]amino]-4-methoxypyridine-2-carboxylate (25 g, 74.34 mmol, 1.00 equip), and $(Ph)_2O$ (200 mL). The resulting solution was stirred for 1 h at 200° C. The reaction mixture was cooled with a water/ice bath. The solids were collected by filtration to yield methyl 8-methoxy-4-oxo-1,4-dihydroquinoline-6-carboxylate as a yellow solid. LCMS (ES, m/z) 234 [M+H]$^+$

STEP 3: methyl 4-bromo-8-methoxyquinoline-6-carboxylate

Into a 500-mL 3-necked round-bottom flask purged and maintained with an inert atmosphere of nitrogen, was placed methyl 8-methoxy-4-oxo-1,4-dihydroquinoline-6-carboxylate (14 g, 60.03 mmol, 1.00 equip), and N,N-dimethylformamide (200 mL). To the resulting mixture was then added $PBr_3$ (17.8 g, 65.76 mmol, 1.10 equip) dropwise with stirring. The resulting solution was stirred for 3 h at 25° C. The reaction was then quenched by the addition of water (1000 mL). The pH value of the solution was adjusted to 8-9 with sodium bicarbonate. The solids were collected by filtration to yield methyl 4-bromo-8-methoxyquinoline-6-carboxylate as a yellow solid. LCMS (ES, m/z) 296 [M+H]$^+$

STEP 4: (4-bromo-8-methoxyquinolin-6-yl)bis(4-chlorophenyl)methanol

Into a 1000-mL 3-necked round-bottom flask, was placed methyl 4-bromo-8-methoxyquinoline-6-carboxylate (13 g, 43.90 mmol, 1.00 equip), tetrahydrofuran (500 mL), and (4-chlorophenyl)magnesium bromide (220 mL, 5.00 equip). The resulting solution was stirred for 3 hr at reflux temperature. The reaction was then quenched by the addition of water (400 mL). The resulting solution was extracted with ethyl acetate (3×300 mL) and the organic layers combined and dried over anhydrous sodium sulfate. The solids were filtered out. The resulting mixture was concentrated under vacuum. The residue was applied onto a silica gel column with ethyl acetate/petroleum ether (2:1) to yield (4-bromo-8-methoxyquinolin-6-yl)bis(4-chlorophenyl)methanol as a yellow solid. LCMS (ES, m/z) 490 [M+H]$^+$

STEP 5: 6-[bis(4-chlorophenyl)methyl]-4-bromo-8-methoxyquinoline

Into a 500-mL 3-necked round-bottom flask, was placed (4-bromo-8-methoxyquinolin-6-yl)bis(4-chlorophenyl)methanol (6 g, 12.27 mmol, 1.00 equip), dichloromethane (200 mL), triethylsilane (8 mL), and trifluoroacetic acid (24 mL). The resulting solution was stirred overnight at 25° C. The resulting solution was diluted with DCM (100 mL). The resulting mixture was washed with saturated sodium bicarbonate (3×100 mL) and dried over anhydrous sodium sulfate. The solids were filtered out. The residue was applied onto a silica gel column with ethyl acetate:petroleum ether (1:1) to yield 6-[bis(4-chlorophenyl)methyl]-4-bromo-8-methoxyquinoline as a yellow solid. LCMS (ES, m/z) 474 [M+H]$^+$

STEP 6: 6-[bis(4-chlorophenyl)methyl]-8-methoxy-N-[1-(trifluoromethane)sulfonylpiperidin-4-yl]quinolin-4-amine Into a 25-mL round-bottom flask purged and maintained with an inert atmosphere of nitrogen, was placed 6-[bis(4-chlorophenyl)methyl]-4-bromo-8-methoxyquinoline (500 mg, 1.06 mmol, 1.00 equip), 1-(trifluoromethane)sulfonylpiperidin-4-amine hydrochloride (425 mg, 1.58 mmol, 1.50 equip), $Pd_2(dba)_3$ (55 mg, 0.05 mmol, 0.05 equip), dppf (100 mg, 0.18 mmol, 0.17 equip), $Cs_2CO_3$ (1000 mg, 3.07 mmol, 3.00 equip), and 1,4-dioxane (10 mL). The resulting solution was stirred overnight at 80° C. The resulting solution was diluted with ethyl acetate (100 mL). The organic layer was washed with water (3×50 mL) and dried over anhydrous sodium sulfate. The solids were filtered out. The filtrate was concentrated under vacuum. The residue was applied onto a silica gel column with dichloromethane/methanol (5:1) to yield 6-[bis(4-chlorophenyl)methyl]-8-methoxy-N-[1-(trifluoromethane)sulfonylpiperidin-4-yl]quinolin-4-amine as a yellow solid.

LCMS (ES, m/z) 624 [M+H]$^+$; $^1$H-NMR (300 MHz, DMSO-D$_6$) δ: 8.336 (d, J=5.4 Hz, 1H), 7.715 (s, 1H), 7.393 (d, J=8.4 HZ, 4H), 7.216 (d, J=8.4 HZ, 4H), 6.801 (s, 1H), 6.758 (d, J=7.8 Hz, 1H), 6.637 (d, J=5.7 Hz, 1H), 5.693 (s, 1H), 3.897-3.853 (m, 3H), 3.772 (s, 3H), 3.435-3.321 (m, 2H), 2.111-2.073 (m, 2H), 1.705-1.655 (m, 2H), 1.301-1.274 (m, 2H).

Example 43

Compound #541

6-(bis(4-chlorophenyl)methyl)-4-((1-((trifluoromethyl)sulfonyl)piperidin-4-yl)amino)quinolin-8-ol

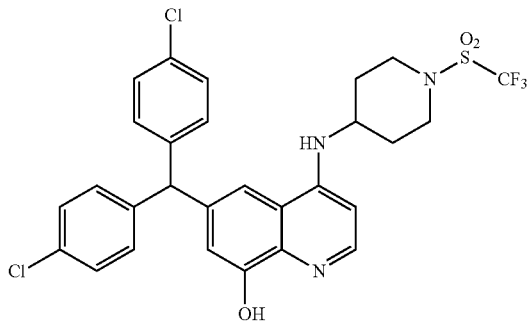 [SMILES: O=S(=O)(N1CCC(Nc2ccnc3c(O)cc(C(c4ccc(Cl)cc4)c4ccc(Cl)cc4)cc23)CC1)C(F)(F)F]

Into a 250-mL round-bottom flask, was placed 6-[bis(4-chlorophenyl)methyl]-8-methoxy-N-[1-(trifluoromethane)sulfonylpiperidin-4-yl]quinolin-4-amine (1 g, 1.60 mmol, 1.00 equip), and dichloromethane (100 mL). To the resulting mixture was then added BBr$_3$ (1.6 g, 6.40 mmol, 4.00 equip) dropwise with stirring at −78° C. The resulting solution was stirred overnight at 25° C. The reaction was then quenched by the addition of water (100 mL). The resulting mixture was concentrated under vacuum. The solids were collected by filtration. The residue was applied onto a silica gel column with dichloromethane:CH$_3$OH (10:1) to yield 6-[bis(4-chlorophenyl)methyl]-4-[[1-(trifluoromethane)sulfonylpiperidin-4-yl]amino]quinolin-8-ol as a yellow solid. LCMS (ES, m/z) 610 [M+H]$^+$;

Example 44

Compound #542

8-(4-aminobutoxy)-6-(bis(4-chlorophenyl)methyl)-N-(1-((trifluoromethyl)sulfonyl)piperidin-4-yl)quinolin-4-amine, trifluoroacetic acid salt

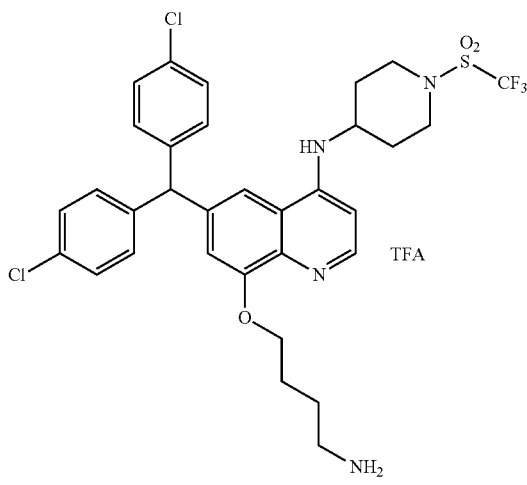 [SMILES: NCCCCOc1cc(C(c2ccc(Cl)cc2)c2ccc(Cl)cc2)cc2c(NC3CCN(S(=O)(=O)C(F)(F)F)CC3)ccnc12]

STEP 1: 2-[4-([6-[bis(4-chlorophenyl)methyl]-4-[[1-(trifluoromethane)sulfonylpiperidin-4-yl]amino]quinolin-8-yl]oxy)butyl]-2,3-dihydro-1H-isoindole-1,3-dione Into a 25-mL round-bottom flask, was placed 6-[bis(4-chlorophenyl)methyl]-4-[[1-(trifluoromethane)sulfonylpiperidin-4-yl]amino]quinolin-8-ol (200 mg, 0.33 mmol, 1.00 equip), N,N-dimethylformamide (10 mL), Cs$_2$CO$_3$ (320 mg, 0.98 mmol, 3.00 equip), and 2-(4-bromobutyl)-2,3-dihydro-1H-isoindole-1,3-dione (140 mg, 0.50 mmol, 1.10 equip). The resulting solution was stirred overnight at 60° C. The reaction was then quenched by the addition of water (100 mL). The solids were collected by filtration to yield 2-[4-([6-[bis(4-chlorophenyl)methyl]-4-[[1-(trifluoromethane)sulfonylpiperidin-4-yl]amino]quinolin-8-yl]oxy)butyl]-2,3-dihydro-1H-isoindole-1,3-dione as a yellow solid. LCMS (ES, m/z) 811 [M+H]$^+$ STEP 2: 8-(4-aminobutoxy)-6-[bis(4-chlorophenyl)methyl]-N-[1-(trifluoromethane)sulfonylpiperidin-4-yl]quinolin-4-amine; trifluoroacetic acid salt Into a 100-mL round-bottom flask, was placed 2-[4-([6-[bis(4-chlorophenyl)methyl]-4-[[1-(trifluoromethane)sulfonylpiperidin-4-yl]amino]quinolin-8-yl]oxy)butyl]-2,3-dihydro-1H-isoindole-1,3-dione (200 mg, 0.25 mmol, 1.00 equip), ethanol (20 mL), and H$_2$N—NH$_2$ (0.2 mL). The resulting solution was stirred overnight at 60° C. The resulting mixture was concentrated under vacuum. The resulting residue was purified by Prep-HPLC with the following conditions (waters2767-5): Column, SunFire Prep C18, 19×150 mm 5 umH; mobile phase, Phase A: water with 0.05% CF$_3$COOH Phase B: CH$_3$CN (35% CH$_3$CN up to 70% for 12 min, hold 95% for 1 min, down to 35% in 1 min, hold 35% in 1 min); Detector, UV220&254 nm to yield 8-(4-aminobutoxy)-6-[bis(4-chlorophenyl)methyl]-N-[1-(trifluoromethane)sulfonylpiperidin-4-yl]quinolin-4-amine, trifluoroacetic acid salt as a white solid.

LCMS (ES, m/z) 681 [M+H]$^+$; $^1$H-NMR (300 MHz, DMSO-D$_6$) δ: 8.401 (d, J=7.2 Hz, 1H), 8.405 (s, 1H), 7.432 (d, J=8.4 Hz, 4H), 7.250-7.222 (m, 5H), 7.085 (d, J=7.2 Hz, 1H), 5.794 (s, 1H), 4.189-4.153 (m, 3H), 3.962-3.920 (m, 2H), 3.443-3.362 (m, 2H), 2.888-2.841 (m, 2H), 2.130-2.092 (m, 2H), 1.846-1.771 (m, 6H).

Example 45

Compound #543

N-(4-((6-(bis(4-chlorophenyl)methyl)-4-((1-((trifluoromethyl)sulfonyl)piperidin-4-yl)amino)quinolin-8-yl)oxy)butyl)acetamide, trifluoroacetic acid salt

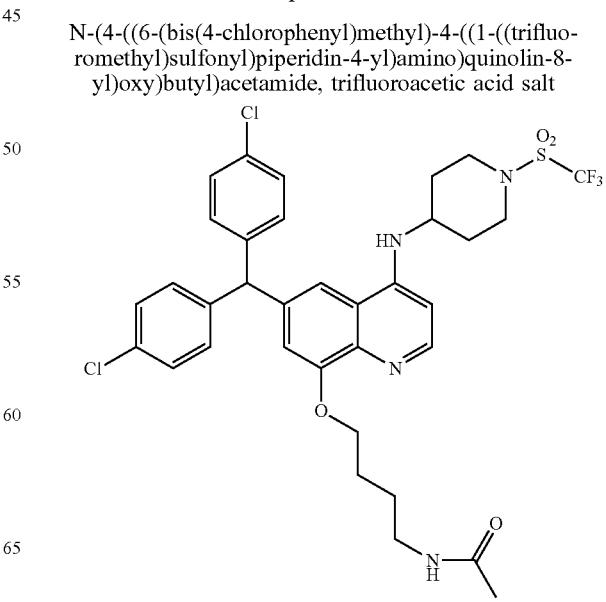

Into a 25-mL round-bottom flask, was placed 8-(4-aminobutoxy)-6-[bis(4-chlorophenyl)methyl]-N-[1-(trifluoromethane)sulfonylpiperidin-4-yl]quinolin-4-amine (130 mg, 0.19 mmol, 1.00 equip), acetic acid (17 mg, 0.28 mmol, 1.50 equip), N,N-dimethylformamide (10 mL), HATU (108 mg, 0.28 mmol, 1.50 equip), and DIPEA (0.1 mL). The resulting solution was stirred overnight at 25° C. The resulting solution was diluted with water (100 mL). The solids were collected by filtration and purified by Prep-HPLC with the following conditions (waters2767-5): Column, SunFire Prep C18, 19×150 mm 5 umH; mobile phase, Phase A: water with 0.05% $CF_3COOH$ Phase: $CH_3CN$ (35% $CH_3CN$ up to 70% in 12 min, hold 95% for 1 min, down to 35% in 1 min, hold 35% for 1 min); Detector, UV220&254 nm to yield N-[4-([6-[bis(4-chlorophenyl)methyl]-4-[[1-(trifluoromethane)sulfonylpiperidin-4-yl]amino]quinolin-8-yl]oxy)butyl]acetamide, trifluoroacetic acid salt as a white solid.

LCMS (ES, m/z) 723 [M+H]$^+$; $^1$H-NMR (300 MHz, DMSO-D$_6$) δ: 8.350 (d, J=7.2 Hz, 1H), 7.973 (s, 1H), 7.427 (d, J=8.4 Hz, 4H), 7.242-7.214 (m, 5H), 7.052 (d, J=6.0 Hz, 1H), 5.785 (s, 1H), 4.185-4.163 (m, 3H), 3.947-3.878 (m, 2H), 3.428-3.345 (m, 2H), 3.125-3.079 (m, 2H), 2.136-2.094 (m, 2H), 1.818-1.759 (m, 7H), 1.601-1.552 (m, 2H).

Example 46

Compound #539 tert-butyl (4-((6-(bis(4-chlorophenyl)methyl)-4-((1-((trifluoromethyl)sulfonyl)piperidin-4-yl)amino)quinolin-8-yl)oxy)butyl)carbamate

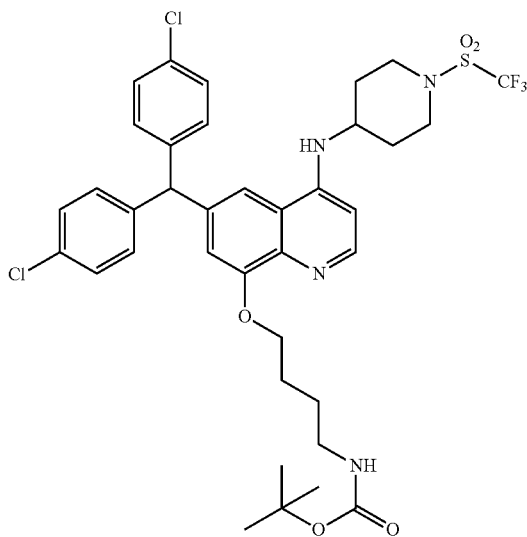 [SMILES: CC(C)(C)OC(=O)NCCCCOc1cc(C(c2ccc(Cl)cc2)c2ccc(Cl)cc2)cc2c(NC3CCN(S(=O)(=O)C(F)(F)F)CC3)ccnc12]

Into a 50-mL round-bottom flask, was placed 6-[bis(4-chlorophenyl)methyl]-4-[[1-(trifluoromethane)sulfonylpiperidin-4-yl]amino]quinolin-8-ol (200 mg, 0.33 mmol, 1.00 equip), N,N-dimethylformamide (20 mL), $Cs_2CO_3$ (320 mg, 0.98 mmol, 3.00 equip), and tert-butyl N-(4-bromobutyl)carbamate (88 mg, 0.35 mmol, 1.10 equip). The resulting solution was stirred for 3 h at 60° C. The resulting solution was diluted with water (150 mL). The solids were collected by filtration. The residue was applied onto a silica gel column with dichloromethane:$CH_3OH$ (10:1) to yield tert-butyl N-[4-([6-[bis(4-chlorophenyl)methyl]-4-[[1-(trifluoromethane)sulfonylpiperidin-4-yl]amino]quinolin-8-yl]oxy)butyl]carbamate as a light brown solid.

LCMS (ES, m/z) 781 [M+H]$^+$; $^1$H-NMR (400 MHz, DMSO-D$_6$) δ: 8.364 (d, J=5.6 Hz, 1H), 7.789 (s, 1H), 7.410 (d, J=8.4 Hz, 4H), 7.211 (d, J=8.4 Hz, 4H), 7.043-6.700 (brm, 2H), 5.709 (s, 1H), 4.010-3.880 (m, 5H), 3.436-3.312 (m, 2H), 2.998-2.951 (m, 2H), 2.111-2.080 (m, 2H), 1.756-1.656 (m, 6H), 1.369 (s, 9H).

Example 47

Compound #540 ethyl 5-((6-(bis(4-chlorophenyl)methyl)-4-((1-((trifluoromethyl)sulfonyl)piperidin-4-yl)amino)quinolin-8-yl)oxy)pentanoate

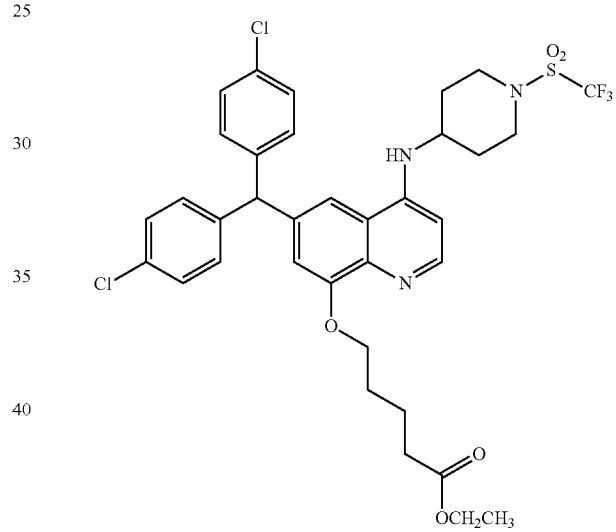

Into a 100-mL round-bottom flask, was placed 6-[bis(4-chlorophenyl)methyl]-4-[[1-(trifluoromethane)sulfonylpiperidin-4-yl]amino]quinolin-8-ol (100 mg, 0.16 mmol, 1.00 equip), N,N-dimethylformamide (20 mL), $Cs_2CO_3$ (160 mg, 0.49 mmol, 3.00 equip), and ethyl 5-bromopentanoate (38 mg, 0.18 mmol, 1.10 equip). The resulting solution was stirred for 3 h at 60° C. The resulting solution was diluted with water (150 mL). The solids were collected by filtration. The residue was applied onto a silica gel column with dichloromethane:$CH_3OH$ (10:1) to yield ethyl 5-([6-[bis(4-chlorophenyl)methyl]-4-[[1-(trifluoromethane)sulfonylpiperidin-4-yl]amino]quinolin-8-yl]oxy)pentanoate as a light yellow solid.

LCMS (ES, m/z) 738 [M+H]$^+$; $^1$H-NMR (300 MHz, DMSO-D$_6$) δ: 8.345 (d, J=5.1 Hz, 1H), 7.699 (s, 1H), 7.395 (d, J=8.4 Hz, 4H), 7.204 (d, J=8.4 Hz, 4H), 6.770 (s, 1H), 6.673-6.608 (m, 2H), 5.674 (s, 1H), 4.069-3.851 (m, 7H), 3.437-3.351 (m, 2H), 2.380-2.334 (m, 2H), 2.111-2.057 (m, 4H), 1.708-1.613 (m, 6H), 1.161 (t, J=7.2 Hz, 3H).

Example 48

Compound #537

5-((6-(bis(4-chlorophenyl)methyl)-4-((1-((trifluoromethyl)sulfonyl)piperidin-4-yl)amino)quinolin-8-yl)oxy)pentanoic acid

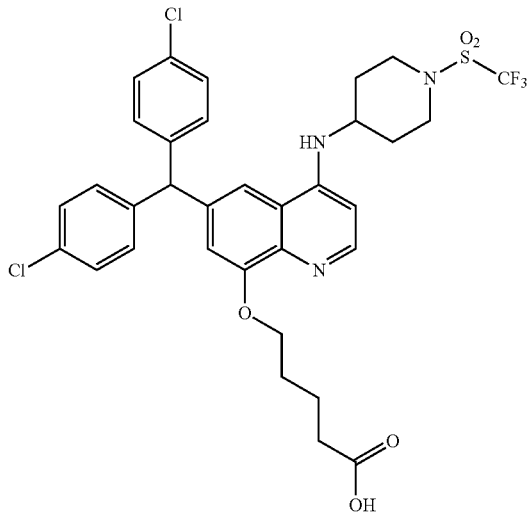 [SMILES: O=C(O)CCCCOc1cc(C(c2ccc(Cl)cc2)c2ccc(Cl)cc2)cc2c(NC3CCN(S(=O)(=O)C(F)(F)F)CC3)ccnc12]

Into a 100-mL round-bottom flask, was placed ethyl 5-([6-[bis(4-chlorophenyl)methyl]-4-[[1-(trifluoromethane)sulfonylpiperidin-4-yl]amino]quinolin-8-yl]oxy)pentanoate (100 mg, 0.14 mmol, 1.00 equip), ethanol (20 mL), and 1M sodium hydroxide (20 mL). The resulting solution was stirred overnight at 25° C. The resulting mixture was concentrated under vacuum. The pH value of the solution was adjusted to 3-4 with 10% HCl. The solids were collected by filtration to yield 5-([6-[bis(4-chlorophenyl)methyl]-4-[[1-(trifluoromethane)sulfonylpiperidin-4-yl]amino]quinolin-8-yl]oxy)pentanoic acid as an off-white solid.

LCMS (ES, m/z) 710 [M+H]$^+$; $^1$H-NMR (300 MHz, DMSO-D$_6$) δ: 8.340 (d, J=5.4 Hz, 1H), 7.720 (s, 1H), 7.392 (d, J=8.4 Hz, 4H), 7.203 (d, J=8.4 Hz, 4H), 6.796-6.720 (m, 2H), 6.649 (d, J=5.7 Hz, 1H), 5.682 (s, 1H), 3.995-3.857 (m, 5H), 3.554-3.351 (m, 2H), 2.340-2.265 (m, 2H), 2.113-2.078 (m, 2H), 1.741-1.570 (m, 6H).

Example 49

Compound #538

5-((6-(bis(4-chlorophenyl)methyl)-4-((1-((trifluoromethyl)sulfonyl)piperidin-4-yl)amino)quinolin-8-yl)oxy)pentanamide

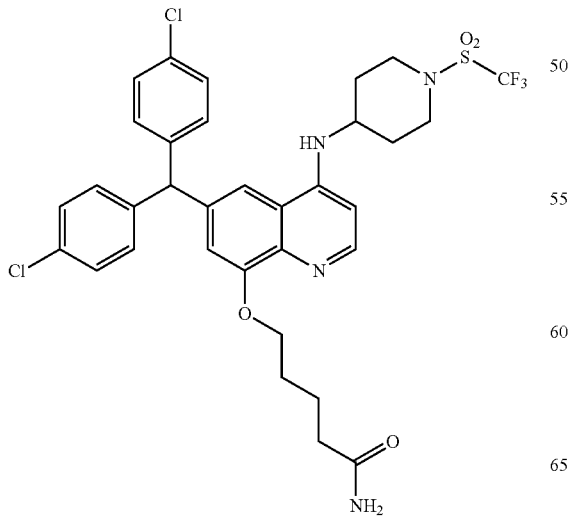

Into a 25-mL round-bottom flask, was placed 5-([6-[bis(4-chlorophenyl)methyl]-4-[[1-(trifluoromethane)sulfonylpiperidin-4-yl]amino]quinolin-8-yl]oxy)pentanoic acid (100 mg, 0.14 mmol, 1.00 equip), NH$_4$Cl (38 mg, 0.71 mmol, 5.00 equip), HATU (80 mg, 0.21 mmol, 1.50 equip), N,N-dimethylformamide (10 mL), and DIEA (0.5 mL). The resulting solution was stirred overnight at 25° C. The resulting solution was diluted with water (100 mL). The solids were collected by filtration. The residue was applied onto a silica gel column with dichloromethane/methanol (10:1) to yield 5-([6-[bis(4-chlorophenyl)methyl]-4-[[1-(trifluoromethane)sulfonylpiperidin-4-yl]amino]quinolin-8-yl]oxy)pentanamide as an off-white solid.

LCMS (ES, m/z) 709 [M+H]$^+$; $^1$H-NMR (300 MHz, DMSO-D$_6$) δ: 8.342 (d, J=6.9 Hz, 1H), 7.914 (s, 1H), 7.428 (d, J=8.4 Hz, 4H), 7.230 (d, J=8.4 Hz, 4H), 7.130 (s, 1H), 6.983 (d, J=6.9 Hz, 1H), 5.767 (s, 1H), 4.121-4.103 (m, 3H), 3.948-3.845 (m, 4H), 3.429-3.345 (m, 2H), 2.188-2.097 (m, 4H), 1.803-1.680 (m, 6H).

Example 50

Compound #530 and #110

6-(bis(4-chlorophenyl)methyl)-2-(2-methoxyethoxy)-N-(1-((trifluoromethyl)sulfonyl)piperidin-4-yl)quinolin-4-amine and 6-(bis(4-chlorophenyl)methyl)-1-(2-methoxyethyl)-4-((1-((trifluoromethyl)sulfonyl)piperidin-4-yl)amino)quinolin-2(1H)-one

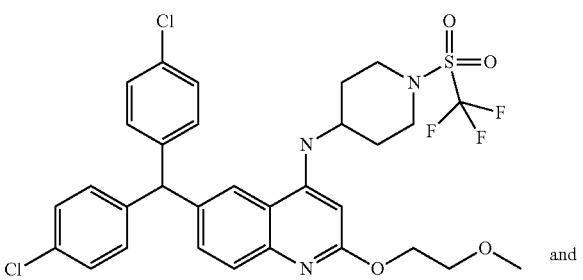 and

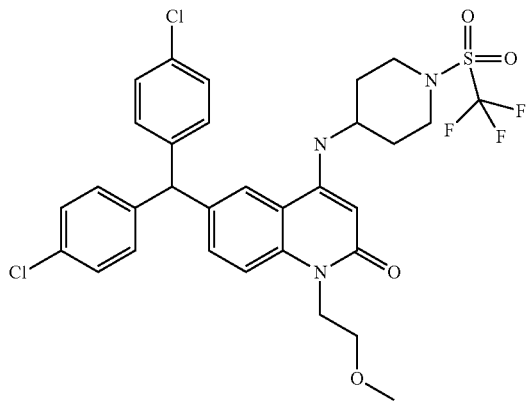

A mixture of 6-(bis(4-chlorophenyl)methyl)-4-((1-((trifluoromethyl)sulfonyl)piperidin-4-yl)amino)quinolin-2(1H)-one (66.7 mg, 0.109 mmol), and 1-bromo-2-methoxyethane (0.0123 mL, 0.131 mmol) in CH$_3$CN (2 mL) was heated at 75° C. overnight. Additional 1-bromo-2-methoxyethane (0.006 mL) was added and the reaction mixture stirred for another 24 h. The reaction mixture was diluted with EtOAc and water. The aqueous layer was extracted with EtOAc twice. The combined organics were concentrated and purified by silica column (25% EtOAc/hexanes) to yield 6-(bis(4-chlorophenyl)methyl)-2-(2-methoxyethoxy)-N-(1-((trifluoromethyl)sulfonyl)piperidin-4-yl)quinolin-4-amine and (80% EtOAc/hexanes) 6-(bis(4-chlorophenyl)methyl)-1-(2-methoxyethyl)-4-((1-((trifluoromethyl)sulfonyl)piperidin-4-yl)amino)quinolin-2(1H)-one.

(M+H)$^+$: 668, 670. $^1$H NMR (CDCl$_3$) δ: 7.68 (d, J=8.6 Hz, 1H), 7.29 (d, J 15=8.1, 4H), 7.25 (m, 2H), 7.04 (d, J=8.1 Hz, 4H), 6.02 (s, 1H), 5.64 (s, 1H), 4.56-4.67 (m, 2H), 4.46 (d, J=7.1 Hz, 1H), 4.00 (m, 2H), 3.71-3.85 (m, 2H), 3.62 (m, 1H), 3.46 (s, 3H), 3.11-3.33 (m, 2H), 2.27 (m, 2H), 1.59-1.70 (m, 2H).

Example 51

Compound #9

4-(3-chlorophenethyl)-6-((4-chlorophenyl)(thiazol-2-yl)methyl)-1-methylquinolin-2(1H)-one

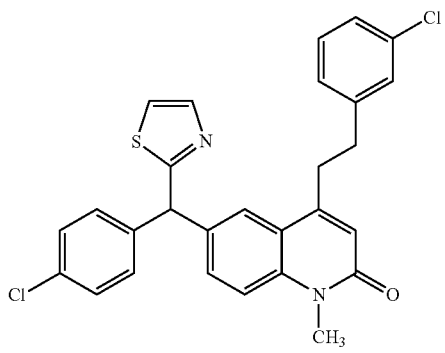 [SMILES: Cn1c(=O)cc(CCc2cccc(Cl)c2)c2cc(C(c3ccc(Cl)cc3)c3nccs3)ccc21]

STEP 1: 4-(3-chlorophenethyl)-6-((4-chlorophenyl)(hydroxy)(thiazol-2-yl)methyl)-1-methylquinolin-2(1H)-one To a solution of thiazole (195 mg, 2.292 mmol, 2.00 equip) in THF (10 mL) at −78° C. was added n-butyllithium (1.6 M in hexanes, 1.447 mL, 2.315 mmol, 2.02 equip) dropwise. After 30 minutes, a solution of 6-(4-chlorobenzoyl)-4-(3-chlorophenethyl)-1-methylquinolin-2(1H)-one (500 mg, 1.146 mmol, 1 equip, prepared as described in ANGIBAUD, P. R., et al., PCT Publication WO2002/051835 A1, published 4 Jul., 2002) in HMPA (8 mL) was added dropwise and the reaction mixture was warmed to room temperature. The reaction was stirred overnight, then quenched with water and the resulting mixture extracted with dichloromethane (3×). The combined organic extracts were washed with brine, dried (Na$_2$SO$_4$), and concentrated. The residue was purified by MPLC using methanol-dichloromethane as the eluent to yield 4-(3-chlorophenethyl)-6-((4-chlorophenyl)(hydroxy)(thiazol-2-yl)methyl)-1-methylquinolin-2(1H)-one as a tan solid.

STEP 2: 4-(3-chlorophenethyl)-6-((4-chlorophenyl)(thiazol-2-yl)methyl)-1-methylquinolin-2(1H)-one To a solution of tin(II) chloride dihydrate (268 mg, 1.189 mmol, 4 equip) and concentrated HCl (0.373 ml) in AcOH (4 ml) was added 4-(3-chlorophenethyl)-6-((4-chlorophenyl)(hydroxy)(thiazol-2-yl)methyl)-1-methylquinolin-2(1H)-one (160 mg, 0.307 mmol, 1 equip). The resulting solution was heated to 110° C. for 45 minutes. The reaction was cooled to room temperature and concentrated. The residue was purified by MPLC using dichloromethane-methanol as the eluent to yield 4-(3-chlorophenethyl)-6-((4-chlorophenyl)(thiazol-2-yl)methyl)-1-methylquinolin-2(1H)-one.

$^1$H NMR (400 MHz, d6-DMSO) δ 7.85 (2H, d), 7.70 (1H, d), 7.60-7.53 (2H, m), 7.43-7.27 (7H, m), 7.16 (1H, d), 6.56 (1H, s), 6.23 (1H, s), 3.58 (3H, s), 3.05-3.01 (2H, m), 2.87-2.83 (2H, m); ES, m/z) 505, 507 [M+H]$^+$

Example 52

Compound #8

4-(3-chlorophenethyl)-6-((4-chlorophenyl)(hydroxy)(thiazol-2-yl)methyl)quinolin-2(1H)-one

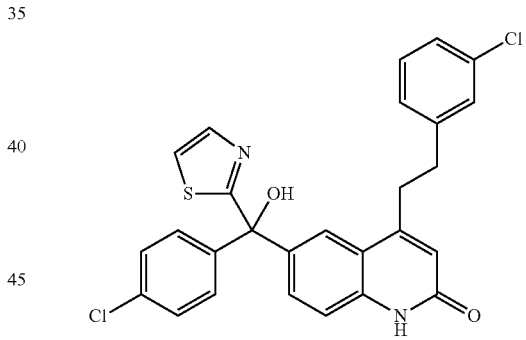

To a solution of thiazole (201 mg, 2.368 mmol, 4.00 equip) in THF (10 mL) at −78° C. was added n-butyllithium (1.6 M in hexanes, 1.495 mL, 2.392 mmol, 4.04 equip) dropwise. After 30 minutes, a solution of 6-(4-chlorobenzoyl)-4-(3-chlorophenethyl)quinolin-2(1H)-one (250 mg, 0.592 mmol, 1 equip, prepared as described in ANGIBAUD, P. R., et al., PCT Publication WO2002/051835 A1, published 4 Jul., 2002) in HMPA (4 mL) was added dropwise and the reaction mixture was warmed to room temperature. The reaction was stirred overnight, then quenched with water and the resulting mixture extracted with dichloromethane (3×). The combined organic extracts were washed with brine, dried (Na$_2$SO$_4$), and concentrated. The residue was purified by MPLC using methanol-dichloromethane as the eluent to yield 4-(3-chlorophenethyl)-6-((4-chlorophenyl)(hydroxy)(thiazol-2-yl)methyl)quinolin-2(1H)-one as a tan solid.

(ES, m/z) 507, 509 [M+H]$^+$

Example 53

Compound #11

4-(3-chlorophenethyl)-6-((4-chlorophenyl)(thiazol-2-yl)methyl)quinolin-2(1H)-one

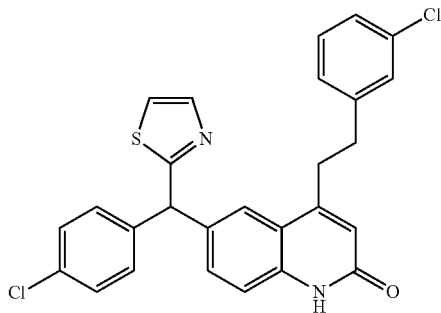 [SMILES: O=c1cc(CCc2cccc(Cl)c2)c2cc(C(c3ccc(Cl)cc3)c3nccs3)ccc2[nH]1]

To a solution of tin(II) chloride dihydrate (121 mg, 0.536 mmol, 4 equiv) and concentrated HCl (0.168 ml) in AcOH (4 ml) was added 4-(3-chlorophenethyl)-6-((4-chlorophenyl)(hydroxy)(thiazol-2-yl)methyl)-1-methylquinolin-2(1H)-one (68 mg, 0.134 mmol, 1 equiv). The resulting solution was heated to 110° C. for 45 minutes. The reaction was cooled to room temperature and concentrated. The residue was taken up in dichloromethane, washed with saturated NaHCO$_3$, dried (Na$_2$SO$_4$), and concentrated. The residue was purified by MPLC using dichloromethane-methanol as the eluent to yield a tacky, off-white solid. The solid was triturated repeatedly with ethyl ether to yield 4-(3-chlorophenethyl)-6-((4-chlorophenyl)(thiazol-2-yl)methyl)quinolin-2(1H)-one as a white solid.
$^1$H NMR (400 MHz, d6-DMSO) δ 7.84 (1H, d), 7.76 (1H, d), 7.69 (1H, d), 7.48-7.27 (7H, m), 7.16 (1H, d), 6.42 (1H, s), 6.16 (1H, s), 3.02-2.98 (2H, m), 2.87-2.83 (2H, m); (ES, m/z) 491, 493 [M+H]$^+$

Example 54

Compound #25

(E)-6-((4-chlorophenyl)(thiazol-2-yl)methyl)-4-styrylquinolin-2(1H)-one

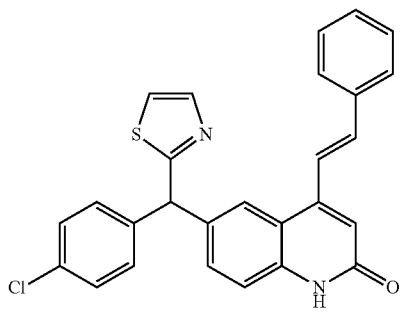 [SMILES: O=c1cc(/C=C/c2ccccc2)c2cc(C(c3ccc(Cl)cc3)c3nccs3)ccc2[nH]1]

STEP 1: 2-(4-chlorophenyl)-2-(4-nitrophenyl)acetonitrile

To a solution of 4-chlorobenzylcyanide (5.909 g, 38.979 mmol, 1.1 equiv) in THF (100 mL) was added potassium t-butoxide (9.941 g, 88.589 mmol, 2.5 equiv) and the solution was stirred for 10 minutes. 4-Fluoronitrobenzene (5.000 g, 35.435 mmol, 1 equiv) was added and the reaction mixture stirred at room temperature overnight. The resulting mixture was acidified to pH 7 with 1N HCl, ethyl acetate and water were added, and the layers were separated. The aqueous layer was extracted 1× with ethyl acetate, and the organic layers were combined, dried (Na$_2$SO$_4$), and concentrated. The residue was purified by MPLC using an ethyl acetate-heptane gradient to yield 2-(4-chlorophenyl)-2-(4-nitrophenyl)acetonitrile as an orange-yellow solid.

STEP 2: 2-(4-chlorophenyl)-2-(4-nitrophenyl)ethanethioamide

A solution of 2-(4-chlorophenyl)-2-(4-nitrophenyl)acetonitrile (1.000 g, 3.667 mmol, 1 equiv) and phosphorus pentasulfide (1.63 g, 7.334 mmol, 2 equiv) in EtOH (20 mL) was heated at reflux temperature for 20 h. The reaction mixture was cooled to room temperature and concentrated. The residue was triturated with hot ethyl ether to yield 2-(4-chlorophenyl)-2-(4-nitrophenyl)ethanethioamide as a yellow solid.

STEP 3: 2-((4-chlorophenyl)(4-nitrophenyl)methyl)thiazole

A solution of 2-(4-chlorophenyl)-2-(4-nitrophenyl)ethanethioamide (800 mg, 2.608 mmol, 1 equiv) and bromoacetaldehyde diethyl acetal (2.055 g, 10.431 mmol, 4 equiv) in acetic acid (12.09 mL) and water (0.47 mL) was heated at 100° C. for 45 minutes. The reaction mixture was poured into water and extracted with ethyl acetate (3×). The combined organic extracts were washed with water, saturated sodium bicarbonate, and then dried over Na$_2$SO$_4$, filtered, and concentrated. The residue was purified by MPLC using ethyl acetate-heptane as eluent to yield 2-((4-chlorophenyl)(4-nitrophenyl)methyl)thiazole as a viscous brown oil.

STEP 4: 4-((4-chlorophenyl)(thiazol-2-yl)methyl)aniline

A solution of 2-((4-chlorophenyl)(4-nitrophenyl)methyl)thiazole (550 mg, 1.663 mmol, 1 equiv) and tin(II) chloride dihydrate (2.321 g, 9.976 mmol, 6 equiv) in MeOH (11 mL) and concentrated HCl (1 ml) was heated at reflux temperature until analytical HPLC showed conversion to the desired product. The reaction mixture was made basic with excess triethylamine. The resulting thick precipitate was filtered through CELITE and the filter pad washed thoroughly with methanol. The filtrate was concentrated and the residue was purified by MPLC using ethyl acetate-heptane as the eluent to yield 4-((4-chlorophenyl)(thiazol-2-yl)methyl)aniline as a white solid (250 mg, 50%). (ES, m/z) 301, 303 [M+H]$^+$

STEP 5: 5-(((4-((4-chlorophenyl)(thiazol-2-yl)methyl)phenyl)amino)methylene)-2,2-dimethyl-1,3-dioxane-4,6-dione To a suspension of 4-((4-chlorophenyl)(thiazol-2-yl)methyl)aniline (220 mg, 0.731 mmol, 1 equiv) in isopropanol (6 mL) was added 2,2-dimethyl-1,3-dioxane-4,6-dione (140 mg, 0.951 mmol, 1.3 equiv) and triethyl orthoformate (443 mg, 2.925 mmol, 4 equiv) and the resulting mixture was heated at 100° C. for 3 h. The reaction mixture was cooled to room temperature and concentrated. The residue was purified by MPLC using dichloromethane-methanol as eluent to yield 5-(((4-((4-chlorophenyl)(thiazol-2-yl)methyl)phenyl)amino)methylene)-2,2-dimethyl-1,3-dioxane-4,6-dione as a pale yellow foam. $^1$H NMR (400 MHz, d6-DMSO) δ 11.25 (1H, d), 8.55 (1H, d), 7.82 (1H, d), 7.69 (1H, d), 7.52 (2H, d), 7.38 (2H, d), 7.38-7.30 (4H, m), 6.19 (1H, s), 1.67 (6H, s).

STEP 6: 6-((4-chlorophenyl)(thiazol-2-yl)methyl)quinolin-4-ol 5-(((4-((4-Chlorophenyl)(thiazol-2-yl)methyl)phenyl)amino)methylene)-2,2-dimethyl-1,3-dioxane-4,6-dione (1.8 g, 3.957 mmol) was added as a solid portionwise over 3-4 minutes to DOWTHERM (75 mL) at 220° C. The resulting mixture was heated for 20 minutes, cooled to room temperature, and treated with excess heptane (30 mL) with stirring. After allowing the solid to settle, the supernatant was decanted and the process repeated 3 times. After concentrating to remove heptane, the residue was purified by MPLC using a dichloromethane-methanol gradient to yield 6-((4-chlorophenyl)(thiazol-2-yl)methyl)quinolin-4-ol. (ES, m/z) 352, 354 [M+H]$^+$ STEP 7: 2-((4-bromoquinolin-6-yl)(4-chlorophenyl)methyl)thiazole 6-((4-chlorophenyl)(thiazol-2-yl)methyl)quinolin-4-ol (500 mg, 1.417 mmol, 1 equip) was dissolved in DMF (4 mL) and phosphorus tribromide (766 mg, 2.834 mmol, 2 equip) was added dropwise. A red-brown precipitate formed immediately and was collected to yield 2-((4-bromoquinolin-6-yl)(4-chlorophenyl)methyl)thiazole which was used in the next step without purification.

STEP 8: 4-bromo-6-((4-chlorophenyl)(thiazol-2-yl)methyl)quinoline 1-oxide

A solution of 2-((4-bromoquinolin-6-yl)(4-chlorophenyl)methyl)thiazole (900 mg, 2.165 mmol, 1 equip) and meta-chloroperoxybenzoic acid (578 mg, 3.247 mmol, 1.5 equip) in dichloromethane (30 mL) was stirred at room temperature for 1 h, at which point additional meta-chloroperoxybenzoic acid (578 mg, 3.247 mmol, 1.5 equip) was added and the solution stirred for an additional 3 h. The reaction mixture was washed with 10% $Na_2CO_3$ and the aqueous layer extracted with dichloromethane (2×). The combined organic extracts were washed with water, dried over $Na_2SO_4$, and concentrated to yield 4-bromo-6-((4-chlorophenyl)(thiazol-2-yl)methyl)quinoline 1-oxide as a pale yellow semi-solid.

STEP 9: 4-bromo-6-((4-chlorophenyl)(thiazol-2-yl)methyl)quinolin-2(1H)-one p-Toluenesulfonyl chloride (628 mg, 3.293 mmol, 1.5 equip) was added to a biphasic mixture of 4-bromo-6-((4-chlorophenyl)(thiazol-2-yl)methyl)quinoline 1-oxide in dichloromethane (6 mL) and 10% $Na_2CO_3$ (42 mL) and the resulting mixture stirred for 1 h. The reaction mixture was diluted with dichloromethane and water, the layers were separated, and the aqueous layer was extracted with dichloromethane. The combined organic extracts were dried over $Na_2SO_4$, filtered, and concentrated. The residue was purified by MPLC to yield 4-bromo-6-((4-chlorophenyl)(thiazol-2-yl)methyl)quinolin-2(1H)-one as a white solid.

STEP 10: (E)-6-((4-chlorophenyl)(thiazol-2-yl)methyl)-4-styrylquinolin-2(1H)-one 4-Bromo-6-((4-chlorophenyl)(thiazol-2-yl)methyl)quinolin-2(1H)-one (50 mg, 0.116 mol, 1 equip), trans-beta-styreneboronic acid (35 mg, 0.232 mmol, 2 equip), SPhos (9.7 mg, 0.023 mmol, 0.2 equip), tripotassium phosphate (49.2 mg, 0.232 mmol, 2 equip), and palladium acetate (2.6 mg, 0.012 mmol, 0.1 equip) were added to 1,4-dioxane (5 mL) and the resulting mixture stirred for 2 h. Additional trans-beta-styreneboronic acid (35 mg, 0.232 mmol, 2 equip), SPhos (9.7 mg, 0.023 mmol, 0.2 equip), tripotassium phosphate (49.2 mg, 0.232 mmol, 2 equip), and palladium acetate (2.6 mg, 0.012 mmol, 0.1 equip) were added and the resulting mixture was stirred overnight. The reaction mixture was diluted with water and ethyl acetate and the layers were separated. The organic phase was washed with saturated sodium bicarbonate, then water, dried over $Na_2SO_4$, filtered and concentrated. The residue was purified by MPLC using a dichloromethane-methanol gradient to yield (E)-6-((4-chlorophenyl)(thiazol-2-yl)methyl)-4-styrylquinolin-2(1H)-one.

$^1$H NMR (400 MHz, d6-DMSO) δ 8.10 (1H, d), 7.83 (1H, d), 7.74-7.60 (4H, m), 7.52-7.32 (10H, m), 6.80 (1H, s), 6.15 (1H, s); (ES, m/z) 455, 457 [M+H]

Example 55

Compound #28

(E)-6-((4-chlorophenyl)(thiazol-2-yl)methyl)-4-(4-(trifluoromethyl)styryl)quinolin-2(1H)-one

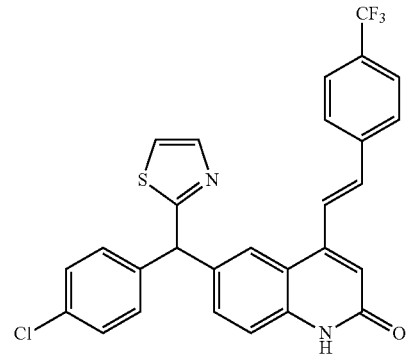 [SMILES: O=c1cc(/C=C/c2ccc(C(F)(F)F)cc2)c2cc(C(c3ccc(Cl)cc3)c3nccs3)ccc2[nH]1]

4-Bromo-6-((4-chlorophenyl)(thiazol-2-yl)methyl)quinolin-2(1H)-one (80 mg, 0.185 mol, 1 equip), trans-2-[4-(trifluoromethyl)phenyl]vinylboronic acid (80 mg, 0.371 mmol, 2 equip), SPhos (15.5 mg, 0.037 mmol, 0.2 equip), tripotassium phosphate (78.7 mg, 0.371 mmol, 2 equip), and palladium acetate (4.2 mg, 0.019 mmol, 0.1 equip) were added to 1,4-dioxane (5 mL) and the resulting mixture stirred for 2 h. Additional trans-2-[4-(trifluoromethyl)phenyl]vinylboronic acid (80 mg, 0.371 mmol, 2 equip), SPhos (15.5 mg, 0.037 mmol, 0.2 equip), tripotassium phosphate (78.7 mg, 0.371 mmol, 2 equip), and palladium acetate (4.2 mg, 0.019 mmol, 0.1 equip) were added and the resulting mixture was stirred overnight. The reaction mixture was diluted with water and ethyl acetate and the layers were separated. The organic phase was washed with saturated sodium bicarbonate, then water, dried over $Na_2SO_4$, filtered and concentrated. The residue was purified by RP-HPLC to yield (E)-6-((4-chlorophenyl)(thiazol-2-yl)methyl)-4-(4-(trifluoromethyl)styryl)quinolin-2(1H)-one.

¹H NMR (600 MHz, d6-DMSO) δ 7.98 (1H, d), 7.86 (2H, d), 7.77-7.70 (4H, m), 7.59 (1H, d), 7.50 (1H, d), 7.40-7.35 (4H, m), 7.32 (2H, d), 6.80 (1H, s), 6.10 (1H, s); (ES, m/z) 522, 524 [M+H]⁺

Example 56

Compound #38

(E)-6-((4-chlorophenyl)(thiazol-2-yl)methyl)-4-(3-fluorostryl)quinolin-2(1H)-one

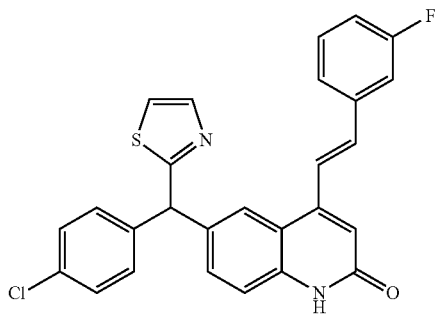 [SMILES: O=c1cc(/C=C/c2cccc(F)c2)c2cc(C(c3ccc(Cl)cc3)c3nccs3)ccc2[nH]1]

4-Bromo-6-((4-chlorophenyl)(thiazol-2-yl)methyl)quinolin-2(1H)-one (80 mg, 0.185 mol, 1 equip), trans-2-(3-fluorophenyl)vinylboronic acid (61.5 mg, 0.371 mmol, 2 equip), SPhos (15.5 mg, 0.037 mmol, 0.2 equip), tripotassium phosphate (78.7 mg, 0.371 mmol, 2 equip), and palladium acetate (4.2 mg, 0.019 mmol, 0.1 equip) were added to 1,4-dioxane (5 mL) and the resulting mixture stirred for 72 h. The reaction mixture was diluted with water and ethyl acetate and the layers were separated. The organic phase was washed with saturated sodium bicarbonate, then water, dried over Na₂SO₄, filtered and concentrated. The residue was purified by RP-HPLC and the fractions were lyophilized. The lyophilized product was washed with hot hexanes to remove residual SPhos, filtered, and dried under vacuum to yield (E)-6-((4-chlorophenyl)(thiazol-2-yl)methyl)-4-(3-fluorostyryl)quinolin-2(1H)-one as an off-white solid.

¹H NMR (400 MHz, d6-DMSO) δ 8.15 (1H, d), 7.80 (1H, d), 7.74-7.62 (3H, m), 7.56-7.32 (9H, m), 7.21 (1H, m), 6.80 (1H, s), 6.12 (1H, s); (ES, m/z) 473, 475 [M+H]

Example 57

Compound #511

(E)-2-((4-chlorophenyl)(4-strylquinolin-6-yl)methyl)thiazole

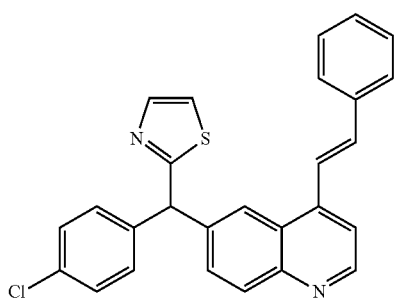 [SMILES: Clc1ccc(C(c2ccc3nccc(/C=C/c4ccccc4)c3c2)c2nccs2)cc1]

A mixture of 2-((4-bromoquinolin-6-yl)(4-chlorophenyl)methyl)thiazole (28 mg, 0.0674 mmol), (E)-styrylboronic acid (19.9 mg, 0.135 mmol), Pd(OAc)₂ (1.5 mg, 0.00674 mmol), SPhos (5.5 mg, 0.022 mmol) and K₃PO₄ (28.6 mg, 0.135 mmol) was stirred at room temperature overnight under argon. The reaction was diluted with EtOAc and water. The aqueous layer was extracted with EtOAc twice. The organic layers combined were concentrated and the crude material was purified by silica column chromatography (25% EtOAc/hexanes) to yield (E)-2-((4-chlorophenyl)(4-styrylquinolin-6-yl)methyl)thiazole.
(M+H)⁺: 439, 440, 442.

Example 58

Compound #501

(E)-bis(4-chlorophenyl)(4-styrylquinolin-6-yl)methanol

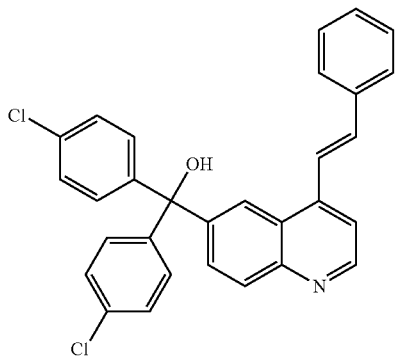 [SMILES: OC(c1ccc(Cl)cc1)(c1ccc(Cl)cc1)c1ccc2nccc(/C=C/c3ccccc3)c2c1]

STEP 1: 5-(((4-(4-chlorobenzoyl)phenyl)amino)methylene)-2,2-dimethyl-1,3-dioxane-4,6-dione A solution of Meldtrum's acid (0.467 g, 3.24 mmol) and triethylorthoformate (2 mL) was heated in a sealed tube to 145° C. After 1h, the solution was allowed to cool to 50° C. and (4-aminophenyl)(4-chlorophenyl)methanone in (0.5 g, 2.16 mmol) was added at once. The reaction mixture was heated to 145° C. for 2 hr, and then cooled to room temperature. The white precipitates were filtered and washed with hexanes to yield 5-(((4-(4-chlorobenzoyl)phenyl)amino)methylene)-2,2-dimethyl-1,3-dioxane-4,6-dione. (M+Na)⁺:408.

STEP 2: 6-(4-chlorobenzoyl)quinolin-4(1H)-one

To a flask with DOWTHERM at 245° C. was added 5-(((4-(4-chlorobenzoyl)phenyl)amino)methylene)-2,2-dimethyl-1,3-dioxane-4,6-dione (3.3 g, 8.55 mmol) in portions. The resulting solution was heated for 10 min and cooled down to room temperature. Solids were precipitated from the solution. To the reaction mixture was added hexanes and the solids filtered. The solids were washed thoroughly with Et₂O and hexanes and dried under vacuum to yield 6-(4-chlorobenzoyl)quinolin-4(1H)-one. (M+H)⁺: 284, 286.

STEP 3: (4-bromoquinolin-6-yl)(4-chlorophenyl)methanone

To a suspension of 6-(4-chlorobenzoyl)quinolin-4(1H)-one (1.26 g, 4.45 mmol) in DMF (8 mL) at room temperature was added slowly phosphorous tribromide. The resulting mixture was stirred under argon for 30 min. The reaction mixture was made basic by the addition of solid NaHCO$_3$ until pH was greater than 10, diluted with water and filtered. The product was washed with several portion of water and dried to yield (4-bromoquinolin-6-yl)(4-chlorophenyl) methanone. (M+H)$^+$: 346, 348.

STEP 4: (4-bromoquinolin-6-yl)bis(4-chlorophenyl)methanol

To a solution of (4-bromoquinolin-6-yl)(4-chlorophenyl) methanone (0.25 g, 0.72 mmol) in THF (5 mL) was slowly added (4-chlorophenyl)magnesium bromide (1.08 mL, 1 M in THF) at 0° C. under the argon. The resulting solution was kept at 0° C. for 3 hr. The reaction was quenched with saturated NH$_4$Cl at 0° C. and the aqueous mixture was extracted with EtOAc 2 times. The combined organics were concentrated and purified by silica column chromatography (20-30% EtOAc/hexanes) to yield (4-bromoquinolin-6-yl) bis(4-chlorophenyl)methanol. (M+H)$^+$: 458, 460.

STEP 5: (E)-bis(4-chlorophenyl)(4-strylquinolin-6-yl)methanol

A mixture of (4-bromoquinolin-6-yl)bis(4-chlorophenyl) methanol (50 mg, 0.109 mmol), (E)-styrylboronic acid (25.8 mg, 0.17 mmol), Pd(OAc)$_2$ (2.44 mg, 0.0109 mmol), SPhos (8.9 mg, 0.022 mmol) and K$_3$PO$_4$ (46 mg, 0.218 mmol) was warmed to 30° C. for 7 hr under argon and then stirred at room temperature overnight. The reaction was quenched with water. The solids were filtered. The aqueous layer was extracted with EtOAc twice. The organic layers and solids (which were dissolved in EtOAc) together were concentrated and the crude material was purified by silica column chromatography (35% EtOAc/hexanes) to yield (E)-bis(4-chlorophenyl)(4-styrylquinolin-6-yl)methanol. (M+H)$^+$: 482, 484.

Example 59

Compound #503

(E)-6-(bis(4-chlorophenyl)methyl)-4-styrylquinoline

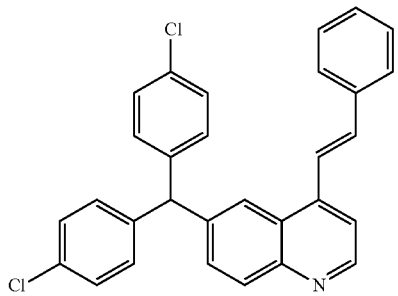 [SMILES: Clc1ccc(C(c2ccc(Cl)cc2)c2ccc3nccc(/C=C/c4ccccc4)c3c2)cc1]

To a suspension of (E)-bis(4-chlorophenyl)(4-styrylquinolin-6-yl)methanol (18 mg, 0.0373 mmol) and triethylsilane (0.0238 mL, 0.149 mmol) in CH$_2$Cl$_2$ (1 mL) at −78° C. was dropwise added titanium chloride (0.0102 mL, 0.0933 mmol). The resulting mixture was warmed to 0° C. for 20 min. To the reaction was slowly added aq. NaHCO$_3$, ice at 0° C. and CH$_2$Cl$_2$. 1N NaOH was added until the aqueous solution was basic. The aqueous layer was extracted with CH$_2$Cl$_2$ twice. The organics were concentrated and purified by silica column chromatography (20-25% EtOAc/hexanes). The product was found to contain ~7% cis-isomer based on NMR. The resulting mixture was recrystallized from EtOAc/hexanes to remove the Cis isomer.
(M+H)$^+$: 466, 468

Example 60

Compound #513 tert-butyl 4-(6-((4-chlorophenyl)(thiazol-2-yl) methyl)quinolin-4-yl)-5,6-dihydropyridine-1 (2H)-carboxylate

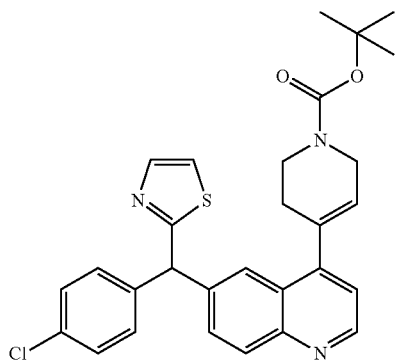 [SMILES: CC(C)(C)OC(=O)N1CC=C(c2ccnc3ccc(C(c4ccc(Cl)cc4)c4nccs4)cc23)CC1]

A mixture of 2-((4-bromoquinolin-6-yl)(4-chlorophenyl) methyl)thiazole (28 mg, 0.0674 mmol), tert-butyl 4-(4,4,5,5-tetramethyl-1,3,2-dioxaborolan-2-yl)-5,6-dihydropyridine-1(2H)-carboxylate (37.5 mg, 0.121 mmol), Pd(dppf) Cl$_2$.CH$_2$Cl$_2$ (5.5 mg, 0.00674), Na$_2$CO$_3$ (14.3 mg, 0.135 mmol) in 1,4-dioxane (0.8 mL) and water (0.4 mL) was heated at 95° C. for 5 hr under argon. The reaction was cooled to room temperature and diluted with EtOAc and water. The aqueous layer was extracted with EtOAc once. The combined organics were concentrated and purified by silica column chromatography (50% EtOAc/hexanes) to yield tert-butyl 4-(6-((4-chlorophenyl)(thiazol-2-yl)methyl) quinolin-4-yl)-5,6-dihydropyridine-1(2H)-carboxylate.
(M+H)$^+$: 518, 519, 520

Example 61

Compound #510

(2-(tert-butoxy)-4-(4-(trifluoromethoxy)benzyl)quinolin-6-yl)(4-chlorophenyl)(thiazol-2-yl)methanol

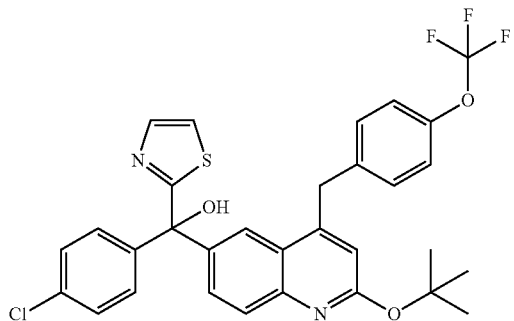 [SMILES: CC(C)(C)Oc1cc(Cc2ccc(OC(F)(F)F)cc2)c2cc(C(O)(c3ccc(Cl)cc3)c3nccs3)ccc2n1]

A mixture of (4-bromo-2-(tert-butoxy)quinolin-6-yl)(4-chlorophenyl)(thiazol-2-yl)methanol (79 mg, 0.157 mmol) and 4,4,5,5-tetramethyl-2-(4-(trifluoromethoxy)benzyl)-1,3,2-dioxaborolane (80.5 mg, 0.267 mmol) in the presence of Pd(dppf)Cl$_2$.CH$_2$Cl$_2$ (512 mg, 0.0157 mmol), Na$_2$CO$_3$ (33 mg, 0.314 mmol) in 1,4-dioxane (1 mL) and water (0.25 mL) was heated at 80° C. overnight. The reaction was diluted with EtOAc and water. The organics were concentrated and purified by silica column (80% EtOAc/hexanes) chromatography to yield (2-(tert-butoxy)-4-(4-(trifluoromethoxy)benzyl)quinolin-6-yl)(4-chlorophenyl)(thiazol-2-yl)methanol.

(M−Bu$^t$)$^+$: 543, 546; (M+H)$^+$: 599, 601.

Example 62

Compound #515

6-((4-chlorophenyl)(thiazol-2-yl)methyl)-4-(4-(trifluoromethoxy)benzyl)quinolin-2(1H)-one

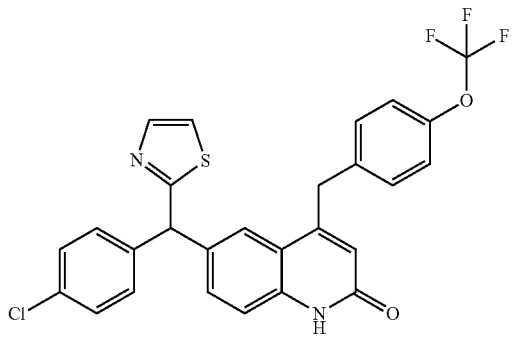 [SMILES: O=c1cc(Cc2ccc(OC(F)(F)F)cc2)c2cc(C(c3ccc(Cl)cc3)c3nccs3)ccc2[nH]1]

(2-(tert-Butoxy)-4-(4-(trifluoromethoxy)benzyl)quinolin-6-yl)(4-chlorophenyl)(thiazol-2-yl)methanol (55 mg, 0.0918 mmol) and tin(II) chloride dihydrate (83 mg, 0.367 mmol) were combined in AcOH (2 mL). HCl (conc. 36%, 0.115 mL) was then added. The solution was heated to 110° C. After 45 min the reaction was cooled to room temperature and concentrated. The residue was taken up in CH$_2$Cl$_2$ and washed with NaHCO$_3$ (satd), dried (Na$_2$SO$_4$) and concentrated. The resulting residue was purified by silica column (70-80% EtOAc/hexanes) chromatography to yield 6-((4-chlorophenyl)(thiazol-2-yl)methyl)-4-(4-(trifluoromethoxy)benzyl)quinolin-2(1H)-one.

(M+H)$^+$: 527, 528, 530

Example 63

Compound #504

(E)-(4-methoxyphenyl)(4-styrylquinolin-6-yl)(thiazol-2-yl)methanol

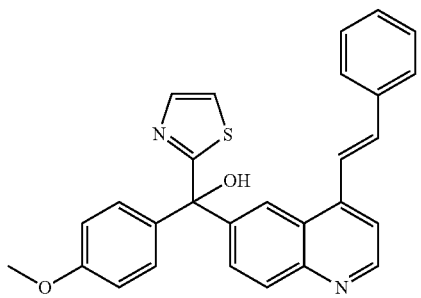 [SMILES: COc1ccc(C(O)(c2ccc3nccc(/C=C/c4ccccc4)c3c2)c2nccs2)cc1]

STEP 1:
4-bromo-N-methoxy-N-methylquinoline-6-carboxamide

To a mixture of 4-bromoquinoline-6-carboxylic acid (5 g), CH$_3$ONH(CH$_3$) hydrochloride salt (1.8 eq. 3.5 g), and HATU (1.15 eq. 8.67 g) in CH$_2$Cl$_2$ (100 mL) was slowly added triethylamine (4 eq. 11 mL) at 0° C. and the resulting reaction mixture was stirred at room temperature overnight. The reaction was diluted with CH$_2$Cl$_2$ and water. The combined organics were washed with water several times, concentrated and then purified by chromatography (60-70% EtOAc/hexanes) to yield 4-bromo-N-methoxy-N-methylquinoline-6-carboxamide as a white solid.

STEP 2: (E)-N-methoxy-N-methyl-4-styrylquinoline-6-carboxamide

A mixture of 4-bromo-N-methoxy-N-methylquinoline-6-carboxamide (155 mg, 0.525 mmol), (E)-styrylboronic acid (155 mg, 1.05 mmol), Pd(OAc)$_2$ (11.8 mg, 0.053 mmol), SPhos (43 mg, 0.105 mmol) and K$_3$PO$_4$.H$_2$O (334 mg, 1.58 mmol) in anhydrous THF (5 mL) was heated at 35° C. overnight. The reaction was diluted with DCM and water. The organics were washed with water and concentrated. The resulting residue was purified by silica column chromatography (40-55% EtOAc/hexanes) to yield (E)-N-methoxy-N-methyl-4-styrylquinoline-6-carboxamide. (ES, m/z) 319.0 [M+H]$^+$ STEP 3: (E)-(4-methoxyphenyl)(4-styrylquinolin-6-yl)methanone To a solution of (E)-N-methoxy-N-methyl-4-styrylquinoline-6-carboxamide (150 mg, 0.47 mmol) in anhydrous THF (2 mL) was dropwise added dropwise (4-chlorophenyl)magnesium bromide (0.5 M, 1.23 mL, 0.61 mmol) at 0° C. under N$_2$ and the resulting reaction mixture was stirred at 0° C. for 3 hr. The reaction was diluted with CH$_2$Cl$_2$ and water. The aqueous layer was extracted with CH$_2$Cl$_2$ and the combined organics were concentrated and purified by chromatography (15-20% EtOAc/hexanes) to yield (E)-(4-methoxyphenyl)(4-styrylquinolin-6-yl)methanone. (ES, m/z) 366.0 [M+H]$^+$ STEP 4: (E)-(4-methoxyphenyl)(4-styrylquinolin-6-yl)(thiazol-2-yl)methanol To a solution of thiazole (0.021 mL, 0.288 mmol) in anhydrous THF (1.5 mL) was added dropwise n-BuLi (1.6M in hexane, 0.18 mmol) at −78° C. under the argon. The resulting yellow mixture was stirred at this temperature for 30 min and then a solution of (E)-(4-methoxyphenyl)(4-styrylquinolin-6-yl)methanone (52.7 mg, 0.144 mmol) in THF (0.5 mL) was added dropwise. The reaction was slowly warmed to room temperature and continuously stirred for 1.5 hr. The reaction was quenched with saturated NH$_4$Cl$_2$ and extracted with CH$_2$Cl$_2$. The combined organics were concentrated and purified by chromatography (60% EtOAc/hexanes) to yield (E)-(4-methoxyphenyl)(4-styrylquinolin-6-yl)(thiazol-2-yl)methanol as a white solid.

(ES, m/z) 451.0 [M+H]$^+$

Example 64

Compound #505

(E)-2-((4-methoxyphenyl)(4-strylquinolin-6-yl)methyl)thiazole

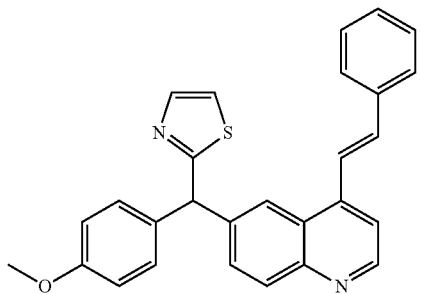 [SMILES: COc1ccc(C(c2ccc3nccc(/C=C/c4ccccc4)c3c2)c2nccs2)cc1]

To a solution of (E)-(4-methoxyphenyl)(4-styrylquinolin-6-yl)(thiazol-2-yl)methanol (33 mg, 0.0732 mmol) and triethylsilane (0.035 mL, 0.22 mmol) in $CH_2Cl_2$ (2 mL) at −78° C. was added dropwise $TiCl_4$ (0.22 mL, 0.22 mmol). The resulting mixture (turned to dark green suspension) was kept at −78° C. for 20 min and then warmed to 0° C. The reaction was maintained at 0° C. for 1 hr and then quenched with ice, $CH_2Cl_2$ and aqueous NaOH until the aqueous layer became basic. The aqueous layer was extracted with $CH_2Cl_2$ twice. The combined organics were concentrated and purified by chromatography (silica column, 25% EtOAc/$CH_2Cl_2$) to yield (E)-2-((4-methoxyphenyl)(4-styrylquinolin-6-yl)methyl)thiazole.

(ES, m/z) 435.0, 437.1 [M+H]$^+$

Example 65

Compound #512

(E)-(2-(tert-butoxy)-4-styrylquinolin-6-yl)(4-chlorophenyl)(4-methoxyphenyl)methanol

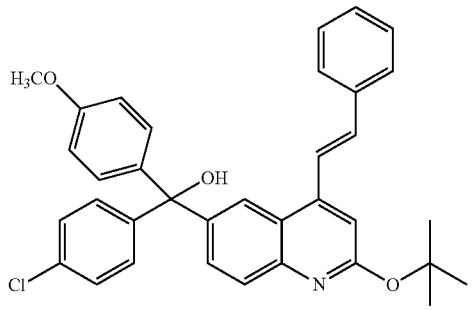 [SMILES: COc1ccc(C(O)(c2ccc(Cl)cc2)c2ccc3nc(OC(C)(C)C)cc(/C=C/c4ccccc4)c3c2)cc1]

A mixture of (4-bromo-2-(tert-butoxy)quinolin-6-yl)(4-chlorophenyl)(4-methoxyphenyl)methanol (107 mg, 0.203 mmol), (E)-styrylboronic acid (60 mg, 0.406 mmol), Pd(OAc)$_2$ (4.56 mg, 0.0203 mmol), SPhos (16.7 mg, 0.0406 mmol) and $K_3PO_4·H_2O$ (86.2 mg, 0.406 mmol) in anhydrous THF (1 mL) was heated at 35° C. overnight. The reaction was diluted with DCM and water. The organics were washed with water and concentrated. The crude material was purified by silica column (40-55% EtOAc/hexanes) to yield (E)-(2-(tert-butoxy)-4-styrylquinolin-6-yl)(4-chlorophenyl)(4-methoxyphenyl)methanol.

(ES, m/z) 550, 551 [M+H]$^+$; 494, 495 (M−Bu$^t$)$^+$.

Example 66

Compound #514

(E)-6-((4-chlorophenyl)(4-methoxyphenyl)methyl)-4-styrylquinolin-2(1H)-one

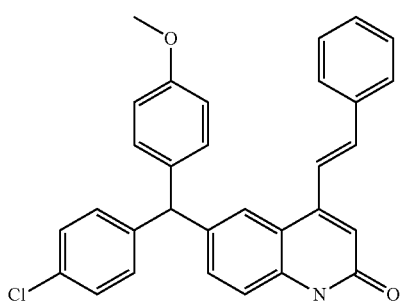 [SMILES: COc1ccc(C(c2ccc(Cl)cc2)c2ccc3[nH]c(=O)cc(/C=C/c4ccccc4)c3c2)cc1]

To a solution of (E)-(4-methoxyphenyl)(4-styrylquinolin-6-yl)(thiazol-2-yl)methanol (50 mg, 0.0909 mmol) and triethylsilane (0.029 mL, 0.182 mmol) in $CH_2Cl_2$ (2 mL) at −78° C. was added dropwise $TiCl_4$ (0.27 mL, 0.273 mmol). The resulting mixture (turned to dark green suspension) was kept at −78° C. for 20 min and then warmed to 0° C. The reaction was continued at 0° C. for 1 hr and then quenched with ice, $CH_2Cl_2$ and aq. NaOH until the aqueous layer became basic. The aqueous layer was extracted with $CH_2Cl_2$ twice. The combined organics were concentrated and purified by chromatography (silica column, 75% EtOAc/$CH_2Cl_2$) to yield (E)-6-((4-chlorophenyl)(4-methoxyphenyl)methyl)-4-styrylquinolin-2(1H)-one.

(ES, m/z) 478.0, 480.1 [M+H]$^+$

Example 67

Compound #14

6-(bis(4-chlorophenyl)methyl)-4-(1-(2,2,2-trifluoroacetyl)-1,2,3,6-tetrahydropyridin-4-yl)quinolin-2(1H)-one

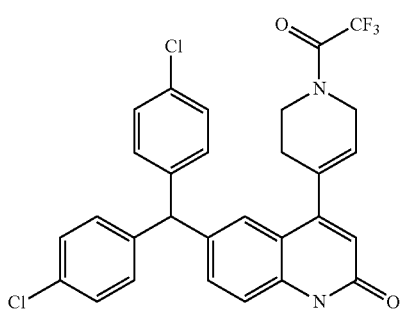 [SMILES: O=C(N1CC=C(c2cc(=O)[nH]c3ccc(C(c4ccc(Cl)cc4)c4ccc(Cl)cc4)cc23)CC1)C(F)(F)F]

STEP 1: 6-(bis(4-chlorophenyl)methyl)-4-(1,2,3,6-tetrahydropyridin-4-yl)quinolin-2(1H)-one To a solution of tert-butyl 4-(6-(bis(4-chlorophenyl)methyl)-2-oxo-1,2-dihydroquinolin-4-yl)-5,6-dihydropyridine-1(2H)-carboxylate (80 mg, 0.142 mmol) in DCM (1 mL) was added TFA (0.35 mL) and the resulting mixture was stirred at room temperature for 2 hr. The reaction was concentrated and dried under the high vacuum to yield 6-(bis(4-chlorophenyl)methyl)-4-(1,2,3,6-tetrahydropyridin-4-yl)quinolin-2(1H)-one, which was used in the next step without further purification. (ES, m/z) 461, 463 [M+H]$^+$ STEP 2: 6-(bis(4-chlorophenyl)methyl)-4-(1-(2,2,2-trifluoroacetyl)-1,2,3,6-tetrahydropyridin-4-yl)quinolin-2(1H)-one To a solution of 6-(bis(4-chlorophenyl)methyl)-4-(1,2,3,6-tetrahydropyridin-4-yl)quinolin-2 (1H)-one (41 mg, 0.0713 mmol) in CH$_2$Cl$_2$ (1 mL) was added TEA (0.06 mL, 0.428 mmol) at 0° C. under argon followed by addition of trifluoroacetic anhydride (0.093 mL, 0.093 mmol, 1M in CH$_2$Cl$_2$ solution). The reaction mixture was stirred for 3 hr at room temperature. A saturated NaHCO$_3$ solution was added and the resulting mixture was stirred for 2 min. The organics were concentrated and purified (65% EtOAc/hexanes) to yield 6-(bis(4-chlorophenyl)methyl)-4-(1-(2,2,2-trifluoroacetyl)-1,2,3,6-tetrahydropyridin-4-yl)quinolin-2(1H)-one.

(ES, m/z) 557, 559 [M+H]$^+$

Example 68

Compound #17 and #519

6-(bis(4-chlorophenyl)methyl)-4-(1-((trifluoromethyl)sulfonyl)-1,2,3,6-tetrahydropyridin-4-yl)quinolin-2(1H)-one and 6-(bis(4-chlorophenyl)methyl)-4-(1-((trifluoromethyl)sulfonyl)-1,2,3,6-tetrahydropyridin-4-yl)quinolin-2-yl trifluoromethanesulfonate

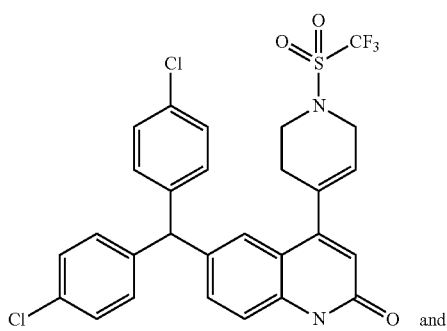

and

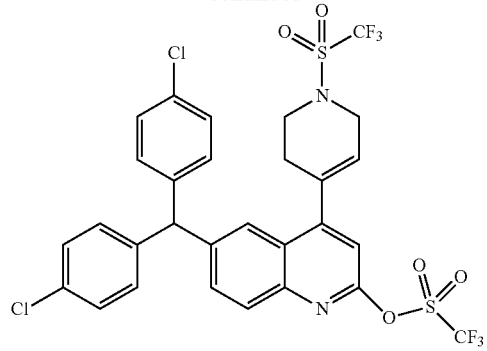

STEP 1: 6-(bis(4-chlorophenyl)methyl)-4-(1,2,3,6-tetrahydropyridin-4-yl)quinolin-2(1H)-one A mixture of 6-(bis(4-chlorophenyl)methyl)-4-(1-(2,2,2-trifluoroacetyl)-1,2,3,6-tetrahydropyridin-4-yl)quinolin-2 (1H)-one (23 mg, 0.041 mmol), Na$_2$CO$_3$ (22.8 mg, 0.165 mmol) in THF (0.8 mL), MeOH (0.5 mL) and a couple of drops of water was stirred at 30° C. for 3 hr. The solvent was evaporated and to the residue was added DCM and water. The organics were dried over anhydrous Na$_2$SO$_4$, filtered and concentrated to yield 6-(bis(4-chlorophenyl)methyl)-4-(1,2,3,6-tetrahydropyridin-4-yl)quinolin-2(1H)-one. (ES, m/z) [M+H]$^+$ 461.1, 463.0.

STEP 2: 6-(bis(4-chlorophenyl)methyl)-4-(1-((trifluoromethyl)sulfonyl)-1,2,3,6-tetrahydropyridin-4-yl)quinolin-2(1H)-one and 6-(bis(4-chlorophenyl)methyl)-4-(1-((trifluoromethyl)sulfonyl)-1,2,3,6-tetrahydropyridin-4-yl)quinolin-2-yl trifluoromethanesulfonate To a solution of 6-(bis(4-chlorophenyl)methyl)-4-(1,2,3,6-tetrahydropyridin-4-yl)quinolin-2(1H)-one (15.4 mg, 0.033 mmol) in CH2Cl2 90.8 mL) was added TEA (0.0139 mL, 0.1 mmol) at 0° C. under Argon followed by triflic anhydride (0.0434 mL, 0.0434 mmol, 1 M in CH$_2$Cl$_2$). The reaction mixture was stirred for 3 hr at room temperature. A saturated NaHCO$_3$ solution was added and the resulting mixture was stirred for 2 min. The organics were concentrated and purified by silica gel chromatography (eluent of 30% EtOAc/hexanes) to yield 6-(bis(4-chlorophenyl)methyl)-4-(1-((trifluoromethyl)sulfonyl)-1,2,3,6-tetrahydropyridin-4-yl)quinolin-2-yl trifluoromethanesulfonate $^1$H NMR (CDCl$_3$) d: 8.01 (d, J=8.8 Hz, 1H), 7.60 (dd, J=8.8, 2.0 Hz, 1H), 7.27-7.38 (m, 5H), 6.96-7.07 (m, 5H), 5.75-5.83 (m, 1H), 5.69 (s, 1H), 4.01-4.29 (m, 2H), 3.62 (m, 2H), 2.49 (m, 2H)

followed by 75% EtOAc/hexanes to yield 6-(bis(4-chlorophenyl)methyl)-4-(1-((trifluoromethyl)sulfonyl)-1,2,3,6-tetrahydropyridin-4-yl)quinolin-2(1H)-one.

(ES, m/z) [M+H]$^+$ 595, 597; $^1$H NMR (CDCl$_3$) d: 11.55 (br. s., 1H), 7.27-7.39 (m, 6H), 6.94-7.07 (m, 5H), 6.48 (s, 1H), 5.73 (m, 1H), 5.55 (s, 1H), 3.95-4.24 (m, 2H), 3.57 (m, 2H), 2.40 (m, 2H);

Example 69

Compound #516 and #517

(Z)-(4-chlorophenyl)(4-styrylquinolin-6-yl)(thiazol-4-yl)methanol and (E)-(4-chlorophenyl)(4-styrylquinolin-6-yl)(thiazol-4-yl)methanol

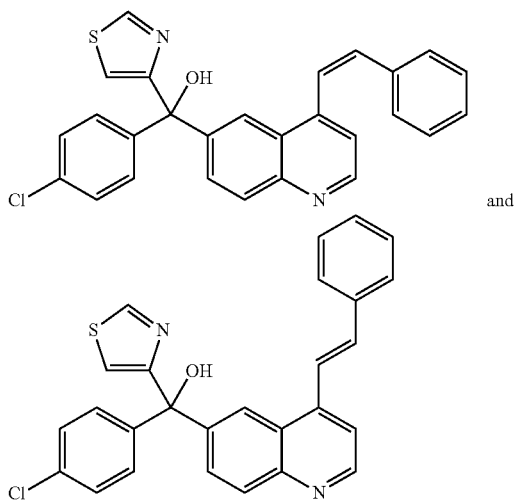

STEP 1: N-methoxy-N-methylthiazole-4-carboxamide

To a mixture of thiazole-4-carboxylic acid (1 g, 7.74 mmol), N,O-dimethylhydroxylamine (1.51 g, 15.5 mmol), and HATU(3.83 g, 10.07 mmol) in $CH_2Cl_2$ (25 mL) was added TEA (4.84 mL, 34.85 mmol). The reaction was stirred at room temperature overnight. The reaction was diluted with $CH_2Cl_2$ and water. The organics were concentrated and purified by chromatography (60-70% EtOAc/hexanes) to yield N-methoxy-N-methylthiazole-4-carboxamide as a clear oil. $^1$H NMR ($CDCl_3$) δ: 8.83 (s, 1H), 8.10 (s, 1H), 3.79 (s, 3H), 3.46 (s, 3H)

STEP 2: (4-chloroquinolin-6-yl)(thiazol-4-yl)methanone

To a solution of 6-bromo-4-chloroquinoline (0.459 g, 1.89 mmol) in THF (8 mL) was added n-BuLi (1.12 mL, 1.80 mmol, 1.6M in hexane) at −78° C. under argon and the resulting mixture was stirred for 2 hr. A solution of N-methoxy-N-methylthiazole-4-carboxamide (0.39 g, 2.27 mmol) in THF (2 mL) was added and the resulting mixture was allowed to warm to room temperature and stirred at room temperature for 2 hr. The reaction mixture was quenched with ice and saturated $NH_4Cl$. The aqueous layer was extracted with $CH_2Cl_2$. The combined organics were concentrated and purified by column chromatography (40-50% EtOAc/hexanes) to yield (4-chloroquinolin-6-yl)(thiazol-4-yl)methanone. (ES, m/z) [M+H]$^+$ 275, 277.

STEP 3: (4-chlorophenyl)(4-chloroquinolin-6-yl)(thiazol-4-yl)methanol

To a solution of (4-chloroquinolin-6-yl)(thiazol-4-yl)methanone (52 mg, 0.189 mmol) in THF (2 mL) was slowly added (4-chlorophenyl)magnesium bromide (0.246 mL, 0.246 mmol, 1M in THF) and the resulting solution was kept at 0° C. for 2 hr. The reaction was quenched with saturated $NH_4Cl$ at 0° C. and the aqueous mixture was extracted with EtOAc twice. The combined organics were concentrated and purified by silica column (40% EtOAc/hexanes) chromatography to yield (4-chlorophenyl)(4-chloroquinolin-6-yl)(thiazol-4-yl)methanol. (ES, m/z) [M+H]$^+$ 387, 389.

STEP 4: (Z)-(4-chlorophenyl)(4-styrylquinolin-6-yl)(thiazol-4-yl)methanol and (E)-(4-chlorophenyl)(4-styrylquinolin-6-yl)(thiazol-4-yl)methanol A mixture of (4-chlorophenyl)(4-chloroquinolin-6-yl)(thiazol-4-yl)methanol (65 mg, 0.168 mmol), (E)-styrylboronic acid (39.74 mg, 0.269 mmol), Pd(OAc)$_2$ (3.77 mg, 0.0168 mmol), SPhos (13.8 mg, 0.0336 mmol), and $K_3PO_4 \cdot H_2O$ (71.25 mg, 0.336 mmol) in anhydrous THF (1.5 mL) was stirred at 30° C. overnight. The reaction was diluted with EtOAc and water. The organics were concentrated and purified by REDSEP GOLD silica column (40% EtOAc/heptanes) to yield (Z)-(4-chlorophenyl)(4-styrylquinolin-6-yl)(thiazol-4-yl)methanol
(ES, m/z) [M+H]$^+$ 455, 457; 1H NMR ($CDCl_3$) δ: 8.85-8.92 (m, 2H), 8.22 (d, J=2.2 Hz, 1H), 8.07 (d, J=8.8 Hz, 1H), 7.58-7.70 (m, 3H), 7.54 (d, J=7.1 Hz, 2H), 7.39-7.46 (m, 2H), 7.28-7.39 (m, 6H), 6.89 (d, J=2.0 Hz, 1H), 4.23 (s, 1H)
and (E)-(4-chlorophenyl)(4-styrylquinolin-6-yl)(thiazol-4-yl)methanol.
(ES, m/z) [M+H]$^+$ 455, 457; $^1$H NMR ($CDCl_3$) δ: 8.84-8.90 (m, 2H), 8.21 (d, J=2.0 Hz, 1H), 8.06 (d, J=8.8 Hz, 1H), 7.56-7.68 (m, 3H), 7.49-7.56 (m, 2H), 7.41 (t, J=7.5 Hz, 2H), 7.28-7.37 (m, 5H), 7.23-7.27 (m, 1H), 6.90 (d, J=2.0 Hz, 1H), 4.42 (s, 1H).

Example 70

Compound #518

(E)-(2-(tert-butoxy)-4-(3-fluorostyryl)quinolin-6-yl)(4-chlorophenyl)(thiophen-3-yl)methanol

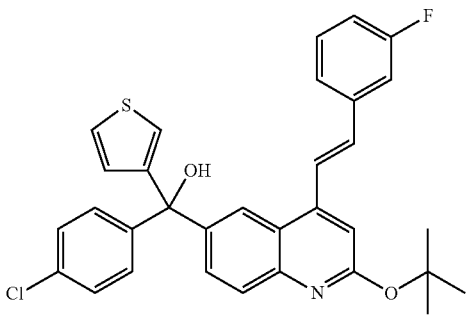 [SMILES: CC(C)(C)Oc1cc(/C=C/c2cccc(F)c2)c2cc(C(O)(c3ccc(Cl)cc3)c3ccsc3)ccc2n1]

STEP 1: (E)-(2-(tert-butoxy)-4-styrylquinolin-6-yl)(4-chlorophenyl)methanone A mixture of (4-bromo-2-(tert-butoxy)quinolin-6-yl)(4-chlorophenyl)methanone (157 mg, 0.375 mmol), (E)-(3-fluorostyryl)boronic acid (105.8 mg, 0.637 mmol), Pd(OAc)$_2$ (8.42 mg, 0.0375 mmol), SPhos (30.79 mg, 0.0375 mmol), and $K_3PO_4 \cdot H_2O$ (159 mg, 0.75 mmol) in anhydrous THF (2.5 mL) was stirred at 30° C. overnight.

The reaction was diluted with EtOAc and water. The organics were concentrated and purified by silica column chromatography (20% EtOAc/heptanes) to yield (E)-(2-(tert-butoxy)-4-styrylquinolin-6-yl)(4-chlorophenyl)methanone.
(ES, m/z) [M−tBu]⁺ 404, 405, 407

STEP 2: (E)-(2-(tert-butoxy)-4-(3-fluorostyryl)quinolin-6-yl)(4-chlorophenyl)(thiophen-3-yl)methanol To a solution of (E)-(2-(tert-butoxy)-4-(3-fluorostyryl)quinolin-6-yl)(4-chlorophenyl)methanone (90 mg, 0.196 mmol) in THF (2 mL) was slowly added thiophen-3-ylmagnesium bromide (1.04 mL, 0.313 mmol, 0.3M in toluene) and the resulting solution was kept at 0° C. for 3 hr. The reaction was quenched with saturated NH₄Cl at 0° C. and the aqueous layer was extracted with EtOAc. The combined organics were purified by silica column chromatography (20-30% EtOAc/hexanes) to yield (E)-(2-(tert-butoxy)-4-(3-fluorostyryl)quinolin-6-yl)(4-chlorophenyl)(thiophen-3-yl)methanol.

(ES, m/z) [M−tBu]⁺488, 490; [M+H]⁺ 544, 545, 547.

Example 71

Compound #39

6-((4-chlorophenyl)(thiazol-2-yl)methyl)-4-(piperidin-4-ylamino)quinolin-2(1H)-one

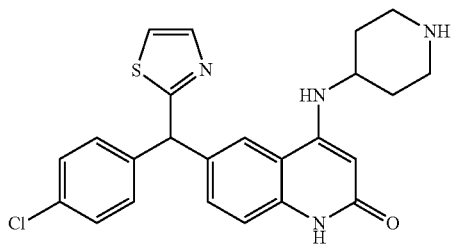 [SMILES: O=c1cc(NC2CCNCC2)c2cc(C(c3ccc(Cl)cc3)c3nccs3)ccc2[nH]1]

Ethyl 4-((6-((4-chlorophenyl)(thiazol-2-yl)methyl)-2-oxo-1,2-dihydroquinolin-4-yl)amino)piperidine-1-carboxylate (114 mg) was dissolved in concentrated HBr solution (48%) and the resulting mixture was heated to ~100° C. for 2 hr. The reaction mixture was cooled to room temperature and concentrated to a yellow/orange slurry. The residue was neutralized carefully with aq. NaOH (3 N). The resulting precipitates were filtered to yield 6-((4-chlorophenyl)(thiazol-2-yl)methyl)-4-(piperidin-4-ylamino)quinolin-2(1H)-one as the corresponding HBr salt as a tan solid.

(ES, m/z) [M+H]⁺ 451, 453. ¹H NMR (CH₃OD) δ: 8.05 (s, 1H), 7.80 (d, J=3.4 Hz, 1H), 7.55 (d, J=3.4 Hz, 1H), 7.18-7.43 (m, 6H), 5.97 (s, 1H), 5.59 (s, 1H), 3.50-3.67 (m, 1H), 2.98-3.19 (m, 2H), 2.66-2.83 (m, 2H), 2.07 (d, J=12.7 Hz, 2H), 1.47-1.65 (m, 2H).

Example 72

Compound #525

6-(bis(4-chlorophenyl)methyl)-N⁴,N⁸-bis(1-((trifluoromethyl)sulfonyl)piperidin-4-yl)quinoline-4,8-diamine

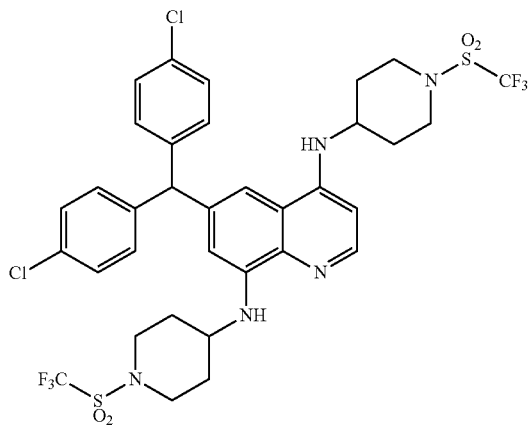 [SMILES: O=S(=O)(N1CCC(Nc2ccnc3c(NC4CCN(S(=O)(=O)C(F)(F)F)CC4)cc(C(c4ccc(Cl)cc4)c4ccc(Cl)cc4)cc23)CC1)C(F)(F)F]

A mixture of 6-(bis(4-chlorophenyl)methyl)-4,8-dibromoquinoline (50 mg, 0.0958 mmol), 1-((trifluoromethyl)sulfonyl)piperidin-4-amine (38.6 mg, 0.144 mmol), Pd₂(dba)₃ (8.77 mg, 0.00958 mmol), dppf (18.58 mg, 0.0335 mmol), and NaOt-Bu (23.01 mg, 0.239 mmol) in 1,4-dioxane (0.9 mL) was heated to 85° C. for 4 hr. No more starting materials remained and the reaction was cooled to room temperature and diluted with EtOAc and water. The organics were concentrated and purified by silica column chromatography (35% EtOAc/hexanes) to yield 6-(bis(4-chlorophenyl)methyl)-N⁴,N⁸-bis(1-((trifluoromethyl)sulfonyl)piperidin-4-yl)quinoline-4,8-diamine.
(ES, m/z) [M+H]⁺ 824.7, 826.7.

Example 73

Compound #107 and #108

6-(bis(4-chlorophenyl)methyl)-8-(2-oxopyrrolidin-1-yl)-4-((1-((trifluoromethyl)sulfonyl)piperidin-4-yl)amino)quinolin-2(1H)-one and 4-((6-(bis(4-chlorophenyl)methyl)-2-oxo-4-((1-((trifluoromethyl)sulfonyl)piperidin-4-yl)amino)-1,2-dihydroquinolin-8-yl)amino)butanoic acid

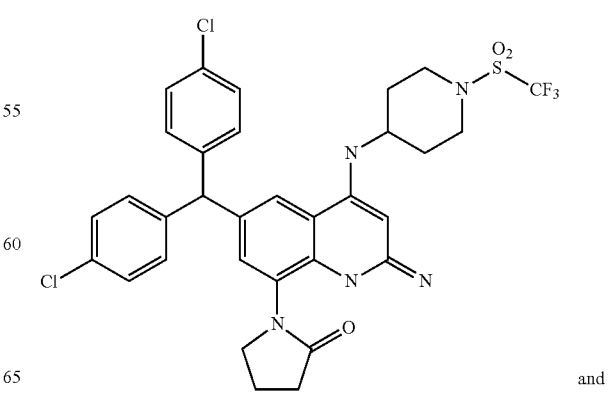

and

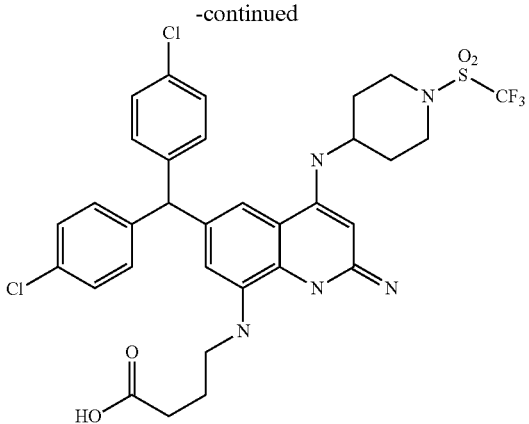

To a solution of ethyl 4-((6-(bis(4-chlorophenyl)methyl)-2-oxo-4-((1-((trifluoromethyl)sulfonyl)piperidin-4-yl)amino)-1,2-dihydroquinolin-8-yl)amino)butanoate (20 mg, 0.027 mmol) in THF (1 mL) was added 1N NaOH solution (0.12 mL) and mixture was stirred at room temperature for 3.5 hr. No more starting material was observed. The reaction was concentrated and neutralized to pH=5 with 1N HCl aqueous solution. The solid was extracted with EtOAc three times. The organics were concentrated and purified by chromatography (silica gel column, 100% EtOAc to yield 6-(bis(4-chlorophenyl)methyl)-8-(2-oxopyrrolidin-1-yl)-4-((1-((trifluoromethyl)sulfonyl)piperidin-4-yl)amino)quinolin-2(1H)-one.

(ES, m/z) [M+H]$^+$ 693, 695; 1H NMR (CDCl$_3$) δ: 9.11 (br. s., 1H), 7.20-7.35 (m, 4H), 7.12 (s, 1H), 6.91-7.06 (m, 5H), 5.61 (s, 1H), 5.56 (s, 1H), 4.56 (d, J=6.6 Hz, 1H), 3.97 (m, 2H), 3.67 (t, J=6.6 Hz, 2H), 3.57 (m, 1H), 3.12-3.30 (m, 2H), 2.61 (t, J=7.8 Hz, 2H), 2.19-2.36 (m, 4H), 1.61 (m, 2H)

and 10% MeOH/EtOAc to yield 4-((6-(bis(4-chlorophenyl)methyl)-2-oxo-4-((1-((trifluoromethyl)sulfonyl)piperidin-4-yl)amino)-1,2-dihydroquinolin-8-yl)amino)butanoic acid.

(ES, m/z) [M+H]$^+$ 711.2, 713; 1H NMR (DMSO-d6) δ: 10.01 (br. s., 1H), 7.37 (d, J=8.1 Hz, 4H), 7.10-7.23 (m, 5H), 6.40 (d, J=8.1 Hz, 1H), 6.31 (s, 1H), 5.51 (s, 1H), 5.47 (s, 1H), 3.83-3.86 (m, 2H), 3.70 (br. s., 1H), 3.36-3.40 (m, 2H) 2.93 (br. s., 2H), 2.24-2.38 (m, 2H), 2.04 (m, 2H), 1.69-1.82 (m, 2H), 1.60 (m, 2H)

Example 74

Compound #119

(Z)-tert-butyl ((4-((6-(bis(4-chlorophenyl)methyl)-2-oxo-1,2-dihydroquinolin-4-yl)amino)piperidin-1-yl)((tert-butoxycarbonyl)imino)methyl)carbamate

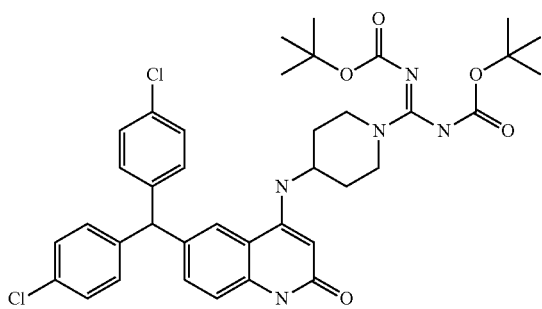 [SMILES: CC(C)(C)OC(=O)/N=C(/NC(=O)OC(C)(C)C)N1CCC(Nc2cc(=O)[nH]c3ccc(C(c4ccc(Cl)cc4)c4ccc(Cl)cc4)cc23)CC1]

To a mixture of 6-(bis(4-chlorophenyl)methyl)-4-(piperidin-4-ylamino)quinolin-2(1H)-one (250 mg, 0.523 mmol0, N,N'-bis-tert-butoxycarbonylthiourea (158.8 mg, 0.575 mmol) and triethylamine (0.22 mL, 1.57 mmol) in 3 mL DMF was added mercuric chloride (170.2 mg, 0.63 mmol) at 0° C. The reaction was stirred for 3 h at 0° C. and then quenched with EtOAc. The reaction was filtered through CELITE. The filtrate was washed two times with water, then dried over anhydrous Na$_2$SO$_4$, filtered and concentrated. The resulting residue was purified on ISCO with MeOH—CH$_2$Cl$_2$ and re-purified on HPLC (40-90% CH$_3$CN(0.1% TFA)/H$_2$O (0.1% TFA)) to yield (Z)-tert-butyl ((4-((6-(bis(4-chlorophenyl)methyl)-2-oxo-1,2-dihydroquinolin-4-yl)amino)piperidin-1-yl)((tert-butoxycarbonyl)imino)methyl)carbamate.

(ES, m/z) [M+H]$^+$ 720, [M+Na]$^+$ 743

Example 75

Compound #118

4-((6-(bis(4-chlorophenyl)methyl)-2-oxo-1,2-dihydroquinolin-4-yl)amino)piperidine-1-carboximidamide

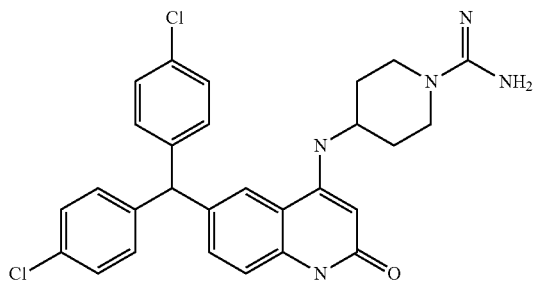 [SMILES: N=C(N)N1CCC(Nc2cc(=O)[nH]c3ccc(C(c4ccc(Cl)cc4)c4ccc(Cl)cc4)cc23)CC1]

(Z)-tert-butyl ((4-((6-(bis(4-chlorophenyl)methyl)-2-oxo-1,2-dihydroquinolin-4-yl)amino)piperidin-1-yl)((tert-butoxycarbonyl)imino)methyl)carbamate was combined (154 mg, 0.21 mmol) with 30% TFA in CH$_2$Cl$_2$ (7 mL) at room temperature and the resulting mixture was stirred for 0.5 hr. The solvent was removed and the residue was triturated with diethyl ether. The white solid was collected and purified on a Gilson (20-90% CH$_3$CN (0.1% TFA)/H$_2$O) (0.1% TFA)) to yield 4-((6-(bis(4-chlorophenyl)methyl)-2-oxo-1,2-dihydroquinolin-4-yl)amino)piperidine-1-carboximidamide as a white solid.

(ES m/z) [M+H]$^+$521

Example 76

Compound #102 ethyl 2-((4-((6-(bis(4-chlorophenyl)methyl)-2-oxo-1,2-dihydroquinolin-4-yl)amino)piperidin-1-yl)sulfonyl)acetate

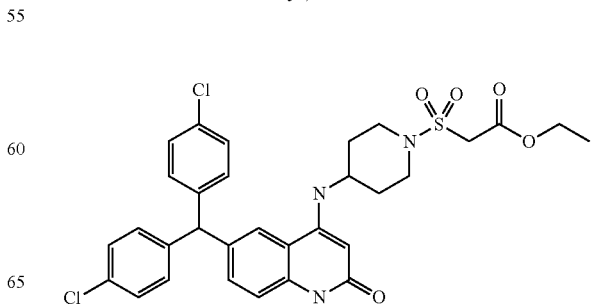

STEP 1: 6-(bis(4-chlorophenyl)methyl)-4-(piperidin-4-ylamino)quinolin-2(1H)-one

To a 500-mL three-neck round bottom flask with stir bar, heating mantel, reflux condenser with $N_2$ outlet, septa with $N_2$ inlet (needle) and temperature probe was added 6-(bis(4-chlorophenyl)methyl)-4-(1-(trifluoromethylsulfonyl)piperidin-4-ylamino)quinolin-2(1H)-one (6.06 g; 9.93 mmol) and THF (120 mL). To this solution was added LAH (pellets, 1.48 g; 38.99 mmol) at room temperature and the resulting mixture was heated to reflux while stirring for 8 hr and cooled room temperature overnight. A 2nd charge of LAH (0.45 g; 11.86 mmol) was added and the resulting mixture was maintained at 60° C. for 6 hr. A 3rd charge of LAH (0.45 g; 11.86 mmol) was added and the resulting mixture was maintained at 60° C. for additional 3 h. The reaction was stopped and cooled to 0° C. with ice bath. Water (2.6 mL) (Note: highly exothermic) was added, then 15% NaOH (2.6 mL), then water (7.5 mL). The resulting mixture was stirred for 15 min and then $Na_2SO_4$ and THF was added. The reaction solution was filtered through CELITE. The filtrate was concentrated and the resulting solid residue was triturated with DCM (10 mL)/diethyl ether (25 mL) in an ice bath for 20 min to yield 6-(bis(4-chlorophenyl)methyl)-4-(piperidin-4-ylamino)quinolin-2(1H)-one as a pink solid.

STEP 2: ethyl 2-((4-((6-(bis(4-chlorophenyl)methyl)-2-oxo-1,2-dihydroquinolin-4-yl)amino)piperidin-1-yl)sulfonyl)acetate To a 25-mL one-neck round bottom flask with stir bar was added 6-(bis(4-chlorophenyl)methyl)-4-(piperidin-4-ylamino)quinolin-2(1H)-one (0.1 g, 0.209 mmol), pyridine (0.02 mL; 0.247 mmol) and THF (3 mL) at 0° C. To the resulting solution was added a solution of ethyl 2-(chlorosulfonyl)acetate (43 mg; 0.23 mmol) in dichloromethane (1 mL) over 10 min. The reaction was then warmed to room temperature. The reaction was quenched with 1N HCl (10 mL) and DCM (10 mL). The aqueous layer was extracted with DCM and the organics were concentrated. The resulting residue was purified by silica gel column chromatography (0-10% MeOH/DCM) to yield ethyl 2-((4-((6-(bis(4-chlorophenyl)methyl)-2-oxo-1,2-dihydroquinolin-4-yl)amino)piperidin-1-yl)sulfonyl)acetate as an orange oil.

LCMS (ESI): 628.2 (M+H)$^+$ 1H NMR (400 MHz, CDCl$_3$): δ 1.33 (t, J=7.07 Hz, 3H), 1.70 (m, 2H), 2.01 (s, 2H), 2.21 (d, J=10.61 Hz, 2H), 3.09 (br. t., 2H), 3.46-3.63 (m, 1H), 3.86 (d, J=12.63 Hz, 2H), 3.96 (s, 2H), 4.27 (q, J=7.07 Hz, 2H), 4.55 (s, 1H), 5.56 (s, 1H), 5.65 (s, 1H), 7.01 (d, J=8.59 Hz, 4H), 7.09-7.20 (m, 2H), 7.21-7.32 (m, 5H), 10.64-10.80 (m, 1H).

Example 77

Compound #103 tert-butyl 2-(4-((6-(bis(4-chlorophenyl)methyl)-2-oxo-1,2-dihydroquinolin-4-yl)amino)piperidin-1-yl)acetate

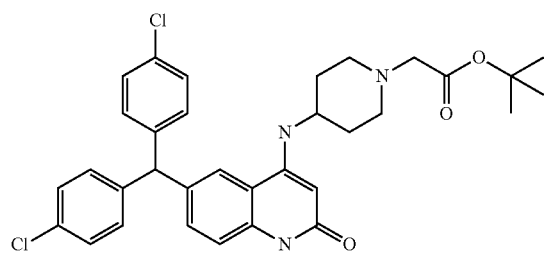 [SMILES: CC(C)(C)OC(=O)CN1CCC(Nc2cc(=O)[nH]c3ccc(C(c4ccc(Cl)cc4)c4ccc(Cl)cc4)cc23)CC1]

To a mixture of 6-(bis(4-chlorophenyl)methyl)-4-(piperidin-4-ylamino)quinolin-2(1H)-one (0.1 g 0.209 mmol) and cesium carbonate (80 mg; 0.245 mmol) in acetone (2 mL) was added a solution of chloroacetic acid, 1,1-dimethylethyl ester (0.04 mL; 0.279 mmol) in dichloromethane (0.1 mL) by syringe. The reaction mixture was stirred at 40° C. in a sand bath for 16 h, cooled to room temperature and concentrated. The reaction was diluted with DCM and water. The organics were concentrated and purified by ISCO (0-10% MeOH/DCM) to yield tert-butyl 2-(4-((6-(bis(4-chlorophenyl)methyl)-2-oxo-1,2-dihydroquinolin-4-yl)amino)piperidin-1-yl)acetate.

LCMS: 593 (M+H); 1H NMR (400 MHz, CDCl$_3$) δ ppm 1.47 (s, 9H) 1.59 (s, 2H) 2.03-2.16 (m, 2H) 2.26-2.43 (m, 2H) 2.84-2.99 (m, 2H) 3.14 (s, 2H) 3.35-3.50 (m, 1H) 4.42-4.54 (m, 1H) 5.57 (s, 1H) 5.65 (s, 1H) 6.96-7.11 (m, 4H) 7.20 (s, 2H) 7.24-7.34 (m, 5H) 10.27-10.40 (m, 1H)

Example 78

Compound #114 tert-butyl 3-(4-((6-(bis(4-chlorophenyl)methyl)-2-oxo-1,2-dihydroquinolin-4-yl)amino)piperidin-1-yl)propanoate

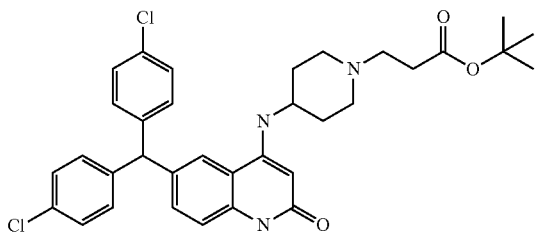 [SMILES: CC(C)(C)OC(=O)CCN1CCC(Nc2cc(=O)[nH]c3ccc(C(c4ccc(Cl)cc4)c4ccc(Cl)cc4)cc23)CC1]

To a solution of 6-(bis(4-chlorophenyl)methyl)-4-(piperidin-4-ylamino)quinolin-2(1H)-one (200 mg) in methanol (0.3 mL) and dichloromethane (0.3 mL) was added a solution of t-butyl acrylate (1.80 mL; 1.57 g) in methanol (0.8 mL) and dichloromethane (0.4 mL) in 1 min. The reaction was heated to 70° C. for 24 hr. The reaction was cooled to room temperature and concentrated. The resulting residue was purified by silica column (ISCO) (5% MeOH/CH$_2$Cl$_2$) to yield tert-butyl 3-(4-((6-(bis(4-chlorophenyl)methyl)-2-oxo-1,2-dihydroquinolin-4-yl)amino)piperidin-1-yl)propanoate.

LCMS: 606 (M+); 1H NMR (400 MHz, CDCl$_3$) δ ppm 1.42-1.49 (m, 9H) 1.49-1.60 (m, 2H) 2.04-2.13 (m, 2H) 2.19 (br. s., 2H) 2.36-2.48 (m, 2H) 2.62-2.72 (m, 2H) 2.75-2.90 (m, 2H) 3.34-3.47 (m, 1H) 4.41-4.52 (m, 1H) 5.56 (s, 1H) 5.65 (s, 1H) 6.97-7.10 (m, 4H) 7.17 (d, J=2.02 Hz, 2H) 7.20-7.36 (m, 5H) 10.77-10.93 (m, 1H).

Example 79

Compound #550

3-(6-(bis(4-chlorophenyl)methyl)-2-methoxy-4-((1-((trifluoromethyl)sulfonyl)piperidin-4-yl)amino)quinolin-8-yl)propan-1-ol

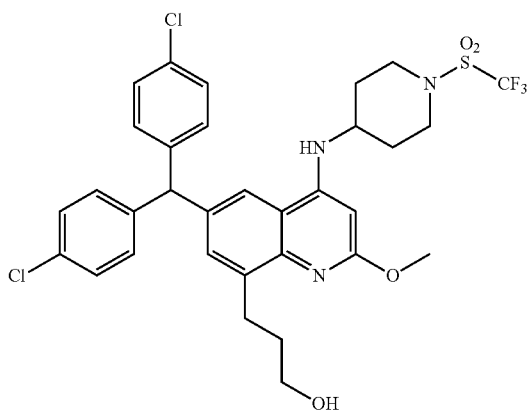 [SMILES: COc1cc(NC2CCN(S(=O)(=O)C(F)(F)F)CC2)c2cc(C(c3ccc(Cl)cc3)c3ccc(Cl)cc3)cc(CCCO)c2n1]

STEP 1: [8-[(1E)-3-[(tert-butyldimethylsilyl)oxy]prop-1-en-1-yl]-2-methoxy-4-[[1-(trifluoromethane)sulfonylpiperidin-4-yl]amino]quinolin-6-yl]bis(4-chlorophenyl)methanol Into a 25-mL round-bottom flask, was placed (8-bromo-2-methoxy-4-[[1-(trifluoromethane)sulfonylpiperidin-4-yl]amino]quinolin-6-yl)bis(4-chlorophenyl)methanol (500 mg, 0.70 mmol, 1.00 equip), Pd(dppf)Cl$_2$*CH$_2$Cl$_2$ (29 mg, 0.04 mmol, 0.05 equip), potassium carbonate (290 mg, 2.10 mmol, 3.00 equip), tert-butyldimethyl[(2E)-3-(tetramethyl-1,3,2-dioxaborolan-2-yl)prop-2-en-1-yl]oxysilane (250 mg, 0.84 mmol, 1.20 equip), 1,4-dioxane (10 mL) and water (4 mL). The resulting solution was stirred overnight at 80° C. The reaction was then quenched by the addition of saturated sodium bicarbonate (50 mL). The resulting solution was extracted with ethyl acetate (100 mL) and the organic layers combined and dried over anhydrous sodium sulfate. The solids were filtered out. The resulting mixture was concentrated under vacuum. The residue was applied onto a silica gel column with ethyl acetate/petroleum ether (1:4) to yield [8-[(1E)-3-[(tert-butyldimethylsilyl)oxy]prop-1-en-1-yl]-2-methoxy-4-[[1-(trifluoromethane)sulfonylpiperidin-4-yl]amino]quinolin-6-yl]bis(4-chlorophenyl)methanol as a yellow solid. LCMS (ES, m/z) 810 [M+H]

STEP 2: (8-[3-[(tert-butyldimethylsilyl)oxy]propyl]-2-methoxy-4-[[1-(trifluoromethane)sulfonylpiperidin-4-yl]amino]quinolin-6-yl)bis(4-chlorophenyl)methanol Into a 100-mL round-bottom flask, was placed a solution of [8-[(1E)-3-[(tert-butyldimethylsilyl)oxy]prop-1-en-1-yl]-2-methoxy-4-[[1-(trifluoromethane)sulfonylpiperidin-4-yl]amino]quinolin-6-yl]bis(4-chlorophenyl)methanol (380 mg, 0.47 mmol, 1.00 equip) in dichloromethane (30 mL). To the resulting mixture was then added 2-nitrobenzene-1-sulfonohydrazide (2.04 g, 9.39 mmol, 20.00 equip), in portions. To this was added TEA (1 mL) dropwise with stirring. The resulting solution was stirred for 5 h at room temperature. The resulting solution was diluted with DCM (100 mL). The resulting mixture was washed with water (2×50 mL). The organic phase was separated and dried over anhydrous sodium sulfate. The solids were filtered out. The resulting mixture was concentrated under vacuum. The residue was applied onto a silica gel column with ethyl acetate/petroleum ether (1:2) to yield (8-[3-[(tert-butyldimethylsilyl)oxy]propyl]-2-methoxy-4-[[1-(trifluoromethane)sulfonylpiperidin-4-yl]amino]quinolin-6-yl)bis(4-chlorophenyl)methanol as a yellow solid. LCMS (ES, m/z) 812 [M+H]$^+$ STEP 3: 3-[6-[bis(4-chlorophenyl)methyl]-2-methoxy-4-[[1-(trifluoromethane)sulfonylpiperidin-4-yl]amino]quinolin-8-yl]propan-1-ol Into a 100-mL round-bottom flask, was placed a solution of (8-[3-[(tert-butyldimethylsilyl)oxy]propyl]-2-methoxy-4-[[1-(trifluoromethane)sulfonylpiperidin-4-yl]amino]quinolin-6-yl)bis(4-chlorophenyl)methanol (370 mg, 0.46 mmol, 1.00 equip) in dichloromethane (30 mL). The solution was bubbled with nitrogen for 30 min to remove air. To the resulting mixture was then added Et$_3$SiH (5.3 g, 45.58 mmol, 100.00 equip), in portions under a nitrogen atmosphere. To the resulting mixture was added trifluoroacetic acid (1 g, 8.85 mmol, 20.00 equip) dropwise with stirring at 0° C. The resulting solution was stirred for 4 h at room temperature. The reaction was then quenched by the addition of saturated sodium bicarbonate (50 mL). The resulting solution was extracted with DCM (100 mL) and the organic layers combined and dried over anhydrous sodium sulfate. The solids were filtered out. The resulting mixture was concentrated under vacuum. The resulting residue was purified by Prep-TLC with ethyl acetate:petroleum ether=1:2 to yield 3-[6-[bis(4-chlorophenyl)methyl]-2-methoxy-4-[[1-(trifluoromethane)sulfonylpiperidin-4-yl]amino]quinolin-8-yl]propan-1-ol as an off-white solid.

LCMS (ES, m/z) 682 [M+H]$^+$

Example 80

Compound #137

6-((4-chlorophenyl)(4-phenylpiperazin-1-yl)methyl)-4-((1-((trifluoromethyl)sulfonyl)piperidin-4-yl)amino)quinolin-2(1H)-one

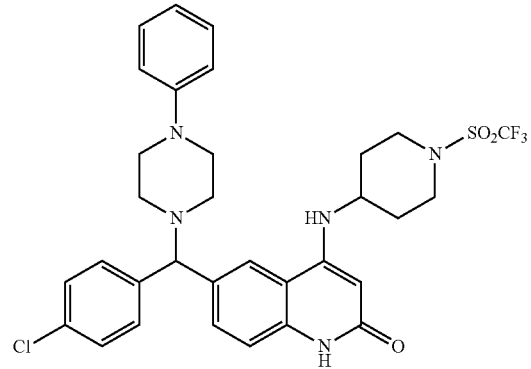

STEP A: 6-(chloro(4-chlorophenyl)methyl)-4-((1-((trifluoromethyl)sulfonyl)piperidin-4-yl)amino)quinolin-2(1H)-one Into a 100-mL round-bottom flask, was placed a solution of 6-[chloro(4-chlorophenyl)methyl]-4-[[1-(trifluoromethane)sulfonylpiperidin-4-yl]amino]-1,2-dihydroquinolin-2-one (200 mg, 0.37 mmol, 1.00 equip) in dichloromethane (30 mL). To the resulting mixture was then added thionyl dichloride (450 mg, 3.78 mmol, 10.00 equip) dropwise with stirring at 0° C. The resulting solution was stirred for 2 h at 45° C. The reaction was then quenched by the addition of saturated sodium bicarbonate (100 mL). The resulting solution was extracted with ethyl acetate (2×100 mL) and the organic layers combined and dried over anhydrous sodium sulfate. The solids were filtered out. The resulting mixture was concentrated under vacuum. The resulting residue was applied onto a silica gel column with ethyl acetate/petroleum ether (1:2), to yield 0.1 g (50%) of 6-[chloro(4-chlorophenyl)methyl]-4-[[1-(trifluoromethane)sulfonylpiperidin-4-yl]amino]-1,2-dihydroquinolin-2-one as a yellow solid. LCMS (ES, m/z) 534 [M+H]$^+$ STEP B: 6-((4-chlorophenyl)(4-phenylpiperazin-1-yl)methyl)-4-((1-((trifluoromethyl)sulfonyl)piperidin-4-yl)amino)quinolin-2(1H)-one Into a 25-mL round-bottom flask, was placed a solution of 6-[chloro(4-chlorophenyl)methyl]-4-[[1-(trifluoromethane)sulfonylpiperidin-4-yl]amino]-1,2-dihydroquinolin-2-one (100 mg, 0.19 mmol, 1.00 equip) in dichloromethane (10 ml), 1-phenylpiperazine (55 mg, 0.34 mmol, 2.00 equip) and TEA (51 mg, 0.50 mmol, 3.00 equip). The resulting solution was stirred overnight at room temperature. The reaction was then quenched by the addition of water (30 mL). The resulting solution was extracted with ethyl acetate (3×50 mL) and the organic layers combined. The resulting mixture was washed with water (2×30 mL) and then with brine (1×30 mL). The resulting mixture was dried over sodium sulfate and concentrated under vacuum. The resulting residue was applied onto a silica gel column with dichloromethane/methanol (20:1), to yield 30 mg (24%) of 6-[(4-chlorophenyl)(4-phenylpiperazin-1-yl)methyl]-4-[[1-(trifluoromethane)sulfonylpiperidin-4-yl]amino]-1,2-dihydroquinolin-2-one as an off-white solid.

LCMS (ES, m/z) 660 [M+H]$^+$, H-NMR (300 MHz, DMSO) δ 10.750 (s, 1H), 7.987 (s, 1H), 7.551-7.512 (m, 3H), 7.405-7.377 (m, 2H), 7.218-7.167 (m, 3H), 6.907-6.879 (m, 2H), 6.784-6.735 (m, 1H), 6.557 (d, J=7.5 Hz, 1H), 5.461 (s, 1H), 4.317 (s, 1H), 3.907-3.864 (m, 2H), 3.745 (br, 1H), 3.450-3.316 (m, 2H), 3.220-3.155 (m, 4H), 2.448-2.350 (m, 4H), 2.190-2.088 (br, 2H), 1.700-1.623 (m, 2H)

Additional representative compounds of the present invention were similarly prepared according to the procedures as in the Examples above, selecting and substituting suitably substituted reagents as would be readily recognized by those skilled in the art. Table EX below lists the names and structures of the compounds thus prepared, along with measured physical properties as noted.

TABLE EX

Representative Compounds of the Present Invention

| ID No. | Compound IUPAC name | Prepared as in Example # | Analytical Data |
| --- | --- | --- | --- |
| 506 | 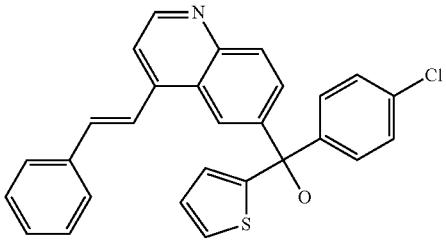 [SMILES: OC(c1ccc(Cl)cc1)(c1ccc2nccc(/C=C/c3ccccc3)c2c1)c1cccs1] (4-Chlorophenyl){4-[(E)-2-phenylethenyl]quinolin-6-yl}thiophen-2-ylmethanol | 63 | (ES, m/z): [M + H]$^+$ 454, 456 |
| 507 | 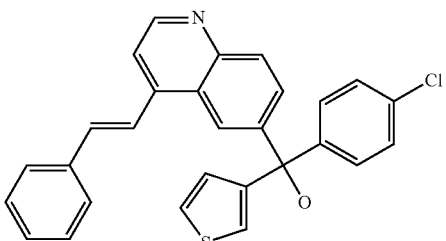 (4-Chlorophenyl){4-[(E)-2-phenylethenyl]quinolin-6-yl}thiophen-3-ylmethanol | 63 | (ES, m/z): [M + H]$^+$ 454, 456 |

TABLE EX-continued

Representative Compounds of the Present Invention

| ID No. | Compound IUPAC name | Prepared as in Example # | Analytical Data |
|---|---|---|---|
| 508 | 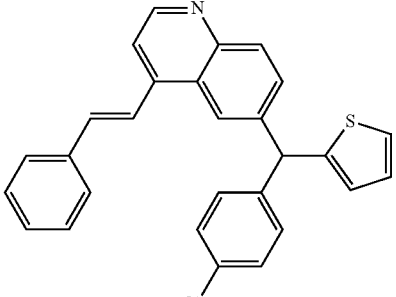<br>6-[(4-Chlorophenyl)(thiophen-2-yl)methyl]-4-[(E)-2-phenylethenyl]quinoline | 64 | (ES, m/z): [M + H]+ 438, 440 |
| 509 | 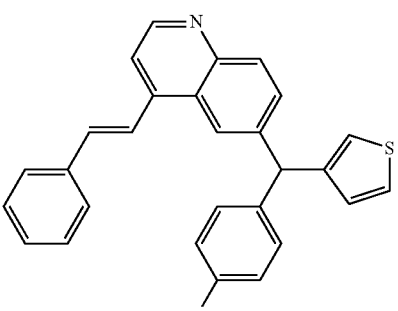<br>6-[(4-Chlorophenyl)(thiophen-3-yl)methyl]-4-[(E)-2-phenylethenyl]quinoline | 64 | (ES, m/z): [M + H]+ 438, 440; 1H NMR (CDCl3) Shift: 8.86 (d, J = 4.6 Hz, 1H), 8.06 (d, J = 8.8 Hz, 1H), 7.90 (s, 1H), 7.51-7.66 (m, 5H), 7.42 (t, J = 7.5 Hz, 2H), 7.27-7.38 (m, 5H), 7.08-7.18 (m, 2H), 6.91 (d, J = 4.9 Hz, 1H), 6.72-6.83 (m, 1H), 5.72 (s, 1H) |
| 13 | 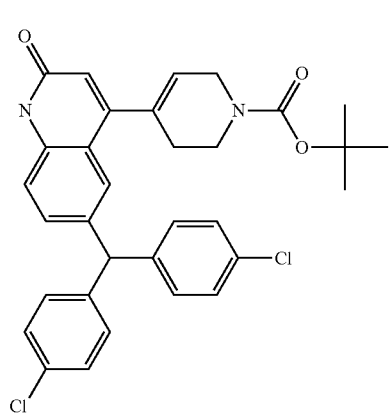 [SMILES: CC(C)(C)OC(=O)N1CC=C(c2cc(=O)[nH]c3ccc(C(c4ccc(Cl)cc4)c4ccc(Cl)cc4)cc23)CC1]<br>tert-Butyl 4-{6-[bis(4-chlorophenyl)methyl]-2-oxo-1,2-dihydroquinolin-4-yl}-3,6-dihydropyridine-1(2H)-carboxylate | 56 | (ES, m/z): [M + H]+ 561, 563 |

TABLE EX-continued

Representative Compounds of the Present Invention

| ID No. | Compound IUPAC name | Prepared as in Example # | Analytical Data |
|---|---|---|---|
| 15 | 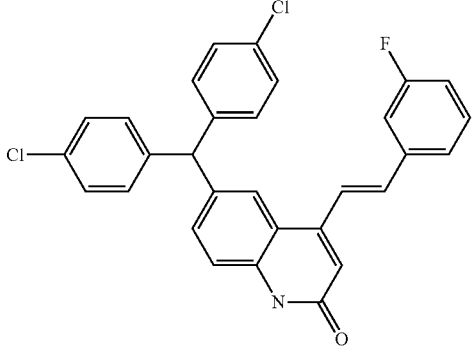 [SMILES: O=c1cc(/C=C/c2cccc(F)c2)c2cc(C(c3ccc(Cl)cc3)c3ccc(Cl)cc3)ccc2[nH]1]<br>6-[Bis(4-chlorophenyl)methyl]-4-[(E)-2-(3-fluorophenyl)ethenyl]quinolin-2(1H)-one | 66 | (ES, m/z): [M + H] + 500, 502 |
| 16 | 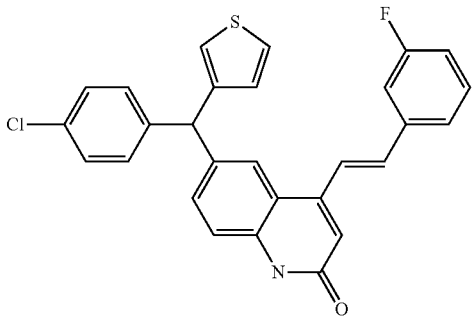 [SMILES: O=c1cc(/C=C/c2cccc(F)c2)c2cc(C(c3ccc(Cl)cc3)c3ccsc3)ccc2[nH]1]<br>6-[(4-Chlorophenyl)(thiophen-3-yl)methyl]-4-[(E)-2-(3-fluorophenyl)ethenyl]quinolin-2(1H)-one | 66 | (ES, m/z): [M + H] + 472, 474; 1H NMR (CDCl3) d: 12.15 (br. s., 1H), 7.56 (d, J = 1.5 Hz, 1H), 7.31-7.43 (m, 4H), 7.26-7.31 (m, 4H), 7.18-7.24 (m, 1H), 7.08-7.17 (m, 3H), 7.02-7.08 (m, 1H), 6.83-6.92 (m, 2H), 6.70-6.78 (m, 1H), 5.60 (s, 1H) |
| 520 | 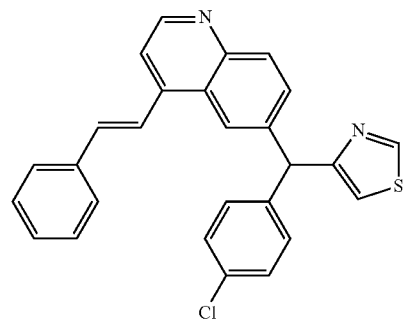 [SMILES: Clc1ccc(C(c2ccc3nccc(/C=C/c4ccccc4)c3c2)c2cscn2)cc1]<br>6-[(4-Chlorophenyl)(1,3-thiazol-4-yl)methyl]-4-[(E)-2-phenylethenyl]quinoline | 64 | (ES, m/z): [M + H] + 439, 440, 442 |

TABLE EX-continued

Representative Compounds of the Present Invention

| ID No. | Compound IUPAC name | Prepared as in Example # | Analytical Data |
|---|---|---|---|
| 18 | 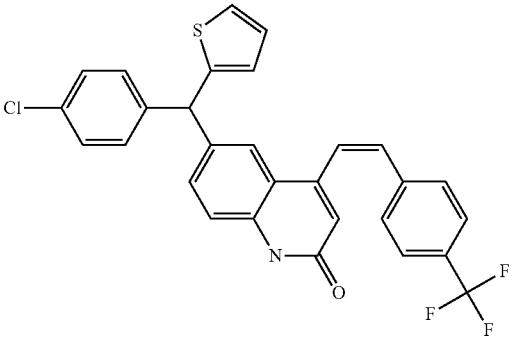 [SMILES: O=c1cc(/C=C\c2ccc(C(F)(F)F)cc2)c2cc(C(c3ccc(Cl)cc3)c3cccs3)ccc2[nH]1]<br>6-[(4-Chlorophenyl)(thiophen-2-yl)methyl]-4-{(Z)-2-[4-(trifluoromethyl)phenyl]ethenyl}quinolin-2(1H)-one | 55 | 1H NMR (CDCl3) d: 11.09 (br. s., 1H), 7.41 (dd, J = 5.0, 3.1 Hz, 3H), 7.31-7.36 (m, 1H), 7.29 (s, 1H), 7.17-7.25 (m, 5H), 6.99 (d, J = 8.3 Hz, 2H), 6.90 (dd, J = 5.0, 3.5 Hz, 1H), 6.87 (d, J = 12.5 Hz, 1H), 6.69 (dd, J = 12.5, 1.2 Hz, 1H), 6.57 (s, 1H), 6.52 (d, J = 3.4 Hz, 1H), 5.61 (s, 1H); (ES, m/z): [M + H] + 522, 523 |
| 19 | 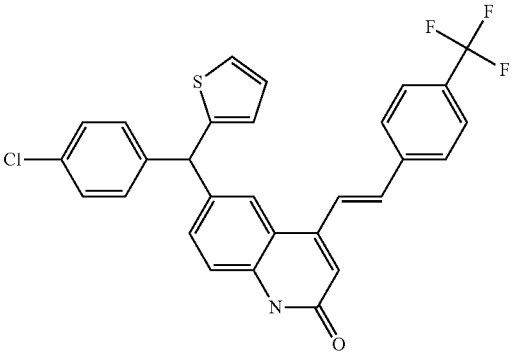 [SMILES: O=c1cc(/C=C/c2ccc(C(F)(F)F)cc2)c2cc(C(c3ccc(Cl)cc3)c3cccs3)ccc2[nH]1]<br>6-[(4-Chlorophenyl)(thiophen-2-yl)methyl]-4-{(E)-2-[4-(trifluoromethyl)phenyl]ethenyl}quinolin-2(1H)-one | 55 | 1H NMR (CDCl3) d: 12.49 (br. s., 1H), 7.63-7.73 (m, 2H), 7.54-7.63 (m, 3H), 7.36-7.48 (m, 3H), 7.30 (d, J = 8.3 Hz, 2H), 7.12-7.25 (m, 4H), 6.97 (dd, J = 5.1, 3.7 Hz, 1H), 6.90 (s, 1H), 6.70 (d, J = 3.7 Hz, 1H), 5.77 (s, 1H); (ES, m/z): [M + H] + 522, 523, 525 |
| 20 | 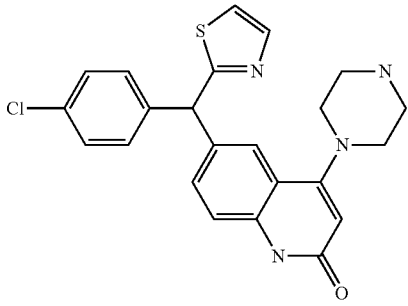 [SMILES: O=c1cc(N2CCNCC2)c2cc(C(c3ccc(Cl)cc3)c3nccs3)ccc2[nH]1]<br>6-[(4-Chlorophenyl)(1,3-thiazol-2-yl)methyl]-4-piperazin-1-ylquinolin-2(1H)-one | 16 | (ES, m/z): [M + H] + 437, 439 |

| ID No. | Compound IUPAC name | Prepared as in Example # | Analytical Data |
|---|---|---|---|
| 21 | 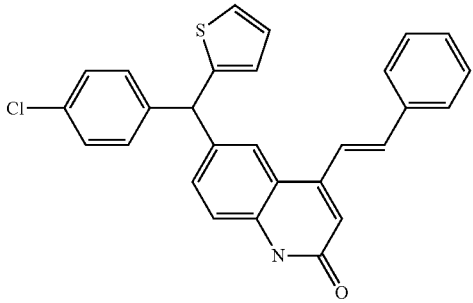 [SMILES: O=c1cc(/C=C/c2ccccc2)c2cc(C(c3ccc(Cl)cc3)c3cccs3)ccc2[nH]1]<br>6-[(4-Chlorophenyl)(thiophen-2-yl)methyl]-4-[(E)-2-phenylethenyl]quinolin-2(1H)-one | 55 | (ES, m/z): [M + H] + 454, 456 |
| 26 | 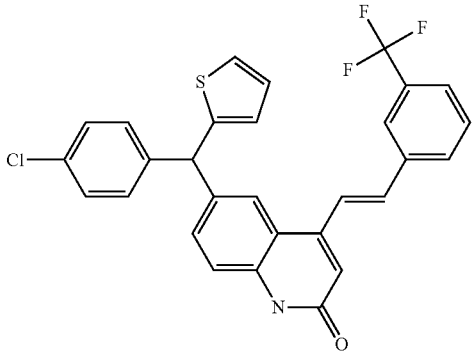 [SMILES: O=c1cc(/C=C/c2cccc(C(F)(F)F)c2)c2cc(C(c3ccc(Cl)cc3)c3cccs3)ccc2[nH]1]<br>6-[(4-Chlorophenyl)(thiophen-2-yl)methyl]-4-{(E)-2-[3-(trifluoromethyl)phenyl]ethenyl}quinolin-2(1H)-one | 55 | (ES, m/z): [M + H] + 522, 525 |
| 27 | 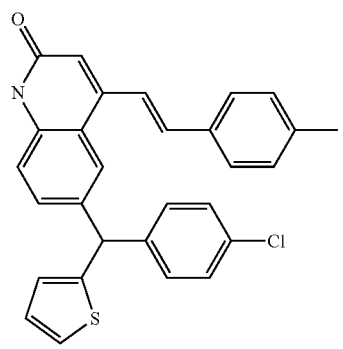 [SMILES: Cc1ccc(/C=C/c2cc(=O)[nH]c3ccc(C(c4ccc(Cl)cc4)c4cccs4)cc23)cc1]<br>6-[(4-Chlorophenyl)(thiophen-2-yl)methyl]-4-[(E)-2-(4-methylphenyl)ethenyl]quinolin-2(1H)-one | 55 | (ES, m/z): [M + H] + 468, 470 |

TABLE EX-continued

Representative Compounds of the Present Invention

| ID No. | Compound IUPAC name | Prepared as in Example # | Analytical Data |
|---|---|---|---|
| 29 | 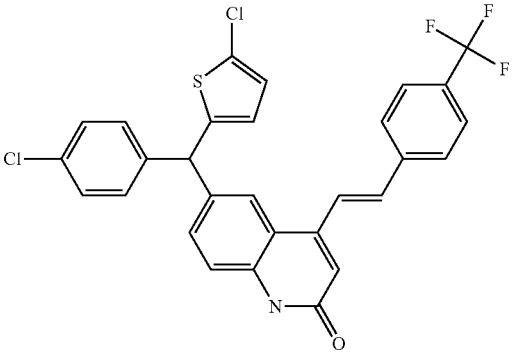 [SMILES: O=c1cc(/C=C/c2ccc(C(F)(F)F)cc2)c2cc(C(c3ccc(Cl)cc3)c3ccc(Cl)s3)ccc2[nH]1]<br>6-[(4-Chlorophenyl)(5-chlorothiophen-2-yl)methyl]-4-{(E)-2-[4-(trifluoromethyl)phenyl]ethenyl}quinolin-2(1H)-one | 55 | (ES, m/z): [M + H] + 556, 557, 558, 560; 1H NMR (DMSO-d6) d: 11.81 (s, 1H), 8.02 (s, 1H), 7.91-7.98 (m, J = 8.1 Hz, 2H), 7.74-7.85 (m, 3H), 7.49 (d, J = 15.9 Hz, 1H), 7.41 (d, J = 8.6 Hz, 3H), 7.35 (d, J = 8.6 Hz, 1H), 7.26-7.32 (m, J = 8.3 Hz, 2H), 7.00 (d, J = 3.7 Hz, 1H), 6.84 (s, 1H), 6.60 (d, J = 3.7 Hz, 1H), 5.89 (s, 1H) |
| 30 | 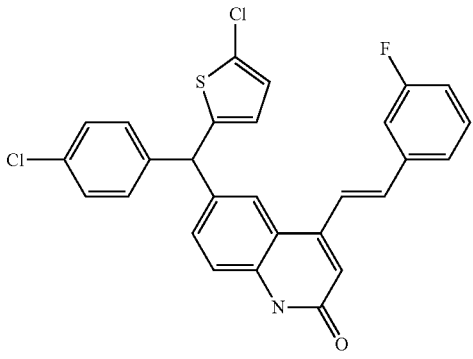 [SMILES: O=c1cc(/C=C/c2cccc(F)c2)c2cc(C(c3ccc(Cl)cc3)c3ccc(Cl)s3)ccc2[nH]1]<br>6-[(4-Chlorophenyl)(5-chlorothiophen-2-yl)methyl]-4-[(E)-2-(3-fluorophenyl)ethenyl]quinolin-2(1H)-one | 55 | (ES, m/z): [M + H] + 506, 507, 508, 510 |
| 31 | 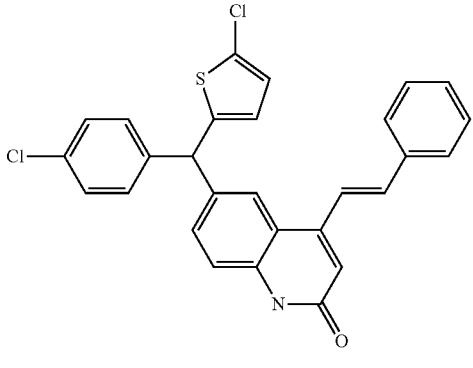 [SMILES: O=c1cc(/C=C/c2ccccc2)c2cc(C(c3ccc(Cl)cc3)c3ccc(Cl)s3)ccc2[nH]1]<br>6-[(4-Chlorophenyl)(5-chlorothiophen-2-yl)methyl]-4-[(E)-2-phenylethenyl]quinolin-2(1H)-one | 55 | (ES, m/z): [M + H] + 488, 490 |

TABLE EX-continued

Representative Compounds of the Present Invention

| ID No. | Compound IUPAC name | Prepared as in Example # | Analytical Data |
|---|---|---|---|
| 521 | 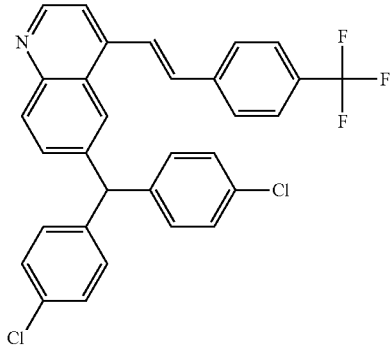 [SMILES: FC(F)(F)c1ccc(/C=C/c2ccnc3ccc(C(c4ccc(Cl)cc4)c4ccc(Cl)cc4)cc23)cc1]<br>6-[Bis(4-chlorophenyl)methyl]-4-{(E)-2-[4-(trifluoromethyl)phenyl]ethenyl}quinoline | 57 | (ES, m/z): [M + H] + 534, 536 |
| 32 | 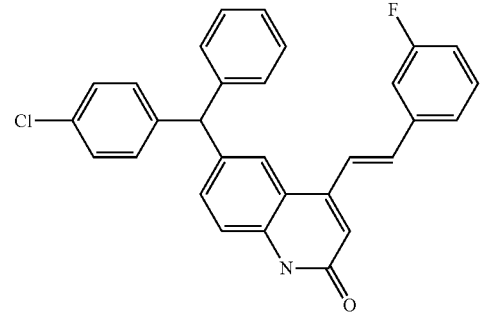 [SMILES: O=c1cc(/C=C/c2cccc(F)c2)c2cc(C(c3ccccc3)c3ccc(Cl)cc3)ccc2[nH]1]<br>6-[(4-Chlorophenyl)(phenyl)methyl]-4-[(E)-2-(3-fluorophenyl)ethenyl]quinolin-2(1H)-one | 57 | (ES, m/z): [M + H] + 466, 468 |
| 33 | 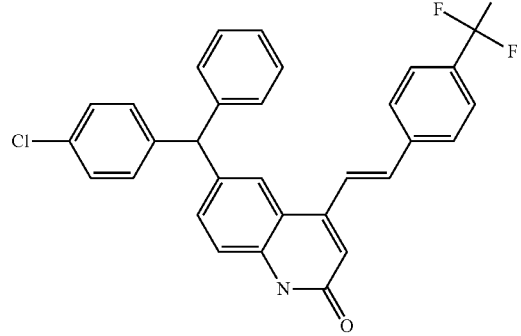<br>6-[(4-Chlorophenyl)(phenyl)methyl]-4-{(E)-2-[4-(trifluoromethyl)phenyl]ethenyl}quinolin-2(1H)-one | 57 | (ES, m/z): [M + H] + 516, 518 |

TABLE EX-continued

Representative Compounds of the Present Invention

| ID No. | Compound IUPAC name | Prepared as in Example # | Analytical Data |
|---|---|---|---|
| 34 | 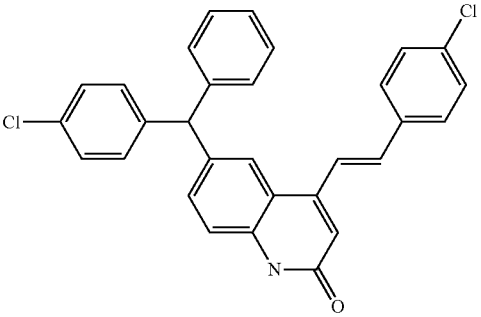 [SMILES: O=c1cc(/C=C/c2ccc(Cl)cc2)c2cc(C(c3ccccc3)c3ccc(Cl)cc3)ccc2[nH]1]<br>4-[(E)-2-(4-Chlorophenyl)ethenyl]-6-[(4-chlorophenyl)(phenyl)methyl]quinolin-2(1H)-one | 57 | (ES, m/z): [M + H] + 482, 484 |
| 35 | 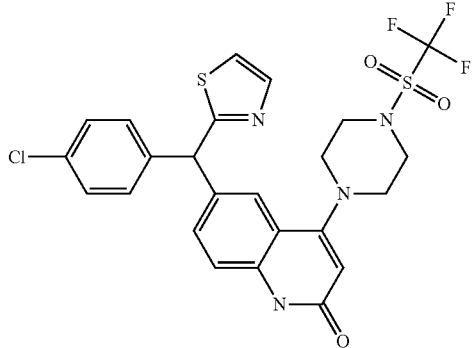 [SMILES: O=c1cc(N2CCN(S(=O)(=O)C(F)(F)F)CC2)c2cc(C(c3ccc(Cl)cc3)c3nccs3)ccc2[nH]1]<br>6-[(4-Chlorophenyl)(1,3-thiazol-2-yl)methyl]-4-{4-[(trifluoromethyl)sulfonyl]piperazin-1-yl}quinolin-2(1H)-one | 68 | (ES, m/z): [M + H] + 569, 570, 572; 1H NMR (CDCl3) d: 11.55 (br. s., 1H), 7.83 (d, J = 3.4 Hz, 1H), 7.37-7.42 (m, 1H), 7.33 (d, J = 8.6 Hz, 5H), 7.19 (d, J = 8.3 Hz, 2H), 6.10 (s, 1H), 5.90 (s, 1H), 3.55 (m, 4H), 3.12 9m, 4H) |
| 522 | 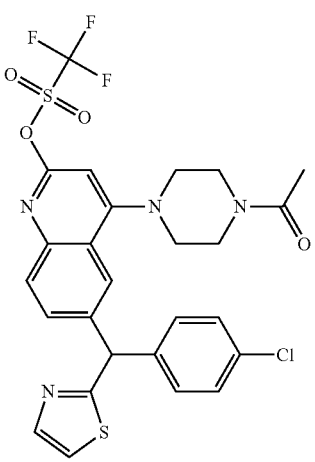 [SMILES: CC(=O)N1CCN(c2cc(OS(=O)(=O)C(F)(F)F)nc3ccc(C(c4ccc(Cl)cc4)c4nccs4)cc23)CC1]<br>4-(4-Acetylpiperazin-1-yl)-6-[(4-chlorophenyl)(1,3-thiazol-2-yl)methyl]quinolin-2-yl trifluoromethanesulfonate | 68 | (ES, m/z): [M + H] + 611, 613 |

TABLE EX-continued

Representative Compounds of the Present Invention

| ID No. | Compound IUPAC name | Prepared as in Example # | Analytical Data |
|---|---|---|---|
| 37 | 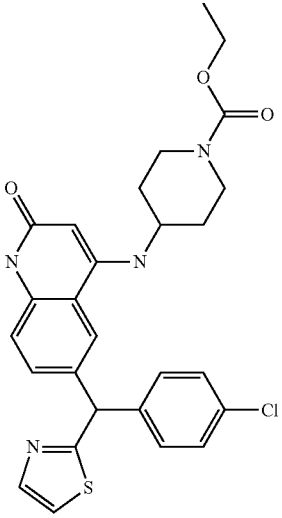 [SMILES: CCOC(=O)N1CCC(Nc2cc(=O)[nH]c3ccc(C(c4ccc(Cl)cc4)c4nccs4)cc23)CC1]<br>Ethyl 4-({6-[(4-chlorophenyl)(1,3-thiazol-2-yl)methyl]-2-oxo-1,2-dihydroquinolin-4-yl}amino)piperidine-1-carboxylate | 8 | (ES, m/z): [M + H] + 523, 525; 1H NMR (CDCl3) d: 11.17 (br. s., 1H), 7.82 (d, J = 3.2 Hz, 1H), 7.34-7.40 (m, 2H), 7.28-7.34 (m, 4H), 7.17 (d, J = 8.3 Hz, 2H), 5.87 (s, 1H), 5.70 (s, 1H), 4.68 (d, J = 7.1 Hz, 1H), 4.14 (m, 4H), 3.56 (m, 1H), 2.96 (m, 2H), 2.14 (m, 2H), 1.47 (m, 2H), 1.07-1.37 (m, 3H) |
| 40 | 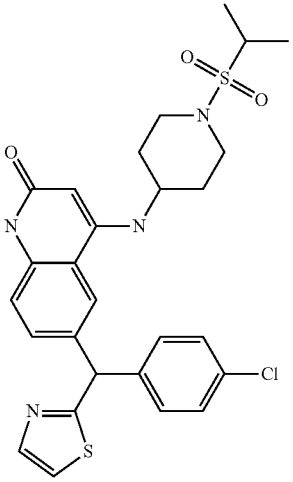 [SMILES: CC(C)S(=O)(=O)N1CCC(Nc2cc(=O)[nH]c3ccc(C(c4ccc(Cl)cc4)c4nccs4)cc23)CC1]<br>6-[(4-Chlorophenyl)(1,3-thiazol-2-yl)methyl]-4-({1-[(1-methylethyl)sulfonyl]piperidin-4-yl}amino)quinolin-2(1H)-one | 1 | (ES, m/z): [M + H] + 557, 559 |

TABLE EX-continued

Representative Compounds of the Present Invention

| ID No. | Compound IUPAC name | Prepared as in Example # | Analytical Data |
|---|---|---|---|
| 42 | 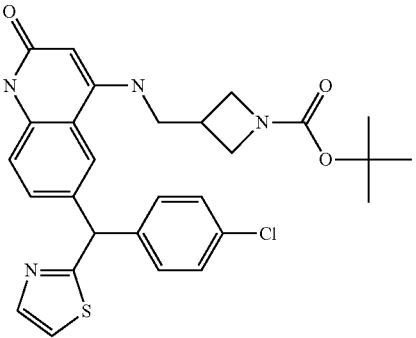 [SMILES: CC(C)(C)OC(=O)N1CC(CNc2cc(=O)[nH]c3ccc(C(c4ccc(Cl)cc4)c4nccs4)cc23)C1]<br>tert-Butyl 3-[({6-[(4-chlorophenyl)(1,3-thiazol-2-yl)methyl]-2-oxo-1,2-dihydroquinolin-4-yl}amino)methyl]azetidine-1-carboxylate | 1 | (ES, m/z): [M + H] + 537, 539 |
| 43 | 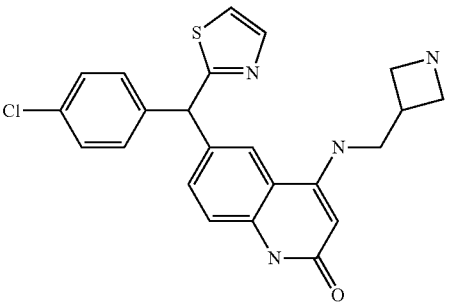 [SMILES: O=c1cc(NCC2CNC2)c2cc(C(c3ccc(Cl)cc3)c3nccs3)ccc2[nH]1]<br>4-[(Azetidin-3-ylmethyl)amino]-6-[(4-chlorophenyl)(1,3-thiazol-2-yl)methyl]quinolin-2(1H)-one | 16 | (ES, m/z): [M + H] + 437, 439 |
| 45 | 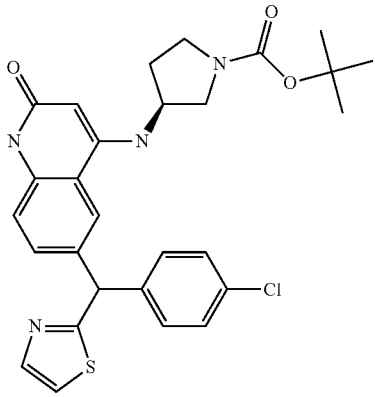 [SMILES: CC(C)(C)OC(=O)N1CC[C@H](Nc2cc(=O)[nH]c3ccc(C(c4ccc(Cl)cc4)c4nccs4)cc23)C1]<br>tert-Butyl (3S)-3-({6-[(4-chlorophenyl)(1,3-thiazol-2-yl)methyl]-2-oxo-1,2-dihydroquinolin-4-yl}amino)pyrrolidine-1-carboxylate | 1 | (ES, m/z): 537, 539 [M + H]+ |

| ID No. | Compound IUPAC name | Prepared as in Example # | Analytical Data |
|---|---|---|---|
| 46 | 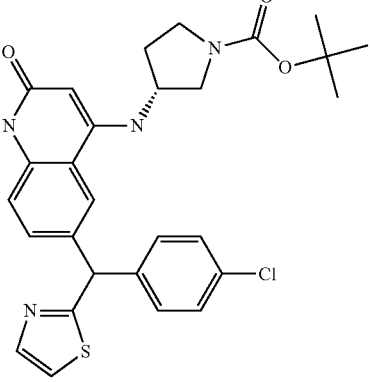<br>tert-Butyl (3R)-3-({6-[(4-chlorophenyl)(1,3-thiazol-2-yl)methyl]-2-oxo-1,2-dihydroquinolin-4-yl}amino)pyrrolidine-1-carboxylate | 1 | (ES, m/z): 537, 539 [M + H]+ |
| 47 | 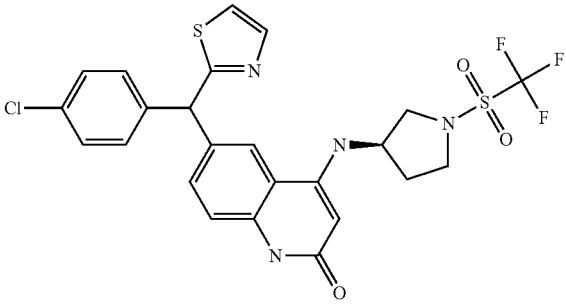 [SMILES: O=c1cc(N[C@@H]2CCN(S(=O)(=O)C(F)(F)F)C2)c2cc(C(c3ccc(Cl)cc3)c3nccs3)ccc2[nH]1]<br>6-[(4-Chlorophenyl)(1,3-thiazol-2-yl)methyl]-4-({(3R)-1-[(trifluoromethyl)sulfonyl]pyrrolidin-3-yl}amino)quinolin-2(1H)-one | 68 | (ES, m/z) 569 [M + H]+<br>1H-NMR (400 MHz, DMSO) δ 10.931 (s, 1H), 8.029 (s, 1H), 7.818 (s, 1H), 7.810 (s, 1H), 7.690 (s, 1H), 7.418-7.281 (m, 5H), 7.220 (d, J = 6.6 Hz, 1H), 6.725 (br, 1H), 5.916 (s, 1H), 5.429 (s, 1H), 4.329-4.316 (m, 1H), 3.870-3.832 (m, 1H), 3.770-3.749 (m, 1H), 3.661-3.644 (m, 1H), 3.549-3.532 (m, 1H), 2.406-2.337 (m, 1H), 2.213-2.166 (m, 1H) |
| 48 | 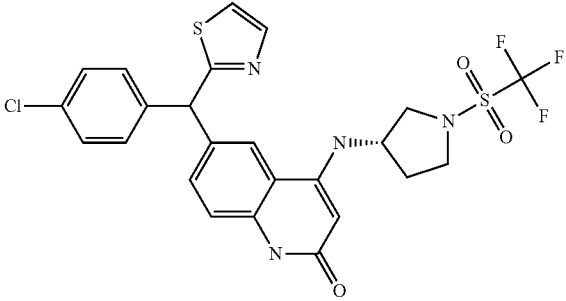 [SMILES: O=c1cc(N[C@H]2CCN(S(=O)(=O)C(F)(F)F)C2)c2cc(C(c3ccc(Cl)cc3)c3nccs3)ccc2[nH]1]<br>6-[(4-Chlorophenyl)(1,3-thiazol-2-yl)methyl]-4-({(3S)-1-[(trifluoromethyl)sulfonyl]pyrrolidin-3-yl}amino)quinolin-2(1H)-one | 68 | (ES, m/z): 569, 571 [M + H]+ |

TABLE EX-continued

Representative Compounds of the Present Invention

| ID No. | Compound IUPAC name | Prepared as in Example # | Analytical Data |
|---|---|---|---|
| 50 | 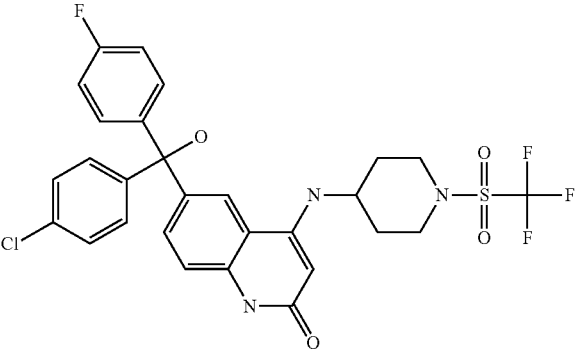 [SMILES: O=c1cc(NC2CCN(S(=O)(=O)C(F)(F)F)CC2)c2cc(C(O)(c3ccc(F)cc3)c3ccc(Cl)cc3)ccc2[nH]1]<br>6-[(4-Chlorophenyl)(4-fluorophenyl)hydroxymethyl]-4-({1-[(trifluoromethyl)sulfonyl]piperidin-4-yl}amino)quinolin-2(1H)-one | 11 | (ES, m/z): 610 [M + H]+; |
| 52 | 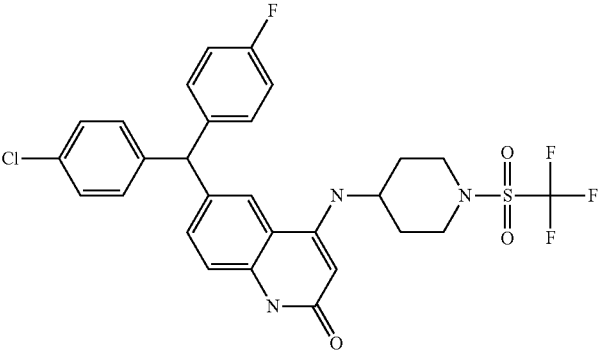 [SMILES: O=c1cc(NC2CCN(S(=O)(=O)C(F)(F)F)CC2)c2cc(C(c3ccc(F)cc3)c3ccc(Cl)cc3)ccc2[nH]1]<br>6-[(4-Chlorophenyl)(4-fluorophenyl)methyl]-4-({1-[(trifluoromethyl)sulfonyl]piperidin-4-yl}amino)quinolin-2(1H)-one | 9 | (ES, m/z) 594 [M + H]+; 1H-NMR (300 MHz, DMSO) δ 10.759 (s, 1H), 7.912 (s, 1H), 7.384 (d, J = 8.4 Hz, 2H), 7.108-7.203 (m, 8H), 6.623 (d, J = 7.8 Hz, 1H), 5.616 (s, 1H), 5.472 (s, 1H), 3.860 (d, J = 12.9 Hz, 2H), 3.732 (br, 1H), 3.354-3.439 (m, 2H), 2.076 (d, J = 11.4 Hz, 2H), 1.571-1.638 (m, 2H) |
| 55 | 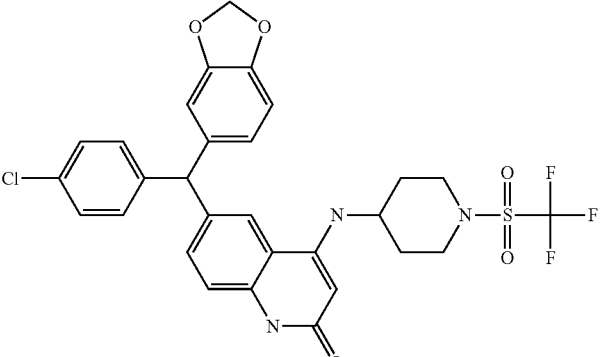<br>6-[1,3-Benzodioxol-5-yl(4-chlorophenyl)methyl]-4-({1-[(trifluoromethyl)sulfonyl]piperidin-4-yl}amino)quinolin-2(1H)-one | 9 | (ES, m/z) 620 [M + H]+; 1H-NMR (300 MHz, DMSO) δ 10.750 (s, 1H), 7.894 (s, 1H), 7.374 (d, J = 8.4 Hz, 2H), 7.198-7.101 (m, 4H), 6.854 (d, J = 8.1 HZ, 1H), 6.682 (s, 1H), 6.568-6.513 (m, 2H), 5.986 (s, 2H), 5.516 (S, 1H), 5.470 (s, 2H), 3.881-3.837 (m, 2H), 3.737 (br, 1H), 3.439-3.399 (m, 2H), 2.095-2.056 (m, 2H), 1.666-1.546 (m, 2H). |

TABLE EX-continued

Representative Compounds of the Present Invention

| ID No. | Compound IUPAC name | Prepared as in Example # | Analytical Data |
|---|---|---|---|
| 58 | 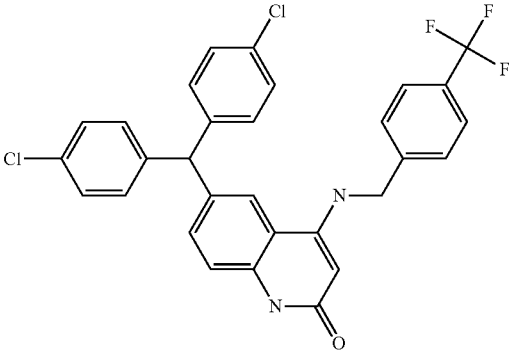 [SMILES: O=c1cc(NCc2ccc(C(F)(F)F)cc2)c2cc(C(c3ccc(Cl)cc3)c3ccc(Cl)cc3)ccc2[nH]1]  6-[Bis(4-chlorophenyl)methyl]-4-{[4-(trifluoromethyl)benzyl]amino}quinolin-2(1H)-one | 5 | (ES, m/z) 553 [M + H]+; 1H-NMR (300 MHz, DMSO) δ 10.773 (s, 1H), 7.913 (s, 1H), 7.717-7.622 (m, 3H), 7.554-7.527 (m, 2H), 7.415-7.387 (d, J = 8.4 Hz,, 4H), 7.187-7.160 (d, J = 8.1 Hz, 6H), 5.647 (s, 1H), 5.080 (s, 1H), 4.512 (d, J = 4.8 Hz, 2H) |
| 62 | 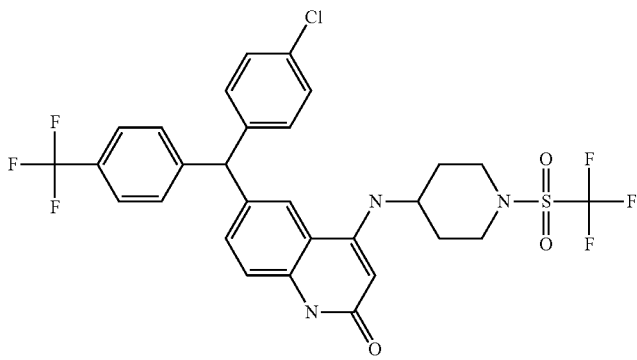 [SMILES: O=c1cc(NC2CCN(S(=O)(=O)C(F)(F)F)CC2)c2cc(C(c3ccc(Cl)cc3)c3ccc(C(F)(F)F)cc3)ccc2[nH]1]  6-{(4-Chlorophenyl)[4-(trifluoromethyl)phenyl]methyl}-4-({1-[(trifluoromethyl)sulfonyl]piperidin-4-yl}amino)quinolin-2(1H)-one | 9 | (ES, m/z) 644 [M + H]+; 1H-NMR (300 MHz, DMSO) δ 10.775 (s, 1H), 7.935 (s, 1H), 7.695 (d, J = 8.1 Hz, 2H), 7.416-7.321 (m, 4H), 7.216-7.120 (m, 4H), 6.519 (d, J = 7.8 Hz, 1H), 5.719 (s, 1H), 5.474 (s, 1H), 3.871-3.721 (m, 3H), 3.435-3.332 (m, 2H), 2.089-2.052 (m, 2H), 1.641-1.520 (m, 2H) |
| 63 | 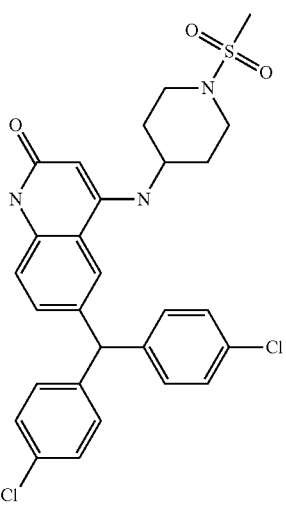 [SMILES: CS(=O)(=O)N1CCC(Nc2cc(=O)[nH]c3ccc(C(c4ccc(Cl)cc4)c4ccc(Cl)cc4)cc23)CC1]  6-[Bis(4-chlorophenyl)methyl]-4-{[1-(methylsulfonyl)piperidin-4-yl]amino}quinolin-2(1H)-one | 13 | (ES, m/z) 556 [M + H]+; 1H-NMR (300 MHz, DMSO) δ 10.749 (s, 1H), 7.929 (s, 1H), 7.388 (d, J = 8.1 Hz, 4H), 7.197-7.111 (m, 6H), 6.502 (d, J = 7.2 Hz, 1H), 5.613 (s, 1H), 5.400 (s, 1H), 3.622-3.538 (m, 3H), 2.938-2.884 (m, 5H), 2.043-1.990 (m, 2H), 1.642-1.539 (m, 2H) |

TABLE EX-continued

Representative Compounds of the Present Invention

| ID No. | Compound IUPAC name | Prepared as in Example # | Analytical Data |
|---|---|---|---|
| 65 | 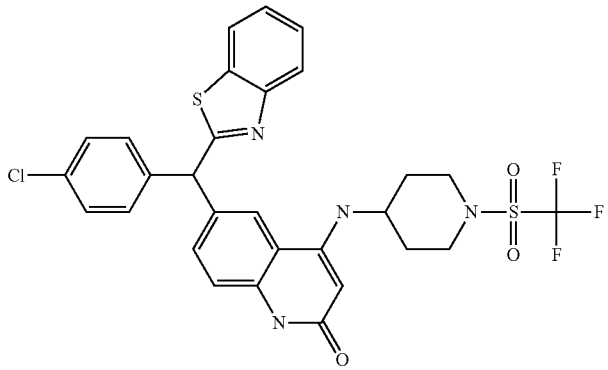 [SMILES: O=c1cc(NC2CCN(S(=O)(=O)C(F)(F)F)CC2)c2cc(C(c3ccc(Cl)cc3)c3nc4ccccc4s3)ccc2[nH]1]<br>6-[1,3-Benzothiazol-2-yl(4-chlorophenyl)methyl]-4-({1-[(trifluoromethyl)sulfonyl]piperidin-4-yl}amino)quinolin-2(1H)-one | 1 | (ES, m/z) 633 [M + H]+; 1H-NMR (300 MHz, DMSO) δ 10.832 (s, 1H), 8.106 (s, 1H), 8.048 (d, J = 6.9 Hz, 1H), 7.957 (d, J = 7.8 Hz, 1H), 7.530-7.329 (m, 7H), 7.233 (d, J = 8.7 Hz, 1H), 6.573 (d, J = 7.5 Hz, 1H), 6.031 (s, 1H), 5.494 (s, 1H), 3.877-3.834 (m, 2H), 3.758-3.735 (m, 1H), 3.437-3.331 (m, 2H), 2.101-2.063 (m, 2H), 1.643-1.536 (m, 2H). |
| 67 | 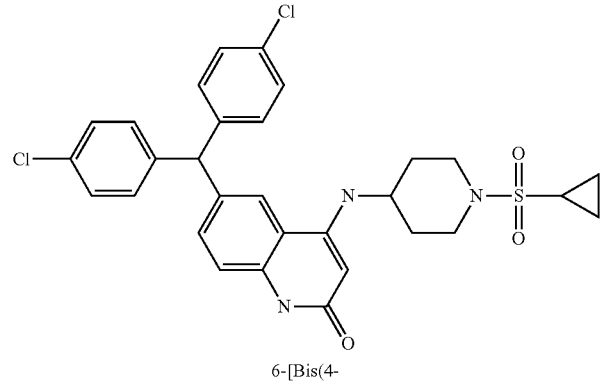<br>6-[Bis(4-chlorophenyl)methyl]-4-{[1-(cyclopropylsulfonyl)piperidin-4-yl]amino}quinolin-2(1H)-one | 13 | (ES, m/z) 582 [M + H]+; 1H-NMR-(300 MHz, DMSO) δ10.753 (s, 1H), 7.933 (s, 1H), 7.385 (d, J = 8.4 Hz, 4H), 7.198-7.109 (m, 6H), 6.601 (d, J = 7.5 Hz, 1H), 5.613 (s, 5H), 5.425 (s, 1H), 3.660-3.620 (m, 3H), 3.061-2.983 (m, 2H), 2.580-2.502 (m, 1H), 2.044-2.004 (d, J = 12 Hz, 2H), 1.635-1.529 (m, 2H), 1.033-0.941 (m, 4H) |
| 68 | 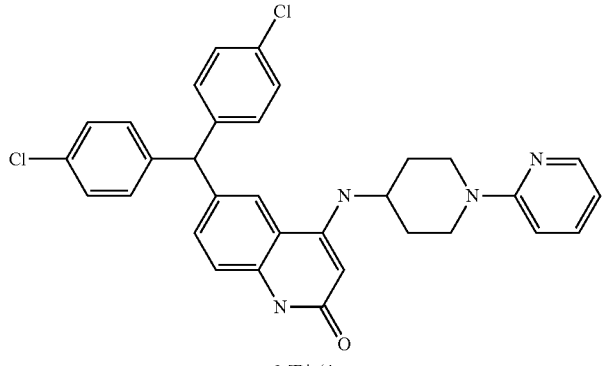<br>6-[Bis(4-chlorophenyl)methyl]-4-[(1-pyridin-2-ylpiperidin-4-yl)amino]quinolin-2(1H)-one | 4 | (ES, m/z) 555 [M + H]+; 1H (300 MHz, DMSO) δ10.711 (s, 1H), 8.108 (d, J = 3.9 Hz 1H), 7.917 (s, 1H), 7.536-7.490 (m, 1H), 7.372 (d, J = 8.4 Hz. 4H), 7.186-7.094 (m, 6H), 6.872 (d, J = 9 Hz, 1H), 6.614-6.574 (m, 1H), 6.443 (d, J = 7.8 Hz, 1H), 5.571 (s, 2H), 5.446 (s, 1H), 4.340 (d, J = 12.3, 2H), 3.714-3.698 (m, 1H), 3.031-2.950 (m, 2H), 1.948 (d, J = 9.9 HZ, 2H), 1.565-1.488 (m, 2H) |

TABLE EX-continued

Representative Compounds of the Present Invention

| ID No. | Compound IUPAC name | Prepared as in Example # | Analytical Data |
|---|---|---|---|
| 69 | 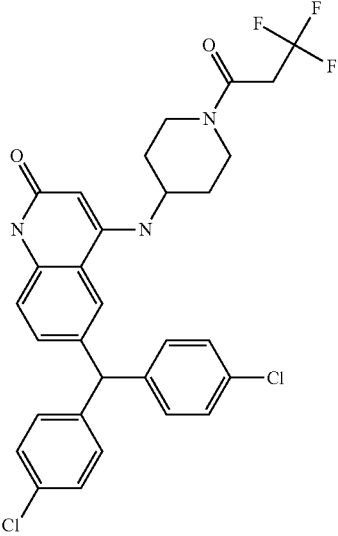 [SMILES: O=C(CC(F)(F)F)N1CCC(Nc2cc(=O)[nH]c3ccc(C(c4ccc(Cl)cc4)c4ccc(Cl)cc4)cc23)CC1]<br>6-[Bis(4-chlorophenyl)methyl]-4-{[1-(3,3,3-trifluoropropanoyl)piperidin-4-yl]amino}quinolin-2(1H)-one | 17 | (ES, m/z) 588 [M + H]+; 1H-NMR-(300 MHz, DMSO) δ10.737 (s, 1H), 7.919 (s, 1H), 7.382 (d, J = 8.1 Hz, 4H), 7.198-7.110 (m, 6H), 6.458 (d, J = 7.8 Hz, 4H), 5.600 (s, 1H), 5.454 (s, 1H), 4.385 (d, J = 12.5 Hz, 1H), 3.900-3.853 (m, 1H), 3.738-3.589 (m, 3H), 3.275-3.158 (m, 1H), 2.814-2.732 (m, 1H), 2.050-1.900 (m, 2H), 1.522-1.342 (m, 2H). |
| 73 | 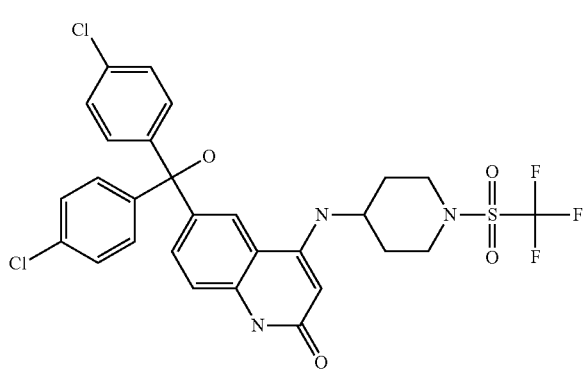<br>6-[Bis(4-chlorophenyl)(hydroxy)methyl]-4-({1-[(trifluoromethyl)sulfonyl]piperidin-4-yl}amino)quinolin-2(1H)-one | 11 | (ES, m/z) 626 [M + H]+; |
| 74 | 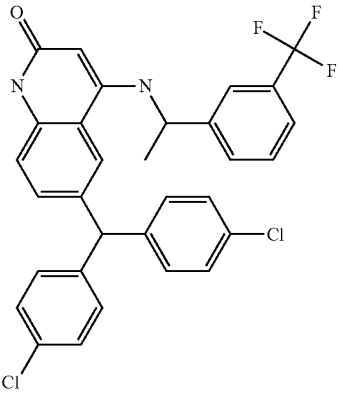 [SMILES: CC(Nc1cc(=O)[nH]c2ccc(C(c3ccc(Cl)cc3)c3ccc(Cl)cc3)cc12)c1cccc(C(F)(F)F)c1] | 5 | (ES, m/z) 567 [M + H]+; 1H-NMR (400 MHz, DMSO) δ10.768 (s, 1H), 8.142 (s, 1H), 7.786 (s, 1 H), 7.720-7.703 (m, 1H), 7.599-7.580 (m, 2H), 7.417-7.401 (d, J = 6.4 Hz, 4H), 7.178-7.113 (m, 6H), 5.675 (s, 1H), 5.071 (s, 1H), 4.780-4.850 (m, 1H), 1.553 (d, J = 6.8 Hz, 3H) |

TABLE EX-continued

Representative Compounds of the Present Invention

| ID No. | Compound IUPAC name | Prepared as in Example # | Analytical Data |
|---|---|---|---|
| 75 | 6-[Bis(4-chlorophenyl)methyl]-4-({1-[3-(trifluoromethyl)phenyl]ethyl}amino)quinolin-2(1H)-one | 3 | (ES, m/z) 539 [M + H]+; H-NMR (400 MHz, DMSO) δ11.201 (s, 1H), 8.785 (s, 1H), 7.912 (s, 1H), 7.639-7.551 (m, 3H), 7.462-7.404 (m, 5H), 7.383 (s, 2H), 7.275-7.152 (m, 4H), 5.798 (s, 1H), 5.683 (s, 1H) |
| 76 | 6-[Bis(4-chlorophenyl)methyl]-4-{[3-(trifluoromethyl)phenyl]amino}quinolin-2(1H)-one | 3 | (ES, m/z) 524 [M + H]+; 1H-NMR (300 MHz, DMSO) δ11.113 (s, 1H), 8.609 (s, 1H), 7.888 (s, 1H), 7.556-7.376 (m, 6H), 7.300-7.144 (m, 7H), 5.668 (s, 1H), 5.616 (s, 1H) |
| | 6-[Bis(4-chlorophenyl)methyl]-4-[(3-chloro-4-fluorophenyl)amino]quinolin-2(1H)-one | | |
| 78 | 6-[Bis(4-chlorophenyl)methyl]-4-({[5-(trifluoromethyl)pyridin-2-yl]methyl}amino)quinolin-2(1H)-one | 5 | (ES, m/z) 554 [M + H]+ |

TABLE EX-continued

Representative Compounds of the Present Invention

| ID No. | Compound IUPAC name | Prepared as in Example # | Analytical Data |
|---|---|---|---|
| 79 | 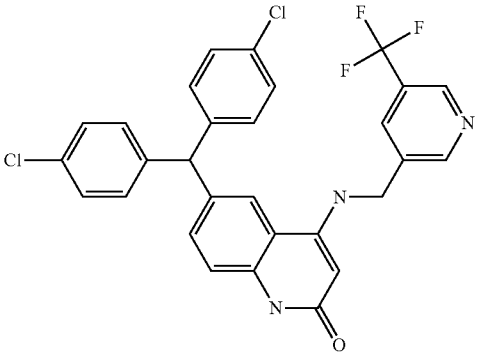 [SMILES: O=c1cc(NCc2cncc(C(F)(F)F)c2)c2cc(C(c3ccc(Cl)cc3)c3ccc(Cl)cc3)ccc2[nH]1]<br>6-[Bis(4-chlorophenyl)methyl]-4-({[5-(trifluoromethyl)pyridin-3-yl]methyl}amino)quinolin-2(1H)-one | 5 | (ES, m/z) 554 [M + H]+; 1H-NMR (300 MHz, DMSO) 10.832 (d, J = 14.1 Hz, 1H), 8.870 (s, 1H), 8.144 (s, 1H), 7.875 (s, 1H), 7.661-7.630 (m, 1H), 7.557-7.540 (m, 4H), 7.188-6.913 (m, 6H), 5.647 (s, 1H), 5.240 (s, 1H), 4.467 (d, J = 5.1 Hz, 2H) |
| 80 | 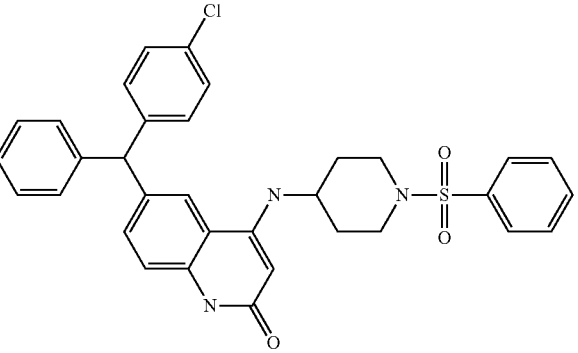<br>6-[Bis(4-chlorophenyl)methyl]-4-{[1-(phenylsulfonyl)piperidin-4-yl]amino}quinolin-2(1H)-one | 16 | (ES, m/z) 618 [M + H]+; 1H-NMR (300 MHz, DMSO) δ10.705 (s, 1H), 7.892 (s, 1H), 7.773-7.641 (m, 5H), 7.394-7.366 (m, 4H), 7.174-7.076 (m, 6H), 6.425 (d, J = 7.5 Hz, 1H), 5.595 (s, 1H), 5.354 (s, 1H), 3.679 (d, J = 12 Hz, 2H), 3.419-3.410 (m, 1H), 2.495-2.420 (m, 2H), 2.006-1.967 (m, 1H), 1.633-1.567 (m, 2H) |
| 82 | 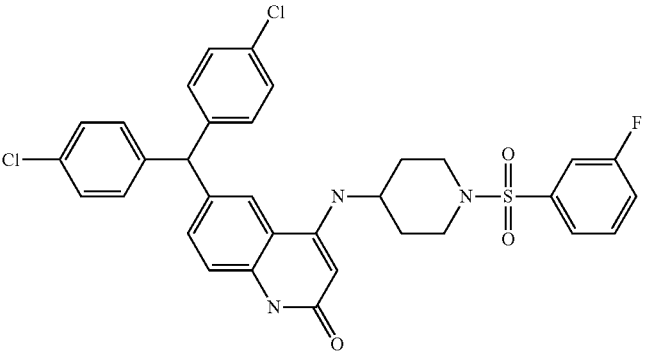 [SMILES: O=c1cc(NC2CCN(S(=O)(=O)c3cccc(F)c3)CC2)c2cc(C(c3ccc(Cl)cc3)c3ccc(Cl)cc3)ccc2[nH]1]<br>6-[Bis(4-chlorophenyl)methyl]-4-({1-[(3-fluorophenyl)sulfonyl]piperidin-4-yl}amino)quinolin-2(1H)-one | 16 | (ES, m/z) 636 [M + H]+; 1H-NMR (300 MHz, DMSO) δ10.712 (s, 1H), 7.897 (s, 1H), 7.774-7.703 (m, 1H), 7.628-7.580 (m, 3H), 7.491-7.336 (m, 4H), 7.180-7.077 (m, 6H), 6.442 (d, J = 8.1 Hz, 1H), 5.597 (s, 1H), 5.364 (s, 1H), 3.714-3.675 (m, 2H), 3.500-3.350 (m, 3H), 2.013-1.973 (m, 2H), 1.632-1.525 (m, 2H) |

TABLE EX-continued

Representative Compounds of the Present Invention

| ID No. | Compound IUPAC name | Prepared as in Example # | Analytical Data |
|---|---|---|---|
| 83 | 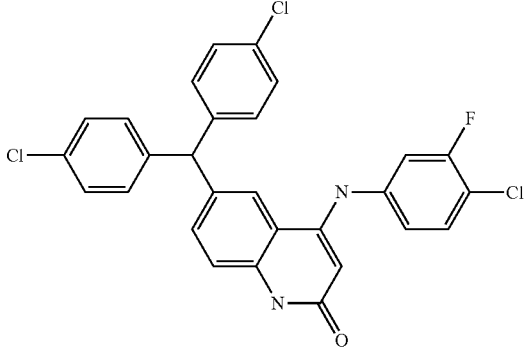 [SMILES: O=c1cc(Nc2ccc(Cl)c(F)c2)c2cc(C(c3ccc(Cl)cc3)c3ccc(Cl)cc3)ccc2[nH]1]<br>6-[Bis(4-chlorophenyl)methyl]-4-[(4-chloro-3-fluorophenyl)amino]quinolin-2(1H)-one | 3 | (ES, m/z) 525 [M + H]+; 1H-NMR (300 MHz, DMSO) δ11.214 (s, 1H), 8.739 (s, 1H), 7.855 (s, 1H), 7.580-7.523 (m, 1H), 7.385 (d, J = 8.4 Hz, 4H), 7.320-7.231 (m, sH), 7.133-7.099 (m, 5H), 5.850 (s, 1H), 5.677 (s, 1H) |
| 84 | 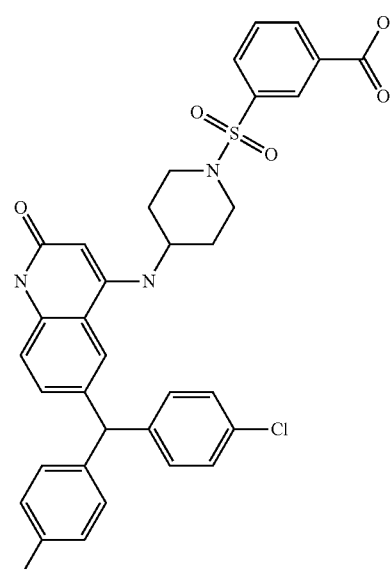<br>3-{[4-({6-[Bis(4-chlorophenyl)methyl]-2-oxo-1,2-dihydroquinolin-4-yl}amino)piperidin-1-yl]sulfonyl}benzoic acid | 29 | (ES, m/z) 662 [M + H]+ |

TABLE EX-continued
Representative Compounds of the Present Invention
| ID No. | Compound IUPAC name | Prepared as in Example # | Analytical Data |
|---|---|---|---|
| 85 | 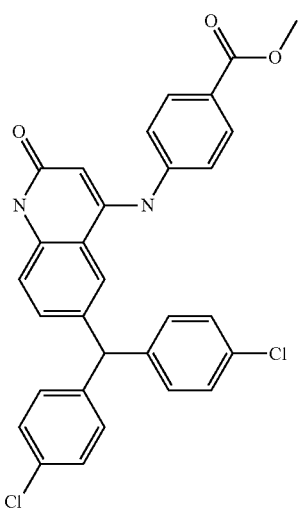 [SMILES: COC(=O)c1ccc(Nc2cc(=O)[nH]c3ccc(C(c4ccc(Cl)cc4)c4ccc(Cl)cc4)cc23)cc1]<br>Methyl 4-({6-[bis(4-chlorophenyl)methyl]-2-oxo-1,2-dihydroquinolin-4-yl}amino)benzoate | 3 | (ES, m/z) 529 [M + H]+: 1H-NMR (300 MHz, DMSO) δ 11.284 (s, 1H), 8.889 (s, 1H), 7.933 (d, J = 8.4 Hz, 2H), 7.854 (s, 1H), 7.396-7.243 (m, 8H), 7.139 (d, J = 8.4 Hz, 4H), 6.029 (s, 1H), 5.676 (s, 1H), 3.85 (s, 3H) |
| 86 | 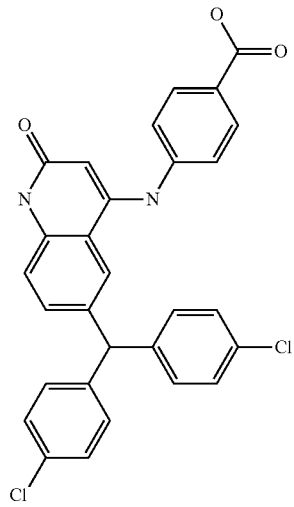<br>4-({6-[Bis(4-chlorophenyl)methyl]-2-oxo-1,2-dihydroquinolin-4-yl}amino)benzoic acid | 24 | (ES, m/z) 515 [M + H]+ |

TABLE EX-continued

Representative Compounds of the Present Invention

| ID No. | Compound IUPAC name | Prepared as in Example # | Analytical Data |
| --- | --- | --- | --- |
| 87 | 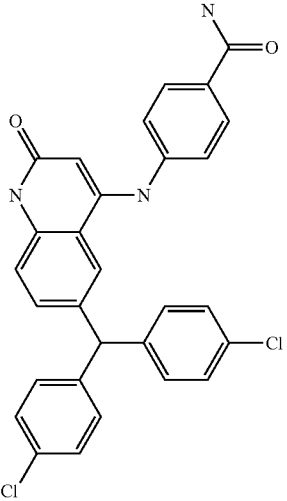 [SMILES: NC(=O)c1ccc(Nc2cc(=O)[nH]c3ccc(C(c4ccc(Cl)cc4)c4ccc(Cl)cc4)cc23)cc1]<br>4-({6-[Bis(4-chlorophenyl)methyl]-2-oxo-1,2-dihydroquinolin-4-yl}amino)benzamide | 25 | (ES, m/z) 514 [M + H]+ |
| 88 | 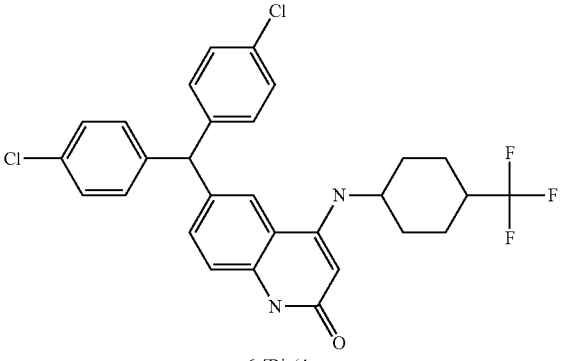<br>6-[Bis(4-chlorophenyl)methyl]-4-{[4-(trifluoromethyl)cyclohexyl]amino}quinolin-2(1H)-one | 7 | (ES, m/z) 545 [M + H]+ |
| 94 | 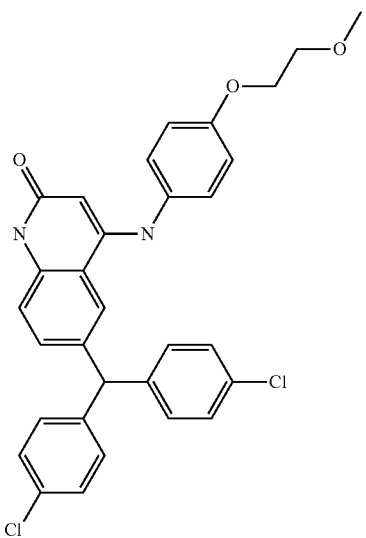 [SMILES: COCCOc1ccc(Nc2cc(=O)[nH]c3ccc(C(c4ccc(Cl)cc4)c4ccc(Cl)cc4)cc23)cc1] | 3 | (ES, m/z): [M + H]+ 545; 1H-NMR: (DMSO-d6, ppm): δ3.328 (s, 3H), 3.668 (dd, J = 4.5 Hz, J = 3.0 Hz, 2H), 4.104 (dd, J = 6.3 Hz, J = 4.5 Hz, 2H), 5.358 (s, 1H), 5.646 (s, 1H), 6.999 (d, J = 9 Hz, 2H), 7.160-7.228 (m, 8H), 7.294 (d, J = 8.4 Hz,, 4H), 7.989 (s, 1H), 8.441 (s, 1H), 10.917 (s, 1H) |

| ID No. | Compound IUPAC name | Prepared as in Example # | Analytical Data |
|---|---|---|---|
| | 6-[Bis(4-chlorophenyl)methyl]-4-{[4-(2-methoxyethoxy)phenyl]amino}quinolin-2(1H)-one 3 | | |
| 95 | 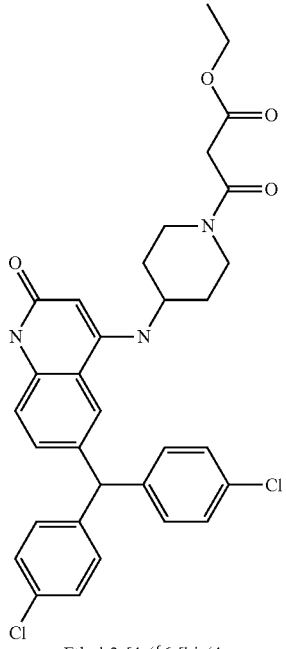<br>Ethyl 3-[4-({6-[bis(4-chlorophenyl)methyl]-2-oxo-1,2-dihydroquinolin-4-yl}amino)piperidin-1-yl]-3-oxopropanoate | 23 | (ES, m/z): [M + H]+ 592; 1H-NMR: (DMSO-d6, ppm): δ1.220 (t, J = 6.9 Hz, 3H), 1.365-1.517 (m, 2H), 1.924-1.966 (m, 2H), 2.727-2.801 (m, 1H), 3.148-3.229 (m, 1H), 3.543 (s, 2H), 3.602-3.683 (m, 1H), 3.767-3.812 (m, 1H), 4.062-4.113 (q, J = 6.9 Hz, 2H), 4.342-4.382 (m, 1H), 5.442 (s, 1H), 5.598 (s, 1H), 6.456 (d, J = 7.8 Hz, 1H), 7.108-7.192 (m, 6H), 7.379 (d, J = 8.7 Hz, 4H), 7.930 (s, 1H), 10.723 (s, 1H) |
| 96 | 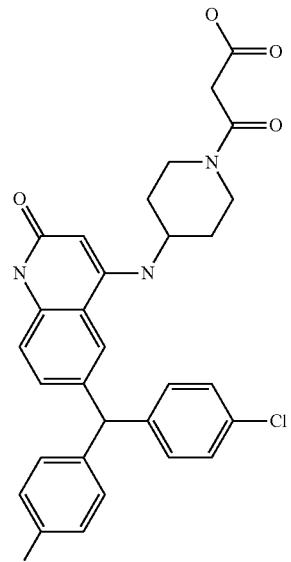<br>3-[4-({6-[Bis(4-chlorophenyl)methyl]-2-oxo-1,2-dihydroquinolin-4-yl}amino)piperidin-1-yl]-3-oxopropanoic acid | 24 | (ES, m/z): [M + H]+ 544, [M + Na]+ 566, [M + H + CH3CN] + 585, [M + Na + CH3CN] + 607 |

TABLE EX-continued

Representative Compounds of the Present Invention

| ID No. | Compound IUPAC name | Prepared as in Example # | Analytical Data |
|---|---|---|---|
| 529 | 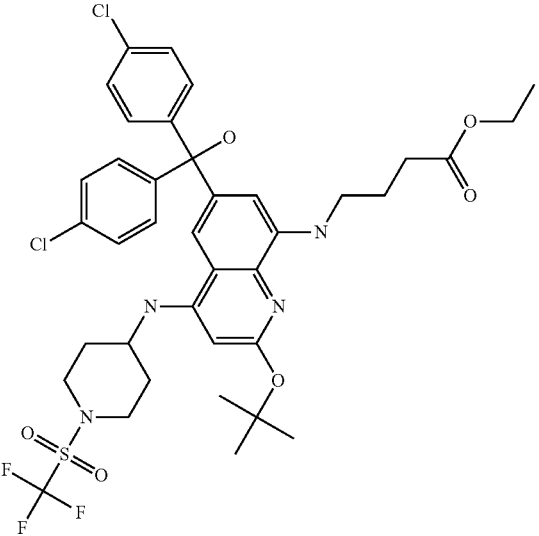 [SMILES: CCOC(=O)CCCNc1cc(C(O)(c2ccc(Cl)cc2)c2ccc(Cl)cc2)cc2c(NC3CCN(S(=O)(=O)C(F)(F)F)CC3)cc(OC(C)(C)C)nc12] Ethyl 4-({6-[bis(4-chlorophenyl)(hydroxy)methyl]-2-tert-butoxy-4-({1-[(trifluoromethyl)sulfonyl]piperidin-4-yl}amino)quinolin-8-yl}amino)butanoate | 38 | (ES, m/z): 811, 813 (M + H)+ |
| 104 | 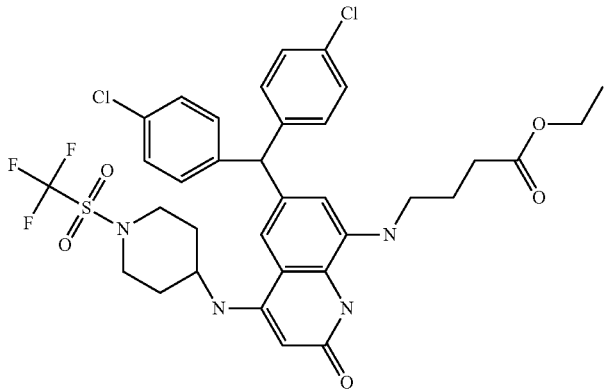 [SMILES: CCOC(=O)CCCNc1cc(C(c2ccc(Cl)cc2)c2ccc(Cl)cc2)cc2c(NC3CCN(S(=O)(=O)C(F)(F)F)CC3)cc(=O)[nH]c12] Ethyl 4-({6-[bis(4-chlorophenyl)methyl]-2-oxo-4-({1-[(trifluoromethyl)sulfonyl]piperidin-4-yl}amino)-1,2-dihydroquinolin-8-yl}amino)butanoate | 38 | (ES, m/z): 739, 741 [M + H]+ |

TABLE EX-continued

Representative Compounds of the Present Invention

| ID No. | Compound IUPAC name | Prepared as in Example # | Analytical Data |
|---|---|---|---|
| 112 | 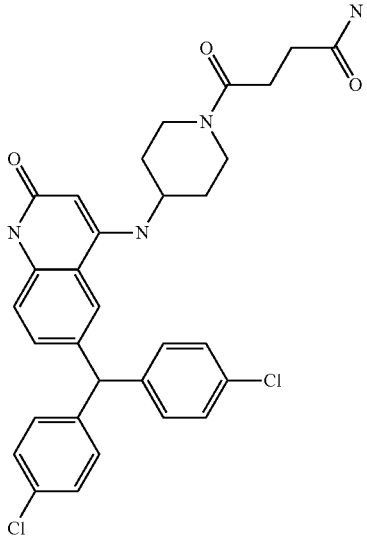 [SMILES: NC(=O)CCC(=O)N1CCC(Nc2cc(=O)[nH]c3ccc(C(c4ccc(Cl)cc4)c4ccc(Cl)cc4)cc23)CC1]<br>4-[4-({6-[Bis(4-chlorophenyl)methyl]-2-oxo-1,2-dihydroquinolin-4-yl}amino)piperidin-1-yl]-4-oxobutanamide | 25 | (ES, m/z): [M + H]+ 577 |
| 113 | 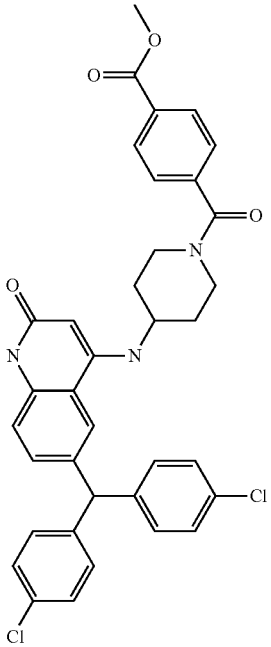 [SMILES: COC(=O)c1ccc(C(=O)N2CCC(Nc3cc(=O)[nH]c4ccc(C(c5ccc(Cl)cc5)c5ccc(Cl)cc5)cc34)CC2)cc1]<br>Methyl 4-{[4-({6-[bis(4-chlorophenyl)methyl]-2-oxo-1,2-dihydroquinolin-4-yl}amino)piperidin-1-yl]carbonyl}benzoate | 17 | (ES, m/z): [M + H]+ 640; 1H-NMR: (DMSO-d6, ppm): δ 1.438-1.511 (m, 2H), 1.867-1.981 (m, 2H), 2.949 (br, 1H), 3.197 (br, 1H), 3.465 (br, 1H), 3.693 (s, 1H), 3.833 (s, 3H), 4.435-4.465 (m, 1H), 5.408 (s, 1H), 5.560 (s, 1H), 6.421 (d, J = 7.8 Hz, 1H), 7.049-7.149 (m, 6H), 7.341 (d, J = 8.1 Hz, 4H), 7.475 (d, J = 8.4 Hz, 2H), 7.878 (s, 1H), 7.989 (d, J = 8.4 Hz, 2H), 10.692 (s, 1 H) |

TABLE EX-continued
Representative Compounds of the Present Invention
| ID No. | Compound IUPAC name | Prepared as in Example # | Analytical Data |
|---|---|---|---|
| 115 | 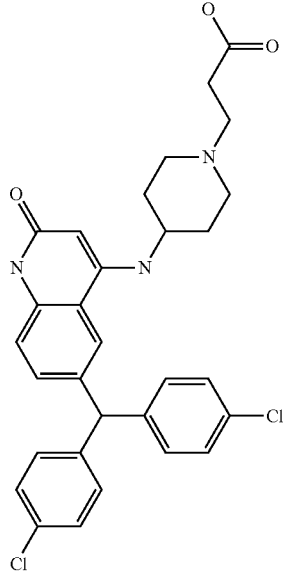 [SMILES: O=C(O)CCN1CCC(Nc2cc(=O)[nH]c3ccc(C(c4ccc(Cl)cc4)c4ccc(Cl)cc4)cc23)CC1]<br>3-[4-({6-[Bis(4-chlorophenyl)methyl]-2-oxo-1,2-dihydroquinolin-4-yl}amino)piperidin-1-yl]propanoic acid | 4 | (ES, m/z): [M + H]+ 550 |
| 116 | 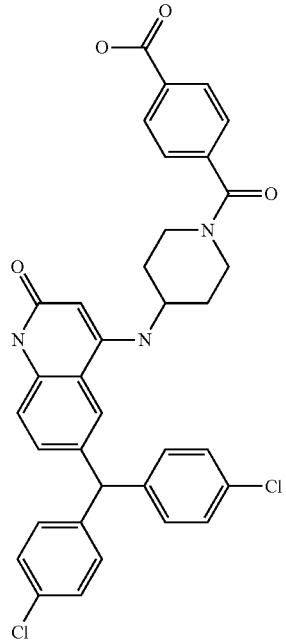 [SMILES: O=C(O)c1ccc(C(=O)N2CCC(Nc3cc(=O)[nH]c4ccc(C(c5ccc(Cl)cc5)c5ccc(Cl)cc5)cc34)CC2)cc1]<br>4-{[4-({6-[Bis(4-chlorophenyl)methyl]-2-oxo-1,2-dihydroquinolin-4-yl}amino)piperidin-1-yl]carbonyl}benzoic acid | 24 | (ES, m/z): [M + H]+ 626 |

| ID No. | Compound IUPAC name | Prepared as in Example # | Analytical Data |
|---|---|---|---|
| 117 | 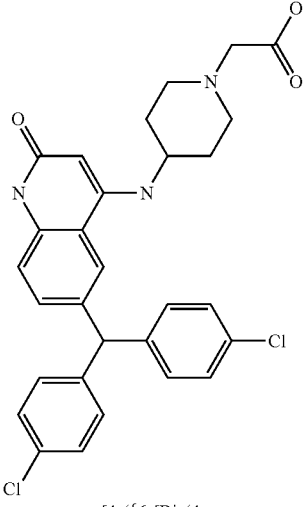 [4-({6-[Bis(4-chlorophenyl)methyl]-2-oxo-1,2-dihydroquinolin-4-yl}amino)piperidin-1-yl]acetic acid | 24 | (ES, m/z): [M + H]+ 536 |
| 531 | 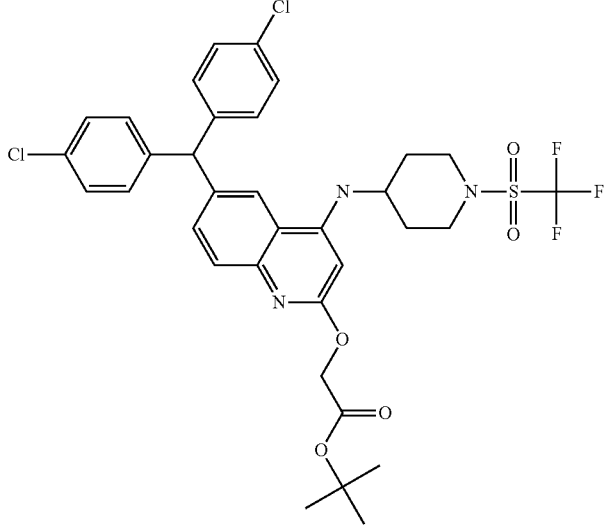 [SMILES: CC(C)(C)OC(=O)COc1cc(NC2CCN(S(=O)(=O)C(F)(F)F)CC2)c2cc(C(c3ccc(Cl)cc3)c3ccc(Cl)cc3)ccc2n1] tert-Butyl ({6-[bis(4-chlorophenyl)methyl]-4-({1-[(trifluoromethyl)sulfonyl]piperidin-4-yl}amino)quinolin-2-yl}oxy)acetate | 50 | (ES, m/z): [M + H]+ 724 |

TABLE EX-continued

Representative Compounds of the Present Invention

| ID No. | Compound IUPAC name | Prepared as in Example # | Analytical Data |
|---|---|---|---|
| 532 | ({6-[Bis(4-chlorophenyl)methyl]-4-({1-[(trifluoromethyl)sulfonyl]piperidin-4-yl}amino)quinolin-2-yl}oxy)acetic acid | 27 | (ES, m/z): [M + H]+ 668 |
| 533 | 2-({6-[Bis(4-chlorophenyl)methyl]-4-({1-[(trifluoromethyl)sulfonyl]piperidin-4-yl}amino)quinolin-2-yl}oxy)-N-methylacetamide | 28 | (ES, m/z): [M + H]+ 681; 1H NMR (CHLOROFORM-d) d: 7.68 (d, J = 8.1 Hz, 1H), 7.27-7.33 (m, 5H), 7.03 (d, J = 8.6 Hz, 4H), 6.50 (br. s., 1H), 5.96 (s, 1H), 5.64 (s, 1H), 4.96 (s, 2H), 4.70 (d, J = 7.1 Hz, 1H), 4.01 (m, 2H), 3.65 (m, 1H), 3.28 (m, 2H), 2.87 (d, J = 4.5 Hz, 3H), 2.27 (m, 2H), 1.59-1.76 (m, 2H) |

| ID No. | Compound IUPAC name | Prepared as in Example # | Analytical Data |
|---|---|---|---|
| 534 | 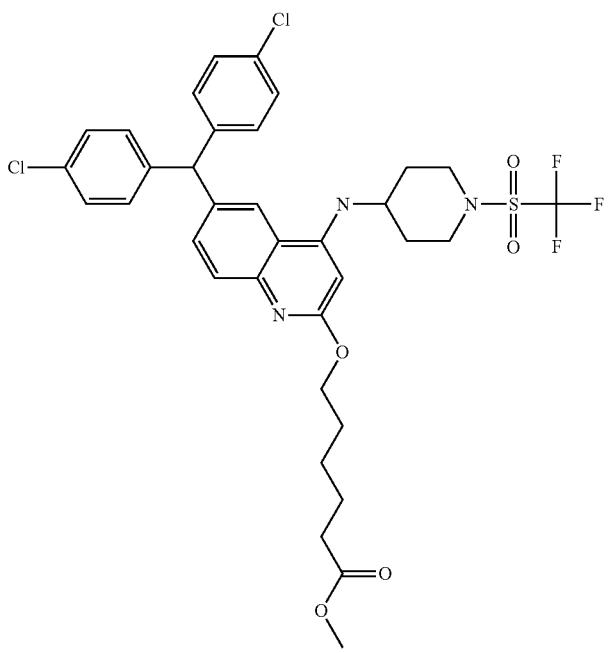 [SMILES: COC(=O)CCCCCOc1cc(NC2CCN(S(=O)(=O)C(F)(F)F)CC2)c2cc(C(c3ccc(Cl)cc3)c3ccc(Cl)cc3)ccc2n1]<br>Methyl 6-({6-[bis(4-chlorophenyl)methyl]-4-({1-[(trifluoromethyl)sulfonyl]piperidin-4-yl}amino)quinolin-2-yl}oxy)hexanoate | 50 | (ES, m/z): [M + H]+ 738, 740 |
| 535 | 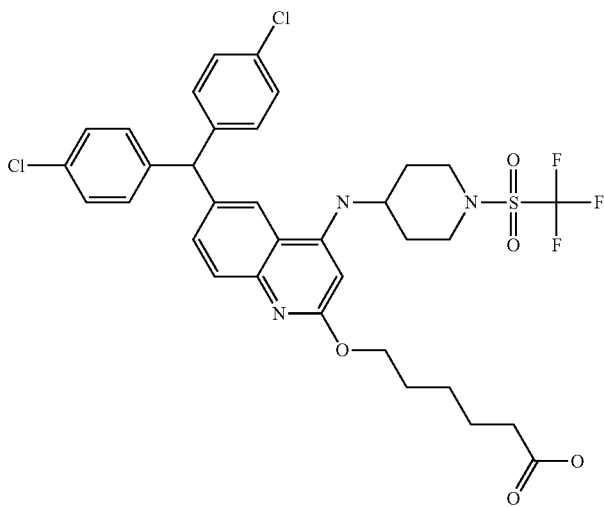 [SMILES: O=C(O)CCCCCOc1cc(NC2CCN(S(=O)(=O)C(F)(F)F)CC2)c2cc(C(c3ccc(Cl)cc3)c3ccc(Cl)cc3)ccc2n1]<br>6-({6-[Bis(4-chlorophenyl)methyl]-4-({1-[(trifluoromethyl)sulfonyl]piperidin-4-yl}amino)quinolin-2-yl}oxy)hexanoic acid | 48 | (ES, m/z): [M + H]+ 724, 726 |

TABLE EX-continued
Representative Compounds of the Present Invention
| ID No. | Compound IUPAC name | Prepared as in Example # | Analytical Data |
|---|---|---|---|
| 120 | 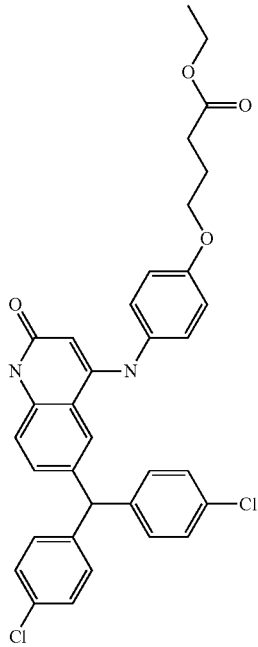 [SMILES: CCOC(=O)CCCOc1ccc(Nc2cc(=O)[nH]c3ccc(C(c4ccc(Cl)cc4)c4ccc(Cl)cc4)cc23)cc1] 4-[4-({6-[bis(4-chlorophenyl)methyl]-2-oxo-1,2-dihydroquinolin-4-yl}amino)phenoxy]butanoate | 26 | (ES, m/z): [M + H]+ 601 |
| 121 | 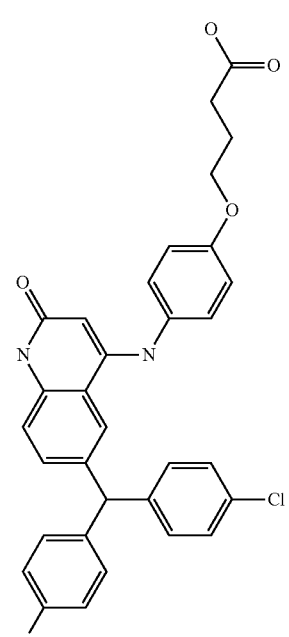 4-[4-({6-[Bis(4-chlorophenyl)methyl]-2-oxo-1,2-dihydroquinolin-4-yl}amino)phenoxy]butanoic acid | 24 | (ES, m/z): [M + H]+ 573 |

TABLE EX-continued

Representative Compounds of the Present Invention

| ID No. | Compound IUPAC name | Prepared as in Example # | Analytical Data |
|---|---|---|---|
| 123 | 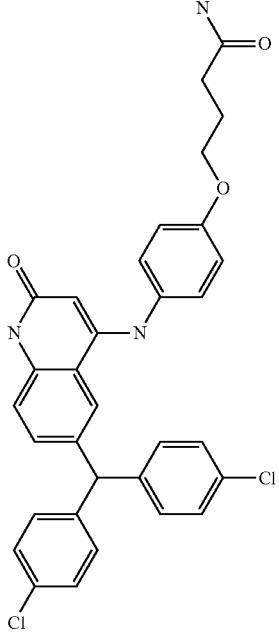 [SMILES: NC(=O)CCCOc1ccc(Nc2cc(=O)[nH]c3ccc(C(c4ccc(Cl)cc4)c4ccc(Cl)cc4)cc23)cc1]<br>4-[4-({6-[Bis(4-chlorophenyl)methyl]-2-oxo-1,2-dihydroquinolin-4-yl}amino)phenoxy]butanamide | 28 | (ES, m/z): [M + H]$^+$ 572 |
| 124 | 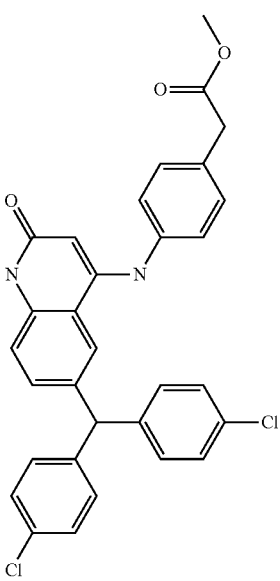 [SMILES: COC(=O)Cc1ccc(Nc2cc(=O)[nH]c3ccc(C(c4ccc(Cl)cc4)c4ccc(Cl)cc4)cc23)cc1]<br>Methyl [4-({6-[bis(4-chlorophenyl)methyl]-2-oxo-1,2-dihydroquinolin-4-yl}amino)phenyl]acetate | 3 | (ES, m/z): [M + H] 543; 1H-NMR: (300 MHz, DMSO, ppm) δ: 11.015 (s, 1H), 8.535 (s, 1H), 7.968 (s, 1H), 7.390 (d, J = 8.4 Hz, 2H), 7.311-7.152 (m, 12H), 5.658 (s, 1H), 5.614 (s, 1H), 3.686 (s, 2H), 3.625 (s, 3H) |

TABLE EX-continued
Representative Compounds of the Present Invention
| ID No. | Compound IUPAC name | Prepared as in Example # | Analytical Data |
|---|---|---|---|
| 125 | 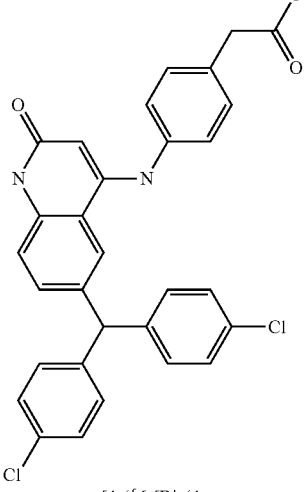<br>[4-({6-[Bis(4-chlorophenyl)methyl]-2-oxo-1,2-dihydroquinolin-4-yl}amino)phenyl]acetic acid | 24 | (ES, m/z): [M + H] + 529 |
| 126 | 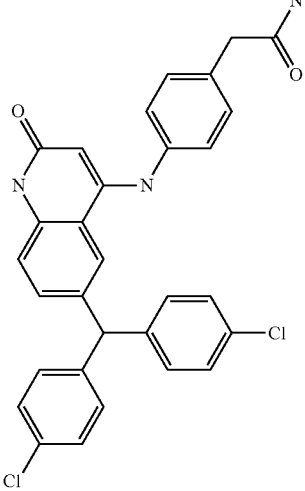<br>2-[4-({6-[Bis(4-chlorophenyl)methyl]-2-oxo-1,2-dihydroquinolin-4-yl}amino)phenyl]acetamide | 25 | (ES, m/z): [M + H] + 528 |

TABLE EX-continued
Representative Compounds of the Present Invention
| ID No. | Compound IUPAC name | Prepared as in Example # | Analytical Data |
|---|---|---|---|
| 127 | 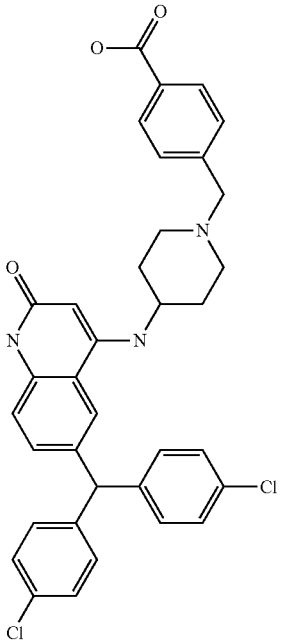 [SMILES: O=C(O)c1ccc(CN2CCC(Nc3cc(=O)[nH]c4ccc(C(c5ccc(Cl)cc5)c5ccc(Cl)cc5)cc34)CC2)cc1]4-{[4-({6-[Bis(4-chlorophenyl)methyl]-2-oxo-1,2-dihydroquinolin-4-yl}amino)piperidin-1-yl]methyl}benzoic acid | 30 | (ES, m/z): [M + H]+ 612 |
| 128 | 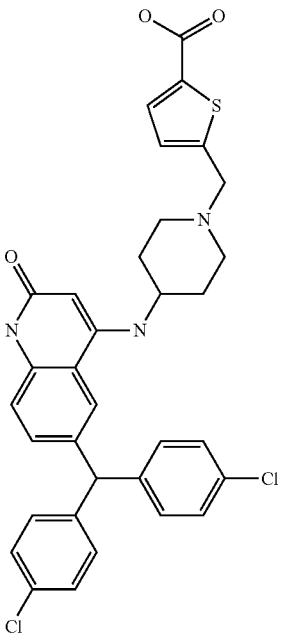 [SMILES: O=C(O)c1ccc(CN2CCC(Nc3cc(=O)[nH]c4ccc(C(c5ccc(Cl)cc5)c5ccc(Cl)cc5)cc34)CC2)s1]5-{[4-({6-[Bis(4-chlorophenyl)methyl]-2-oxo-1,2-dihydroquinolin-4-yl}amino)piperidin-1-yl]methyl}thiophene-2-carboxylic acid | 30 | (ES, m/z): [M + H] + 618 |

TABLE EX-continued

Representative Compounds of the Present Invention

| ID No. | Compound IUPAC name | Prepared as in Example # | Analytical Data |
|---|---|---|---|
| 131 | 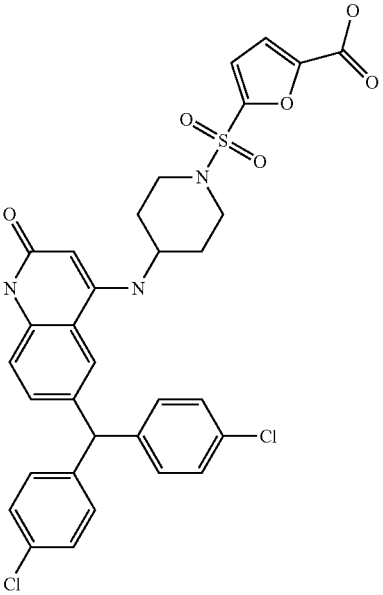 [SMILES: O=C(O)c1ccc(S(=O)(=O)N2CCC(Nc3cc(=O)[nH]c4ccc(C(c5ccc(Cl)cc5)c5ccc(Cl)cc5)cc34)CC2)o1]<br>5-{[4-({6-[Bis(4-chlorophenyl)methyl]-2-oxo-1,2-dihydroquinolin-4-yl}amino)piperidin-1-yl]sulfonyl}furan-2-carboxylic acid | 31 | (ES, m/z): [M + H] + 652 |
| 132 | 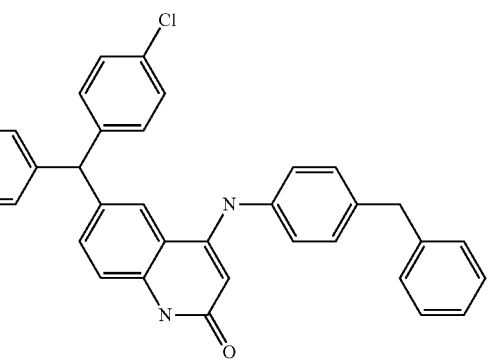<br>4-[(4-Benzylphenyl)amino]-6-[bis(4-chlorophenyl)methyl]quinolin-2(1H)-one | 3 | (ES, m/z): [M + H] + 562 |
| 133 | 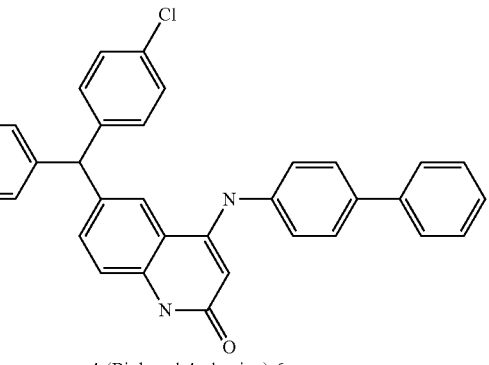<br>4-(Biphenyl-4-ylamino)-6-[bis(4- | 3 | (ES, m/z): [M + H] + 547 |

TABLE EX-continued

Representative Compounds of the Present Invention

| ID No. | Compound IUPAC name | Prepared as in Example # | Analytical Data |
|---|---|---|---|
| | chlorophenyl)methyl]quinolin-2(1H)-one | | |
| 134 | 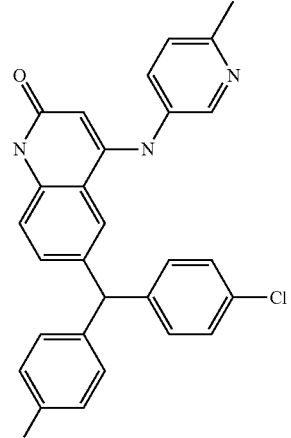<br>6-[Bis(4-chlorophenyl)methyl]-4-[(6-methylpyridin-3-yl)amino]quinolin-2(1H)-one | 3 | (ES, m/z): [M + H] + 486 |
| | 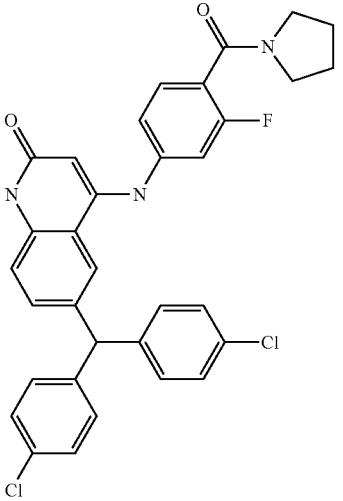 [SMILES: O=C(c1ccc(Nc2cc(=O)[nH]c3ccc(C(c4ccc(Cl)cc4)c4ccc(Cl)cc4)cc23)cc1F)N1CCCC1]<br>6-[Bis(4-chlorophenyl)methyl]-4-{[3-fluoro-4-(pyrrolidin-1-ylcarbonyl)phenyl]amino}quinolin-2(1H)-one | 3 | (ES, m/z): [M + H] + 586 |

BIOLOGICAL ASSAYS

CB$_1$ and CB$_2$ receptors are G$_i$-coupled GPCR. Activation of CB$_1$ and CB$_2$ receptors results in a decrease in cAMP production. An inverse agonist of the CB$_1$ or CB$_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+ TBP-NHS Cryptate (supplied as part of the assay kit). The specific signal (i.e. energy transfer) is inversely proportional to the concentration of cAMP in the standard or sample.

Biological Example 1

CB-1 and CB-2 In Vitro Assay

Preparation of Cells

Human CB$_1$R (Cannabinoid receptor 1) was stably transfected in HEK-293 cells (DiscoveRx, cat: 93-0200C1).

Human CB$_2$R (Cannabinoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/ml Hygromycin B (Invitrogen Cat#10687-010), 600 µg/mL G418 (Invitrogen Cat#10131-035), and 1× Penn/Strep (Invitrogen 15140-122). After cell expansion, aliquots were cryo-stored in media containing 5% DMSO (Pierce Cat#20684).

Plating Cells from Cryostore

One day prior to experiments media was warmed to 37° C. and the cryo-stored cells were thawed in a 37° C. water bath. The cells were then added to media (10× volume) and the mixture was centrifuged at 1000 RPM for 5 min. The supernate was removed and the cells were re-suspended in media. A sample of the cell suspension was evaluated on a Cedex XS automated cell counter (Innovatis Systems) to determine viable cells/ml. Additional media was added to the cells to achieve a final cell density of 4E5 cells/mL. The cells were then plated into 384 well PDL white solid bottom plates (Greiner, Cat#781945) at 20 µL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% CO$_2$, 95% humidity) overnight.

Preparation of Compound Plates

DMSO was added to all wells of 384 well V bottom polystyrene plate (Greiner, Cat#781280) except to columns 1 and 13, rows O and P and wells M13-M23 and N13-N23. Test compounds (60 µL, 10 mM) were added to Column 1 and 13 (A1 through N1 and A13 through L13). Test compounds were serially diluted 1/3 by transferring and mixing 20 µl sample with 40 µL DMSO. This process resulted in a plate of 26 compounds, 11 doses per compound, 10 mM to 0.5 µM.

Preparation of Control Plate

DMSO (40 µL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 µL, 10 mM) was added to O1; and 1-(2,4-dichlorophenyl)-7-[(4-fluorophenyl)methylene]-4,5,6,7-tetrahydro-N-1-piperidinyl-1H-indazole-3-carboxamide (60 µL, 10 mM) was added to N13. The control was serially diluted 1/3 by transferring and mixing 20 µl sample with 40 µL DMSO. This process resulted 11 doses per control, 10 mM to 0.5 µM.

cAMP Assay Protocol

Cells plated the day prior to the assay in clear bottom plates were viewed on an inverse microscope to ensure confluency in the range of 60-75%.

The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma I5879) in Buffer 1; (c) 1 µM cAMP Standard (50 µM stock, Perkin Elmer Cat#AD0262) diluted in Buffer 2 and serially diluted in Buffer 2, 12 doses @½ dilutions resulting in a dose range of 1 µM to 0.5 nM; (d) d2 labelled cAMP (CisBio HTRF Detection Kit Cat #62AM4PEB reconstituted with 6 ml dH$_2$0) diluted 1/20 with lysis buffer (CisBio HTRF Detection Kit Cat #62AM4PEB); (e) anti-cAMP (CisBio HTRF Detection Kit Cat #62AM4PEB reconstituted with 5 ml dH$_2$0) diluted 1/20 with lysis buffer (CisBio HTRF Detection Kit Cat #62AM4PEB); and (f) Forskolin (Sigma Cat#F6886, 10 mM in DMSO) diluted first in DMSO to 1 mM and then to 1.5 µM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 µl per well). Media as "dumped" from the cell plate and 30 µL Buffer 1 was added to each well using a Multidrop. The content of the cell plate was again "dumped" and 10 µL Buffer 2 was added to each well using a Flexdrop. 12.5 nL test compound dilutions or control compound dilutions (10 mM to 0.5 µM) were added to the cell plate using an ECHO 555 (Labcyte). The cell plate was mixed (Speed 6, Lab-Line Instruments Titer Plate Shaker) and centrifuged (1000 RPMs, 1 min). Using the Flexdrop, 2 µl additions were made into the cell plate: Buffer 2 was added to Column 24; and, 1.5 µM Forskolin was added to columns 1 through 23. Final volume of the cell plate was 12 µl with 250 nM Forskolin in all wells except column 12, and serial dilutions of test compound or control ranging from 10 µM to 0.5 nM. The cell plate was again mixed (speed 6) and centrifuged (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 µL d2 labelled cAMP and 6 µL of Anti-cAMP were added to all wells of the cell plate using a BioMek FX (Beckman Coulter). The cell plate was again mixed (speed 6) and centrifuged (1000 RPMs, 1 min) and was incubated for 60 minutes in the dark at room Temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence×10,000 (Normalized signal (NS)). Amount of cAMP in nM was calculated for each well (based on NS) from a cAMP standard curve located on each plate (at P1-12 and P13-24). EC$_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of formula (I), compounds of formula (II), compounds of formula (III) and compounds of formula (IV) of the present invention were tested for activity against the CB-1 and CB-2 receptors, according to assay protocol as outlined in Biological Example 1, with EC$_{50}$ results (in micromolar) as listed in Tables BIO-1, below. Where a compound was tested more than once, the result presented below represents a mean of the individual measurements.

TABLE BIO-1

| CB-1 & CB-2 Biological Activity | | |
|---|---|---|
| ID No. | CB-1 EC$_{50}$ (µM) | CB-2 EC$_{50}$ (µM) |
| 8 | 0.876 | >10 |
| 9 | 0.169 | >10 |

TABLE BIO-1-continued

CB-1 & CB-2 Biological Activity

| ID No. | CB-1 EC$_{50}$ (μM) | CB-2 EC$_{50}$ (μM) |
|---|---|---|
| 11 | 0.121 | >10 |
| 13 | 0.403 | >10 |
| 14 | 0.254 | >10 |
| 15 | 0.702 | 0.66 |
| 16 | 0.083 | 0.09 |
| 17 | 0.827 | 0.08 |
| 18 | 0.875 | >10 |
| 19 | 0.059 | >10 |
| 21 | 4.137 | >10 |
| 25 | 0.816 | >10 |
| 26 | 0.333 | >10 |
| 27 | 0.443 | >10 |
| 28 | 0.397 | >10 |
| 29 | 0.759 | >10 |
| 30 | 1.375 | >10 |
| 31 | 2.280 | >10 |
| 32 | 3.200 | >10 |
| 33 | 1.213 | >10 |
| 34 | 1.465 | >10 |
| 35 | 0.322 | >10 |
| 37 | 0.019 | >10 |
| 38 | 0.497 | >10 |
| 39 | 0.604 | >10 |
| 40 | 0.204 | >10 |
| 41 | 0.015 | 8.15 |
| 42 | 2.330 | |
| 43 | >10 | |
| 44 | 0.008 | 5.23 |
| 45 | 1.172 | >10 |
| 46 | 0.657 | >10 |
| 47 | 0.075 | 4.61 |
| 48 | 0.230 | >3.29989 |
| 49 | 0.024 | >10 |
| 50 | 0.530 | 9.70 |
| 51 | 0.029 | 8.28 |
| 52 | 0.023 | 7.10 |
| 53 | 0.020 | >13.9991 |
| 54 | 0.008 | 1.83 |
| 55 | 0.010 | 0.84 |
| 56 | 0.022 | >10 |
| 57 | 0.011 | 4.10 |
| 58 | 0.045 | >10 |
| 59 | 0.007 | >10 |
| 60 | 0.006 | >10 |
| 61 | 0.007 | 1.81 |
| 62 | 0.029 | 3.23 |
| 63 | 0.094 | 2.66 |
| 64 | 0.028 | 4.50 |
| 65 | 0.064 | 4.30 |
| 66 | 0.022 | 7.69 |
| 67 | 0.015 | >10 |
| 68 | 0.006 | >10 |
| 69 | 0.010 | 4.20 |
| 70 | 0.007 | >10 |
| 71 | 0.007 | >10 |
| 72 | 0.011 | 6.60 |
| 73 | 0.052 | 5.40 |
| 74 | 0.036 | >10 |
| 75 | 0.025 | >10 |
| 76 | 0.010 | >10 |
| 77 | 0.003 | >10 |
| 78 | 0.168 | >10 |
| 79 | 0.054 | 6.75 |
| 80 | 0.014 | >10 |
| 81 | 0.015 | >10 |
| 82 | 0.063 | 3.20 |
| 83 | 0.011 | >10 |
| 84 | 0.269 | 8.96 |
| 85 | 0.070 | >10 |
| 86 | >10 | >10 |
| 87 | 3.147 | >10 |
| 88 | 0.111 | 3.70 |
| 89 | 0.014 | 9.90 |
| 90 | 0.967 | >10 |
| 92 | 0.010 | 0.05 |
| 93 | 0.015 | >10 |
| 94 | 0.055 | >10 |
| 95 | 0.013 | 3.65 |
| 96 | 0.220 | >10 |
| 97 | 0.031 | 9.90 |
| 98 | 0.242 | >10 |
| 99 | >10 | >10 |
| 100 | 0.006 | 0.20 |
| 101 | 0.015 | 0.91 |
| 102 | 0.017 | >10 |
| 103 | 0.005 | >10 |
| 104 | 1.124 | >10 |
| 105 | 0.095 | >10 |
| 106 | 1.547 | 6.50 |
| 107 | 0.052 | 0.67 |
| 108 | 0.310 | 0.46 |
| 109 | 5.122 | >10 |
| 110 | 0.228 | >10 |
| 111 | 0.099 | >10 |
| 112 | 0.302 | >10 |
| 113 | 0.025 | >10 |
| 114 | 0.103 | >10 |
| 115 | >10 | >10 |
| 116 | 0.438 | >10 |
| 117 | 9.701 | >10 |
| 118 | >10 | >10 |
| 119 | 0.128 | >10 |
| 120 | 0.068 | >10 |
| 121 | 1.012 | >10 |
| 122 | 0.159 | 0.24 |
| 123 | 0.219 | >10 |
| 124 | 0.027 | >10 |
| 125 | 2.478 | >10 |
| 126 | 0.079 | 8.10 |
| 127 | 0.876 | >10 |
| 128 | 0.293 | 9.70 |
| 129 | 0.157 | >10 |
| 130 | 0.113 | 0.69 |
| 131 | 0.251 | 3.93 |
| 132 | 0.015 | >10 |
| 133 | 0.073 | >10 |
| 134 | 0.300 | 6.70 |
| 135 | 1.100 | 6.81 |
| 136 | 0.122 | >10 |
| 137 | 0.290 | >10 |
| 138 | 0.227 | 0.75 |
| 139 | >10 | >10 |
| 140 | 0.013 | 0.06 |
| 141 | 0.625 | >10 |
| 501 | >10 | >10 |
| 502 | 0.580 | >10 |
| 503 | 0.191 | >10 |
| 504 | 0.342 | >10 |
| 505 | 0.326 | >10 |
| 506 | >10 | >10 |
| 507 | 5.482 | >10 |
| 508 | 0.375 | >10 |
| 509 | 0.140 | >10 |
| 511 | 0.136 | >10 |
| 512 | >10 | >10 |
| 513 | 1.505 | >10 |
| 514 | 0.426 | >10 |
| 515 | 0.366 | >10 |
| 516 | 3.270 | 0.20 |
| 517 | 0.884 | 0.34 |
| 518 | >10 | 0.54 |
| 519 | >10 | 0.04 |
| 520 | 0.169 | >10 |
| 521 | 0.213 | >10 |
| 522 | >10 | >10 |
| 524 | 0.012 | 0.18 |
| 525 | >13.9991 | >13.9991 |
| 529 | >10 | >10 |
| 530 | 0.023 | >10 |
| 531 | >10 | >10 |
| 532 | 1.284 | 6.70 |
| 533 | 0.038 | >10 |

TABLE BIO-1-continued

CB-1 & CB-2 Biological Activity

| ID No. | CB-1 EC$_{50}$ (µM) | CB-2 EC$_{50}$ (µM) |
|---|---|---|
| 534 | 2.200 | >10 |
| 535 | 0.092 | 0.06 |
| 536 | 0.100 | 0.204 |
| 537 | 0.108 | 2.38 |
| 538 | 0.051 | 8.63 |
| 539 | 0.096 | >20.9991 |
| 540 | 0.081 | 7.10 |
| 541 | 0.339 | >10 |
| 542 | 0.144 | >10 |
| 543 | 0.102 | >10 |
| 544 | 0.126 | 3.40 |
| 545 | 4.9 | >10 |
| 546 | 0.121 | 4.80 |
| 547 | 0.036 | >41.9952 |
| 548 | 0.058 | >41.9952 |
| 549 | 0.036 | 3.80 |
| 550 | 0.031 | 0.115 |

Biological Example 2

CB-1 & CB-2 Receptor Binding Assay

Experimental Procedure CB-1 Membrane Binding:

Into Greiner V bottom polypropylene plates, hCB1-CHO-K1 membranes (2 µg/well final concentration) in assay buffer (50 mM Tris-HCl pH 7.4, 5 mM MgCl$_2$ and 0.5 mg/ml (0.05%) Ultra fatty acid free BSA) were dispensed. Membranes were purchased from Perkin Elmer. Test compounds were then added to each well and then [$^3$H] CP 55, 940 (0.4 nM final well concentration) in assay buffer (50 mM Tris-HCl pH 7.4, 5 mM MgCl$_2$ and 0.5 mg/ml (0.05%) Ultra fatty acid free BSA) was added. Samples were mixed and incubated for 90 min at 30° C. in the Greiner V Bottom Polypropylene plate. After incubation, assay reagents were transferred to a blocked 384 well polypropylene filter plates. The binding reaction was stopped by filtration and washed seven times with ice cold rinse buffer. Filter plates were then dried overnight at room temperature. The next day, plate bottoms were sealed with plate tape and 15 µl MicroScint 20 was added to each well. Plates were incubated for 2 h and radioactivity was measured by Topcount.

Experimental Procedure CB-2 Membrane Binding:

Into Greiner V bottom polypropylene plates, hCB2-HEK293 membranes (2 µg/well final concentration) in assay buffer (50 mM Tris-HCl pH 7.4, 5 mM MgCl$_2$ and 0.5 mg/ml (0.05%) Ultra fatty acid free BSA) were dispensed. Membranes were prepared as described in FELDER, C. C., et al., *Molecular Pharmacology*, 1992, pp 838-845, Vol. 42. Test compounds were then added to each well and then [$^3$H] CP 55, 940 (0.5 nM final well concentration) in assay buffer (50 mM Tris-HCl pH 7.4, 5 mM MgCl$_2$ and 0.5 mg/ml (0.05%) Ultra fatty acid free BSA) was added. Samples were mixed and incubated for 90 min at 30° C. in the Greiner V Bottom Polypropylene plate. After incubation, assay reagents were transferred to a blocked 384 well polypropylene filter plates. The binding reaction was stopped by filtration and washed nine times with ice cold rinse buffer. Filter plates were then dried overnight at room temperature. The next day, plate bottoms were sealed with plate tape and 15 ul MicroScint was added to each well. Plates were incubated for 2 h and radioactivity was measured by Topcount.

Total Binding:

Total Binding levels were achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):

Non-Specific Binding (NSB) levels were achieved by combining membrane, 10 µM final concentration WIN-55, 212 (also known as (R)-(+)-[2,3-Dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H] CP-55,940 (also known as 5-(1,1-dimethylheptyl)-2-[(1R,2R,5R)-5-hydroxy-2-(3-hydroxypropyl)cyclohexyl]-phenol).

Data Analysis:

Top Count raw data files were used for data analysis as follows:

Non-specific binding (NSB=10 µM WIN-55,212+Membrane+[$^3$H] CP-55,940) was used as the negative control, while the Total Binding (TB=DMSO+Membrane+[$^3$H] CP-55,940) was used as the positive control.

Excel data file reports were generated by the PE TopCount and imported into Excel for calculations or were imported into a macro driven Excel template maintained by Lead Generation—Biology.

IC$_{50}$ data was calculated using raw CPM values. Curves were fitted individually from singlet 11 point dosing curves+ 1% DMSO Control. IC$_{50}$ values were fit appropriately and calculated using the following equation:

$$v = V_{min} + \frac{V_0 - V_{min}}{1 + \left(\frac{[I]}{IC_{50}}\right)^h}$$

$V_{min}$, CPM at maximum inhibition; $V_o$, CPM at zero inhibition; IC$_{50}$, inhibitor concentration at 50% inhibition; h, Hill coefficient.

Maximal compound % inhibition of control treated wells was also noted since some compounds exhibited values suitable for calculating IC$_{50}$'s.

% Inhibition of Total Binding=(1−(CPM Compound Treated Well/CPM Control Treated Well))*100

Representative compounds of formula (I), compounds of formula (II), compounds of formula (III) and compounds of formula (IV) of the present invention were tested for activity against the CB-1 and CB-2 receptors, according to assay protocol as outlined in Biological Example 2, with IC$_{50}$ results (in micromolar) as listed in Tables BIO-2, below. Where a compound was tested more than once, the result presented below represents a mean of the individual measurements.

TABLE BIO-2

CB-1 & CB-2 Binding Activity

| ID No. | CB-1 IC$_{50}$ (µM) | CB-2 IC$_{50}$ (µM) |
|---|---|---|
| 8 | >2.5 | |
| 9 | >2.5 | |
| 11 | 0.3321 | |
| 16 | 0.0220 | >5 |
| 19 | 0.0151 | >5 |
| 25 | 0.0346 | >5 |
| 41 | 0.0044 | >5 |
| 44 | 0.0012 | 0.053 |

TABLE BIO-2-continued

CB-1 & CB-2 Binding Activity

| ID No. | CB-1 IC$_{50}$ (μM) | CB-2 IC$_{50}$ (μM) |
|---|---|---|
| 501 | 0.0521 | |
| 502 | 0.0358 | |
| 503 | 0.0041 | |
| 504 | 1.866 | |
| 506 | 0.1008 | |
| 507 | 0.2234 | |
| 508 | 0.0973 | |
| 511 | 0.0551 | >5 |

In Vivo Biological Assays

Animals, Diets and Test Compound:

Male 14-20-week old diet-induced obese mice were ordered from Taconic. Mice were started on a 60% fat diet (D12492, Research Diets, New Brunswick, N.J.) at 6 weeks of age. Mice were single-housed.

Male Sprague Dawley rats were ordered from Charles River (225-250 gm upon arrival). They were fed standard chow diet (Purina 5001) and housed 2 per cage. Male C57bl/6j mice were ordered from Charles River at 22-25 g and housed 3 per cage. They were fed standard chow (Purina 5001). All animals were housed in a temperature-controlled room with 12-hour light/dark cycle. Animals were given food and water ad libitum, except as noted.

Test compounds were formulated in 10% PEG400 and 10% solutol. Test compounds were administered by oral gavage (5 ml kg$^{-1}$).

Biological Example 3

Mouse Fast PK/BBB

Male C57bl/6j mice were dosed with test compounds at 30 mg/kg. Plasma was collected via retro-orbital bleeding at 1 hr and 4 hrs after dosing. Whole brain without cerebellum was collected at 4 hrs after dosing. Wet brain weight was recorded before freezing. Brains were homogenized in saline and sent for analysis for determination of concentration of test compound.

Table BIO-3 below present results for representative compounds of the present invention, tested according to the procedure as described above. Each compound was tested in three animals (N=3) and administered PA at 20 mg/kg

TABLE BIO-3

Mouse Fast PK/BBB Results

| ID No. | Time | PLASMA Mean Conc. (ng/mL) ± Std. Dev (ng/mL) | BRAIN Mean Conc. (ng/mL) ± Std. Dev (ng/mL) |
|---|---|---|---|
| 44 | 1 hr | 1048 ± 122 | 7.62 ± 2.28 |
|    | 4 hr | 1182 ± 147.6 | 11.75 ± 8.99 |
| 41 | 1 hr | 714 ± 188 | 7.43 ± NA |
|    | 4 hr | 291 ± 90.5 | 0 |
| 59 | 1 hr | 2317 ± 1022 | BLOQ ± NA |
|    | 4 hr | 1610 ± 563 | 59.7 ± 9.55 |

BLOQ = below level of quantitation;
NA = Not applicable

Biological Example BIO-4

Chronic DIO Mouse

The test compound was formulated in 10% PEG400 and 10% solutol. DIO mice received vehicle, test compound (@1, 3 and 10 mg/kg) daily for 26 days. At the end of the experiment, the mice were euthanized and blood and tissues were collected.

Body weight and food weight (food intake) were monitored daily for days 1-5 and twice weekly thereafter. Fed blood glucose was measured weekly.

An insulin tolerance test (0.5 U/kg Humulin, ip) was performed on day 19 after a 4 hour food removal. Blood glucose was measured at 0, 15, 30, 60 and 120 minutes after insulin. After an overnight fast, an oral glucose tolerance test (2 g/kg glucose) was performed on day 23. Blood glucose was measured at 0, 30, 60 and 120 minutes after glucose challenge.

Blood glucose was measured from the tail vein with a Lifescan glucometer. Plasma insulin was measured with an ELISA or HTRF kit (Cisbio). Plasma parameters were measured with an Olympus clinical chemistry analyzer.

Compound #44 was tested according to the procedure as described above, with results as listed in Table BIO-4A through Table BIO4-G, below.

TABLE BIO-4A

Mean Daily Food Intake (in Grams (Std Err))

|  | Vehicle | 1 mg/kg | 3 mg/kg | 10 mg/kg |
|---|---|---|---|---|
| Day 2 | 2.64 (0.13) | 2.84 (0.17) | 2.71 (0.13) | 2.24 (0.10) |
| Day 3 | 2.94 (0.12) | 3.00 (0.09) | 2.92 (0.13) | 2.29 (0.16) |
| Day 4 | 2.50 (0.14) | 2.76 (0.17) | 2.44 (0.24) | 1.70 (0.08) |
| Day 5 | 2.57 (0.17) | 2.88 (0.12) | 2.26 (0.20) | 1.58 (0.11) |
| Day 8 | 2.89 (0.07) | 2.50 (0.09) | 2.30 (0.11) | 1.80 (0.12) |
| Day 10 | 2.75 (0.10) | 2.37 (0.07) | 2.14 (0.15) | 2.02 (0.13) |
| Day 11 | 2.59 (0.10) | 2.28 (0.15) | 1.95 (0.11) | 1.94 (0.11) |

TABLE BIO-4B

Mean Body Weight (in Grams (Std Err))

|  | Vehicle | 1 mg/kg | 3 mg/kg | 10 mg/kg |
|---|---|---|---|---|
| Day 1 | 43.22 (0.45) | 43.32 (0.45) | 43.19 (0.39) | 43.26 (0.40) |
| Day 2 | 42.94 (0.42) | 43.28 (0.45) | 42.86 (0.47) | 42.39 (0.36) |
| Day 3 | 43.03 (0.39) | 43.28 (0.42) | 42.71 (0.56) | 41.61 (0.41) |
| Day 4 | 42.66 (0.68) | 43.06 (0.44) | 42.20 (0.65) | 40.76 (0.37) |
| Day 5 | 42.68 (0.66) | 43.21 (0.50) | 41.95 (0.70) | 40.17 (0.39) |
| Day 8 | 42.45 (0.91) | 42.62 (0.48) | 41.06 (0.76) | 38.16 (0.48) |
| Day 10 | 43.82 (0.35) | 42.38 (0.51) | 40.50 (0.74) | 37.47 (0.56) |
| Day 11 | 43.62 (0.34) | 42.07 (0.63) | 40.15 (0.74) | 36.67 (0.55) |

TABLE BIO-4C

Insulin Tolerance Test
Mean Blood Glucose (in mg/dL (Std Err))

|  | Vehicle | 1 mg/kg | 3 mg/kg | 10 mg/kg |
|---|---|---|---|---|
| 0 min | 195.1 (5.7) | 194.0 (6.1) | 189.4 (7.3) | 163.5 (5.9) |
| 15 min | 180.0 (9.4) | 196.1 (18.6) | 178.8 (12.5) | 138.4 (20.0) |
| 30 min | 172.2 (8.4) | 136.7 (10.4) | 121.4 (13.7) | 96.2 (11.0) |
| 60 min | 171.7 (6.9) | 145.1 (11.5) | 119.7 (9.6) | 99.7 (9.7) |

TABLE BIO-4C-continued

Insulin Tolerance Test
Mean Blood Glucose (in mg/dL (Std Err))

| | Vehicle | 1 mg/kg | 3 mg/kg | 10 mg/kg |
|---|---|---|---|---|
| 120 min | 178.5 (11.3) | 151.4 (7.8) | 155.3 (9.5) | 143.5 (8.3) |
| AUC (mg/dL * min) | 21116.3 (181.2) | 18543.8 (1120.6) | 16879.5 (1166.6) | 14258.3 (1152.4) |

TABLE BIO-4D

Intraperitoneal Glucose Tolerance Test
Mean Blood Glucose (in mg/dL (Std Err))

| | Vehicle | 1 mg/kg | 3 mg/kg | 10 mg/kg |
|---|---|---|---|---|
| 0 min | 164.0 (4.3) | 158.1 (6.9) | 161.8 (5.0) | 141.6 (6.5) |
| 30 min | 334.0 (18.9) | 334.6 (14.5) | 352.0 (22.6) | 319.1 (26.9) |
| 60 min | 273.9 (29.1) | 264.8 (19.7) | 264.6 (25.6) | 225.1 (20.3) |
| 120 min | 203.7 (26.0) | 173.4 (13.5) | 169.6 (9.2) | 128.4 (5.7) |
| AUC (mg/dL * min) | 30915.0 (2482.5) | 29525.6 (1477.0) | 29983.1 (1894.8) | 25680.0 (1883.5) |

TABLE BIO-4E

Plasma Insulin (in ng/mL (Std Err))

| | Plasma Insulin |
|---|---|
| Vehicle | 4.05 (0.5) |
| 1 mg/kg | 2.60 (0.3) |
| 3 mg/kg | 2.26 (0.3) |
| 10 mg/kg | 2.14 (0.3) |

TABLE BIO-4F

Fed Blood Glucose (in mg/dL (Std Err))

| | Day 0 | Day 18 |
|---|---|---|
| Vehicle | 173.75 (4.83) | 165.71 (8.30) |
| 1 mg/kg | 162.75 (13.02) | 154.83 (5.98) |
| 3 mg/kg | 167.13 (7.59) | 156.50 (7.39) |
| 10 mg/kg | 161.88 (6.71) | 154.00 (5.53) |

TABLE BIO 4G

Plasma and Brain Concentrations,
2 Hours Post Dose, Day 16

| | Plasma ng/mL (Std Dev) | Brain ng/g (Std Dev) |
|---|---|---|
| 1 mg/kg | 431 (62) | 59.4 (17.6) |
| 3 mg/kg | 1513 (443) | 114 (22) |
| 10 mg/kg | 4437 (337) | 244 (21) |

In a second study, Compound #44 was tested according to the procedure as described above, with results as listed in Tables BIO-5A through 5G, below.

TABLE BIO-5A

Mean Daily Food Intake (in Grams (Std Err))

| | Vehicle | 0.3 mg/kg | 1 mg/kg | 3 mg/kg | 10 mg/kg |
|---|---|---|---|---|---|
| Day 2 | 2.38 (0.10) | 2.51 (0.09) | 2.84 (0.06) | 2.50 (0.11) | 2.07 (0.14) |
| Day 3 | 2.70 (0.15) | 2.92 (0.07) | 2.79 (0.06) | 2.41 (0.09) | 1.63 (0.14) |
| Day 4 | 2.35 (0.12) | 2.76 (0.17) | 2.45 (0.08) | 2.02 (0.13) | 1.48 (0.11) |
| Day 5 | 2.20 (0.14) | 2.64 (0.11) | 2.49 (0.14) | 2.02 (0.15) | 1.38 (0.12) |
| Day 8 | 2.58 (0.15) | 2.80 (0.10) | 2.63 (0.09) | 2.13 (0.09) | 1.64 (0.13) |
| Day 10 | 2.81 (0.10) | 2.81 (0.11) | 2.67 (0.08) | 2.57 (0.10) | 2.08 (0.11) |
| Day 11 | 2.54 (0.11) | 2.68 (0.09) | 2.57 (0.09) | 2.29 (0.12) | 2.12 (0.05) |

TABLE BIO-5B

Mean Body Weight (in Grams (Std Err))

| | Vehicle | 0.3 mg/kg | 1 mg/kg | 3 mg/kg | 10 mg/kg |
|---|---|---|---|---|---|
| Day 1 | 40.82 (0.85) | 40.78 (0.65) | 40.60 (0.65) | 40.54 (0.58) | 40.51 (0.57) |
| Day 2 | 41.09 (0.88) | 40.87 (0.62) | 40.78 (0.62) | 40.47 (0.51) | 39.87 (0.53) |
| Day 3 | 40.93 (0.89) | 40.77 (0.67) | 40.85 (0.62) | 40.24 (0.55) | 39.16 (0.50) |
| Day 4 | 40.21 (0.82) | 40.33 (0.64) | 40.36 (0.64) | 39.39 (0.53) | 38.04 (0.48) |
| Day 5 | 40.20 (0.81) | 40.53 (0.67) | 40.42 (0.66) | 39.11 (0.64) | 27.49 (0.54) |
| Day 8 | 40.48 (0.83) | 40.87 (0.75) | 40.16 (0.74) | 38.59 (0.61) | 35.69 (0.71) |
| Day 10 | 40.81 (0.87) | 41.06 (0.73) | 40.73 (0.81) | 38.48 (0.72) | 35.08 (0.70) |
| Day 11 | 40.93 (0.84) | 41.61 (0.71) | 40.74 (0.70) | 38.13 (0.80) | 34.63 (0.69) |

TABLE BIO-5C

Insulin Tolerance Test, Mean Blood Glucose (in mg/dL (Std Err))

| | Vehicle | 0.3 mg/kg | 1 mg/kg | 3 mg/kg | 10 mg/kg |
|---|---|---|---|---|---|
| 0 min | 190.05 (5.05) | 185.00 (3.58) | 181.70 (5.90) | 161.10 (4.61) | 161.10 (7.94) |
| 15 min | 194.33 (7.35) | 172.38 (6.81) | 193.89 (8.03) | 179.67 (5.47) | 143.90 (12.96) |
| 30 min | 184.67 (6.86) | 164.13 (4.33) | 170.56 (8.02) | 156.33 (6.19) | 133.60 (12.91) |
| 60 min | 180.33 (5.94) | 169.38 (5.38) | 182.78 (6.03) | 167.22 (6.39) | 126.20 (11.09) |
| 120 min | 153.67 (3.61) | 165.13 (8.21) | 179.40 (6.12) | 159.78 (5.72) | 136.10 (11.70) |
| AUC (mg/dL * min) | 21205.83 (451.50) | 20233.13 (601.56) | 21698.33 (582.26) | 19435.83 (408.53) | 16134.75 (1237.70) |

TABLE BIO-5D

Intraperitoneal Glucose Tolerance Test
Mean Blood Glucose (in mg/dL (Std Err))

| | Vehicle | 0.3 mg/kg | 1 mg/kg | 3 mg/kg | 10 mg/kg |
|---|---|---|---|---|---|
| 0 min | 164.20 (6.05) | 155.44 (5.54) | 156.60 (5.76) | 141.30 (5.94) | 149.00 (6.76) |
| 30 min | 201.50 (8.51) | 204.33 (11.35) | 225.20 (5.87) | 224.30 (18.09) | 218.50 (12.49) |

TABLE BIO-5D-continued

Intraperitoneal Glucose Tolerance Test
Mean Blood Glucose (in mg/dL (Std Err))

|  | Vehicle | 0.3 mg/kg | 1 mg/kg | 3 mg/kg | 10 mg/kg |
|---|---|---|---|---|---|
| 60 min | 201.30 (7.06) | 187.67 (7.45) | 185.50 (6.65) | 174.20 (6.66) | 169.60 (7.72) |
| 120 min | 163.50 (5.29) | 154.78 (3.77) | 155.00 (5.19) | 138.90 (5.37) | 146.60 (3.04) |
| AUC (mg/dL * min) | 22471.50 (598.52) | 21550.00 (730.92) | 22102.50 (604.07) | 20854.50 (678.62) | 20820.00 (599.17) |

TABLE BIO-5E

Plasma Insulin (in ng/mL (Std Err))

|  | Plasma Insulin |
|---|---|
| Vehicle | 3.57 (0.29) |
| 0.3 mg/kg | 3.89 (0.31) |
| 1 mg/kg | 3.12 (0.64) |
| 3 mg/kg | 1.74 (0.14) |
| 10 mg/kg | 1.64 (0.32) |

TABLE BIO-5F

Fed Blood Glucose (in mg/dL (Std Err))

|  | Day 0 | Day 18 |
|---|---|---|
| Vehicle | 160.30 (7.07) | 142.70 (4.69) |
| 0.3 mg/kg | 165.4 (8.16) | 161.22 (6.29) |
| 1 mg/kg | 170.80 (5.99) | 151.20 (6.14) |
| 3 mg/kg | 161.8 (6.57) | 142.60 (4.44) |
| 10 mg/kg | 167.9 (4.63) | 144.30 (6.47) |

TABLE BIO 5G

Plasma and Brain Concentrations, 2 Hours Post Dose

|  | Day 2 | | Day 23 | |
|---|---|---|---|---|
|  | Plasma ng/mL (Std Dev) | Brain ng/g (Std Dev) | Plasma ng/mL (Std Dev) | Brain ng/g (Std Dev) |
| 0.3 mg/kg | 61.3 (19.2) | BLOQ* | 192 (33.0) | BLOQ** |
| 1 mg/kg | 310 (48) | BLOQ* | 515 (101) | 36.8 (8.26) |
| 3 mg/kg | 759 (103) | BLOQ* | 1558 (211) | 100 (9.57) |
| 10 mg/kg | 2492 (590) | 62.3 (6.6) | 5282 (742) | 201 (21.8) |

Biological Example 5

Open Field Locomotor Activity in Rats (CNS Activity)

Male SD rats were weighed and transferred to the Activity Chambers with access to water. After a 2-hr acclimation period, the rats were dosed with vehicle or test compound (@3 and 10 mg/kg). The Activity Chamber monitoring software program was initiated and automatically recorded rat activity in each chamber for a period of 4 hours. At the end of the 4 hour monitoring period, the software was stopped and the rats were removed from the activity chambers. The rats were anesthetized and blood samples were obtained via retro-orbital puncture to determine plasma concentration of compounds. The rats were immediately euthanized with $CO_2$ and the brains removed, washed with PBS, frozen on dry ice and stored at −80° C. for receptor occupancy (RO) analysis.

Satellite groups of 3 rats were dosed with test compound at 3 mg/kg and 10 mg/kg respectively. Four hours later, the rats were anesthetized. Blood was collected from these rats and then they were perfused with 400 ml heparinized saline through the left ventricle of the heart. The brains were removed and homogenized in PBS (4 ml/gm tissue). The samples were submitted for determination of plasma and brain compound levels.

Compound #44 was tested in n=8 animals, according to the procedure as described above, with stereotypic counts as listed in Table BIO-5A; and plasma and brain drug levels as listed in Table BIO-5B, below.

TABLE BIO-5A

Stereotypic Counts from Open Field Locomotor Study

| Compound No. | Stereotypic Counts (MEAN) | Stereotypic Counts (SEM) |
|---|---|---|
| Vehicle | 3022 | 406 |
| #44 | 3250 | 329 |
| #44 | 2850 | 162 |

TABLE BIO-5B

Plasma and Brain Concentrations (4 Hrs. Post Dosing)

|  | Plasma (ng/mL) Mean ± Std Dev | Brain (ng/g) Mean ± Std Dev |
|---|---|---|
| Compound #44 @ 3 mg/kg | 126 ± (28) | 9.85 ± (17.1) |
| Compound #44 @ 10 mg/kg | 501 ± (148) | 22.7 ± (19.9) |

Formulation Example 1

Solid, Oral Dosage Form—Prophetic Example

As a specific embodiment of an oral composition, 100 mg of the Compound 44, prepared as in Example 2, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (B)

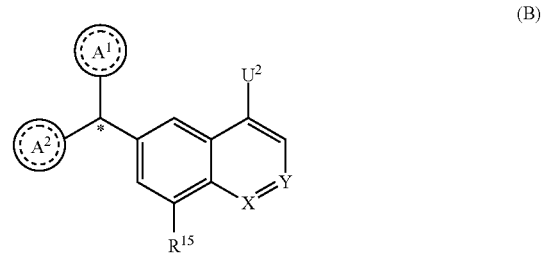

(B)

wherein
U² is selected from the group consisting of

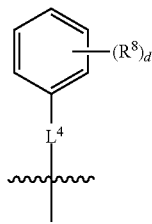 and 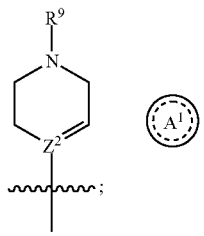;

is selected from the group consisting of phenyl, furyl, thienyl, thiazolyl, pyridyl, benzothiazolyl and benzo[d][1,3]dioxolyl;
  wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;
  wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^C$R$^D$; wherein R$^C$ and R$^D$ are each independently selected from the group consisting of hydrogen, $C_{1-4}$alkyl and —($C_{2-4}$alkyl)-O—($C_{1-4}$alkyl); provided that each substituent is bound to a carbon atom of the ring;
R$^{15}$ is selected from the group consisting of hydrogen, halogen, —OH, —$C_{1-4}$alkyl, —O—($C_{1-4}$alkyl), —NH$_2$, —NH($C_{1-4}$alkyl) and —N($C_{1-4}$alkyl)$_2$;
provided that when U² is

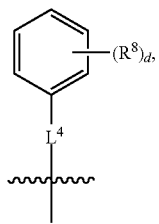

then R$^{15}$ is selected from the group consisting of hydrogen and —O—($C_{1-4}$alkyl);

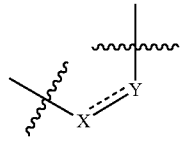

is selected from the group consisting of

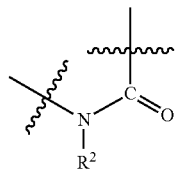 and 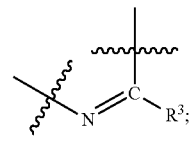;

R² is selected from the group consisting of hydrogen, —($C_{1-4}$alkyl), —($C_{2-4}$alkyl)-O—($C_{1-4}$alkyl), —($C_{1-4}$alkyl)-CO$_2$H, —($C_{1-4}$alkyl)-C(O)O—($C_{1-4}$alkyl) and —($C_{1-4}$alkyl)-C(O)—NR$^L$R$^M$; wherein R$^L$ and R$^M$ are each independently selected from the group consisting of hydrogen and $C_{1-4}$alkyl;

R³ is selected from the group consisting of hydrogen and —OR⁴;

wherein R⁴ is selected from the group consisting of —$C_{1-12}$alkyl, -(hydroxy substituted $C_{2-12}$alkyl), —($C_{1-12}$ alkyl)-N$_3$, —($C_{2-12}$alkyl)-NR$^J$R$^K$, —($C_{2-12}$alkyl)-O—($C_{1-12}$alkyl), —($C_{2-12}$alkyl)-O—($C_{2-12}$alkyl)-CN, —($C_{2-12}$alkyl)-O—($C_{1-12}$alkyl)-CO$_2$H, —($C_{2-12}$alkyl)-O—($C_{1-12}$alkyl)-C(O)—O—($C_{1-6}$alkyl), —($C_{1-12}$ alkyl)-O—($C_{1-12}$alkyl)-C(O)—NR$^J$R$^K$, —($C_{1-12}$ alkyl)-CO$_2$H, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—NR$^J$R$^K$, —($C_{1-12}$alkyl)-C(O)—NR$^J$R$^K$, —($C_{2-12}$alkyl)-NR$^J$—C(O)—($C_{1-6}$alkyl), —($C_{2-12}$ alkyl)-NR$^J$—C(O)—($C_{1-12}$alkyl)-OH, —($C_{2-12}$ alkyl)-NR$^J$—SO$_2$—($C_{1-6}$alkyl), and —SO$_2$-(halogenated $C_{1-12}$alkyl); wherein R$^J$ and R$^K$ are each independently selected from the group consisting of hydrogen, $C_{1-6}$alkyl and hydroxy substituted $C_{2-6}$alkyl;

provided that when that when R$^{15}$ is other than hydrogen, then R² is hydrogen;

L⁴ is selected from the group consisting of —CH$_2$—, —CH$_2$CH$_2$— and —CH=CH—;

d is an integer from 0 to 2; and each R⁸ is independently selected from the group consisting of halogen, cyano, $C_{1-4}$alkyl, halogenated $C_{1-4}$alkyl, $C_{1-4}$alkoxy and halogenated $C_{1-4}$alkoxy;

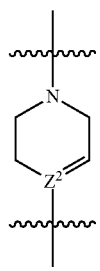

is selected from the group consisting of

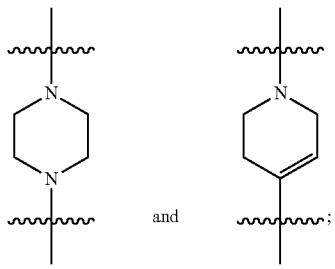 [SMILES: *N1CCN(*)CC1 ; *C1=CCN(*)CC1]

and;

wherein $Z^2$ is N and "----" represents a single bond or alternatively, $Z^2$ is C and "----" represents a double bond;
$R^9$ is selected from the group consisting of hydrogen, —C(O)O—($C_{1-4}$alkyl), —C(O)—($C_{1-4}$alkyl), —C(O)-(halogenated $C_{1-4}$alkyl) and —SO$_2$-(halogenated $C_{1-4}$alkyl);
provided that when

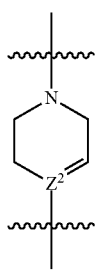

is piperazin-1-yl, then $R^9$ is other than hydrogen;
or a stereoisomer, tautomer or pharmaceutically acceptable salt thereof.

2. A compound as in claim 1 of the formula (III)

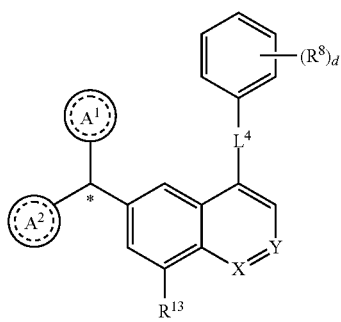

(III)

wherein

is selected from the group consisting of phenyl, furyl, thienyl, thiazolyl, pyridyl, benzothiazolyl and benzo[d][1,3]dioxolyl;
  wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^A$R$^B$; wherein R$^A$ and R$^B$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;
  wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and NR$^C$R$^D$; wherein R$^C$ and R$^D$ are each independently selected from the group consisting of hydrogen, $C_{1-4}$alkyl and —($C_{2-4}$alkyl)-O—($C_{1-4}$alkyl); provided that each substituent is bound to a carbon atom of the ring;
$R^{13}$ is selected from the group consisting of hydrogen and —O—($C_{1-4}$alkyl);

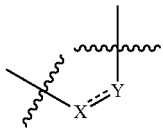

is selected from the group consisting of

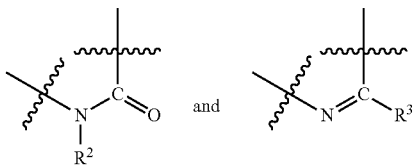

and;

$R^2$ is selected from the group consisting of hydrogen, —($C_{1-4}$alkyl), —($C_{2-4}$alkyl)-O—($C_{1-4}$alkyl), —($C_{1-4}$alkyl)-CO$_2$H, —($C_{1-4}$alkyl)-C(O)O—($C_{1-4}$alkyl) and —($C_{1-4}$alkyl)-C(O)—NR$^L$R$^M$; wherein R$^L$ and R$^M$ are each independently selected from the group consisting of hydrogen and $C_{1-4}$alkyl;
$R^3$ is selected from the group consisting of hydrogen and —OR$^4$;
  wherein R$^4$ is selected from the group consisting of —$C_{1-12}$alkyl, -(hydroxy substituted $C_{2-12}$alkyl), —($C_{1-12}$ alkyl)-N$_3$, —($C_{2-12}$alkyl)-NR$^J$R$^K$, —($C_{2-12}$alkyl)-O—($C_{1-12}$alkyl), —($C_{2-12}$alkyl)-O—($C_{1-12}$alkyl)-CN, —($C_{2-12}$alkyl)-O—($C_{1-12}$alkyl)-CO$_2$H, —($C_{2-12}$alkyl)-O—($C_{1-12}$alkyl)-C(O)—O—($C_{1-6}$alkyl), —($C_{2-12}$ alkyl)-O—($C_{1-12}$alkyl)-C(O)—NR$^J$R$^K$, —($C_{1-12}$ alkyl)-CO$_2$H, —($C_{1-12}$alkyl)-C(O)

O—(C$_{1-6}$alkyl), —(C$_{2-12}$alkyl)-OC(O)—(C$_{1-6}$alkyl), —(C$_{2-12}$alkyl)-OC(O)—NR$^J$R$^K$, —(C$_{1-12}$alkyl)-C(O)—NR$^J$R$^K$, —(C$_{2-12}$alkyl)-NR$^J$—C(O)—(C$_{1-6}$ alkyl), —(C$_{2-12}$ alkyl)-NR$^J$—C(O)—(C$_{1-12}$alkyl)-OH, —(C$_{2-12}$ alkyl)-NR$^J$—SO$_2$—(C$_{1-6}$alkyl), and —SO$_2$-(halogenated C$_{1-12}$alkyl); wherein R$^J$ and R$^K$ are each independently selected from the group consisting of hydrogen, C$_{1-6}$alkyl and hydroxy substituted C$_{2-6}$alkyl;

provided that when R$^{13}$ is —O—(C$_{1-4}$alkyl), then R$^2$ is hydrogen;

L$^4$ is selected from the group consisting of —CH$_2$—, —CH$_2$CH$_2$— and —CH=CH—;

d is an integer from 0 to 2;

each R$^8$ is independently selected from the group consisting of halogen, cyano, C$_{1-4}$alkyl, halogenated C$_{1-4}$alkyl, C$_{1-4}$alkoxy and halogenated C$_{1-4}$alkoxy;

or stereoisomer, tautomer or pharmaceutically acceptable salt thereof.

3. A compound as in claim 2, wherein

is selected from the group consisting of phenyl, thiazolyl and benzothiazolyl;

wherein the phenyl or thiazolyl is optionally substituted with one to two substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, and NR$^A$R$^B$; wherein R$^A$ and R$^B$ are each independently selected from the group consisting of hydrogen, C$_{1-4}$alkyl and —(C$_2$alkyl)-O—(C$_{1-2}$alkyl); provided that each substituent is bound to a carbon atom of the ring;

is selected from the group consisting of phenyl, thiazolyl and benzothiazolyl;

wherein the phenyl or thiazolyl is optionally substituted with one to two substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, and NR$^A$R$^B$; wherein R$^A$ and R$^B$ are each independently selected from the group consisting of hydrogen, C$_{1-4}$alkyl and —(C$_2$alkyl)-O—(C$_{1-2}$alkyl); provided that each substituent is bound to a carbon atom of the ring R$^{13}$ is selected from the group consisting of hydrogen and —O—(C$_{1-2}$alkyl);

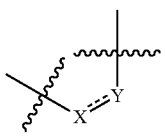

is selected from the group consisting of

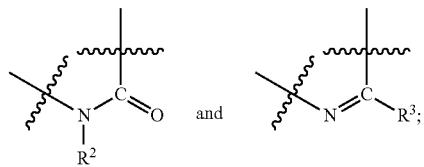

R$^2$ is selected from the group consisting of hydrogen, —(C$_{1-4}$alkyl), —(C$_2$alkyl)-O—(C$_{1-2}$alkyl), —(C$_{1-2}$alkyl)-CO$_2$H, —(C$_{1-2}$alkyl)-C(O)O—(C$_{1-4}$alkyl) and —(C$_{1-4}$alkyl)-C(O)—NR$^L$R$^M$; wherein R$^L$ and R$^M$ are each independently selected from the group consisting of hydrogen and C$_{1-2}$alkyl;

R$^3$ is selected from the group consisting of hydrogen and —OR$^4$;

wherein R$^4$ is selected from the group consisting of —C$_{1-6}$alkyl, -(hydroxy substituted C$_{2-4}$alkyl), —(C$_{2-4}$alkyl)-NR$^J$R$^K$, —(C$_{2-4}$alkyl)-O—(C$_{1-4}$alkyl)-CO$_2$H, (C$_{1-4}$alkyl)-C(O)—O—(C$_{1-4}$alkyl), —(C$_{2-4}$alkyl)-O—(C$_{1-4}$alkyl)-C(O)—NR$^J$R$^K$, —(C$_{1-6}$alkyl)-CO$_2$H, —(C$_{1-6}$alkyl)-C(O)O—(C$_{1-4}$alkyl), —(C$_{1-4}$alkyl)-C(O)—NR$^J$R$^K$, —(C$_{2-4}$alkyl)-NR$^J$—C(O)—(C$_{1-4}$alkyl) and —SO$_2$-(fluorinated C$_{1-2}$alkyl); wherein R$^J$ and R$^K$ are each independently selected from the group consisting of hydrogen, C$_{1-6}$alkyl;

provided that when R$^{13}$ is —O—(C$_{1-2}$alkyl), then R$^2$ is hydrogen;

L$^4$ is selected from the group consisting of —CH$_2$—, —CH$_2$CH$_2$— and —CH=CH—;

d is an integer from 0 to 1;

each R$^8$ is independently selected from the group consisting of halogen, cyano, C$_{1-4}$alkyl, fluorinated C$_{1-2}$alkyl, C$_{1-4}$alkoxy and fluorinated C$_{1-2}$alkoxy;

or stereoisomer, tautomer or pharmaceutically acceptable salt thereof.

4. A compound as in claim 3, wherein

is phenyl; wherein the phenyl is substituted with a substituent selected from the group consisting of halogen and C$_{1-2}$alkoxy;

is selected from the group consisting of phenyl, thiazolyl and thienyl; wherein the phenyl or thienyl is optionally substituted with a substituent selected from the group consisting of halogen and C$_{1-2}$alkoxy;

R$^{13}$ is hydrogen;

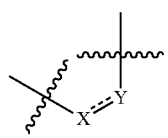

is selected from the group consisting of

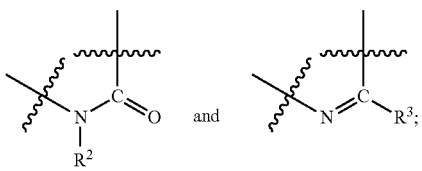 and

R² is selected from the group consisting of hydrogen and C$_{1-2}$alkyl;

R³ is selected from the group consisting of hydrogen and —OR⁴; wherein R⁴ is selected from the group consisting of C$_{1-4}$alkyl;

L⁴ is selected from the group consisting of —CH$_2$—, —CH$_2$CH$_2$—, —CH=CH—, cis-CH=CH— and trans-CH=CH—;

d is an integer from 0 to 1;

R⁸ is selected from the group consisting of halogen, C$_{1-2}$alkyl, fluorinated C$_{1-2}$alkyl and fluorinated C$_{1-2}$alkoxy;

or stereoisomer, tautomer or pharmaceutically acceptable salt thereof.

5. A compound as in claim 4, wherein

is selected from the group consisting of 4-chlorophenyl and 4-methoxyphenyl;

is selected from the group consisting of phenyl, 4-chlorophenyl, 4-methoxyphenyl, thiazol-2-yl, thiazol-4-yl, thien-2-yl, thien-3-yl and 5-chloro-thien-2-yl;

R¹³ is hydrogen;

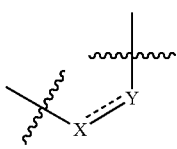

is selected from the group consisting of

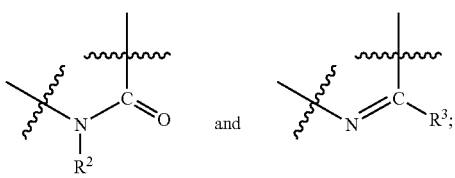 and

R² is selected from the group consisting of hydrogen and methyl;

R³ is hydrogen;

L⁴ is selected from the group consisting of —CH$_2$—, —CH$_2$CH$_2$—, —CH=CH—, cis-CH=CH— and trans-CH=CH—;

d is an integer from 0 to 1;

R⁸ is selected from the group consisting of 3-fluoro, 3-chloro, 4-chloro, 4-methyl, 3-trifluoromethyl, 4-trifluoromethyl and 4-trifluoromethoxy;

or stereoisomer, tautomer or pharmaceutically acceptable salt thereof.

6. A compound as in claim 5, wherein

is selected from the group consisting of 4-chlorophenyl and 4-methoxyphenyl;

is selected from the group consisting of phenyl, 4-chlorophenyl, 4-methoxyphenyl, thien-2-yl and thien-3-yl;

R¹³ is hydrogen;

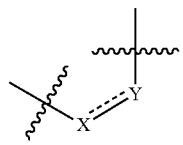

is selected from the group consisting of

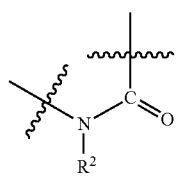 and

R² is selected from the group consisting of hydrogen and methyl;

R³ is hydrogen;

L⁴ is selected from the group consisting of —CH$_2$CH$_2$—, —CH=CH—, cis-CH=CH— and trans-CH=CH—;

d is an integer from 0 to 1;

R⁸ is selected from the group consisting of 3-fluoro, 3-chloro, 4-methyl, 3-trifluoromethyl, 4-trifluoromethyl and 4-trifluoromethoxy.

7. A compound as in claim 5, wherein

is 4-chlorophenyl;

is selected from the group consisting of 4-chlorophenyl, thiazol-4-yl and thien-3-yl;

R$^{13}$ is hydrogen;

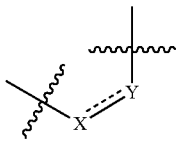

is selected from the group consisting of

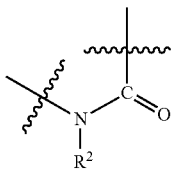 and 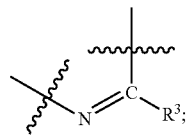

R$^2$ is selected from the group consisting of hydrogen and methyl;
R$^3$ is hydrogen;
L$^4$ is selected from the group consisting of —CH$_2$CH$_2$—, —CH═CH—, cis-CH═CH— and trans-CH═CH—;
d is an integer from 0 to 1;
R$^8$ is selected from the group consisting of 3-fluoro, 3-chloro and 3-trifluoromethyl;
or stereoisomer, tautomer or pharmaceutically acceptable salt thereof.

8. A compound as in claim 5, wherein

is selected from the group consisting of 4-chlorophenyl and 4-methoxyphenyl;

is selected from the group consisting of 4-chlorophenyl, thien-2-yl and thien-3-yl;

R$^{13}$ is hydrogen;

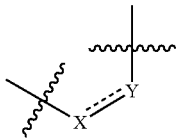

is selected from the group consisting of

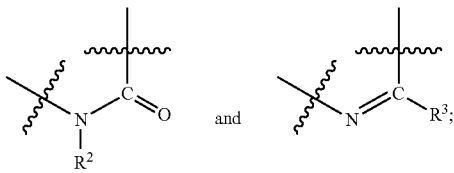

R$^2$ is hydrogen;
R$^3$ is hydrogen;
L$^4$ is selected from the group consisting of —CH$_2$CH$_2$—, —CH═CH—, cis-CH═CH— and trans-CH═CH—;
d is an integer from 0 to 1;
R$^8$ is selected from the group consisting of 3-fluoro, 3-chloro and 3-trifluoromethyl;
or a pharmaceutically acceptable salt thereof.

9. A compound as in claim 1 of the formula (IV)

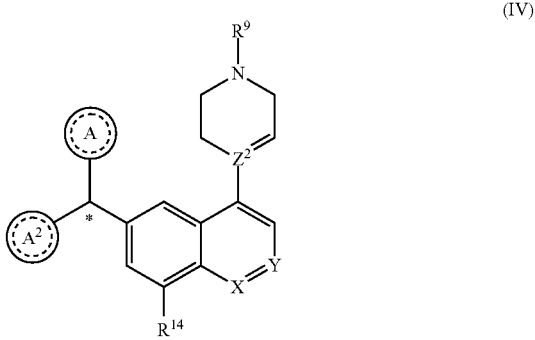

(IV)

wherein

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, cyano, —C(O)OH, C(O)O—C$_{1-4}$alkyl and NR$^A$R$^B$; wherein R$^A$ and R$^B$ are each independently selected from the group consisting of hydrogen, C$_{1-4}$alkyl and —(C$_{2-4}$alkyl)-O—(C$_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, C$_{1-4}$alkyl, fluorinated C$_{1-4}$alkyl, C$_{1-4}$alkoxy, fluorinated C$_{1-4}$alkoxy, cyano, —C(O)OH, C(O)O—C$_{1-4}$alkyl and NR$^C$R$^D$; wherein R$^C$ and R$^D$ are each independently selected from the group consisting of hydrogen, C$_{1-4}$alkyl and —(C$_{2-4}$alkyl)-O—(C$_{1-4}$alkyl); provided that each substituent is bound to a carbon atom of the ring;

R$^{14}$ is selected from the group consisting of hydrogen, halogen, —OH, —C$_{1-4}$alkyl, —O—(C$_{1-4}$alkyl), —NH$_2$, —NH(C$_{1-4}$alkyl) and —N(C$_{1-4}$alkyl)$_2$;

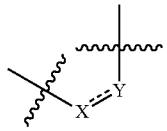

is selected from the group consisting of

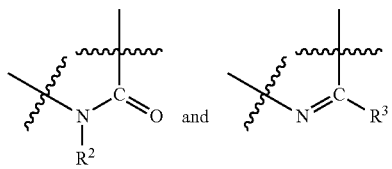

and;

R$^2$ is selected from the group consisting of hydrogen, —(C$_{1-4}$alkyl), —(C$_{2-4}$alkyl)-O—(C$_{1-4}$alkyl), —(C$_{1-4}$alkyl)-CO$_2$H, —(C$_{1-4}$alkyl)-C(O)O—(C$_{1-4}$alkyl) and —(C$_{1-4}$alkyl)-C(O)—NR$^L$R$^M$; wherein R$^L$ and R$^M$ are each independently selected from the group consisting of hydrogen and C$_{1-4}$alkyl;

R$^3$ is selected from the group consisting of hydrogen and —OR$^4$;

wherein R$^4$ is selected from the group consisting of —C$_{1-12}$alkyl, -(hydroxy substituted C$_{2-12}$alkyl), —(C$_{1-12}$ alkyl)-N$_3$, —(C$_{2-12}$alkyl)-NR$^J$R$^K$, —(C$_{2-12}$ alkyl)-O—(C$_{1-12}$alkyl), —(C$_{2-12}$alkyl)-O—(C$_{2-12}$ alkyl)-CN, —(C$_{2-12}$alkyl)-O—(C$_{1-12}$alkyl)-CO$_2$H, —(C$_{2-12}$alkyl)-O—(C$_{1-12}$alkyl)-C(O)—O—(C$_{1-6}$ alkyl), —(C$_{1-12}$ alkyl)-O—(C$_{1-12}$alkyl)-C(O)—NR$^J$R$^K$, —(C$_{1-12}$ alkyl)-CO$_2$H, —(C$_{1-12}$alkyl)-C(O) O—(C$_{1-6}$alkyl), —(C$_{2-12}$alkyl)-OC(O)—(C$_{1-6}$alkyl), —(C$_{2-12}$alkyl)-OC(O)—NR$^J$R$^K$, —(C$_{1-12}$alkyl)-C (O)—NR$^J$R$^K$, —(C$_{2-12}$alkyl)-NR$^J$—C(O)—(C$_{1-6}$ alkyl), —(C$_{2-12}$ alkyl)-NR$^J$—C(O)—(C$_{1-12}$alkyl)-OH, —(C$_{2-12}$ alkyl)-NR$^J$—SO$_2$—(C$_{1-6}$alkyl), and —SO$_2$-(halogenated C$_{1-12}$alkyl); wherein R$^J$ and R$^K$ are each independently selected from the group consisting of hydrogen, C$_{1-6}$alkyl and hydroxy substituted C$_{2-6}$alkyl;

provided that when R$^{14}$ is other than hydrogen, then R$^2$ is hydrogen;

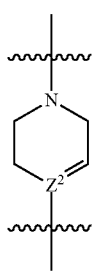

is selected from the group consisting of

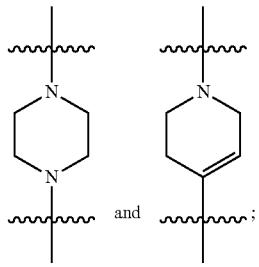

wherein Z$^2$ is N and "----" represents a single bond or alternatively, Z$^2$ is C and "----" represents a double bond; R$^9$ is selected from the group consisting of hydrogen, —C(O)O—(C$_{1-4}$alkyl), —C(O)—(C$_{1-4}$alkyl), —C(O)-(halogenated C$_{1-4}$alkyl) and —SO$_2$-(halogenated C$_{1-4}$alkyl);

provided that when

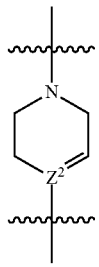

is piperazin-1-yl, then R$^9$ is other than hydrogen;
or stereoisomer, tautomer or pharmaceutically acceptable salt thereof.

10. A compound as in claim 9, wherein

is selected from the group consisting of phenyl, thiazolyl and benzothiazolyl;
wherein the phenyl or thiazolyl is optionally substituted with one to two substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, and NR$^A$R$^B$; wherein R$^A$ and R$^B$ are each independently selected from the group consisting of hydrogen, C$_{1-4}$alkyl and —(C$_2$alkyl)-O—(C$_{1-2}$alkyl); provided that each substituent is bound to a carbon atom of the ring;

is selected from the group consisting of phenyl, thiazolyl and benzothiazolyl;
wherein the phenyl or thiazolyl is optionally substituted with one to two substituents independently selected from the group consisting of halogen, hydroxy, C$_{1-4}$alkyl, fluorinated C$_{1-2}$alkyl, C$_{1-4}$alkoxy, fluorinated C$_{1-2}$alkoxy, and NR$^A$R$^B$; wherein R$^A$ and R$^B$ are each independently selected from the group consisting of hydrogen, C$_{1-4}$alkyl and —(C$_2$alkyl)-O—(C$_{1-2}$alkyl); provided that each substituent is bound to a carbon atom of the ring;

R$^{14}$ is selected from the group consisting of hydrogen, halogen, —C$_{1-2}$alkyl, —NH$_2$, —NH(C$_{1-2}$alkyl) and —N(C$_{1-2}$alkyl)$_2$;

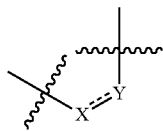

is selected from the group consisting of

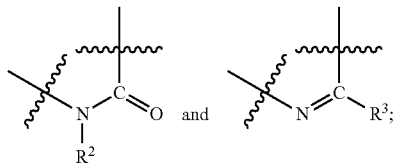

R$^2$ is selected from the group consisting of hydrogen, —(C$_{1-4}$alkyl), —(C$_2$alkyl)-O—(C$_{1-2}$alkyl), —(C$_{1-2}$alkyl)-CO$_2$H, —(C$_{1-2}$alkyl)-C(O)O—(C$_{1-4}$alkyl) and —(C$_{1-4}$alkyl)-C(O)—NR$^L$R$^M$; wherein R$^L$ and R$^M$ are each independently selected from the group consisting of hydrogen and C$_{1-2}$alkyl;

R$^3$ is selected from the group consisting of hydrogen and —OR$^4$;

wherein R$^4$ is selected from the group consisting of —C$_{1-6}$alkyl, -(hydroxy substituted C$_{2-4}$alkyl), —(C$_{2-4}$alkyl)-N$^J$R$^K$, —(C$_{2-4}$alkyl)-O—(C$_{1-4}$alkyl), —(C$_{2-4}$alkyl)-O—(C$_{1-4}$alkyl)-CO$_2$H, —(C$_{2-4}$alkyl)-O—(C$_{1-4}$alkyl)-C(O)O—(C$_{1-4}$alkyl), —(C$_{2-4}$alkyl)-O—(C$_{1-4}$alkyl)-C(O)—NR$^J$R$^K$, —(C$_{1-6}$alkyl)-CO$_2$H, —(C$_{1-6}$alkyl)-C(O)O—(C$_{1-4}$alkyl), —(C$_{1-4}$alkyl)-C(O)—NR$^J$R$^K$, —(C$_{2-4}$alkyl)-NR$^J$—C(O)—(C$_{1-4}$alkyl) and —SO$_2$-(fluorinated C$_{1-2}$alkyl); wherein R$^J$ and R$^K$ are each independently selected from the group consisting of hydrogen, C$_{1-6}$alkyl;

provided that when R$^{14}$ is other than hydrogen, then R$^2$ is hydrogen;

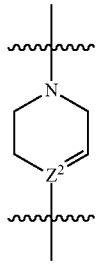

is selected from the group consisting of

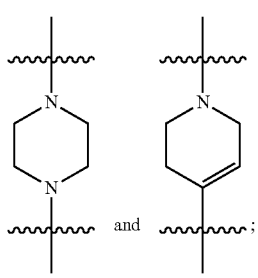

wherein Z$^2$ is N and "- - -" represents a single bond or alternatively, Z$^2$ is C and "- - -" represents a double bond;

R$^9$ is selected from the group consisting of hydrogen, —C(O)O—(C$_{1-4}$alkyl), —C(O)—(C$_{1-4}$alkyl), —C(O)-(fluorinated C$_{1-2}$alkyl) and —SO$_2$-(fluorinated C$_{1-2}$alkyl);

provided that when

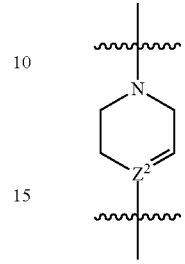

is piperazin-1-yl, then R$^9$ is other than hydrogen;

or stereoisomer, tautomer or pharmaceutically acceptable salt thereof.

11. A compound as in claim 10, wherein

is phenyl; wherein the phenyl is substituted with a halogen;

is selected from the group consisting of phenyl and thiazolyl; wherein the phenyl is substituted with a halogen;

R$^{14}$ is hydrogen;

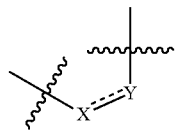

is selected from the group consisting of

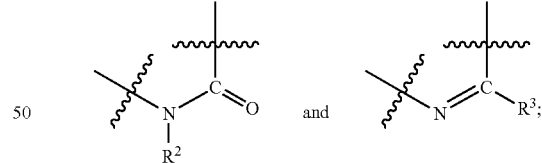

R$^2$ is hydrogen;

R$^3$ is selected from the group consisting of hydrogen and —OR$^4$; wherein R$^4$ is —SO$_2$-(fluorinated C$_{1-2}$alkyl);

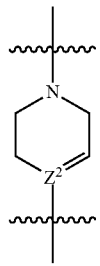

is selected from the group consisting of

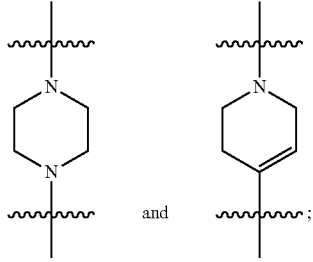

wherein $Z^2$ is N and "-----" represents a single bond or alternatively, $Z^2$ is C and "-----" represents a double bond;

$R^9$ is selected from the group consisting of hydrogen, —C(O)O—($C_{1-4}$alkyl), —C(O)—($C_{1-2}$alkyl), —C(O)-(fluorinated $C_{1-2}$alkyl) and —$SO_2$-(fluorinated $C_{1-2}$alkyl);

provided that when

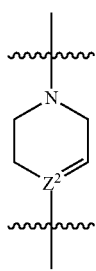

is piperazin-1-yl, then $R^9$ is other than hydrogen;

or stereoisomer, tautomer or pharmaceutically acceptable salt thereof.

12. A compound as in claim 11, wherein

is 4-chlorophenyl;

is selected from the group consisting of 4-chlorophenyl and thiazol-2-yl;

$R^{14}$ is hydrogen;

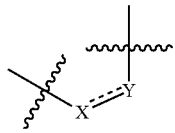

is selected from the group consisting of

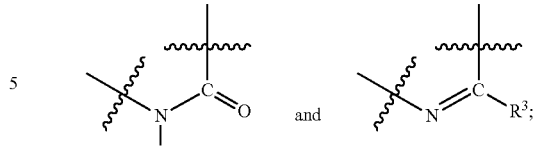

$R^2$ is hydrogen;

$R^3$ is selected from the group consisting hydrogen and —O—$SO_2$—$CF_3$;

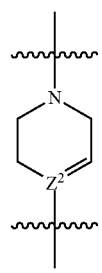

is selected from the group consisting of

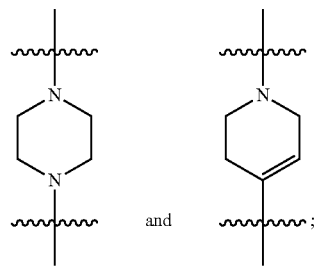

wherein $Z^2$ is N and "-----" represents a single bond or alternatively, $Z^2$ is C and "-----" represents a double bond;

$R^9$ is selected from the group consisting of hydrogen, —C(O)O-t-butyl, —C(O)-methyl, —C(O)—$CF_3$ and —$SO_2$—$CF_3$;

provided that when

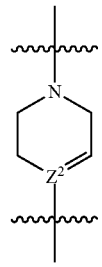

is piperazin-1-yl, then $R^9$ is other than hydrogen;

or stereoisomer, tautomer or pharmaceutically acceptable salt thereof.

13. A compound as in claim 11, wherein

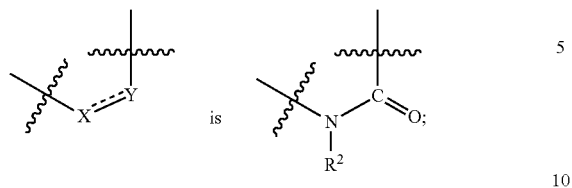

R⁹ is selected from the group consisting of —C(O)O-t-butyl, —C(O)—CF$_3$ and —SO$_2$—CF$_3$;

or stereoisomer, tautomer or pharmaceutically acceptable salt thereof.

14. A pharmaceutical composition comprising a pharmaceutically acceptable carrier and a compound of claim 1.

15. A pharmaceutical composition made by mixing a compound of claim 1 and a pharmaceutically acceptable carrier.

16. A process for making a pharmaceutical composition comprising mixing a compound of claim 1 and a pharmaceutically acceptable carrier.

* * * * *